US010526411B2

(12) United States Patent
King et al.

(10) Patent No.: US 10,526,411 B2
(45) Date of Patent: Jan. 7, 2020

(54) METHODS AND COMPOSITIONS RELATING TO ANTI-CCR7 ANTIGEN BINDING PROTEINS

(71) Applicant: AMGEN INC., Thousand Oaks, CA (US)

(72) Inventors: Chadwick Terence King, North Vancouver (CA); Gordon Ng, Vancouver (CA); Shaw-Fen Sylvia Hu, Thousand Oaks, CA (US); Hung Nguyen, Chandler, AZ (US); Jeannie Jung, Prosper, TX (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 15/665,139

(22) Filed: Jul. 31, 2017

(65) Prior Publication Data
US 2017/0342155 A1 Nov. 30, 2017

Related U.S. Application Data

(63) Continuation of application No. 14/776,670, filed as application No. PCT/US2014/026537 on Mar. 14, 2014, now abandoned.

(60) Provisional application No. 61/962,296, filed on Mar. 15, 2013.

(51) Int. Cl.
C07K 16/00 (2006.01)
C12P 21/08 (2006.01)
C07K 16/28 (2006.01)
A61K 39/00 (2006.01)

(52) U.S. Cl.
CPC ...... C07K 16/2866 (2013.01); A61K 39/0005 (2013.01); A61K 2039/5156 (2013.01); C07K 2317/14 (2013.01); C07K 2317/21 (2013.01); C07K 2317/24 (2013.01); C07K 2317/34 (2013.01); C07K 2317/51 (2013.01); C07K 2317/515 (2013.01); C07K 2317/56 (2013.01); C07K 2317/565 (2013.01); C07K 2317/76 (2013.01)

(58) Field of Classification Search
None
See application file for complete search history.

(56) References Cited

U.S. PATENT DOCUMENTS

| 3,773,919 | A | 11/1973 | Boswell et al. |
|---|---|---|---|
| 4,474,893 | A | 10/1984 | Reading |
| 4,518,584 | A | 5/1985 | Mark et al. |
| 4,737,462 | A | 4/1988 | Mark et al. |
| 4,751,180 | A | 6/1988 | Cousens et al. |
| 4,935,233 | A | 6/1990 | Bell et al. |
| 4,946,778 | A | 8/1990 | Ladner et al. |
| 4,965,195 | A | 10/1990 | Namen et al. |
| 4,968,607 | A | 11/1990 | Dower et al. |
| 5,011,912 | A | 4/1991 | Hopp et al. |
| 5,225,539 | A | 7/1993 | Winter |
| 5,260,203 | A | 11/1993 | Ladner et al. |
| 5,457,035 | A | 10/1995 | Baum et al. |
| 5,545,806 | A | 8/1996 | Lonberg et al. |
| 5,569,825 | A | 10/1996 | Lonberg et al. |
| 5,582,996 | A | 12/1996 | Curtis |
| 5,807,706 | A | 9/1998 | Carter et al. |
| 5,814,318 | A | 9/1998 | Lonberg et al. |
| 5,821,337 | A | 10/1998 | Carter et al. |
| 5,859,205 | A | 1/1999 | Adair et al. |
| 5,869,619 | A | 2/1999 | Studnicka |
| 5,959,083 | A | 9/1999 | Bosslet et al. |
| 6,010,902 | A | 1/2000 | Ledbetter et al. |
| 6,106,833 | A | 8/2000 | Ring et al. |
| 6,558,661 | B1 | 5/2003 | Ashkenazi et al. |
| 6,881,557 | B2 | 4/2005 | Foote |
| 8,865,170 | B2 * | 10/2014 | Nishiguchi ........ C07K 16/2866 424/135.1 |
| 2002/0155109 | A1 | 10/2002 | Lynch |
| 2003/0195154 | A1 | 10/2003 | Walker et al. |
| 2010/0159587 | A1 | 6/2010 | Brinkmann et al. |
| 2013/0129722 | A1 | 5/2013 | Lowy et al. |
| 2013/0186797 | A1 | 7/2013 | Walsh et al. |
| 2013/0195869 | A1 | 8/2013 | Nishiguchi et al. |

FOREIGN PATENT DOCUMENTS

| CA | 2813203 A1 | 4/2012 |
|---|---|---|
| EP | 036676 A1 | 9/1981 |
| EP | 058481 A1 | 8/1982 |
| EP | 088046 A2 | 9/1983 |
| EP | 133988 A2 | 3/1985 |
| EP | 143949 A1 | 6/1985 |
| EP | 367566 A1 | 5/1990 |
| EP | 460846 A1 | 12/1991 |
| WO | 198801649 A1 | 3/1988 |

(Continued)

OTHER PUBLICATIONS

Paul, Fundamental Immunology, 3rd Edition, 1993, pp. 292-295, under the heading "Fv Structure and Diversity in Three Dimensions" (Year: 1993).*
Rudikoff et al (Proc. Natl. Acad. Sci.USA, 79(6):1979-1983, Mar. 1982) (Year: 1982).*
Colman P. M. (Research in Immunology, 145:33-36, 1994) (Year: 1994).*
Barrios et al (J Molecular Recognition 17: 332-338, 2004) (Year: 2004).*
U.S. Appl. No. 08/759,620, Jakobovits.
Adams et al., The c-myc oncogene driven by immunoglobulin enhancers induces lymphoid malignancy in transgenic mice, Nature, vol. 318, (1985): 533-538.
Alexander, W.S., et al., (1987), *Mol Cell Biol.* 7, 1436-44.

(Continued)

*Primary Examiner* — Shulamith H Shafer
(74) *Attorney, Agent, or Firm* — Nathan A. Machin

(57) ABSTRACT

The present invention provides compositions and methods relating to antigen binding proteins against CCR7, including antibodies, nucleic acids, vectors, methods of making the antigen binding proteins, and methods of using the antigen binding proteins.

5 Claims, 51 Drawing Sheets
Specification includes a Sequence Listing.

(56) References Cited

FOREIGN PATENT DOCUMENTS

| WO | 1993/10151 A1 | 5/1993 |
|---|---|---|
| WO | 1993/15722 A1 | 8/1993 |
| WO | 1994/10308 A1 | 5/1994 |
| WO | 1998/24893 A2 | 6/1998 |
| WO | 2000/09560 A2 | 2/2000 |
| WO | 2000/76310 A1 | 12/2000 |
| WO | 2007/003216 A1 | 1/2007 |
| WO | 2008/097461 A2 | 8/2008 |
| WO | 2009/105269 A1 | 8/2009 |
| WO | 2009/139853 A2 | 11/2009 |
| WO | 2010/075238 A1 | 7/2010 |
| WO | 2012/043533 A1 | 4/2012 |
| WO | 2012/148547 A1 | 11/2012 |

OTHER PUBLICATIONS

Arbonés, Maria L., et al. "Lymphocyte homing and leukocyte rolling and migration are impaired in L-selectin-deficient mice," *Immunity* 1.4 (1994): 247-260.

Ashkenazi, Avi, et al. "Protection against endotoxic shock by a tumor necrosis factor receptor immunoadhesin," *Proceedings of the National Academy of Sciences* 88.23 (1991): 10535-10539.

Aung, Latt Latt, et al. "Plasmeytoid dendritic cells in multiple sclerosis: chemokine and chemokine receptor modulation by interferon-beta," *Journal of neuroimmunology* 226.1 (2010): 158-164.

Ausubel, Frederick M. *Current protocols in molecular biology*, No. 577.2 CUR. 1987, (TOC).

Ausubel, Frederick M., et al. "Short protocols in molecular biology," (1992): (TOC).

Bauer et al. "A genetic enrichment for mutations constructed by oligodeoxynucleotide-directed mutagenesis", Gene, 37 (1985), pp. 73-81.

Baum, Peter R., et al. "Molecular characterization of murine and human OX40/OX40 ligand systems: identification of a human OX40 ligand as the HTLV-1-regulated protein gp34," *The EMBO Journal* 13.17 (1997): 3992.

Ben-Baruch, Adit, "Site-specific metastasis formation: chemokines as regulators of tumor cell adhesion, motility and invasion," *Cell adhesion & migration* 3.4 (2009): 328-333.

Benoist, Christophe, and Pierre Chambon, "In vivo sequence requirements of the SV40 early promoter region," *Nature* 290 (1981): 304-310.

Bird, Robert E., et al. "Single-chain antigen-binding proteins," *Science* 242.4877 (1988): 423-427.

Bloom, James W., et al. "Intrachain disulfide bond in the core hinge region of human IgG4," *Protein Science* 6.2 (1997): 407-415.

Brennan, Maureen, Peter F. Davison, and Henry Paulus, "Preparation of bispecific antibodies by chemical recombination of monoclonal immunoglobulin G1 fragments," *Science* 229 (1985): 81-84.

Brinster, Ralph L., et al. "Regulation of metallothionein-thymidine kinase fusion plasmids injected into mouse eggs," *Nature* vol. 296 (1982): 39-42.

Byrn, Randal A., et al. "Biological properties of a CD4 immunoadhesin," *Nature* 344.6267 (1990): 667-670.

Carrillo, Humberto, and David Lipman, "The multiple sequence alignment problem in biology," *SIAM Journal on Applied Mathematics* 48.5 (1988): 1073-1082.

Chen, Jianzhu, et al. "Immunoglobulin gene rearrangement in B cell deficient mice generated by targeted deletion of the JH locus," *International immunology* 5.6 (1993): 647-656.

Cheung, Ramsey C., et al. "Epitope-specific antibody response to the surface antigen of duck hepatitis B virus in infected ducks," *Virology* 176.2 (1990): 546-552.

Choi, Ted K., et al. "Transgenic mice containing a human heavy chain immunoglobulin gene fragment cloned in a yeast artificial chromosome," *Nature genetics* 4.2 (1993): 117-123.

Chu, Gilbert, and Phillip A. Sharp, "SV40 DNA transfection of cells in suspension: analysis of the efficiency of transcription and translation of T-antigen," *Gene* 13.2 (1981): 197-202.

Cosman, David, et al. "Cloning, sequence and expression of human interleukin-2 receptor," (1984): 768-771.

Craik, "Use of Oligonucleotides for Site-Specific Mutagenesis", BioTechniques, Jan./Feb. 1985, pp. 12-19.

Davis, C. Geoffrey, Michael L. Gallo, and Jose RF Corvalan, "Transgenic mice as a source of fully human antibodies for the treatment of cancer," *Cancer and Metastasis Reviews* 18.4 (1999): 421-425.

Davis, C. Geoffrey, et al. "Production of human antibodies from transgenic mice," *Antibody Engineering: Methods and Protocols* (2004): 191-200.

Davis, Leonard, *Methods in molecular biology*, Elsevier, 1986, (TOC).

Dayhoff et al., Atlas of Protein Sequence and Structure, vol. 5, Suppl. 3, (1978), pp. 345-352; (TOC).

De Boer, Herman A., Lisa J. Comstock, and Mark Vasser, "The tac promoter: a functional hybrid derived from the trp and lac promoters," *Proceedings of the National Academy of Sciences* 80.1 (1983): 21-25.

de Graaf, Michelle, et al. "34 Expression of scFvs and scFv Fusion Proteins in Eukaryotic Cells," *Antibody Phage Display: Methods and Protocols* (2002): 379-387.

Devereux, John, Paul Haeberli, and Oliver Smithies, "A comprehensive set of sequence analysis programs for the VAX," *Nucleic acids research* 12.1Part1 (1984): 387-395.

Eppstein, Deborah A., et al. "Biological activity of liposome-encapsulated murine interferon gamma is mediated by a cell membrane receptor," *Proceedings of the National Academy of Sciences* 82.11 (1985): 3688-3692.

Evans, Vanessa A., et al. "HIV persistence: Chemokines and their signalling pathways," *Cytokine & growth factor reviews* 23.4 (2012): 151-157.

Fanslow, William C., et al. "Structural characteristics of CD40 ligand that determine biological function," *Seminars in immunology*, vol. 6, No. 5, Academic Press, 1994.

Fishwild, Dianne M., et al. "High-avidity human lgGx monoclonal antibodies from a novel strain of minilocus transgenic mice," *Nature biotechnology* 14.7 (1996): 845-851.

Gallo, Michael L., et al. "The human immunoglobulin loci introduced into mice: V (D) and J gene segment usage similar to that of adult humans," *European journal of immunology* 30.2 (2000): 534-540.

Glennie, Martin J., et al. "Preparation and performance of bispecific F (ab'gamma) 2 antibody containing thioether-linked Fab'gamma fragments," *The Journal of Immunology* 139.7 (1987): 2367-2375.

Gluzman, Yakov, "SV40-transformed simian cells support the replication of early SV40 mutants," *Cell* 23.1 (1981): 175-182.

Edward S. Golub and Douglas R. Green, Immunology: A Synthesis, 2nd ed. (Sunderland, Mass.: Sinauer, 1991), (TOC).

Gomperts et al., "Fibrocytes in lung disease," *Journal of Leukocyte Biology* vol. 82, Sep. 2007, pp. 449-456.

Graham, Frank L., and Alex J. van der Eb, "A new technique for the assay of infectivity of human adenovirus 5 DNA," *Virology* 52.2 (1973): 456-467.

Green, L. L., et al. "Antigen-specific human monoclonal antibodies from mice engineered with human Ig heavy and light chain YACs," *Nature genetics* 7.1 (1994): 13-21.

Green, Larry L., and Aya Jakobovits "Regulation of B cell development by variable gene complexity in mice reconstituted with human immunoglobulin yeast artifical chromosomes," *Journal of Experimental Medicine* 188.3 (1998): 483-495.

Green, Larry L. "Antibody engineering via genetic engineering of the mouse: XenoMouse strains are a vehicle for the facile generation of therapeutic human monoclonal antibodies," *Journal of immunological methods* 231.1 (1999): 11-23.

Gribskov and Devereux, eds. "Sequence Analysis Primer", 1991, New York: M. Stockton Press, TOC.

Griffin, Annette M., and Hugh G. Griffin, "Computer analysis of sequence data, Part 1 / edited by Annette M. Griffin and Hugh G. Griffin," *Methods in molecular biology*, v. 24, (TOC).

Grossehedl, Rudolf, et al. "Introduction of a μ immunoglobulin gene into the mouse germ line: specific expression in lymphoid cells and synthesis of functional antibody," *Cell* 38.3 (1984): 647-658.

(56) References Cited

OTHER PUBLICATIONS

Hammer, Robert E., et al. "Diversity of alpha-fetoprotein gene expression in mice is generated by a combination of separate enhancer elements," *Science* 235 (1987): 53-58.

Hanahan, Douglas, "Heritable formation of pancreatic β-cell tumours in transgenic mice expressing recombinant insulin/simian virus 40 oncogenes," *Nature* 315.6015 (1985): 115-122.

Harding, Fiona A., and Nils Lonberg, "Class switching in human immunoglobulin transgenic mice," *Annals of the New York Academy of Sciences* 764.1 (1995): 536-546.

Harlow and Lane, Antibodies, A Laboratory Manual, Cold Spring Harbor Press, Cole Spring Harbor, N.Y. (1988), (1990), (TOC).

Henikoff, Steven, and Jorja G. Henikoff, "Amino acid substitution matrices from protein blocks," *Proceedings of the National Academy of Sciences* 89.22 (1992): 10915-10919.

Hollenbaugh, Diane, and Alejandro Aruffo, "Construction of immunoglobulin fusion proteins," *Current protocols in immunology* (2002): 10-19.

Hoppe, Hans-Jürgen, Paul N. Barlow, and Kenneth BM Reid, "A parallel three stranded α-helical bundle at the nucleation site of collagen triple-helix formation," *FEBS letters* 344.2-3 (1994): 191-195.

Huston, James S., et al. "Protein engineering of antibody binding sites: recovery of specific activity in an anti-digoxin single-chain Fv analogue produced in *Escherichia coli,*" *Proceedings of the National Academy of Sciences* 85.16 (1988): 5879-5883.

International Preliminary Report on Patentability dated Sep. 15, 2015.

Jakobovits, Aya, "Production and selection of antigen-specific fully human monoclonal antibodies from mice engineered with human Ig loci," *Advanced drug delivery reviews* 31.1 (1998): 33-42.

Jakobovits, Aya, et al. "Germ-line transmission and expression of a human-derived yeast artificial chromosome," *Nature* 362.6417 (1993): 255.

Jakobovits, Aya, et al. "Analysis of homozygous mutant chimeric mice: deletion of the immunoglobulin heavy-chain joining region blocks B-cell development and antibody production," *Proceedings of the National Academy of Sciences* 90.6 (1993): 2551-2555.

Jakobovits, Aya, "Tools of the Trade YAC Vectors: Humanizing the mouse genome," *Current Biology* 4.8 (1994): 761-763.

Jakobovits, Aya, "The long-awaited magic bullets: therapeutic human monoclonal antibodies from transgenic mice," *Expert opinion on investigational drugs* 7.4 (1998): 607-614.

Kawakami, Masaki, et al. "The role of CCR7 in allergic airway inflammation induced by house dust mite exposure," *Cellular immunology* 275.1 (2012): 24-32.

Kearney, John F., et al. "A new mouse myeloma cell ine that has lost immunoglobulin expression but permits the construction of antibody-secreting hybrid cell lines," *The Journal of Immunology* 123.4 (1979): 1548-1550.

Kellermann, Sirid-Aimée, and Larry L. Green, "Antibody discovery: the use of transgenic mice to generate human monoclonal antibodies for therapeutics," *Current Opinion in Biotechnology* 13.6 (2002): 593-597.

Kelsey, Gavin D., et al. "Species-and tissue-specific expression of human alpah I-antitrypsin in transgenic mice," *Genes & development* 1.2 (1987): 161-171.

Kennett, Roger H., and Thomas J. McKearn, eds. *Monoclonal antibodies*, Plenum Press (1980)—TOC.

Kirkland, Theo N., et al. "Analysis of the fine specificity and cross-reactivity of monoclonal anti-lipid A antibodies," *The Journal of Immunology* 137.11 (1986): 3614-3619.

Kollias, George, et al. "Regulated expression of humay Aγ-, β-, and hybrid γβ-globin genes in transgenic mice: manipulation of the developmental expression patterns," *Cell* 46.1 (1986): 89-94.

Kortt, Alexander A., et al. "Dimeric and trimeric antibodies: high avidity scFvs for cancer targeting," *Biomolecular engineering* 18.3 (2001): 95-108.

Kortt, Alexander A., et al. "Single-chain Fv fragments of anti-neuraminidase antibody NC10 containing five-and ten-residue linkers from dimers and with zero-residue linker a trimer," *Protein Engineering* 10.4 (1997): 423-433.

Kostelny et al., Formation of a Bispecific Antibody by the use of Leucine Zippers, J. Immunol. vol. 148, 1547-1553, No. 5, (Mar. 1, 1992).

Kriangkum, Jitra, et al. "Bispecific and bifunctional single chain recombinant antibodies," *Biomolecular engineering* 18.2 (2001): 31-40.

Krumlauf, R., et al. "Developmental regulation of alpha-fetoprotein genes in transgenic mice," *Molecular and cellular biology* 5.7 (1985): 1639-1648.

Landschultz, W. H., P. F. Johnson, and S. L. McKnight, "The Leucine Zipper: A Hypothetical Structure Common to a New Class of DNA Binding Protein," *Science* 240 (1988): 1759-1764.

Langer, Robert, "Controlled release of macromolecules," *Chemtech* 12.2 (1982): 98-105.

Langer, Robert et al. "Biocompatibility of polymeric delivery systems for macromolecules," *Journal of Biomedical Materials Research*, vol. 15, 267-277 (1981).

Lantto, Johan, et al. "Chain shuffling to modify properties of recombinant immunoglobulins," *Antibody Phage Display: Methods and Protocols* (2002): 303-316.

Larrick, James W., et al. "Polymerase chain reaction using mixed primers: cloning of human monoclonal antibody variable region gens from single hybridoma cells," *Bio/technology* 7.9 (1989): 934-938.

Leder, Aya, et al. "Consequences of widespread deregulation of the c-myc gene in transgenic mice: multiple neoplasma and normal development," *Cell* 45.4 (1986): 485-495.

Lesk, A. *Computational molecular biology*, Oxford University Press, Inc., (1988), (TOC).

Liu, Xiaosun, et al. "Tolerance induction towards cardiac allografts under constimulation blockade is impaired in CCR7-deficient animals but can be restored by adoptive transfer of syngeneic plasmacytoid dendritic cells," *European journal of immunology* 41.3 (2011): 611-623.

Liu, Alvin Y., et al. "Chimeric mouse-human IgG1 antibody that can mediate lysis of cancer cells," *Proceedings of the National Academy of Sciences* 84.10 (1987): 3439-3443.

N. Lonberg, 1994, Transgenic Approaches to Human Monoclonal Antibodies in Handbook of Experimental Pharmacology 11333: 49-101.

Lo et al., "Chemokines and Their Receptors in Human Renal Allotransplantation", *Transplantation*, vol. 91, No. 1, Jan. 15, 2011, pp. 70-77.

Lonberg, Nils, et al. "Antigen-specific human antibodies from mice comprising four distinct genetic modifications," *Nature* 368.6474 (1994): 856-859.

Lonberg, Nils, and Dennis Huszar, "Human antibodies from transgenic mice," *Intern. Rev. Immunol.* 13, (1995): 65-93.

Luchtefeld, Maren, et al. "Chemokine Receptor 7 Knockout Attenuates Atherosclerotic Plaque DevelopmentClinical Perspective," *Circulation* 122.16 (2010): 1621-1628.

Lunde, E., et al. "Troybodies and pepbodies," (2002): 500-506.

MacDonald, Raymond J. "Expression of the pancreatic elastase I gene in transgenic mice," *Hepatology* 7.S1 (1987).

Magram, Jeanne, Kiran Chada, and Frank Costantini, "Developmental regulation of a cloned adult β-globin gene in transgenic mice," *Nature* vol. 315 (1985): 338-340.

Maniatis, Tom, Stephen Goodbourn, and Janice A. Fischer, "Regulation of inducible and tissue-specific gene expression," *Science* 236 (1987): 1237-1246.

Marks, James D., et al. "By-passing immunization: building high affinity human antibodies by chain shuffling," *Bio/technology (Nature Publishing Company)* 10.7 (1992): 779-783.

Mason, Anthony J., et al. "The hypogonadal mouse: reproductive functions restored by gene therapy," Science, (1986) vol. 234, pp. 1372-1378.

McMahan, Catherine J., et al. "A novel IL-1 receptor, cloned from B cells by mammalian expression, is expressed in many cell types," *The EMBO journal* 10.10 (1991): 2821.

(56) References Cited

OTHER PUBLICATIONS

Mendez, Michael J., et al. "Functional transplant of megabase human immunoglobulin loci recapitulates human antibody response in mice," *Nature genetics* 15.2 (1997): 146-156.
Milstein, C., and A. C. Cuello, "Hybrid hybridomas and their use in immunohistochemistry," *Nature* 305.5934 (1983): 537-540.
Moldenhauer, G., et al. "Identity of HML-1 Antigen on Intestinal Intraepithelial T Cells and of B-ly7 Antigen on Hairy Cell Leukaemia," *Scandinavian journal of immunology* 32.2 (1990): 77-82.
Morel, Guillemette A., et al. "Monoclonal antibodies to bovine serum albumin: affinity and specificity determinations," *Molecular immunology* 25.1 (1988): 7-15.
Moschovakis, Georgios Leandros, and Reinhold Föster, "Multifaceted activities of CCR7 regulate T-cell homeostasis in health and disease," *European journal of immunology* 42.8 (2012): 1949-1955.
Needleman, Saul B., and Christian D. Wunsch, "A general method applicable to the search for similarities in the amino acid sequence of two proteins," *Journal of molecular biology* 48.3 (1970): 443-453.
Neuberger, 1996, Nature Biotechnology 14: 826.
Ornitz, D. M., Palmiter, R. D., Messing, A., Hammer, R. E., Pinkert, C. A., & Brinster, R. L. (Jan. 1985), Elastase I promoter directs expression of human growth hormone and SV40 T antigen genes to pancreatic acinar cells in transgenic mice, In *Cold Spring Harbor symposia on quantitative biology* (vol. 50, pp. 399-409), Cold Spring Harbor Laboratory Press.
Padlan, Eduardo A., C. Abergel, and J. P. Tipper, "Identification of specificity-determining residues in antibodies," *The FASEB journal* 9.1 (1995): 133-139.
Pinkert, Carl A., et al. "An albumin enhancer located 10 kb upstream functions along with its promoter to direct efficient, liver-specific expression in transgenic mice," *Genes & development* 1.3 (1987): 268-276.
Pouweis, Pieter Hendrik, Betty E. Enger-Valk, and William John Brammar, *Cloning vectors: a laboratory manual*, Amsterdam etc.: Elsevier, 1985, (TOC).
Readhead, Carol, et al. "Expression of a myelin basis protein gene in transgenic shiverer mice: correction of the dysmyelinating phenotype," *Cell* 48.4 (1987): 703-712.
Riechmann, Lutz, et al. "Reshaping human antibodies for therapy," *Nature* 332.6162 (1988): 323-327.
Remington's Pharmaceutical Sciences, 16th Edition, 1980, Mack Publishing Company.
Remington's Pharmaceutical Sciences, 18th Edition, (A.R. Gennaro, ed.), 1990 Mack Publishing Company (TOC).
Remington: The Science and Practice of Pharmacy, 20th Edition, (A.R. Gennaro, ed.), 2000, Philadelphia College of Pharmacy and Science.
Russell, Nina D., et al. "Production of protective human antipneumococcal antibodies by transgenic mice with human immunoglobulin loci," *Infection and immunity* 68.4 (2000): 1820-1826.
Sambrook, Joseph, and William Russell David, "Molecular cloning: a laboratory manual," *Cold Spring Harbor Laboratory Press*, New York, (2001), (TOC).
Saunders, R., et al. "Airway smooth muscle chemokine receptor expression and function in asthma," *Clinical & Experimental Allergy* 39.11 (2009: 1684-1692.
Schier et al., "Isolaation of Picomolar Affinity Anti-c-erbB-2 Singlechain Fv Molecular Evolution of the Complementarity Determining regions in the Center of the Antibody Binding Site," 1996, J. Mol. Biol 263: 551-567.
Shani, Moshe, "Tissue-specific expression of rat myosin light-chain 2 gene in transgenic mice," *Nature* 314 (1985): 283-286.
Sidman, Kenneth R., et al. "Controlled release of macromolecules and pharmaceuticals from synthetic polypeptides based on glutamic acid," *Biopolymers* 22.1 (1983): 547-556.
Biocomputing: Informatics and Genome Projects (1994), pp. 119-174 by A. K. Konopka edited by D. Smith, (TOC).
Genetic Engineering: Principles and Methods, Plenum Press, 1981, TOC.
Songsivilai, S., and P. J. Lachmann, "Bispecific antibody: a tool for diagnosis and treatment of disease," *Clinical and experimental immunology* 79.3 (1990): 315.
Stähli, C., et al. "[20] Distinction of epitopes by monoclonal antibodies," *Methods in enzymology* 92 (1983): 242-253.
Swift, Galvin H., et al. "Tissue-specific expression of the rat pancreatic elastase I gene in transgenic mice," *cell* 38.3 (1984): 639-646.
Tamura, Midori, et al. "Structural correlates of an anticarcinoma antibody: identification of specificity-determining residues (SDRs) and development of a minimally immunogenic antibody variant by retention of SDRs only," *the Journal of Immunology* 164.3 (2000): 1432-1441.
Taylor, Lisa D., et al. "Human immunoglobulin transgenes undergo rearrangement, somatic mutation and class switching in mice that lack endogenous IgM," *International Immunology* 6.4 (1994): 579-591.
Taylor, Lisa D., et al. "A transgenic mouse that expresses a diversity of human sequence heavy and light chain immunoglobulins," *Nucleic acids research* 20.23 (1992): 6287-6295.
Thomsen, Darrel R., et al. "Promoter-regulatory region of the major immediate early gene of human cytomegalovirus," *Proceedings of the Nanomal Academy of Sciences* 81.3 (1984): 659-663.
Tomizuka, Kazuma, et al. "Function expression and germline transmission of fragments in chimaeric mice," *Nature genetics* 16 (1997): 133.
Tomizuka, Kazuma, et al. "Double trans-chromosomic mice: maintenance of two individual human chromosome fragments containing Ig heavy and κ loci and expression of fully human antibodies," *Proceedings of the National Academy of Sciences* 97.2 (2000): 722-727.
Tsuda, Hirohisa, et al. "Inactivation of the MouseHPRTLocus by a 203-bp Retroposon Insertion and a 55-kb Gene-Targeted Deletion: Establishment of New HPRT-Deficient Mouse Embryonic Stem Cell Lines," *Genomics* 42.3 (1997): 413-421.
Tuaillon, Nadine, et al. "Biased utilization of DHQ52 and JH4 gene segments in a human Ig transgenic minilocus is independent of antigenic selection," *The Journal of Immunology* 152.6 (1994): 2912-2920.
Tuaillon, Nadine, et al. "Human immunoglobulin heavy-chain minilocus recombination in transgenic mice: gene-segment use in mu and gamma transcripts," *Proceedings of the National Academy of Sciences* 90.8 (1993): 3720-3724.
Villa-Komaroff, Lydia, et al. "A bacterial clone synthesizing proinsulin," *Proceedings of the National Academy of Sciences* 75.8 (1978): 3727-3731.
Von Heijne, Gunnar, ed. *Sequence analysis in molecular biology: treasure trove or trivial pursuit*, Elsevier, (1987)—TOC.
Voss, Stephan D., Uwe Schlokat, and Peter Gruss, "The role of enhancers in the regulation of cell-type-specific transcriptional control," *Trends in Biochemical Sciences* 11.7 (1986): 287-289.
Wagner, Michael J., Janice A. Sharp, and William C. Summers, "Nucleotide sequence of the thymidine kinase gene of herpes simplex virus type 1," *Proceedings of the National Academy of Sciences* 78.3 (1981): 1441-1445.
Walder et al., "Oligodeoxynucleotide-directed mutagenesis using the yeast transformation system", Gene, 42 (1986), pp. 133-139.
Ward, E. Sally, et al. "Binding activities of a repertoire of single immunoglobulin variable domains secreted from *Escherichia coli,*" *Nature* 341.6242 (1989): 544-546.
Winter, Greg, and William J. Harris, "Humanized antibodies," *Trends in pharmacological sciences* 14.5 (1993): 139-143.
Yamamoto, Tadashi, Benoit de Crombrugghe, and Ira Pastan, "Identification of a functional promoter in the long terminal repeat of Rous sarcoma virus," *Cell* 22.3 (1980): 787-797.
Yuling, H., et al. "Essential role of sphingosine-I-phosphate receptor I-bearing CD8+ CD44+ CCR7+ T cells in acute skin allograft rejection," *American journal of transplantation: official journal of the American Society of Transplantation and the American Society of Transplant Surgeons* 8.7 (2008): 1401-1412.
Zabel, Brian A., et al. "The novel chemokine receptor CXCR7 regulates trans-endothelial migration of cancer cells," *Molecular cancer* 10.1 (2011): 73-80.

(56) References Cited

OTHER PUBLICATIONS

BioLegend, "APC anti-human CD197( CCR7) Product Data Sheet", [retrieved from internet], <URL: http://www.biolegend.com/pop_pdf_php?id=id-7536>published on Apr. 8, 2014 as per Wayback Machine #.

* cited by examiner

FIGURE 1A

| SEQ ID NO: | Sequence | Type | Organism | Name |
|---|---|---|---|---|
| 1 | ATGGACATGAGGGTGCCCGCTCAGCTCCTGGGGCTCTTGCTGCTCTGGCTGTGCTGAGAGGTGCGCGCTGTT CCTATGAGCTGACTCAGCCACCCTCAGTGCCGTGCCGTCCTGGTATCCGTTCCCAGGACAGAGGCCAGAATCACCTGCTC TGGAGATAAATTGGGGGATAAATATGCTTCCTGGTATCAGCAGAAGCCAGGCCAGTCCCCTGTCCTACTG GTCATCTATCAAGATAGCAAGCGGCCCTCAGGGATCCCTGAGCGATTCTCTGGCTCCAACTCTGGAA ACACAGCCACTCTGACCATCAGCGGACTCCAGGCTGAGGGACCAAACTGACCGTCCTAGGTCAGCCAAGGCGTG GGGCAGCAGCACTGTGATATTCGGCGGAGGGACCAAACTGACCGTCCTAGTCAGCCAAGGCCAA CCCACTGTCACTCTGTTCCCGCCCTCTCTGAGGAGCTCAATAAGGCCACACTAGTGTGT CTGATCAGTGACTTCTACCCGGGAGCTGTGACAGTGGCCTGGAAGGCAGATGGCAGCCGTCAAG GCGGGAGTGGAGACCACCAAACCCTCCAAACAGAGCAACAACAAGTACGCGGCCAGCAGTACCTG ACCGTGACGCCGAGCAGTGGAAGTCCACAAGTCTGCCAGGTCACGCATGAAGGGAGC ACCGTGGAGAAGACAGTGGCCCCTACAGAATGTTCA | DNA | Human | 6B4.1 LC |
| 2 | MDMRVPAQLLGLLLLWLRGARCSYELTQPPSVSVSPGQRARITCSGDKLGDKYASWYQQKPGQSPLLVI YQDSKRPSGIPERFSGSNSGNTATLTISGTQAMDEADYYCQAWGSSTVIFGGGTKLTVLGQPKANPTVTL FPPSSEELQANKATLVCLISDFYPGAVTVAWKADGSPVKAGVETTKPSKQSNNKYAASSYLSLTPEQWKS HRSYSCQVTHEGSTVEKTVAPTECS | PRT | Human | 6B4.1 LC |
| 3 | TCTGGAGATAAATTGGGGGATAAATATGCTTCC | DNA | Human | 6B4.1 LC CDR1 |
| 4 | SGDKLGDKYAS | PRT | Human | 6B4.1 LC CDR1 |
| 5 | CAAGATAGCAAGCGGCCCTCA | DNA | Human | 6B4.1 LC CDR2 |
| 6 | QDSKRPS | PRT | Human | 6B4.1 LC CDR2 |
| 7 | CAGGCGTGGGGCAGCAGCACTGTGATA | DNA | Human | 6B4.1 LC CDR3 |
| 8 | QAWGSSTVI | PRT | Human | 6B4.1 LC CDR3 |
| 9 | ATGGACATGAGGGTGCCCGCTCAGCTCCTGGGGCTCTTGCTGCTCTGGCTGCGAGGTGCGCGCTGTT ATGAGCTGACTCAGCCACCCTCAGTGCCGTGCCGTCCTGGTATCCCCAGGACAGAGGCCAGAATCACCTGCTCTGG AGATAAATTGGGGGATAAATATGCTTCCTGGTATCAGCAGAAGCCAGGCCAGTCCCCTGTCCTACTGGTC ATCTATCAAGATAGCAAGCGGCCCTCAGGGATCCCTGAGCGATTCTCTGGCTCCAACTCTGGAAACA CAGCCACTCTGACCATCAGCGGACTCCAGGCTATGGATGAGGCTGACTATTACTGTCAGGCGTGGGGG CAGCAGCACTGTGATATTCGGCGGAGGGACCAAACTGACCGTCCTAGGTCAGCCCAAGGCCAACCC CACTGTCACTCTGTTCCCGCCCTCTCTGAGGAGCTCCAAGCAAATAAGGCCACACTAGTGTGTCTG ATCAGTGACTTCTACCCGGGAGCTGTGACAGTGGCCTGGAAGGCAGATAGCGGCCAGCAGTACCTGACC GTGACGCCGAGCAGTGGAAGTCCCAAACAGAGCAACAACAAGTACGCGGCCAGCAGTACCTGAGC CTGACGCCGAGCAGTGGAAGTCCCACAAGTCTGCCAGGTCACGCATGAAGGGAGCACC GTGGAGAAGACAGTGGCCCCTACAGAATGTTCA | DNA | Human | 6B4.1 LC desS |
| 10 | MDMRVPAQLLGLLLLWLRGARCYELTQPPSVSVSPGQRARITCSGDKLGDKYASWYQQKPGQSPLLVIY QDSKRPSGIPERFSGSNSGNTATLTISGTQAMDEADYYCQAWGSSTVIFGGGTKLTVLGQPKANPTVTLFPP SSEELQANKATLVCLISDFYPGAVTVAWKADGSPVKAGVETHKPSKQSNNKYAASSYLSLTPEQWKSH RSYSCQVTHEGSTVEKTVAPTECS | PRT | Human | 6B4.1 LC desS |
| 11 | TCTGGAGATAAATTGGGGGATAAATATGCTTCC | DNA | Human | 6B4.1 LC desS CDR1 |
| 12 | SGDKLGDKYAS | PRT | Human | 6B4.1 LC desS CDR1 |
| 13 | CAAGATAGCAAGCGGCCCTCA | DNA | Human | 6B4.1 LC desS CDR2 |

FIGURE 1B

| SEQ ID NO: | Sequence | Type | Organism | Name |
|---|---|---|---|---|
| 14 | QDSKRPS | PRT | Human | 6B4.1 LC desS CDR2 |
| 15 | CAGGCGTGGGCAGCAGCACTGTGATA | DNA | Human | 6B4.1 LC desS CDR3 |
| 16 | QAWGSSTVI | PRT | Human | 6B4.1 LC desS CDR3 |
| 17 | ATGGACATGAGGGTGCCCGCTCAGCTCCTGCTGCTGGGCCTCCTGCTGCTGTGGCTGAGAGGTGCGCGCTGTTCCTATGAGCTGACTCAGCCACCCTCAGTTCCGTCCCGTGTCCCAGGACAGAAGCCAGCATCACCTGCTCTGGAGATAAATTGGGGGATAAATATGCTTCCTGGTATCAGCAGAAGCCAGGCCAGTCCCCTCTACTGGTCATCTATCAAGATGGCAAGCGGCCCTCAGGGATCCCTGAGCGATTCTCTGGCTCCAACTCTGAAACACAGCCACTCTGACCATCAGCGGGACCCAGGCTATGGATGAGGCTGACTATTACTGTCAGGCGTGGGCCAGCAGCACTGTGATATTCGGCGGAGGGACCAAACTGACCGTCCTAGGTCAGCCCAAGGCTGCCCCCTCGGTCACTCTGTTCCCGCCCTCTCTGAGGAGCTCTGATAGTCAGTTGACAGTGGCTGCAAGTCACCCCAAAGCTGGGAGTGCAGATGGCAGTTGCGGCCAGAGCTACCTGAGCCTGACGCCCGAGCAGTGGAAGTCCACAGAGTCCCAAACAGAGCAACAACAAGTACGCGGCCAGCAGCTACCTGAGCCTGACGCCCGAGCAGTGGAAGTCACACAGAGCAACAACAAGTACGCGGCCAGCAGCTACCTGAGCCTGACGCCCGAGCAGTGGAAGTCCACCCCTGAGCCTGACGCCCGAGCAGTGGAAGTCACCAAGCTGAGCCTGACGCCCGAGCAGTGGAAGTCAGCAGCACCGTGACCTGCCAGGTCACGCATGAAGGGAGCACCGTGGAGAAGACAGTGGCCCCTACAGAATGTTCA | DNA | Human | 6B5.1 LC |
| 18 | MDMRVPAQLLGLLLLWLRGARCSYELTQPPSVSVSPGQTASITCSGDKLGDKYASWYQQKPGQSPLLVIYQDGKRPSGIPERFSGSNSGNTATLTISGTQAMDEADYYCQAWGSSTVIFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | PRT | Human | 6B5.1 LC |
| 19 | TCTGGAGATAAATTGGGGGATAAATATGCTTCC | DNA | Human | 6B5.1 LC CDR1 |
| 20 | SGDKLGDKYAS | PRT | Human | 6B5.1 LC CDR1 |
| 21 | CAAGATGGCAAGCGGCCCTCA | DNA | Human | 6B5.1 LC CDR2 |
| 22 | QDGKRPS | PRT | Human | 6B5.1 LC CDR2 |
| 23 | CAGGCGTGGGCAGCAGCACTGTGATA | DNA | Human | 6B5.1 LC CDR3 |
| 24 | QAWGSSTVI | PRT | Human | 6B5.1 LC CDR3 |
| 25 | ATGGACATGAGGGTGCCCGCTCAGCTCCTGCTGCTGTGGCTGGGCCTCCTGCTGCTGTGGCTGAGAGGTGCGCGCTGTTCCTATGAGCTGACTCAGCCACCCTCAGTGTCCGTGTCCCCAGGACAGACAGCCAGCATCACCTGCTCTGGAAATAAATTGGGGGATAAACAAGCCTTCTGGTATCATCAGAAGCCAGGCCAGTCCCCTGTGCTGGTCATCTATCAAGATAACAAGCGGCCCTCAGGGATCCCTGAGCGATTCTCTGGCTCCAACTCTGGAAACACAGCCACTCTGACCATCAGCGGGACCCAGGCTATGGATGAGGCTGACTATTTCTGTCAGGCGTGGGACAGGACTGTGGTTATTCGGCGGAGGGACCAAACTGACCGTCCTAGGTCAGCCCAAGGCCAACCCCACTGTCACTCTGTTCCCGCCCTCCTCTGAGGAGCTCCAAGCCAACAAGGCCACACTGGTGTGTCTGATAAGTGACTTCTACCCGGGAGTGGCCGTGAAGCAGATGGCAGTTCAGCCCGTCAAGGCGGGAGTGGAGACCACCAAACCCTCCAAACAGAGCAACAACAAGTACGCGGCCAGCAGCTACCTGAGCCTGACGCCCGAGCAGTGGAAGTCCCACAGAAGCTACAGCTGCCAGGTCACGCATGAAGGGAGCACCGTGGAGAAGACAGTGGCCCCTACAGAATGTTCA | DNA | Human | 6E1.2 LC |
| 26 | MDMRVPAQLLGLLLLWLRGARCSYELTQPPSVSVSPGQTASITCSGNKLGDKYASWYHQKPGQSPVLVIYQDNKRPSGIPERFSGSNSGNTATLTISGTQTMDEADYFCQAWDRTVPGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | PRT | Human | 6E1.2 LC |

FIGURE 1C

| SEQ ID NO: | Sequence | Type | Organism | Name |
|---|---|---|---|---|
| 27 | TCTGGAAATAAATTGGGGGATAAATATGCTTCC | DNA | Human | 6E1.2 LC CDR1 |
| 28 | SGNKLGDKYAS | PRT | Human | 6E1.2 LC CDR1 |
| 29 | CAAGATAACAAGCGGCCCTCA | DNA | Human | 6E1.2 LC CDR2 |
| 30 | QDNKRPS | PRT | Human | 6E1.2 LC CDR2 |
| 31 | CAGGCGTGGGACAGGACTGTGGTA | DNA | Human | 6E1.2 LC CDR3 |
| 32 | QAWDRTVV | PRT | Human | 6E1.2 LC CDR3 |
| 33 | ATGGACATGAGGGTGCCCGCCAGCTCCTGGGCTCCTCTGCTGCTGTGGCTGAGAGGTGCGCGCTGTTCCTATGAGCTGACTCAGCTGACCTCAGTGTCCGTGTCCCCAGGACAGACAGCCAGCATCACCTGCTCTGGAAATAAATTGGGGGATAAATATGCTTCCTGGTATCAGCAGAAGCCAGGCCAGTCCCCTGTGCTGGTCATCTATCAAGATAACAAGCGGCCCTCAGGGATCCCTGAGCGATTCTCTGCCTCAACTCTGGAACAGCCACTCTGACCATCAGCGGGACCCAGACTATGGACGCAGGGCCAACCTGGACAGGACTGTGTTATTCGGCGGAGGGACCAAACTGACCGTCCTAGGTCAGCCAAGGCCAACCCCACTGTCACTCTGTTCCCGCCCTCCTGTGACAGTGGCTGGAAGGCAGATGGCAGCCCGTCAAGGCGATCAGTGACTTCTACCCGGGAGCTGTGACAGAGCAATGGCCAGCAGTACGCGCCAGCAGTCACCTGAGCGGTGGAGACCACCAAACCCTCCAAACAGAAGAAGCTCCACAGAAGCTACAGTCCAGTGCCCAGGTTCACGCATGAAGGGAGCACCGTGGAGAAGACAGTGGCCCCTACGAATTGTTCA | DNA | Human | 6E1.2 LC H36Q |
| 34 | MDMRVPAQLLGLLLLWLRGARCSYELTQPPSVSVSPGQTASITCSGNKLGDKYASWYQQKPGQSPVLVIYQDNKRPSGIPERFSGSNSGNTATLTISGTQTMDEADYFCQAWDRTVVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | PRT | Human | 6E1.2 LC H36Q |
| 35 | TCTGGAAATAAATTGGGGGATAAATATGCTTCC | DNA | Human | 6E1.2 LC H36Q CDR1 |
| 36 | SGNKLGDKYAS | PRT | Human | 6E1.2 LC H36Q CDR1 |
| 37 | CAAGATAACAAGCGGCCCTCA | DNA | Human | 6E1.2 LC H36Q CDR2 |
| 38 | QDNKRPS | PRT | Human | 6E1.2 LC H36Q CDR2 |
| 39 | CAGGCGTGGGACAGGACTGTGGTA | DNA | Human | 6E1.2 LC H36Q CDR3 |
| 40 | QAWDRTVV | PRT | Human | 6E1.2 LC H36Q CDR3 |

FIGURE 1D

| SEQ ID NO: | Sequence | Type | Organism | Name |
|---|---|---|---|---|
| 41 | ATGGACATGAGGGTGCCCGCTCAGCTCCTGGGGCTCCTGCTGCTGTGGCTGAGAGGTGCGCGCTGTC AGGTGCAGCTGGTGGAGTCTGGGGGAGGCGTGGTCCAGCCTGGGAGGTCCCTGAGACTCTCCTGTGC AGCGTCTGGATTCACCTTCAGTAGCTATGGCATGCACTGGGTCCGCCAGGCTCCAGGCAAGGGGCTG GAGTGGGTGGCAGTTATATGGTATGATGGAAGTAAAAAATATTATGCAGACTCCGTGAAGGGCCGA TTCACCATCTCCAGAGACAATTCCAAAAACACTGTATCTGCAAATGAACAGCCTGAGAGCCGAG GACACGGCTGTGTATTACTGTGCGAGAGATGGGGGTATAGCAGTATTTTTACAGGACAATTGGTTCG ACCCCTGGGGCCAGGGAACCCTGGTCACCGTCTCCTCAGCCTCCACCAAGGGCCCATCGGTCTTCCC CCTGGCGCCCTGCTCCAGGAGCACCTCCGAGAGCACAGCGGCCCTGGGCTGCCTGGTCAAGGACTAC TTCCCCGAACCGGTGACGGTGTCGTGGAACTCAGGCGCTGACCAGCGGCGTGCACACCTTCCCAG CTGTCCTACAGTCCTCAGGACTCTACTCCCTCAGCAGCGTGGTGACCGTGCCCTCCAGCAACTTCGGC ACCCAGACCTACACCTGCAACGTAGATCACAAGCCCAGCAACACCAAGGTGGACAAGACAGTTGAG CGCAAATGTTGTGTCGAGTGCCCACCGTGCCCAGCACCTGTGGCAGGACCGTCAGTTCCTCT TCCCCCCAAAACCCAAGGACACACCCTCATGATCTCCCGGACCCCTGAGGTCACGTGCGTGGTGGA CGTGAGCCACGAAGACCCCGAGGTCCAGTTCAACTGGTACGTGGACGGCGTGGAGGTGCATAATGC CAAGACAAAGCCACGGGAGGAGCAGTTCAACAGCACGTTCGTGTGGTCAGCGTCCTCACCGTTGT CACCAGGACTGGCTGAACGGCAAGGAGTACAAGTGCAAGGTCTCCAACAAAGGCCTCCAGCCC ATCGAGAAAACCATCTCCAAAACCAAAGGGCAGCCCCGAGAACCAGGTGTACACCCTGCCCCCA TCCCGGGAGGAGATGACCAAGAACCAGGTCAGCCTGACCTGCCTGGTCAAAGGCTTCTACCCCAG CGACATCGCCGTGGAGTGGGAGAGCAATGGGCAGCCGGAGAACAACTACAAGACCACGCCTCCCGT GCTGGACTCCGACGGCTCCTTCTTCCTCTACAGCAAGCTCACCGTGGACAAGAGCAGGTGGCAGCAG GGGAACGTCTTCTCATGCTCCGTGATGCATGAGGCTCTGCACAACCACTACACGCAGAAGAGCCTCT CCCTGTCTCCGGGTAAA | DNA | Human | 6B4.1 HC |
| 42 | MDMRVPAQLLGLLLLWLRGARCQVQLVESGGGVVQPGRSLRLSCAASGFTFSSYGMHWVRQAPGKGL EWVAVIWYDGSKKYYADSVKGRFTISRDNSKNTLYLQMNRLRAEDTAVYYCARDGGIAVFLQDNWFDP WGQGTLVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKDTL MISRTPEVTCVVVDVSHEDPEVQFNWYVDGVEVHNAKTKPREEQFNSTFRVVSVLTVVHQDWLNGKEY KCKVSNKGLPAPIEKTISKTKGQPREPQVYTLPPSREEMTKNQVSLTCLVKGFYPSDIAVEWESNGQPENN YKTTPPMLDSDGSFFLYSKLTVDKSRWQQGNVFSCSVMHEALHNHYTQKSLSLSPGK | PRT | Human | 6B4.1 HC |
| 43 | AGCTATGGCATGCAC | DNA | Human | 6B4.1 HC CDR1 |
| 44 | SYGMH | PRT | Human | 6B4.1 HC CDR1 |
| 45 | GTTATATGGTATGATGGAAGTAAAAAATATTATGCAGACTCCGTGAAGGGC | DNA | Human | 6B4.1 HC CDR2 |
| 46 | VIWYDGSKKYYADSVKG | PRT | Human | 6B4.1 HC CDR2 |
| 47 | GATGGGGGTATAGCAGTATTTTTACAGGACAATTGGTTCGACCCC | DNA | Human | 6B4.1 HC CDR3 |
| 48 | DGGIAVFLQDNWFDP | PRT | Human | 6B4.1 HC CDR3 |

FIGURE 1E

| SEQ ID NO: | Sequence | Type | Organism | Name |
|---|---|---|---|---|
| 49 | ATGGACATGAGGGTGCCCGCTCAGCTCCTGGGGCTCCTGCTGCTGTGGCTGAGAGGTGCGCGCTGTC AGGTGCAGCTGGTGGAGTCTGGGGGAGGCGTGGTCCAGCCTGGGAGGTCCCTGAGACTCTCTGTGC AGCGTCTGGATTCACCTTCAGAAGCTATGGCATGCACTGGGTCCGCCAGGCTCCAGGCAAGGGGCTG GAGTGGGTGGCAGTTATATGGTATGATGGAAGTAAAAATATTATGCAGACTCCGTGAAGGGCCGA TTCACCATCTCCAGAGACAACTCCAAAAACACACTGTATCTGCAAATGAACAGACTGAGAGCGGAG GACACGGCTGTGTATTACTGTGCGAGAGATGGGGGTATAGCAGTAGTTTTTTAGAGGACAATTGGTTCG ACCCCTGGGGCCAGGGAACCCTGGTCACCGTCTCTAGTGCCTCCACCAAGGGCCCATCGGTCTTCCC CCTGGCGCCCTGCTCCAGGAGCACCTCTGGGGGCACAGCGGCCCTGGGCTGCCTGGTCAAGGACTAC TTCCCCGAACCGGTGACGGTGTCGTGGAACTCAGGCGCCCTGACCAGCGGCGTGCACACCTTCCCGG CTGTCCTACAGTCCTCAGGACTCTACTCCCTCAGCAGCGTGGTGACCGTGCCCTCCAGCAACTTCGGC ACCCAGACCTACACCTGCAACGTAGATCACAAGCCCAGCAACACCAAGGTGGACAAGACCGTTAGAG CGCAAATGTTGTGCGAGTGCCCACCGTGCCCAGCACCTGAGCTCCTGGGGGGACCGTCAGTCTTCCTCTT TCCCCCCAAAACCCAAGGACACCCTCATGATCTCCCGGACCCCTGAGGTCACGTGCGTGGTGGTGGA CGTGAGCCACGAAGACCCTGAGGTCAAGTTCAACTGGTACGTGGACGGCGTGGAGGTGCATAATGC CAAGACAAAGCCGCGGGAGGAGCAGTACAACAGCACGTTCCGTGTGGTCAGCGTCCTCACCGTCGT CACCAGGACTGGCTGAATGGCAAGGAGTACAAGTGCAAGGTCTCCAACAAAGGCCTCCCAGCCCC CATCGAGAAAACCATCTCCAAAGCCAAAGGGCAGCCCCGAGAACCACAGGTGTACACCCTGCCCCC ATCCCGGGAGGAGATGACCAAGAACCAGGTCAGCCTGACCTGCCTGGTCAAAGGCTTCTACCCCAG CGACATCGCCGTGGAGTGGGAGAGCAATGGGCAGCCGGAGAACAACTACAAGACCACGCCTCCCGT GCTGGACTCCGACGGCTCCTTCTTCCTCTACAGCAAGCTCACCGTGGACAAGAGCAGGTGGCAGCAG GGGAACGTCTTCTCATGCTCCGTGATGCATGAGGCTCTGCACAACCACTACACGCAGAAGAGCCTCT CCCTGTCTCCGGGTAAA | DNA | Human | 6B5.1 HC |
| 50 | MDMRVPAQLLGLLLLWLRGARCQVQLVESGGGVVQPGRSLRLSCAASGFTFRSYGMHWVRQAPGKGL EWVAVIWYDGSKKYYADSVKGRFTISRDNSKNTLYLQMNRLRAEDTAVYYCARDGGIAVFLEDNWFDP WGQGTLVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKDTL MISRTPEVTCVVVDVSHEDPEVQFNWYVDGVEHNAKTKPREEQFNSTFRVVSVLTVVHQDWLNGKEY KCKVSNKGLPAPIEKTISKTKGQPREPQVYTLPPSREEMTKNQVSLTCLVKGFYPSDIAVEWESNGQPENN YKTTPPMLDSDGSFFLYSKLTVDKSRWQQGNVFSCSVMHEALHNHYTQKSLSLSPGK | PRT | Human | 6B5.1 HC |
| 51 | AGCTATGGCATGCAC | DNA | Human | 6B5.1 HC CDR1 |
| 52 | SYGMH | PRT | Human | 6B5.1 HC CDR1 |
| 53 | GTTATATGGTATGATGGAAGTAAAAATATTATGCAGACTCCGTGAAGGGC | DNA | Human | 6B5.1 HC CDR2 |
| 54 | VIWYDGSKKYYADSVKG | PRT | Human | 6B5.1 HC CDR2 |
| 55 | GATGGGGGTATAGCAGTAGTTTTTTAGAGGACAATTGGTTTGACCCC | DNA | Human | 6B5.1 HC CDR3 |
| 56 | DGGIAVFLEDNWFDP | PRT | Human | 6B5.1 HC CDR3 |

FIGURE 1F

| SEQ ID NO: | Sequence | Type | Organism | Name |
|---|---|---|---|---|
| 57 | ATGGACATGAGGGTGCCCGCTCAGCTCCTGGGGCTCCTGCTGCTGTGGCTGAGAGGTGCGCGCTGTC AGGGGCAGCTGTGGAGTCTGGGGGAGGCGTGGTCCAGCCTGGGAGGTCCCTGAGACTCTCCTGTG CAGCGTCTGGATTCACCTTCACTAGCTATGGCATGCACTGGGTCCGCCAGGCTCCAGGCAAGGGGCT GGAGTGGGTGGCAGTTATATGGTATGATGGAAGTAAAAATACTATGCAGACTCCGTGAAGGGCCG ATTCACCATCTCCAGAGACAATTCCAAGAACACGCTGTTTCTGCAAATGAACAGCCTGAGAGCCGAG GACACGGCTGTGTATTACTGTGCGAGAGATGGGGGTATAGCAGCATTTTTACAGGACAACTGGTTCG ACCCCTGGGGCCAGGGAACCCTGGTCACCGTCTCCTCAGCCTCCACCAAGGGCCCATCGGTCTTCCC CCTGGCGCCCTGCTCCAGGAGCACCTCCGAGAGCACAGCGGCCCTGGGCTGCCTGGTCAAGGACTAC TTCCCCGAACCGGTGACGGTGTCGTGGAACTCAGGCGCCCTGACCAGCGGCGTGCACACCTTCCCAG CTGTCCTACAGTCCTCAGGACTCTACTCCCTCAGCAGCGTGGTGACCGTGCCCTCCAGCAACTTCGGC ACCCAGACCTACACCTGCAACGTAGATCACAAGCCCAGCAACACCAAGGTGGACAAGACAGTTGAG CGCAAATGTTGTGTCGAGTGCCCACCGTGCCCAGCACCACCTGTGCCCAGCACCCCTGAGGTCCTCT TCCCCCCAAAACCCAAGGACACCCTCATGATCTCCCGGACCCCTGAGGTCACGTGCGTGGTGGTGGA CGTGAGCCACGAAGACCCCGAGGTCCAGTTCAACTGGTACGTGGACGGCGTGGAGGTGCATAATGC CAAGACAAAGCCACGGGAGGAGCAGTTCAACAGCACGTTCCGTGTGGTCAGCGTCCTCACCGTTGT GCACCAGGACTGGCTGAACGGCAAGGAGTACAAGTGCAAGGTCTCCAACAAAGGCCTCCCAGCCCC CATCGAGAAAACCATCTCCAAAACCAAAGGGCAGCCCCGAGAACCACAGGTGTACACCCTGCCCCC ATCCCGGGAGGAGATGACCAAGAACCAGGTCAGCCTGACCTGCCTGGTCAAAGGCTTCTACCCCAG CGACATCGCCGTGGAGTGGGAGAGCAATGGGCAGCCGGAGAACAACTACAAGACCACACGCCTCCCA GCTGGACTCCGACGGCTCCTTCTTCCTCTACAGCAAGCTCACCGTGGACAAGAGCAGGTGGCAGCAG GGGAACGTCTTCTCATGCTCCGTGATGCATGAGGCTCTGCACAACCACTACACGCAGAAGAGCCTCT CCCTGTCTCCGGGTAAA | DNA | Human | 6E1.2 HC |
| 58 | MDMRVPAQLLGLLLLWLRGARCQGQLVESGGGVVQPGRSLRLSCAASGFTFRSYGMHWVRQAPGKGL EWVAVIWYDGSKKYYADSVKGRFTISRDNSKNTLFLQMNSLRAEDTAVYYCARDGGIAAFLQDNWFDP WGQGTLVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKDTL MISRTPEVTCVVVDVSHEDPEVQFNWYVDGVEVHNAKTKPREEQFNSTFRVVSVLTVVHQDWLNGKEY KCKVSNKGLPAPIEKTISKTKGQPREPQVYTLPPSREEMTKNQVSLTCLVKGFYPSDIAVEWESNGQPENN YKTTPPMLDSDGSFFLYSKLTVDKSRWQQGNVFSCSVMHEALHNHYTQKSLSLSPGK | PRT | Human | 6E1.2 HC |
| 59 | AGCTATGGCATGCAC | DNA | Human | 6E1.2 HC CDR1 |
| 60 | SYGMH | PRT | Human | 6E1.2 HC CDR1 |
| 61 | GTTATATGGTATGATGGAAGTAAAAATACTATGCAGACTCCGTGAAGGGC | DNA | Human | 6E1.2 HC CDR2 |
| 62 | VIWYDGSKKYYADSVKG | PRT | Human | 6E1.2 HC CDR2 |
| 63 | GATGGGGGTATAGCAGCATTTTTACAGGACAACTGGTTCGACCCC | DNA | Human | 6E1.2 HC CDR3 |
| 64 | DGGIAAFLQDNWFDP | PRT | Human | 6E1.2 HC CDR3 |

FIGURE 1G

| SEQ ID NO: | Sequence | Type | Organism | Name |
|---|---|---|---|---|
| 65 | ATGGACATGAGGGTGCCCGCTCAGTCCTCCTGCTGTGTGGCTGTGAGAGGTGCGCGCTGTC AGGTGCAGCTGGTGGAGTCTGGGGGAGGCGTGGTCCAGCCTGGGAGGTCCCTGAGACTCTGTGC AGGGTCTGGATTCACCTTCAGGAGCTATGGCATGCACTGGGTCCGCCAGGCTCCAGGCAAGGGGCTG GAGTGGGTGGCAGTTATATGGTATGATGGAAGTAAAAAATACTATGCAGACTCCGTGAAGGGCCGA TTCACCATCTCCAGAGACAATTCCAAGAACACGCTGTTTCTGCAAATGAACAGCCTGAGAGCCGAGG ACACGGCTGTGTATTACTGTGCGAGAGATGGGGGTATAGCAGCATTTTTACAGGACAACTGGTTCGA CCCCTGGGGCCAGGGAACCCTGGTCACCGTCTCCTCAGTCGCCTCCACCAAGGGCCCATCGGTCTTCCCC CTGGCGCCCTGCTCCAGGAGCACCTCTGGGAACTCCCTGACGGTGACGGTGTCGTGGAACTCAGGCGCCCTGACCAGCGGCGTGCACACCTTCCCAGC TGTCCTACAGTCCTCAGGACTCTACTCCCTCAGCAGCGTGGTGACCGTGCCCTCCAGCAACTTCGGC ACCCAGACCTACACCTGCAACGTAGATCACAAGCCCAGCAACACCAAGGTGGACAAGACAGTTGAG CGCAAATGTTGTGTGCGAAGTGCCCACCGTGCCCAGCACCTCCTGTGCCCAGGACCACCAAGGTAACAAGGTGGACAAGACACAGTCTCTCT TCCCCCCAAAACCCAAGGACACCCTCATGATCTCCCGGACCCCTGAGGTCACATGCGTGGTGGTGGA CGTGAGCCACGAAGACCCCGAGGTCCAGTTCAACTGGTACGTGGACGGCGTGGAGGTGCATAATGC CAAGACAAAGCCACGGGAGGAGCAGTTCAACAGCACGTTCCGTGTGGTCAGCGTCCTCACCGTTGT GCACCAGGACTGGCTGAACGGCAAGGAGTACAAGTGCAAGGTCTCCAACAAAGGCCTCCCAGCCCC CATCGAGAAAACCATCTCAAAACCCAAAGGGCAGCCCCGAGAACCAGGTGTACACCCTGCCCCCA TCCCGGGAGGAGATGACCAAGAACCAGGTCAGCCTGACCTGCCTGGTCAAAGGCTTCTACCCCAG CGACATCGCCGTGGAGTGGGAGAGCAATGGGCAGCCGGAGAACAACTACAAGACCACGCCTCCCAT GCTGGACTCCGACGGCTCCTTCTTCCTCTACAGCAAGCTCACCGTGGACAAGAGCAGGTGGCAGCAG GGGAACGTCTTCTCATGCTCCGTGATGCATGAGGCTCTGCACAACCACTACACGCAGAAGAGCCTCT | DNA | | |
| 66 | MDMRVPAQLLGLLLLWLRGARCQVQLVESGGGVVQPGRSLRLSCAASGFTFRSYGMHWVRQAPGKGL EWVAVIWYDGSKKYYADSVKGRFTISRDNSKNTLFLQMNSLRAEDTAVYYCARDGGIAAFLQDNWFDP WGQGTLVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKDTL MISRTPEVTCVVVDVSHEDPEVQFNWYVDGVEVHNAKTKPREEQFNSTFRVVSVLTVVHQDWLNGKEY KCKVSNKGLPAPIEKTISKTKGQPREPQVYTLPPSREEMTKNQVSLTCLVKGFYPSDIAVEWESNGQPENN YKTTPPMLDSDGSFFLYSKLTVDKSRWQQGNVFSCSVMHEALHNHYTQKSLSLSPGK | PRT | Human | 6E1.2 HC G2V |
| 67 | AGCTATGGCATGCAC | DNA | Human | 6E1.2 HC G2V CDR1 |
| 68 | SYGMH | PRT | Human | 6E1.2 HC G2V CDR1 |
| 69 | GTTATATGGTATGATGGAAGTAAAAAATACTATGCAGACTCCGTGAAGGGC | DNA | Human | 6E1.2 HC G2V CDR2 |
| 70 | VIWYDGSKKYYADSVKG | PRT | Human | 6E1.2 HC G2V CDR2 |
| 71 | GATGGGGGTATAGCAGCATTTTTACAGGACAACTGGTTCGACCCC | DNA | Human | 6E1.2 HC G2V CDR3 |
| 72 | DGGIAAFLQDNWFDP | PRT | Human | 6E1.2 HC G2V CDR3 |

FIGURE 1H

| SEQ ID NO: | Sequence | Type | Organism | Name |
|---|---|---|---|---|
| 73 | ATGGACATGAGGGTGCCCGCTCAGCTCCTGGGGCTCCTGCTGCTGTGGCTGAGAGGTGCGCGCTGT GAGGGCAGCTGGTGGAGTCTGGGGGAGGCGTGGTCCAGCCTGGGAGGTCCCTGAGACTCTCCTGTG CAGCGTCTGGATTCACCTTCAGGAGCTATGGCATGCACTGGGTCCGCCAGGCTCCAGGCAAGGGGCT GGAGTGGGTGGCAGTTATATGGTATGATGGAAGTAAAAATACTATGCAGACTCCGTGAAGGGCCG ATTCACCATCTCCAGAGACAATTCCAAGAACACGCTGTATCTGCAAATGAACAGCCTGAGAGCCGA GGACACGGCTGTGTATTACTGTGCGAGAGATGGGGTATAGCAGCATTTTACAGGACAACTGGTTC GACCCCTGGGGCCAGGGAACCCTGGTCACCGTCTCTAGTGCCTCCACCAAGGGCCCATCGGTCTTC CCCCTGGCGCCCTGCTCCAGGAGCACCTCTGGGGGCACAGCGGCCCTGGGCTGCCTGGTCAAGGACTA CTTCCCCGAACCGGTGACGGTGTCGTGGAACTCAGGCGCTCTGACCAGCGGCGTGCACACCTTCCCA GCTGTCCTACAGTCCTCAGGACTCTACTCCCTCAGCAGCGTGGTGACCGTGCCCTCCAGCAACTTCG GCACCCAGACCTACACCTGCAACGTAGATCACAAGCCCAGCAACACCAAGGTGGACAAGACAGTTG AGCGCAAATGTTGTGTCGAGTGCCCACCGTGCCCAGCACCACCTGTGGCAGGACCGTCAGTCTTCCT CTTCCCCCCAAAACCCAAGGACACCCTCATGATCTCCCGGACCCCTGAGGTCACGTGCGTGGTGGTG GACGTGAGCCACGAAGACCCCGAGGTCCAGTTCAACTGGTACGTGGACGGCGTGGAGGTGCATAAT GCCAAGACAAAGCCACGGGAGGAGCAGTTCAACAGCACGTTCCGTGTGGTCAGCGTCCTCACCGTT GTGCACCAGGACTGGCTGAACGGCAAGGAGTACAAGTGCAAGGTCTCCAACAAAGGCCTCCCAGCC CCCATCGAGAAAACCATCTCCAAAACCAAAGGACAGCCCCGAGAACCAGGTGTACACCCTGCCCC CATCCCGGGAGGAGATGACCAAGAACCAGGTCAGCCTGACCTGCCTGGTCAAAGGCTTCTACCCCA GCGACATCGCCGTGGAGTGGGAGAGCAATGGGCAGCCGGAGAACAACTACAAGACCACGCCTCCCA TGCTGGACTCCGACGGCTCCTTCTTCCTCTACAGCAAGCTCACCGTGGACAAGAGCAGGTGGCAGCA GGGGAACGTCTTCTCATGCTCCGTGATGCATGAGGCTCTGCACAACCACTACACGCAGAAGAGCCTC TCCCTGTCTCCGGGTAAA | DNA | Human | 6E1.2 HC F80Y |
| 74 | MDMRVPAQLLGLLLLWLRGARCQGQLVESGGGVVQPGRSLRLSCAASGFTFRSYGMHWVRQAPGKGL EWVAVIWYDGSKKYYADSVKGRFTISRDNSKNTLYLQMNSLRAEDTAVYYCARDGGIAAFLQDNWFDP WGQGTLVTVSSASTKGPSVFPLAPCSRSTSESTAALGCLVKDYFPEPVTVSWNSGALTSGVHTFPAVLQS SGLYSLSSVVTVPSSNFGTQTYTCNVDHKPSNTKVDKTVERKCCVECPPCPAPPVAGPSVFLFPPKPKDTL MISRTPEVTCVVVDVSHEDPEVQFNWYVDGVEVHNAKTKPREEQFNSTFRVVSVLTVVHQDWLNGKEY KCKVSNKGLPAPIEKTISKTKGQPREPQVYTLPPSREEMTKNQVSLTCLVKGFYPSDIAVEWESNGQPENN YKTTPPMLDSDGSFFLYSKLTVDKSRWQQGNVFSCSVMHEALHNHYTQKSLSLSPGK | PRT | Human | 6E1.2 HC F80Y |
| 75 | AGCTATGGCATGCAC | DNA | Human | 6E1.2 HC F80Y CDR1 |
| 76 | SYGMH | PRT | Human | 6E1.2 HC F80Y CDR1 |
| 77 | GTTATATGGTATGATGGAAGTAAAAATACTATGCAGACTCCGTGAAGGGC | DNA | Human | 6E1.2 HC F80Y CDR2 |
| 78 | VIWYDGSKKYYADSVKG | PRT | Human | 6E1.2 HC F80Y CDR2 |
| 79 | GATGGGGTATAGCAGCATTTTTACAGGACAACTGGTTCGACCCC | DNA | Human | 6E1.2 HC F80Y CDR3 |
| 80 | DGGIAAFLQDNWFDP | PRT | Human | 6E1.2 HC F80Y CDR3 |

FIGURE 11

| SEQ ID NO: | Sequence | Type | Organism | Name |
|---|---|---|---|---|
| 81 | ATGGACATGAGAGGGTGCCCGCTCAGTCCTCTGGGCTCCGCTGCTGTGGCTGAGAGGTGCGCGCTGTCAGGTGCAGCTGGTGGAGTCTGGGGGAGGCGTGGTCCAGCCTGGGAGGTCCCTGAGACTCTCTGTGCAGCCTCTGGATTCACCTTCAGGAGCTATGGCATGCACTGGGTCCGCCAGGCTCCAGGCAAGGGGCTGGAGTGGGTGGCAGTTATATGGTATGATGGAAGTAAAAAATACTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTACTGTGCGAGAGATGGGGGTATAGCAGCATTTTACAGGACAACTGGTTCGACCCCTGGGGCCAGGGAACCCTGGTCACCGTCTCCAGGGCCTCCACCAAGGGCCCATCGGTCTTCCCCCTGGCCCCCTGCTCCAGGAGCACCTCCGAGAGCACAGCGGCCCTGGGCTGCCTGGTCAAGGACTACTTCCCCGAACCGGTGACGGTGTCGTGGAACTCAGGCGCTCTGACCAGCGGCGTGCACACCTTCCCAGCTGTCCTACAGTCCTCAGGACTCTACTCCCTCAGCAGCGTGGTGACCGTGCCCTCCAGCAACTTCGGCACCCAGACCTACACCTGCAACGTAGATCACAAGCCCAGCAACACCAAGGTGGACAAGACAGTTGAGCGCAAATGTTGTGTCGAGTGCCCACCGTGCCCAGCACCTGTGCCAGGACCGTCAGTCTTCCTCTTCCCCCCAAAACCCAAGGACACCCTCATGATCTCCCGGACCCCTGAGGTCACGTGCGTGGTGGTGGACGTGAGCCACGAAGACCCCGAGGTCCAGTTCAACTGGTACGTGGACGGCGTGGAGGTGCATAATGCCAAGACAAAGCCACGGGAGGAGCAGTTCAACAGCACGTTCCGTGTGGTCAGCGTCCTCACCGTTGTGCACCAGGACTGGCTGAACGGCAAGGAGTACAAGTGCAAGGTCTCCAACAAAGGCCTCCCAGCCCCCATCGAGAAAACCATCTCCAAAACCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTCTACCCCAGCGACATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATGCATGAGGCTCTGCACAACCACTACACGCAGAAGAGCCTCTCCCTGTCTCCGGGTAAA | DNA | Human | 6E1.2 HC G2V F80Y |
| 82 | MDMRVPAQLLGLLLLWLRGARCQVQLVESGGGVVQPGRSLRLSCAASGFTFRSYGMHWVRQAPGKGLEWVAVIWYDGSKKYYADSVKGRFTISRDNSKNTLYLQMNSLRAEDTAVYYCARDGGIAAFLQDNWFDPWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK | PRT | Human | 6E1.2 HC G2V F80Y |
| 83 | AGCTATGGCATGCAC | DNA | Human | 6E1.2 HC G2V F80Y CDR1 |
| 84 | SYGMH | PRT | Human | 6E1.2 HC G2V F80Y CDR1 |
| 85 | GTTATATGGTATGATGGAAGTAAAAAATACTATGCAGACTCCGTGAAGGGC | DNA | Human | 6E1.2 HC G2V F80Y CDR2 |
| 86 | VIWYDGSKKYYADSYKG | PRT | Human | 6E1.2 HC G2V F80Y CDR2 |
| 87 | GATGGGGGTATAGCAGCATTTTTACAGGACAACTGGTTCGACCCC | DNA | Human | 6E1.2 HC G2V F80Y CDR3 |
| 88 | DGGIAAFLQDNWFDP | PRT | Human | 6E1.2 HC G2V F80Y CDR3 |

FIGURE 1J

| SEQ ID NO: | Sequence | Type | Organism | Name |
|---|---|---|---|---|
| 89 | GCCTCCACCAAGGGCCCATCGGTCTTCCCCCTGGCACCCTCCTCCAAGAGCACCTCTGGGGGCACAG CGGCCCTGGGCTGCCTGGTCAAGGACTACTTCCCCGAACCGGTGACGGTGTCGTGGAACTCAGGCGC CCTGACCAGCGGCGTGCACACCTTCCCGGCTGTCCTACAGTCCTCAGGACTCTACTCCCTCAGCAGC GTGGTGACCGTGCCATCCAGCAGCTTGGGCACCCAGACCTACATCTGCAACGTGAATCACAAGCCCA GCAACACCAAGGTGGACAAGAAAGTTGAGCCCAAATCTTGTGACAAAACTCACACATGCCCACCGT GCCCAGCACCTGAACTCCTGCGGGGGACCGTCAGTCTTCCTCTTCCCCCCAAAACCCAAGGACACCCT CATGATCTCCCGGACCCCTGAGGTCACATGCGTGGTGGTGGACGTGAGCCACGAAGACCCTGAGGTC AAGTTCAACTGGTACGTGGACGGCGTGGAGGTGCATAATGCCAAGACAAAGCCGCGGGAGGAGCAG TACAACAGCACGTACCGTGTGGTCAGCGTCCTCACCGTCCTGCACCAGGACTGGCTGAATGGCAAGG AGTACAAGTGCAAGGTCTCCAACAAAGCCCTCCCAGCCCCCATCGAGAAAACCATCTCCAAAGCCA AGGGCAGCCCGAGAACCACAGGTGTACACCCTGCCCCCATCCCGGGAGGAGATGACCAAGAACC AGGTCAGCCTGACCTGCCTGGTCAAAGGCTTCTATCCCAGCGACATCGCCGTGGAGTGGGAGAGCA ATGGGCAGCCGGAGAACAACTACAAGACCACGCCTCCCGTGCTGGACTCCGACGGCTCCTTCTTCCT CTATAGCAAGCTCACCGTGGACAAGAGCAGGTGGCAGCAGGGGAACGTCTTCTCATGCTCCGTGAT GCATGAGGCTCTGCACAACCACTACACGCAGAAGAGCCTCTCCCTGTCTCCGGGTAAA | DNA | Human | IgG1"Ala, Ala" Effectorless IgG1z |
| 90 | ASTKGPSVFPLAPSSKSTSGGTAALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELAGAPSVFLFPPKPKDTLMISRTPEVT CVVVDVSHEDPEVKFNWYVDGVEVHNAKTKPREEQYNSTYRVVSVLTVLHQDWLNGKEYKCKVSNKA LPAPIEKTISKAKGQPREPQVYTLPPSREEMTKNQVSLTCLVKGFYPSDIAVEWESNGQPENNYKTTPPVL DSDGSFFLYSKLTVDKSRWQQGNVFSCSVMHEALHNHYTQKSLSLSPGK | PRT | Human | IgG1"Ala, Ala" Effectorless IgG1z |
| 91 | ATGGACATGAGGGTGCCCGCTCAGCTCCTGGGGCTCCTGCTGCTCTGGCTCCCAGGTGCGCGCTGTG ACATCCAGATGACCCAGAGCCCATCAGTCTCTGCTTCCGTGGGAGATCGGGTTACCATTACATG TAGGGCCTCTCAAGACATTGGTCAATCTCAAATGGTATCAGCAGAAACCCGAGAAAGCACCCAA ATTCTCGATCTATGTACATCTTCTGGATTCGGGGTCCCTCACGGTTCTCCGGTTCAGGAGCG GAACCGACTTCACGCTTCACCATCAGCAGCCTGCAGCGGAACCAAGGTCGAGATTACGTACGGTGCTGC GTATGCCACAAGCCCTCTCACATTTGGGCAGGGAACCAAGGTCGAGATTAAGCGTACGGTGGCTGC ACCATCTGTCTTCATCTTCCCGCCATCTGATGAGCAGTTGAAATCTGGAACTGCCTCTGTTGTGTGCC TGCTGAATAACTTCTATCCCAGAGAGGCCAAAGTACAGTGGAAGGTGGATAACGCCCTCCAATCGG GTAACTCCCAGGAGAGTGTCACAGAGCAGGACAGCAAGGACAGCACCTACAGCCTCAGCAGCACC CTGACGCTGAGCAAAGCAGACTACGAGAAACACAAAGTCTACGCCTGCGAAGTCACCCATCAGGGCC TGAGCTCGCCCGTCACAAAGAGCTTCAACAGGGGAGAGTGT | DNA | Antibody Sequence | MAB22_KLC_V1 |
| 92 | MDMRVPAQLLGLLLLWLRGARCDIQMTQSPSSLSASVGDRVTITCRASQDIGSNLNWYQQKPEKAPKSLI YATSSLDSGVPSRFSGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V1 |

FIGURE 1K

| SEQ ID NO: | Sequence | Type | Organism | Name |
|---|---|---|---|---|
| 93 | ATGGACATGAGGGTGCCCGCTCAGCTGCTGGGACTCCTGCTGCTGTGGCTGAGAGGTGCGCGCTGTG ACATCCAGATGACCCAGAGCCCATCTAGTCTCTCTGCTTCCGTGGGAGATCGGGTTACCATTACATG TAGGGCCTCTCAAGACATTGGGTCAAATCGAATTGGCTTCAACAGACATCAGATGAAGTATTAAA CGCCTGATCTACGCTACGTCTCTGGATTCCGGGGTCCCCCTCACGGTTCTCCGGTTCAGGGAGCGG AACCGACTTCACGCTTACAATCTCAAGCCTTCAGCCAGGATTTGCTACCTACACTGTCTGCAGT ATGCCACAAGCCCTCTACATTTGGGACAGGAAACCAAGGTCGAGATTAAGCGTAGGTGGCTGCAC CATCTGTCTTCATCTTCCCGCCATCTGATGAGCAGTGGAAATCTGAACTGCCTCTGTTGTGTCCTG CTGAATAACTTCTATCCCAGAGAGTGTCACAGAGGCCAAAGTACAGCAAGGACAGCAGCCACTACAGCAGCACCCTG AACTCCCAGGAGAGTTCACAGAGCAAGGACAGCAGCAAGTGATAACGCCTCAGCCCTGCCAAAAGACTACGCTGCGAAGTCACCATCAGGCCTG AGCTCGCCCGTCACAAAGAGCTTCAACAGGGAGAGTGT | DNA | Antibody Sequence | MAB22_KLC_V2 |
| 94 | MDMRVPAQLLGLLLLWLRGARCDIQMTQSPSSLSASVGDRVTITCRASQDIGSNLNWLQQTSDGSIKRLI YATSSLLDSGVPSREGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V2 |
| 95 | ATGGACATGAGGGTGCCCGCTCAGCTCCTGGGGCTCCTGCTGCTGTGGCTGAGAGGTGCGCGCTGTG ACATCCAGATGACCCAGAGCCCATCTAGTCTCTCCGTGGGAGATCGGGTTACCATTACATG TAGGGCCTCTCAAGACATTGGGTCAAATCGAATTGGCTCAACAGACAAACGCACCCAA CGCCTGATCTATGCTACATCTCTGGATTCCGGGGTCCCCTTCCGGTTCTCCGGTTCAGGGAGCG GAACCGACTTCACGCTTACAATCTCAGCCAGGAACAAGGTTTGCTACCTACACTGTCTGCA GTATGCCACAAGCCCTCTACATTTGGGCAGGAACCAAGGTTGAAATCTGGAACTGCCTCTGTTGTGTCC ACCATCTGTCTTCATCTTCCCGCCATCTGATGAGCAGTTGAAATCTGGAACTGCCTCTGTTGTGTCC TGCTGAATAACTTCTATCCCAGAGAGGTCACAGAGGCCAAAGTACAGTGGAAGGTGGATAACGCCCTCCAATCGG GTACAGCCTGAGCAAAGCAGATCAGAATCAGAGAAACAACAAGTCTACGCCTGCGAAGTCACCATCAGGGCC TGAGCTCGCCCGTCACAAAGAGCTTCAACAGGGAGAGTGT | DNA | Antibody Sequence | MAB22_KLC_V3 |
| 96 | MDMRVPAQLLGLLLLWLRGARCDIQMTQSPSSLSASVGDRVTITCRASQDIGSNLNWLQQKPEKAPKSLI YATSSLLDSGVPSREGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V3 |

FIGURE 1L

| SEQ ID NO: | Sequence | Type | Organism | Name |
|---|---|---|---|---|
| 97 | ATGGACATGAGGGTGCCCGCTCAGCTCCTCGGGCTCCTGCTGCTGTGGCTGAGAGGTGCGCGCTGTG ACATCCAGATGACCCAGAGCCCATCTAGTCTCTCTGCTTCCGTGGGAGATCGGGTTACCATTACATG TAGGGCCTCTCAAGACATTGGGTCAAATCTGAATTGGTATCAGCAGAAACCCGAGAAAGCACCCAA AAGACTGATCTATGCTGCATCTTCTCTGGATTCCGGGGTCCCCTCACGGTTCTCCGGTTCAGGAGCG GAACCGACTTCACGCTTCACGATCAGCCAGAGGATTTGCTACCTACTACTGTCTGCA GTATGCCACAAGCCCTCTCACATTTGGGCAGGAACCAAGGTCGAGATTAAGCGTACGGTGGCTGC ACCATCTGTCTTCATCTTCCCGCCATCTGATGAGCAGTTGAAATCTGAACTGCCTCTGTTGTGTCC TGCTGAATAACTTCTATCCCAGAGAGGCCAAAGTACAGTGGAAGGTGATAACGCCCTCCAATCGG GTAACTCCCAGGAGAGTCACAGACAGCAGGACAGCAGCAAAGTCTACGCTGAAGTCACCCACC TGAGCCTGAGCAAAGCAGACTACGAGAAACACAAAGTCTACGCCTGCGAAGTCACCCATCAGGGCC TGAGCTCGCCCGTCACAAAGAGCTTCAACAGGGGAGAGTGT | DNA | Antibody Sequence | MAB22_KLC_V4 |
| 98 | MDMRVPAQLLGLLLLWLRGARCDIQMTQSPSSLSASVGDRVTITCRASQDIGSNLNWYQQKPEKAPKRLI YATSSLLDSGVPSRFSGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V4 |
| 99 | ATGGACATGAGGGTGCCCGCTCAGCTCCTCGGGCTCCTGCTGCTGTGGCTGAGAGGTGCGCGCTGTG ACATCCAGATGACCCAGAGCCCATCTAGTCTCTCTGCTTCCGTGGGAGATCGGGTTACCATTACATG TAGGGCCTCTCAAGACATTGGGTCAAATCTGAATTGGTATCAGCAGAAACCCGAGAAAGCACCCAA AAGACTGATCTATGCTGCATCTTCTCTGGATTCCGGGGTCCCCTCACGGTTCTCCGGTTCAGGAGCG GAACCGACTTCACGCTTCAGCCTCAGCCAGAGGATTTGCTACCTACTACTGTCTGCA GTATGCCACAAGCCCTCTCACATTTGGGCAGGAACCAAGGTCGAGATTAAGCGTACGGTGGCTGC ACCATCTGTCTTCATCTTCCCGCCATCTGATGAGCAGTTGAAATCTGAACTGCCTCTGTTGTGTCC TGCTGAATAACTTCTATCCCAGAGAGGCCAAAGTACAGTGGAAGGTGGATAACGCACTCCAATCGG GTAACTCCCAGGAGAGTCACAGACAGCAGGACACAGCAAAGTCACCTCGAAGTCACCCACC TGAGCCTGAGCAAAGCAGACTACGAGAAACACAAAGTCTACGCCTGCGAAGTCACCCATCAGGGCC TGAGCTCGCCCGTCACAAAGAGCTTCAACAGGGGAGAGTGT | DNA | Antibody Sequence | MAB22_KLC_V5 |
| 100 | MDMRVPAQLLGLLLLWLRGARCDIQMTQSPSSLSASVGDRVTITCRASQDIGSNLNWLQQKPEKAPKRLI YATSSLLDSGVPSRFSGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V5 |

FIGURE 1M

| SEQ ID NO: | Sequence | Type | Organism | Name |
|---|---|---|---|---|
| 101 | ATGGACATGAGGGTGCCCGCTCAGCTCCTGGGGCTCCTGCTGCTCTGGCTCCCAGGTGCCGCTGTG ACATCCAGATGACCCAGAGCCCATCTAGTCTCTCTGCTTCCGTGGGAGATCGGGTTACCATTACATG TAGGGCCTCTCAAGACATTGGGTCAAATCTGAATTGGCTCAGCAGAAACCGGCAAAGCACCCAA AAGACTGATCTATGCTACATCTCTGGATTCCGGGGTCCCCTCACGGTTCTCCGGTTCTACTGTCTGCA GAACCGACTTCACGCTTCACCTCCAAGCCTTCAGCAGGATTTTGCTACTACTGTCTGCAA GTATGCCACAAGCCCTCTCACATTTGGGCAGGGAACCAAGGTCGAGATTAAGCGTACGGTGGCTGC ACCATCTGTCTTCATCTTCCCGCCATCTGATGAGCCAGCCAAAGTACAGTGAAATCTGAACTGCCTCTGTGTGTGCC TGCTGAATAACTTCTATCCCAGAGAGGCCAAAGTACAGTGGAAGGTGGATAACGCCCTCCAATCGG GTAACTCCCAGGAGAGTGTCACAGAGCAGGACAGCAAGGACAGCACCTACAGCCTCAGCAGCACC CTGACGCTGAGCAAAGCAGACTACGAGAAAACACAAAGTCTACGCCTGCGAAGTCACCCATCAGGGCC TGAGCTCGCCCGTCACAAAGAGCTTCAACAGGGGAGAGTGT | DNA | Antibody Sequence | MAB22_KLC_V6 |
| 102 | MDMRVPAQLLGLLLLWLRGARCDIQMTQSPSSLSASVGDRVTITCRASQDIGSNLNWLQQKPGKAPKRLI YATSSLDSGVPSRFSGSGSGTDFTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V6 |
| 103 | ATGGACATGAGGGTGCCCGCTCAGCTCCTGGGGCTCCTGCTGCTCTGGCTCCCAGGTGCCGCTGTG ACATCCAGATGACCCAGAGCCCATCTAGTCTCTCTGCTTCCGTGGGAGATCGGGTTACCATTACATG TAGGGCCTCTCAAGACATTGGGTCAAATCTGAATTGGCTCAGCAGAAACCGGAGAAGCACCCAA AAGACTGATCTATGCTACATCTCTGGATTCCGGGGTCCCCTCACGGTTCTCCGGTTCACGGAGCG GAAGCGACTATACGCTTCAAGCCTCTCACATTTGGGCAGGGAACCAAGGTCGAGATTAAGCGTACGGTGGCTGCA GTATGCCACAAGCCCTCTCACATTTGGGCAGGGAACCAAGGTCGAGATTAAGCGTACGGTGGCTGCA ACCATCTGTCTTCATCTTCCCGCCATCTGATGAGCCAGCCAAAGTACAGTGAACTGCCTCTGTGTGTGCC TGCTGAATAACTTCTATCCCAGAGAGGCCAAAGTACAGTGGAAGGTGGATAACGCCCTCCAATCGG GTAACTCCCAGGAGAGTGTCACAGAGCAGGACAGCAAGGACAGCACCTACAGCCTCAGCAGCACC CTGACGCTGAGCAAAGCAGACTACGAGAAAACACAAAGTCTACGCCTGCGAAGTCACCCATCAGGGCC TGAGCTCGCCCGTCACAAAGAGCTTCAACAGGGGAGAGTGT | DNA | Antibody Sequence | MAB22_KLC_V7 |
| 104 | MDMRVPAQLLGLLLLWLRGARCDIQMTQSPSSLSASVGDRVTITCRASQDIGSNLNWLQQKPEKAPKRLI YATSSLDSGVPSRSGSRSGSDYTLTISSLQPEDFATYYCLQYATSPLTEGQGIKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V7 |

FIGURE 1N

| SEQ ID NO: | Sequence | Type | Organism | Name |
|---|---|---|---|---|
| 105 | ATGGACATGAGGGTGCCCGCTCAGCTCCTGCTGCTGTGGCTCCTGGGGCTCCTCTGCTGCTGGGCTGAGAGGTGCGCGCTGTG ACATCCAGATGACCCAGAGCCCATCTAGTCTCTGCTTCCGTGGGAGATCGGGTTACCATTACATG AGGGCCTCCAAGACATTGGGTCAATCTTCTCTGGATTCCGGATCAAATCTGAATGGCTCCAGCAGAAACCCGGCAAAGCACCCAA AAGACTGCTATGCTACAGCTTACAATCTCAAGCCTTCAGCAGGAACCTTCTCCAGAGATTTTGCTACTTACTGTCTGCA GAAGCGACTATACGCTTACAAGCCCCTCTACATTTGGGCAGGGGAACCAAGGTGCAGATTAAGCTCGCTGTTGTGCTC GTATGCCACAAGCCCTCTCATCTTCCCGCCATCTGATGAGCAGTTGAAATCTGGAACTGCTCCTGTTGTGTGC ACCATCTGTCTTCATTCCAGGAGAGTCGACGGAGGGTCAAAGGCCAAATGAACGTACAAGCACCTACAGCCTCAGCAGACCT GTAACTCCAGGAGAGTGTCACAGAGCAGGACAGGAAACACAAGTCTACGCCTCGCGAAGTCACCATCAGGGCC TGACGCTGAGCAAAGCAGACTACGAGAAACATAAGGGGAGTGTC | DNA | Antibody Sequence | MAB22_KLC_V8 |
| 106 | MDMRVPAQLLGLLLLWLRGARCDIQMTQSPSSLSASVGDRVTITCRASQDIGSNLNWLQQKPGKAPKRLI YATSSLDSGVPSRFSGSRSGSDYTLTISSLQPEDFATYYCLQYATSPLTFGQGTKVEIKRTVAAPSVFIFPPS DEQLKSGTASVVCLLNNFYPREAKVQWKVDNALQSGNSQESVTEQDSKDSTYSLSSTLTLSKADYEKHK VYACEVTHQGLSSPVTKSFNRGEC | PRT | Antibody Sequence | MAB22_KLC_V8 |
| 107 | ATGGACATGAGGGTGCCCGCTCAGCTCCTGCTGCTGTGGCTCCTGGGGCTCCTCTGCTGCTGGGCTGAGAGGTGCGCGCTGTG AAGTGCAGCTGGTGGAGAGCGGCGGTGGTCTGGTGAAGCCCGGAGGTCATTGAAGACTCTATGCG CGGCTTCCGGTTCTCTTTCTCCACGCTATGCAATGACTTGGGTGCGCCAGGCCCTGGTAAAGGGCTG GAATGGGTGTCTACGATCTCGGATGCGCTCATATACGTACTATCAGAGTCAGAAGAAGATAGAT TCACTATCAGCAGGGACAATGCCAAGAACAGCCTGTATCTCCAAATGAATAGTGTGCGAGGCCAAAG ATACAGCCGTCTATTACTGCGCAAGAGCGAACTATTGTGACCATGGTGACACAGATGCCATGGATTACTG GGGCCAAGGAACCCATGGTGACTGTGAGCTCAGCCTCCACCAAGGGCCCATCGGTCTTCCCCCTGGCG CCCTGCTCCAGGAGCACCTCCGAGAGCACAGCGGCCCTGGGCTGCCTGGTCAAGGACTACTTCCCG AACCGGTGACGGTGTCGTGGAACTCAGGCGCTGTCACTGTGACCTCAGGTGTCCTCCAGCAGCTTGGGCACCCAG ACAGCTCCTCAGGACTCCTACTCCCTCAGCAGCGTGACTGTGCCCTCCAGCAAGCAGCAAGACATCAATGCACCAGAAAGGTTGAGACGCAAA GGGCTGGACAAGAACCAACATCCACCACAAGGGCCAGGACTCTTGTGACAAGAAACCACATGCCCATCAGTGCACCAGCTGAAGGCC CACGAAGACCCCGAGGTGACTACCCATGCCGAGGCGCTGGAGGTGCATAATGCCAAGACA AGCCACGGGAGGAGCAGTTCAACAGCACGTTCCGTGTGTGTCACCGTGCGAGGTGCATAATGCCAAGACA AGCACGGGAGGAGCAGTTCAACAGCACGTTCCGTGTGTCACCGTGCTCCACCAGGACTGGCTGAATGGCAAGGAGTACAAGTGCAAGGTCTCCAACAAAGCCCTCCCAGCCCCCATCGAGA AAACCATCTCAAAAGGCCAAAGGCCAAAGGCAGCCCCGAGAACCAGGTCAGCCTGACCTGCCTGGTCAAAGGCTTCTACCCCAGCGACATCG CCGTGGAGTGGAGAGCAATGGGCAGCCGGAGAACAACTACAAGACCACGCCTCCCGTGCTGACTCCGACGGCTCCTTCTTCCTCTACAGCAAGCTCACCGTGGACAAGAGCAGGTGGCAGCAGGGGAACGT CTTCTCATGCTCCGTGATGCATGAGGCTCTGCACAACCACTACACGCAGAAGAGCCTCTCCCTGTCT CCGGGTAAA | DNA | Antibody Sequence | MAB22_HC_V1 |

FIGURE 10

| SEQ ID NO: | Sequence | Type | Organism | Name |
|---|---|---|---|---|
| 108 | MDMRVPAQLLGLLLLWLRGARCEVQLVESGGGLVKPGGSLRLSCAASGFSFSRYAMTWVRQAPGKGLE WVSTISDGGSYTYYPDSEKNRFTISRDNAKNSLYLQMNSLRAEDTAVYYCARRAGHMVTFDAMDYWG QGTMVTVSSASTKGPSVFPLAPCSRSTSESTAALGCLVKDYFPEPVTVSWNSGALTSGVHTFPAVLQSSG LYSLSSVVTVPSSNPGTQTYTCNVDHKPSNTKVDKTVERKCCVECPPCPAPPVAGPSVFLFPPKPKDTLMI SRTPEVTCVVVDVSHEDPEVQFNWYVDGVEVHNAKTKPREEQFNSTFRVVSVLTVVHQDWLNGKEYKC KVSNKGLPAPIEKTISKTKGQPREPQVYTLPPSREEMTKNQVSLTCLVKGFYPSDIAVEWESNGQPENNYK TTPPMLDSDGSFFLYSKLTVDKSRWQQGNVFSCSVMHEALHNHYTQKSLSLSPGK | PRT | Antibody Sequence | MAB22_HC_V1 |
| 109 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSSEQAMRCSLI TEHVEAFITIQVAQMVIGFLVPLLAMSFCYLVIIRTLQARNFERNKAIKVHAVVVFHYPQLPYNGVVLA QFVANFNITSSTCELSKQLNIAYDVTYSLACVRCCVNPFLYAFIGVKFRMDLFKLFKDLGCLSQEQLRQWS SCRHRRSSMSVEAEFTTTFSP | PRT | Human | Human CCR7 Protein |
| 110 | GAC GAT TAC ATC GGA GAG AAC ACC ACA GTG GAC TA | DNA | Synthetic Oligo | D35E sense |
| 111 | TAG TCC ACT GTG GTG TTC TCT CCG ATG TAA TCG TC | DNA | Synthetic Oligo | D35E antisense |
| 112 | CAC AGT GGA CTA CAC TTT GTA TGA GTC TTT GTG CTC CAA GAA | DNA | Synthetic Oligo | F44Y sense |
| 113 | TTC TTG GAG CAC AAA GAC TCA TAC AAA GTG TAG TCC ACT GTG | DNA | Synthetic Oligo | F44Y antisense |
| 114 | TGG ACT ACA CTT TGT TCG AGT CTG TGT GCT CCA AGA | DNA | Synthetic Oligo | L47V sense |
| 115 | TCT TGG AGC ACA CAG ACT CGA ACA AAG TGT AGT CCA | DNA | Synthetic Oligo | L47V antisense |
| 116 | TTC GAG TCT TTG TGC TTC AAG AAG GAC GTG CGG | DNA | Synthetic Oligo | S49F sense |
| 117 | CCG CAC GTC CTT CTT GAA GCA CAA AGA CTC GAA | DNA | Synthetic Oligo | S49F antisense |
| 118 | GGGCCT ACA GCG AGG CCA AGT CCT G | DNA | Synthetic Oligo | A118E sense |
| 119 | CAG GAC TTG GCC TCG CTG TAG GCC C | DNA | Synthetic Oligo | A118 antisense |
| 120 | CGG CCA AGT CCT GGA TCT TCG GTG TCC AC | DNA | Synthetic Oligo | V123I sense |
| 121 | GTG GAC ACC GAA GAT CCA GGA CTT GGC CG | DNA | Synthetic Oligo | V123I antisense |

FIGURE 1P

| SEQ ID NO: | Sequence | Type | Organism | Name |
|---|---|---|---|---|
| 122 | GTC CTG GGT CTT CGG TGT CTA TTT TTG CAA GCT CAT CTT TG | DNA | Synthetic Oligo | H127Y sense |
| 123 | CAA AGA TGA GCT TGC AAA AAT AGA CAC CGA AGA CCC AGG AC | DNA | Synthetic Oligo | H127Y antisense |
| 124 | GGG TCT TCG GTG TCC ACT TAT GCA AGC TCA TCT T | DNA | Synthetic Oligo | F128L sense |
| 125 | AAG ATG AGC TTG CAT AAG TGG ACA CCG AAG ACC C | DNA | Synthetic Oligo | F128L antisense |
| 126 | GCT CCT GTA CAG TGG CCT CCA GAG GAG CA | DNA | Synthetic Oligo | D198G sense |
| 127 | TGC TCC TCT GGA GGC CAC TGT ACA GGA GC | DNA | Synthetic Oligo | D198G antisense |
| 128 | CAG TGA CCT CCA GAA GAG CAG CAG TGA GC | DNA | Synthetic Oligo | R201K sense |
| 129 | GCT CAC TGC TGC TCT TCT GGA GGT CAC TG | DNA | Synthetic Oligo | R201K antisense |
| 130 | GTG ACC TCC AGA GGA ACA GCA GTG AGC AAG C | DNA | Synthetic Oligo | S202N sense |
| 131 | GCT TGC TCA CTG CTG TTC CTC TGG AGG TCA C | DNA | Synthetic Oligo | S202N antisense |
| 132 | TCC AGA GGA GCA GCA GCG GTG AGC AAG CGA TG | DNA | Synthetic Oligo | S204G sense |
| 133 | CAT CGC TTG CTC ACC GCT GCT GCT CCT CTG GA | DNA | Synthetic Oligo | S204G antisense |
| 134 | GGA GCA GCA GTG AGG ATG CGA TGC GAT GCT C | DNA | Synthetic Oligo | Q206D sense |
| 135 | GAG CAT CGC ATC GCA TCC TCA CTG CTG CTC C | DNA | Synthetic Oligo | Q206D antisense |
| 136 | AGG AGC AGC AGT GAG CAA ACG ATG CGA TCG | DNA | Synthetic Oligo | A207T sense |
| 137 | GCA TCG CAT CGT TTG CTC ACT GCT GCT CCT | DNA | Synthetic Oligo | A207T antisense |
| 138 | GCA GTG AGC AAG CGT TGC GAT GCT CTC TC | DNA | Synthetic Oligo | M208L sense |
| 139 | GAG AGA GCA TCG CAA CGC TTG CTC ACT GC | DNA | Synthetic Oligo | M208L antisense |
| 140 | GAT GCG ATG CTC TCT CGT CAC AGA GCA TGT GGA | DNA | Synthetic Oligo | I213V sense |

FIGURE 1Q

| SEQ ID NO. | Sequence | Type | Organism | Name |
|---|---|---|---|---|
| 141 | TCC ACA TGC TCT GTG ACG AGA GAG CAT CGC ATC | DNA | Synthetic Oligo | I213V antisense |
| 142 | CGA TGC TCT CTC ATC TCA GAG CAT GTG GAG G | DNA | Synthetic Oligo | T214S sense |
| 143 | CCT CCA CAT GCT CTG AGA TGA GAG AGC ATC G | DNA | Synthetic Oligo | T214S antisense |
| 144 | GCT CTC TCA TCA CAG CGC ATG TGG AGG CCT T | DNA | Synthetic Oligo | E215A sense |
| 145 | AAG GCC TCC ACA TGC GCT GTG ATG AGA GAG C | DNA | Synthetic Oligo | E215A antisense |
| 146 | TCT CTC ATC ACA GAG CAG GAG GCC TTT ATC AC | DNA | Synthetic Oligo | H216Q sense |
| 147 | GTG ATA AAG GCC TCC ACC TGC TCT GTG ATG AGA GA | DNA | Synthetic Oligo | H216Q antisense |
| 148 | CAA CTT CAA CAT CAC CAA TAG CAC CTG TGA GCT CA | DNA | Synthetic Oligo | S295N sense |
| 149 | TGA GCT CAC AGG TGC TAT TGG TGA TGT TGA AGT TG | DNA | Synthetic Oligo | S295 antisense |
| 150 | CAA CAT CAC CAG TAG CAG CTG TGA GCT CAG TAA GC | DNA | Synthetic Oligo | T297S sense |
| 151 | GCT TAC TGA GCT CAC AGC TGC TAC TGG TGA TGT TG | DNA | Synthetic Oligo | T297S antisense |
| 152 | CAC CAG TAG CAC CTG TGA GAC CAG TAA GCA ACT CAA CAT C | DNA | Synthetic Oligo | L300T sense |
| 153 | GAT GTT GAG TTG CTT ACT GGT CTC ACA GGT GCT ACT GGT G | DNA | Synthetic Oligo | L300T antisense |

FIGURE 1R

| SEQ ID NO: | Sequence | Type | Organism | Name |
|---|---|---|---|---|
| 154 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACAACCACAGTGGACTACACTTGTTCGA GTCTTTGTGTCTCAAGAAGGACGTGCGGAACTTTAAAGCCTGGTTCCTCCCTATCATGTACTCCATCA TTTGTTTCGTGGGCCTACTGGGCAATGGCCTGGTCGTGTTGACCTATATCTATTTCAAGAGGCTCAAG ACCATGACCGATACCTACCTGCTCAACCTGGCGGTGGCAGACATCCTCTTCCTGACCCTTGCCCTT CTGGGCCTACAGCGCGGCAAGTCCTGGGTTCGGTGTCCACTTCTTGCAAGCTCATCTTTGCCATCT ACAAGATGAGCTTCTTCAGTGCATGGCTCCTACTTCTTTGCATCAGCATTGACCGCTAGTGGCCATC GTCCAGGCTGTCTTCAGTGCTTCACGCCACAGTGCTCTCCATCCCGTCTTCTTCATCAGCATCTGGG CATCTGGATACTAGCCACAGTGCTCTCCATCCCAGAGCTCCTGTACAGTGACCTCTATCACCATCCAGGTGG AGTGAGCAAGCGATGCAGTCGGCTTTCTGGTCCCCCTGTGCCAACGGTGGAGGCTTTATGAGCTTCTGTTACCTTGTCATCATCGC CCCAGATGGTGATCGGCTTTCTGGTCCCCCTGTGCCAACGGTGGAGGCTTTATGAGCTTCTGTTACCTTGTCATCATCGC ACCCTGCTCCAGGCACGCAACTTTGAGCGCAACAAGGCCATCAAGGTGATCATCGCTGTGGTCGTGG TCTTCATAGTCTTCCAGCTGCCCTACAATGGGGTGGTTCTGGCCCAGACGGTCGAACTTCAACAT CACCAGTAGCACCTGTGAGCTCAGTAAGCAACTCAACATGCCTTCATCGGCGTCAAGTTCCGCAACGATCTCT CAAGCTCTTCAAGGACCTGGCTGCCTCAGCCAGGAGCAGCTCCGGCAGTGGTCTTCCTGTCGGCAC ATCCGGCGCTCCTCATGAGTGTGAGGCGAGAGCCACCACCACCTTCTCCCATAG | DNA | Mutated hCCR7 | pcDNA3.1 Neo-hCCR7 |
| 155 | MDLGKPMKSVLVVALLVIFQVCLCQDEVTDDYIGDNTTVDYTLFESLCSKKDVRNFKAWFLPIMYSIICF VGLLGNGLVLLTYIYFKRLKTMTDTYLLNLAVADILFLLTLPFWAYSAAKSWVFGVHFCKLIFAIYKMSF FSQMLLLLCISIDRYVAIYQAVSAHRHRARVLLJSKLSCVGIWILATVLSIPELLYSDLQRSSSEQAMRCSLI TEHVEAFITIQVAQMVIGFLVPLLAMSFCYLVHRTLLQARNFERNKAIKVHAVVVFIVFQLPYNGVVLA QTVANFNITSSTCELSKQLNIAYDVTYSLACVRCCVNPFLYAFIGVKFRNDLFKLFKDLGCLSQEQLRQWS SCRHIRRSSMSVEAETTTTFSP | PRT | Mutated hCCR7 | pcDNA3.1 Neo-hCCR8 |

FIGURE 1S

| SEQ ID NO. | Sequence | Type | Organism | Name |
|---|---|---|---|---|
| 156 | ATGGACCTGGGGAAACCAATGAAAAGCGTGCTGGTGGCTCTCCTTGTCATTTCCAGGTATGCCTGTGTCAAGATGAGGTCACGGACGATTACAGAGACGTGCTGGCAGAGAGAACCACAGTGACTTGTTCGAGTCTTGTGTGCTTCAAGAAGGACGTGCCAATGGCCTACTACCTGCTCAACCTGGCTGTCGCTGATGGCCTCGGCTGGTCCTATCATGTACTCCATCATTTGTTTCGTGGGCCTACTACCTGCTCAACCTGGCTGTCGCTGATGGCCTCGGCTGGTCCTATCATGTACTCCATCAACCATGACCGATACCTACCTGCTCAACCTGGGTCTTCGCTGGCAGACATCCTCCTCCTGACCCTTCCCTTCTGGGCCTACAGCGCGGCCAAGTCCTGGGTCTTCGGTGTCCATTTCTGCAAGCTCATCTTTGCCATCTACAAGATGAGCTTCTTCAGTGGCATGCTCCTACTTCTTTGCATCAGCATTGACCGCTACGTGGCCATCGTCCAGGCTGTCCAGCTACTAGCCACAGTGCTCTCCATCCCAGAGCTCCTGTACAGTGACCTTTATCACCATCCAGTTGGAGTGAGCAAGCGATGCAGCTTCTTCTGGTCCCGTGGCCATGAGCTTCTGTTCTTACCTTGTCATCATCCGCCCCAGATGGTGATCGGTGATTCGCCCAACTTTGAGGCGAACAAGGCCATCAAGGTGATCATCGCTGTGGTCGTGGTCTTCATATGTCTTGTGGCCACTGTGAGCTCCCTACAATGGGTGTCCTGGCCCAGAGCGGTGCCAACTACAAGCTGCCCAGGTAGCAGCACCTGTGAGCTCAGTGGCCTCAACCCTTTCTGTATACGCCTCAGCCAGGAGCTGCCTCAGGCCAGGCTCCGGGACCACCAACCTACCTTCTCCCATAG | DNA | Mutated hCCR7 | D35E 20100122625 |
| 157 | MDLGKPMKSVLVVALLVIFQVCLCQDEVTDDYIGENTFVDYTLFESLCSKKDVRNFKAWFLPIMYSIICFVGLLGNGLVVLTYIYFKRLKTMTDTYLLNLAVADILFLLTLPFWAYSAAKSWVFGVHFCKLIFAIYKMSFFSGMLLLCISIDRYVAQMVIGFLVPLLAMSFCYLVIRTLLQARNFERNKAIKVIIAVVVFVFQLPYNGVVLATEHYEAFITIQVAQMVIGFLVPLLAMSFCYLVIRTLLQARNFERNKAIKVIIAVVVFVFQLPYNGVVLAQTVANFNITSSTCELSKQLNIAYDVTYSLACVRCCVNPFLYAFIGVKFRNDLFKLFKDLGCLSQEQLRQWSSCRHIRRSSMSVEAETTTFSP | PRT | Mutated hCCR7 | D35E 20100122625 |

FIGURE 1T

| SEQ ID NO: | Sequence | Type | Organism | Name |
|---|---|---|---|---|
| 158 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACCACAGTGGACTACACTTTGTATGA GTCTTTGTGCTCCAAGAAGGACGTGCGGAACTTTAAAGCCTGGTTCCTCCCTATCATGTACTCCATCA TTTGTTTCGTGGGCCTACTGGGCAATGGGCTGGTCGTGTTGACCGTGCAGCTATATCTATTTCAAGAGGCTCAAG ACCATGACGGATACCTACGTGCTCAACCTGGCAGTCGCTGGGGTTCGGTGCCAAGTCCATCTTTGACATCTTTGCCATCT CTGGGCCTACAGCGCGGCCAAGTCCATGGCATGCTCCTACTCTCTTTGCATCAGCATTGACCGCTAGTGCCATC ACAAGATGAGCTCTTCAGCTCGTGTCTCACCGCCACCGTGCTCTCCATCCACCGCGTCTTCTAGCAGTGCTGTCCTGTGTGGG CATCTGGATACTAGCCACCAGTGCTCTCTCGGTCCCCCGCTGCGCCATGAGCTTCTGTTATCCTGTCATCATCCGC AGTGAGCAAGCGATGCGATGCTTTCTGCGCCAATGGGCAACAAGGCCATCAAGGTGATCATCGAGCTTCGTGTGGTCGTGG CCCTGCTCCAGCACGCAACTTTGAGCGCAACAGCATGGGGTGGTCTCGGCCATCGCCTACGACGTCACCTACAGCCTGGCC TCTTCATAGTCTTCCAGTGCCCTACAATGGGGTTCGCCCTTTGGCTCAGGCAGCAGGCTGCCTGTGGCAGGCCGTGGCC CACCAGTAGCACCTGTGAGCTCAGTCAGTAAGCAACTCAACATGCCTACGACGTCACCTACAGCCTGGCC TGCGTCCGCTGCCGTCAAGGACCTGGGCTGCCTCAGCCAGGCAGCTCCGGCAGTGCCGGCAGTGGTCTTCCTGTCGGCAC CAAGCTCTTCAAGGACCTGGGGCTGCCTCAGCCAGGCAGCTCCGGCAGTGCCGGCAGTGGTCTTCCTGTCGGCAC ATCCGGCGCTCCATGAGTGTGGAGGCCGAGACCACCACCACCTTCTCCCCATAG | DNA | Mutated hCCR7 | F44Y 20180128285 |
| 159 | MDLGKPMKSVLVVALLVIFQVCLCQDEVTEDDYIGDNTTVDYTLYESLCSKKDVRNFKAWFLPIMYSHCF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSEQAMRCSLI TEHVEAFITIQVAQMVIGFLVPLLAMSFCYLVIIRTLLQARNFERNKAIKVIHAVVVFIVFQLPYNGVVLA QTVANFNITSSTCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | F44Y 20180128285 |

FIGURE 1U

| SEQ ID NO. | Sequence | Type | Organism | Name |
|---|---|---|---|---|
| 160 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACCACAGTGGACTACACTTTGTTCGA GTCTGTGTGCTCCAAGAAGGACGTGCGGAACTTTAAAGCTTGGGCTTTCCTGCCTATCATGTACTCCATC ATTTGTTTCGTGGGCCTACCTACCGATACCTACCTGGCCAATGGCGCTGTCATGTCTGTTCGACCTATATCTATTTCAAGAGGCTCAA GACCAGAAGACCGATACCTACCTGGCCAATGGCGCTGTGCAACTGCAGATGGTCATTTTCCAGGTCCTGTGTCTGTGTCCCT TCTGGCCTACACAGCGCGCAAGTCCTGGGTCTTCAGTGGCATGCTGCTCACTGTTGCAAGTCATCTTTGCCATC TACAAGATGAGCTTCTTCAGTGGCATGCTCCTACTTCTTTGCATCAGCATTGACCGTCACTGTTGCTGGTGTTTG CGTCCAGGCTGTCTCAGTCTCACCGACCAGTGCTCTCCATCGCCAGAGTCCTGTACAGTCGACCTGTGGAAGGAGCAG CAGTGAGCAAGCGATGCGATTCTCTCATCACAGACATGTGGAGGCCTTTATCAACTGACCCATCCAGTG GCCCAGATGGTGATCGGCTTTCTGGTCCCCCTGCTGGCCAACTTTGAGCGCAACAAGGCCATCAAGGTGATCATCCAGTGGTCGTG CACCGCTCCAGGCACGCAACTTTGAGCGCAACAAGGCCATCAAGGTGATCATCGCTGGTCGTG GTCTTCATAGTCTTCCAGTGCCCTACAATGGGTGTTCCTGGCCCAGACGGTGGCAACTACAACA TCACCAGTAGCACCTGTGAGCTCAGTAAGCAACATGCTAAGCAACATGCTCAACATGCTCAGCCAGCGCCTCAACAATGGCCTTCTGTACGACGTCACTACAGCCTGGC CTGGTCCGCTGCTGCTGCGTCAACCTTTCTTGTACGCCTCATCGGCGTCAAGTTCCGCAACGATCTCT TCAAGGACCTCTTCAAGGACCTGGGCTGCCTCAGCCAGGAGCAGCTCCGGCAGTGGTCTTCCCTGCGGCA CATCCGGCGCTCTCCATGAGTGTGAGGCCGAGACCACCACTTCTCCCCATAG | DNA | Mutated hCCR7 | L47V 20100122626 |
| 161 | MDLGKPMKSVLVVALLVIFQVCLCQDEVTDDYIGDNTTVDYTLFESVCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSSEQAMRCSLI TEHYEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDIJGCLSQEQLRQWS SCRHIRRSSMSVEAETTTTFSP | PRT | Mutated hCCR7 | L47V 20100122626 |

FIGURE IV

| SEQ ID NO: | Sequence | Type | Organism | Name |
|---|---|---|---|---|
| 162 | ATGGACCTGGGAAACCAATGAAAAGCGTGCTGGTGGTGGCTCTCCTTGTCATTTCCAGGTATGCC TGTGTCAAGATGAGGTCACGGACGATTACATCGGAGACGAACAACCACAGTGGACTACACTTTGTTCGA GTCTTTGTGCTTCAAGAAGGACGTGCGGAACTTTAAAGCCTGGTTCCTCCCTATCATGTACTCCATCA TTTGTTTCGTGGGCCTACTGGGCAATGGGCTGTTGTTGACCTATGTATTTCAAGAGGCTCAAG ACCATGACCGATACCTACCTGCTCAACCTGGCGGTGCAGACATCCTCCTTCCTGACCCTTCCCTT CTGGGCCTACAGCGCGGCCAAGTCCTGGGTCTTCGGTGTCCACTTTGCAATGAGCATTGACTTTGCCATCT ACAAGATGAGCTTCTTCAGTGAGCAGATGCTCCGCTCCTACTTCTTTGCCAATGTCCCGCCCTACGTGGCCATC GTCCAGGCTGTCTCAGTCACCGCACAGTGCTCTCCATCCAGAGCTCCTTCCTGTACAGGGCCTTTATCCACAGTGG AGTGAGCAAGCAGATGCGATTGGCTTCTCGTCCCCATGGAGCCTTTATCACCATCCAGGTGG CCCAGATGGTGATCGGCTTCTCGTCCCCATGGAGCCTTCGTTACCTTGTCATCATCCGC CACCTGCTCCAGGCACGCAACTTTGAGCGCAACAAGGCCATCAAGGTGATCATCGCTGTGGTCGTGG TCTTCATAGTCTTCCAGTGCTCCACTACAATGGGTGGCGCCAGACGCTGCCCAACTTCAACAT CACCAGTAGCACCTGTGAGCTCAGTAAGCAACTCAACATCGCTACGACGTCACTCACGCCTGCC TGCGTCCGCTGCTGCGTCAAGAACCTGGCTGCCTCAGCCAGGAGCAGCTCCGGCAGTTCGCAACGATCTCTT CAAGCTCTTCAAGGACCTGGGCTGCCTGAGTGGAGCCGAGACCACCACCACCTTCTCCCCATAG | DNA | Mutated hCCR7 | S49F 20100122627 |
| 163 | MDLGKPMKSVLVVALLVIFQVCLCQDEVTDYIGDNTTVDYTLFESLCFFKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSSEQAMRCSLI TEHVEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | S49F 20100122627 |

FIGURE 1W

| SEQ ID NO. | Sequence | Type | Organism | Name |
|---|---|---|---|---|
| 164 | ATGGACCTGGGGAAACCAATGAAAAGCGTGCTGGTGGCTCTCCTTGTCATTTTCCAGGTATGCC TGTGTCAAGATGAGGTCACGGACGATTACATCGGAGACAACACCACAGTGGACTACACTTTGTTCGA GTCTTGTGTCTGCAAGAAGGACGTGCGGAACTTTAAAGCCTGGTTCCTCCCTATCATGTACTCCATCA TTTGTTTCGTGGGCCTACTACCTGCTCAATGGGCTGGTCGGTGTTGACCTATATCTATTTCAAGAGGCTCAAG ACCATGACCGATACCTACCTGCTCAACCTGCTGGCGTCTTCGGTCGCAGACATCTCTATCGACCGCTACGT CTGGGCCTACAGCGCGAGCCAAGCTCCGGCATGGCATGCGCCACCGCGTCCTACTCTTGCATCAGCATTGACCGCTACGTGGCCATC ACAAGATGAGTCTTCAGTGGCATGCCTCCTACTTCTTTGCATCAGCATTGACCGCTACGTGGCCATC GTCCAGGCTCTCTCAGCTACTAGCCACAGTGCTCTCTCCATCCAGAGCTCCTGTACAGTGGAGCCTTTATCACCATCCAGTGG CATCTGGATACTAGCCACAGTGCTCTCTCCATCCAGAGCTCCTGTACAGTGGAGCCTTTATCACCATCCAGTGG AGTGAGCAAGTGGTTGATGCGGCTTTCTGGTCCCCCTGCTGGCCATGAGCTTCTGTTACCTTGTCATCATCCGC CCAGATGGTGATCGGCTTTCTGGTCCCCCTGCTGGCCATGAGCTTCTGTTACCTTGTCATCATCCGC ACCCTGCTCCAGGCCACGCAACTTTGAGCGCAACAAGGCCATCAAGGTGATCATGCTGTGGTCGTGG TCTTCATAGTCTTCCAGCTGCCCTACAATGGGGTGGTCTCTGGCCCAGACGGTGCCAACTTCAACAT CACCAGTAGCACCACCTGTGAGCTCAGTAAGCAACTTTCTGTACGCCTTCATCGGCGTCAAGTTCCGGAACGACCTGTTCAAGGACCTGTTT TGCCTCCGCTGCGTCAACCCTTTCTTGTACGCCTTCATCGGCGTCAAGTTCCGGAACGACCTGTTT AAGGTCTTCAAGGACCTGGGCTGCCTCAGCCAGGAGCAGCTCCGGCAGTGGTCTTCCTGTCGGCAC ATCCGGCGCTCCTCCATGAGTGTGGAGGCCGAGACCACCACCTTCCTCCCCATAG | DNA | Mutated hCCR7 | A118E 20100130760 |
| 165 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSEAKSWVFGVHFCKLIFAIYKMSF FSGMLLLLCISIDRYVAQMVIGFLVPLLAMSFCYLVIIRTLLQARNFERNKAIKVIIAVVVFIVFQLPYNGVVLA TEHYEAFTIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHIRRSSMSVEAETTTFSP | PRT | Mutated hCCR7 | A118E 20100130760 |

FIGURE IX

| SEQ ID NO: | Sequence | Type | Organism | Name |
|---|---|---|---|---|
| 166 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACCACCAGTGGACTACACTTGTTCGA GTCTTTGTGCTCCAAGAGGACTGCGGAACTTTAAAGCCTGGTTCTCCCTATCATGTACTCCATCA TTTGTTCGTGGGCCTACTGGCCTACTGCTCAACCTGCGTGTCGTGTTGACCTATATCTATTTCAAGAGGCTCAAG ACCATGACCGATACCTACTTGCTCTCAACCTGCGGTGGCAGACATCCTCCTTGCAAGCTCATCTTTGCCATCT CTGGGCTACAGCGGCCAAGTCTGGATCTTCGGTGTCCACTTTTGCAAGCTCATCTTTGCCATCT ACAAGATGAGCTTCTTCAGTGACATGGCATGCTCCTACTTCTTGCATCAGCATTGACCGCTACGTGGCCATC GTCCAGGCTGTCTCAGCTACACCGCCACGTGCTCTCCATCCAGAGCTCCTCCATCCAGAGCTCTCTCAGAGCTATGGAGGCCTTTATCACCAGGAGGCAGC AGTGAGCAAGCGATGCGATGCTCTCTCAGTCCGTGGACGATGCTCTGCTCGTGCAACTTCGTGCACGCAACTTTGAGCGCAACAAGGCCATCAAGGTGACTCAGGTGACATCAAGGTGACATCAAGGTGACATCAAGGTGACTCTTGATCATCCGC CCCAGATGGTGATCGGCTTTCTGGTCCCGCTGCTGGCCATGAGCTTCTGTTACCTTGTCATCATCCGC ACCCTGCTCCAGGCACGCAACTTTGAGCGCAACAAGGCCATCAAGGTGATCATCGTGTGGTCGTGG TCTCATAGTCTTCCAGTGCCCTCACAATGGGGTGTCCTGGCCCAGACGGTGGCAACTTCAACAT CACCAGTAGCACCTGTGAGCTCAGTAAGCAACTCAACATGCTACGACGTCACTCACGTCTGGCC TGCGTCCGCTGCTGCGTCAAGCCCTTTCTTGTACGCCTCATCGGCGTCAAGTTCCGACAAGATCTCTT CAAGCTCTTCAAGGACCTGGGCTGCCTCAGCCAGGAGCTCCGGCAGTCCGGCAGTGGTCTTCCTGTGGGCAC ATCCGGCGCTCCTCCATGAGTGTGGAGGCCGAGACCACCACCACCTTCTCCCCATAG | DNA | Mutated hCCR7 | V1231 20100126473 |
| 167 | MDLGKPMKSVLVVALLVIFQVCLCQDEVTDDYIGDNTTVDYTLFESLCSKKDVRNFKAWFLPIMYSHCF VGLLGNGLVVLTYIYFKRLKTMTDTYLLNLAVADILFLLTLPFWAYSAAKSWIFGVHFCKLIFAIYKMSFF SGMLLLCISIDRYVAIVQAVSAHRHRARVLLISKLSCVGIWILATVLSIPELLYSDLQRSSSEQAMRCSLIT EHVEAFITIQVAQMVIGFLVPLLAMSFCYLVHRTLLQARNFERNKAIKVHAVVVFIVFQLPYNGVVLAQ TVANFNITSSTCELSKQLNIAYDVTYSLACVRCCVNPFLYAFIGVKFRNDLFKLFKDLGCLSQEQLRQWSS CRHIRRSSSMSVEAETTTTFSP | PRT | Mutated hCCR7 | V1231 20100126473 |

FIGURE 1Y

| SEQ ID NO: | Sequence | Type | Organism | Name |
|---|---|---|---|---|
| 168 | ATGGACCTGGGGAAACCAATGAAAAGCGTGCTGGTGGTGGCTCTCCTTGTCATTTCCAGGTATGCC TGTGTCAAGATGAGGTCACGGACGATTACATCGGAGACAACACCACAGTGGACTACACTTGTTCGA GTCTTTGTCTCCAAGAAGGACGTGCGGAATCCTGGTTCCTCCCCTATCATGTACTCCATCA TTTGTTCGTGGGCCTACTGGCAATGGCGTGGTCGTGTTGACCTATCTATTTCAAGAGGCTCAAG ACCATGACCGATACCTACCTGCTCAACCTGGCGGTGGCAGACATCCTCCTCCTGACCCTTCCCTT CTGGGCCTACAGCGCGGCCAAGTCCTGGGTCTTCGGTGTCTTCTGCATCAGCATTGACCGCTACGTGGCCATC ACAAGATGAGCTTCTTCAGTGGCATGCTCCTACTTCTTTGCCGCGTCCTTCATCAGCATGTCCTGTGGG CATCCAGGCTGTCTCAGTCACTAGCCACCAGTGCTCTCTCATCACAGAGAGCATGTGGAGGCCTTATCACCATCCAGTGG AGTGAGCAAGCGATGCGATGCTTTCTGTCTCCCGTGCTCCCATGGCCATGAGCTTCTGTTACCTTGTCATCATCGC CCCAGATGGTGATCGGCTTTCTGTCTCCCGTGCTCCCATGGCCATGAGCTTCTGTTACCTTGTCATCATCGC ACCTGCTCCAGGCACGCAACTTGAGCGCAACAAGGCCATCAAGGTGATCATCGCTGTGGTCGTGA TCTTCATAGTTCTTCCAGTGCCCTACAATGGGGTGGTCCTGGCCAGACGTGGCAACTTCAACAT CACCAGTAGCACCTGTGAGTCAGTAAGCAACTCAAACATCGCCTACGACGTCACTACAGCCTGGCC TGCGTCCGCTGCTGCGTCAACAGTGGCGTCAACAGTTCGCAACGATCTCTT CAAGCTCTTCAAGGACCTGGCTGCCTCAGCCAGGAGCCGAGAACCACCACCACCTTCTCCCCATAG | DNA | Mutated hCCR7 | H127Y 20:00135009 |
| 169 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVYFCKLIFAIYKMSF FSGMLLLLCISIDRYVAIVQAVSAHRHRARVLLISKLSCVGIWILATVLSIPELLYSDLQRSSEQAMRCSLI TEHVEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | H127Y 20:00135009 |

FIGURE 1Z

| SEQ ID NO. | Sequence | Type | Organism | Name |
|---|---|---|---|---|
| 170 | ATGGACCTGGGGAAACCAATGAAAAGCGTGCTGGTGGTGGCTCTCCTTGTCATTTCCAGGTATGCC TGTGTCAAGATGAGGTCACGACGATTACATCCGGAGACAACACAGTGGACTACACTTGTTCGA GTCTTTGTGCTCCAAGAAGACGTGCGAACTTTAAAGCCTGGTTCCTCCCATCATGTACTCCATCA TTTGTTTCGTGGCCTACTGGGCAATGGGCTGTGTCGGTTGACCTATCTTATTTCAAGAGGCTCAAG ACCATGACCGATACCTACCTGCTCAACCTGGCGGCAGACATCCTCTTCCTCTGACCCTTCCCTT CTGGGCCTACAGCGCGGCCAAGTCCTGGGTCTTCGGTGTCCACTTGTGTAAGCTCATCTTTGCCATCT ACAAGATGAGCTTTCAGTGGCATGCCTCCTACTTCTTTGCATCAGCATTGACCGCTACGTGGCCATC GTCCAGGCTGTCTCAGCCCACCGCCACGTGTCTCCAGAGCTCTCCATCCAGAGCATGTGGAGGCAGC AGTGAGCAAGCAATGCGATGCTCTCTCATCACAGAGCATGTGGAGGCCTTTATCACCATCCAGGTGG CCCAGATGGTGATCGGCTTTCTGGTCCCCCTGCTGGCCATGAGCTTCTGTTACCTTGTCATCATCCGC ACCCTGCTCCAGGCACGGAACTTTGAGCGCAACAAGGCCATCAAGGTGATCATCCTGTGGTCGTGG TCTTCATAGTCTTCCAGCTGCCCTACAATGGTGGTCTGCCTACAATATCCGCCAGAGACGGTGCCAACTTCAACAT CACCAGTAGCACCTGTGAGCTCAGTAAGCAACTCAACATCGCCTACGACGTCACTACAGCCTGGCC TGCCTCCGCTGCGTCAAGGACCTGTTCAAGCGCTTCTGTACGCCTCAGCCAGGAGCAGCTCCGGCAGTCCGGCAGTGGTCTTCCTGTCGGCAC AATCCGGCGCTCCTCCATGAGTTGTGAGGCCGAGACCACCACCACCTTCTCCCCATAG | DNA | Mutated hCCR7 | F128L 20100126472 |
| 171 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHLCKLIFAIYKMSF FSGMLLLLCISIDRYVAQMVIGFLVPLLAMSFCYLVIIRTLLQARNFERNKAIKVIIAVVVFIVFQLPYNGVVLA TEHVEAFITHQVAQMVIGFLVPLLAMSFCYLVIIRTLLQARNFERNKAIKVIIAVVVFIVFQLPYNGVLA QTVANFNITSSTCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | F128L 20100126472 |

FIGURE 1AA.

| SEQ ID NO: | Sequence | Type | Organism | Name |
|---|---|---|---|---|
| 172 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGAGACAACCACAGTGGACTACACTTTGTTCGA GTCTTTGTGCTCCAAGAAGGACGTGCCGAATCTTTAAAGCCTGGTTCCTCTGCCTATCATGTACTCCATCA TTTGTTTCGTGGGCCTACTGGGCCATGCGCTGCTCAACCTGCCATGGGGCTGCTCGTGTTGACCTATCATTCAAGAGGCTCAAG ACCATGACCGATACCTACCTGCTGAACCTCAACGTGGCGGTGGCAGACATCCTCTTCCTGACCCTTCCCTT CTGGGCCTACAGCGCGGCCAAGTCCTGGGTCTTCGGTGTCCACTTTTGCAAGCTCATCTTTGCCATCT ACAAGATGAGCTTCTTCAGTGGCATGCTCCTACTTCTTTGCATCAGCATTGACCGCTACGTGGCCATC GTCCAGGCTGTCCAGATGGTCGGCTTCCTGGTCCCGTATGGCTTATCACACAGCATGTGGAGGCTTTATCACGCCATCATCCGC CCCAGATGGTGGCTTCTGTCCCAGTGGGCCATGAGCTTCTGTTAGCCTTGATCTGGATATTGATTCAAGAGGAGCAGCC ACCCTGCTCCAGGCACGCAACTTTGAGGCGAACAAGGCCATCAAGGTGATCATCCGTGTGCTGTTCTTGCCAACT TCTTCATAGTCTTCCAGCTGCCCTACAATGGTGTTCTGGCCCAGACGGTGCCAACTTCAACAT CACCAGTAGCACCTGTGAGCTCAGTAAGCAACTCAACATCGCCTACGACGTGACTTACAGCCTGGCC TGCCTCCCGTGCGTCAAGCCTTTCTGTACGCCTTCATCGGCGTCAAGTTCCGCAACGATCTCTT CAAGCTCTTCAAGGACCTGGGCTGCCTCAGCCAGGAGCAGCTCCGGCAGTGGTCTTCCTGTCGGCAC ATCCGGCGCTCCTCAATGAGTGTGGAGGCCGAGACCACCACCTTCTCCCCATAG | DNA | Mutated hCCR7 | D198G 20110009482 |
| 173 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHIRRSSMSVEAETTTFSP | PRT | Mutated hCCR7 | D198G 20110009482 |

FIGURE 1AB

| SEQ ID NO: | Sequence | Type | Organism | Name |
|---|---|---|---|---|
| 174 | ATGGACCTGGGAAACCAATGAAAAGGCTGTGCTGGTGGCTCTCCTTGTCATTTCCAGGTATGCCTGTGTCAAGATGAGGTCACGGACGATTACATCGGAGACAACACCAGTGGACTACACTTTGTTCGAGTCTTTGCTCCAAGAAGGACGTGCCGGAACTTTAAAGCCTGGTTCCTCCCTATCATGTACTCCATCATTTGTTTCGTGGGCCTACTGGCAATGGCTGTGGTCGTGATTGACCTATATCTATTTCAAGAGGCTCAAGACCATGACCGATACCTACCTGCTCAACCTGCCGGTGGCAGACATCCTTCCTCTGACCCTTCCCTTCTGGGCCTACAGCGCGGCCAAGTCCTGGGTCTTCGGTGTCCACTTTGCAAGCTCATCTTTGCCATCTACAAGATGAGCTTCTTCAGTGGCATGCTCCTACTTCTTTGCATCAGCATTGACCGCTACGTGGCCATCGTCCAGGCTGTCTCAGCTCACCGCCACGGTGCCCGTCCTTCTCATCAGCAAGCTGTCTCTGTGTGGGCATCTGGATACTAGCCACAGTGCTCTCTCATCACAGAGCATGTGGAGGCCTTTATCACAGTCCAGGTGGAGTGAGCAAGCATGGCGATGCTCTCGTGGTCCATCCCCCTGCTGGCCATGAGCTTCTGTTACCTTGTCATCATCCGCACCCTGCTCCAGGCAGCAACTTTGAGCGCAACAAGGCCATCAAGGTGATCATCGCTGTGGTCGTGGTCTTCATAGTCTTCCAGTGCCCTACAATGGGTGGTCCTGGCCCAGACGGTGGTCCTCAACTTCAACATCACCAGTAGCACCTGTGAGCTCAGTAAGCAACTGAACATCGCCTTCATCGCGGTCAAGGTCACCGTCAAGATCTCTTGCCTCCGCTGCTGCGTCAACCCTTTCTTGTACGCCTCAGCGCCTGCCTCAGCCAGGAGCAGCTCCGGCAGCTCCATGAGTGTCCTGTCGGCACATCCGGCGGCTCCTCATGAGTGTGGAGGCCGAGACCACCACCACCTTCTCTCCCCATAG | DNA | Mutated hCCR7 | R201K 20100171268 |
| 175 | MDLGKPMKSVLVVALLVIFQVCLCQDEVTDDYIGDNTTVDYTLFESLCSKKDVRNFKAWFLPIMYSHCFVGLLGNGLVVLTYIYFKRLKTMTDTYLLNLAVADILFLLTLPFWAYSAAKSWVFGVHFCKLIFAIYKMSFSGMLLLLCISIDRYVAQMVIGFLVPLLAMSFCYLVIIRTLLQARNFERNKAIKVIIAVVVFHVFQLPYNGVVLAQTVANFNITSSTCELSKQLNIAYDVTYSLACVRCCVNPFLYAFIGVKFRNDLFKLFKDLGCLSQEQLRQWSSCRHIRRSSMSVEAETTTTFSP | PRT | Mutated hCCR7 | R201K 20100171268 |

FIGURE 1AC

| SEQ ID NO: | Sequence | Type | Organism | Name |
|---|---|---|---|---|
| 176 | ATGGACCTGGGGAAACCAATGAAAAGCGTGCTGGTGGTGGCTCTCCTTGTCATTTCCAGGTATGCC TGTGTCAAGATGAGGTCTCCAAGAAGGATGTTACGACGATTACATCGGAGACAACCACAGTGGACTACTTTGTCGA GTCTTTGTGTCGTGGGCCTACTGGGCAATGGGCGTGGTCGTGTTGACCTATCTATTTCAAGAGGCTCAAG TTTGTTCGTGTGGGCCTACTGGGCAATGGGCGTGGTCGTGTTGACCTATCTATTTCAAGAGGCTCAAG ACCATGACCGATACCTACCTGCTCAACCTGGCGGTTGGCAGACATCCTCCACTTTGCAAGCTCATCTTTGCCATCT CTGGGCCTACAGCGCGGCCAAGTCCTGGGCTTCGGTGTCCACTTTGCATCAGCATTGACCGCTACGTGGCCATC ACAAGATGAGCTTCTTCAGTGACATGCTCCTACTTCTTTGCATCAGCATTGACCGCTACGTGGCCATC GTCCAGGCTGTCTCAGCTCACCGCCACGTGCCCGGTGCCGGTCTTCTCCATCAGCAGTCCTGTACAGGCATGTGGG CATCTGGATACTAGCCACAGTGCTCTCTCATCACAGAGCATGTGGAGGCCTTTATCATCCAAGGTTG AGTGAGCAAGCAATGGATGCGATTCGGTTCTGCCATGAGCTTCTGTTACCTTGTCATCATCCGC CCCAGATGGTGATCGGCTTTCTGGTCCCGGCTTGAGCGCCCTCTGTTACCTTGTCATCATCCGC ACCCTGCTCCAGGCACGCAACTTTGAGCGCAACAAGGCCATCAAGTTGATCATCGCTGTGGTCGTGG TCTTCATAGTCTTCCAGCTGCCCTACAATGGGTGTCCTGGCCCAGACGGTGGCCAACTTCAACAT CACCAGTAGCACCTGTGAGCTCAGTAAGCAACTCAACATCCCTCAAACATCGCTTCATCGCCATCATCGCC TGGCTCCGCTGCTGCGTCAAACCCTTCTTGTACGCCTGTGTACGCCTGTCATCGGGTCAAGTTCCGCAACGATCTT CAAGCTCTCAAGAAGACCTGGGCTGCCAGCGCCAGGAGACCACCACCTTCTCCCATAG | DNA | Mutated hCCR7 | S202N 20110009483 |
| 177 | MDLGKPMKSVLVVALLVIFQVCLCQDEVTDDYIGDNTTVDYFVESLCSKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRNSSEQAMRCSLI TEHVEAFIT

FIGURE 1AD

| SEQ ID NO: | Sequence | Type | Organism | Name |
|---|---|---|---|---|
| 178 | ATGGACCTGGGAAACCAATGAAAAGCGTGCTGGTGGTGGCTCTCCTTGTCATTTCCAGGTATGCC TGTGTCAAGATGAGGTCACGACGATTACATCGGAGACAACACCAGTGGACTACACTTTGTTCGA GTCTTTGTGCTCCAAGAAGGACGTGCGGAACTTTAAAGCCTGGTTCCTCCCTATCATGTACTCCATCA TTTGTTTCGTGGGGCCTACTGGCAATGGGCTGTTGTGGTGTTGACCTATCTATTTCAAGAGGCTCAAG ACCATGACGATACCTACCTGCTCAACCTGGCCGTGGCAGACATCCTCTTCCTGACCCTTCCCTT CTGGGCCTACAGCGCGGCCAAGTCCTGGGTCTTCGGTGTCCATTTCTGCAAGCTCATCTTTGCCATCT ACAAGATGAGCTTCTTCAGTGGCATGCTCCTACTTCTTTGCATCAGCATTGACCGCTACGTGGCCATC GTCCAGGCTGTCTCAGCTACTAGCCACGGATGCGATGCTCTCTCATCACAGAGCATGTGGAGGCCTTT ATCAGTTGAGCAAGCAAGGTAGCAAATCACAAAGCCATATGTGGAGGCCTTATCACAGAGCAGGTGG CCCAGAGTGGTGATCGGCTTCTCGTCCCGCCATGAGCTTCTGTTACCTTGTCATCATCCGC ACCCTGCTCCAGGCACGCAACTTTGAGGCGCAACAAGGCATCAAGGTGATCATCGCTGTGGTCGTGG TCTTCATAGTTCTCCAGTGCTTCTACCTGCCCTACAATGGGTTGTCCTGGCCAGACGGGGCAACTTCAACAT CACCAGTAGCACCTGTGAGTCAGTAAGCAACCCTTTCTTGTACGCCTTCATCGGGGTCAAGTTCCGCAACGATCTCTT CAAGCTCTTCAAGGACCTGGCTGCCTCAGCCAGGAGCAGCTCCGGCACCACCACCTCTCCCATAG | DNA | Mutated hCCR7 | S204G 20100171269 |
| 179 | MDLGKPMKSVLVVALLVIFQVCLCQDEVTIDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSGEQAMRCSLI TEHVEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHRRSSMSVEAEFTTTFSP | PRT | Mutated hCCR7 | S204G 20100171269 |

FIGURE 1AE

| SEQ ID NO: | Sequence | Type | Organism | Name |
|---|---|---|---|---|
| 180 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACACAGTGGACTACACTTGTTCGA GTCCTTGTGCTCCAAGAAGGACGTGCGGAATGGAACTTTAAAGCCTGGTTCCTCCATCATGTACTCCATCA TTTGTTTCGTGGGCCTACTACCTGGGCAATGGGCTGGTCGTGCTGGTTGACCTATATCTATTTCAAGAGGCTCAAG ACCATGACCGATACCTACCTGCTCAACCTGGGCGGTGGCAGACATCTCTCTCCTGACCTCCCTT CTGGGCCTACAGCGCGGCAAGTCCTGGGGTCTTCGGTGTCCACTTTGCATCAGCATTGACCGCTGGCCATC ACAAGATGAGCTCTCTCAGTTCGATACTAGCCACAGTCGCTCCACCGTCCATCCAGAGCTCTGTATCCAGTCAGCCATCAGCATCAGCAGCAGCCATCACCATCCAGTGT GTCCAGGCTGTCTCAGTCAGCTAGCCAGCAGTCGAGTGCCATGTCTCTCTCATCACAGACGTGATGCTCTTCTGTGAGGCCTTTATCACCATCCAGTTGG AGTGAGGATGCGATGGATGCCCAGATTGATCGGCTTTCGGCTTCTGGCTGTCCCTCCAGCAACCTTGAGCGCAACAAGGCAACAGTGGATCATCGCTGTCATCCGC ACCCTGCTCCAGAGCTCTTCCAGTGCCCTACAATGGGTGTCCTGGCCCAGACGACGTCAACTACAAGCTGGCC TCCTTCATAGTCTTCCAGTGCCCTACAATGGGTGAGCTCAGTAAGCAACTCAACATCCAACAGTCCAAGTTCCGCAACGATCTCTT TGCCTCCGCCAAGGTCATCCTGGCCGTCAACCCTTTCTTGTACCGTTTGCATCCAGCCTCATCGCCGGAGCAGCTCCCGGCCAGTGGCCTCGTCCCGGCAC CAAGCTCTCAAGGACCTGGCCTGCTCAGCCAGGAGCAGCTGAGCCAGCTCCGGCAGTGGTCTTCCTGTCGGCAC ATCCGGCGCTCCTCCATGAGTGTGGAGGCCGAGACCACCACCACCTTCTCCCATAG | DNA | Mutated hCCR7 | Q206D 20110009484 |
| 181 | MDLGKPMKSVLVVALLVIFQVCLCQDEVTDDYIGDNFTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAMVIGFLVPLLAMSFCYLVIRTLLQARNFERNKAIKVILAVVVFIVFQLPYNGVVLA QTVANFNITSSTCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | Q206D 20110009484 |

FIGURE 1AF

| SEQ ID NO. | Sequence | Type | Organism | Name |
|---|---|---|---|---|
| 182 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACAGTGGACTACTTGTTCGA GTCTTTGTGTCCAAGAAGGACGTGCGCAATGGCGGAACTTTAAAGCTGCCTATCATGTACTCCATCA TTTGTTTCGTGGGCCTACTGGGCAATGGCCTGCTCAACCTGGTCGCGTGTTGACCTACTATTTCAAGAGGCTCAAG ACCATGACCGATACCTACCTGCTCAACCTGGCGGTGGCAGACATCCTCTTCCTCTGACCCTTCCCTT CTGGGCCTACAGCGCGGCCAAGTCCTGGGTCTTCGGTGTCCACTTTTGCAAGTCATCTTTGCCATCT ACAAGATGAGCTTCTTCAGTGGCATGCTCCTACTTCTTTGCATCAGCATTGACCGCTACGTGGCCATC GTCCAGGCTGTCTCAGCTCACCGCCACCGTGCCCAGTCCTTCTTCATCAGCAGTGACCTTTATCACCAT CATCTGGATACTAGCCACCAGTGCGATGTCTCTCCATCCCAGAGCTCTGTGGAGGCATGTTGGAGGCCTTTATCACCATCCAGTGG AGTGAGCAAACGATGCTTCGGTTGATCGGTTTCTGTCCCATGAGCTTCTTTATCAGTTTACTTGTCATCCGC CCCAGATGGTTGATCGGTTTTCTGTCCATGAGCTTCTGTTACTTGTCATCCGC ACCTGCTCCAGGCACGCAACTTTGAGGCGAACAAGGCCATCAAGGTGATCATCGCTGTGGTCGTGG TCTTCATAGTCTTCCAGCTGCCCTACAATGGGGTCGTCCTGGCCCAGACGGTGGCCAACTTCAACAT CACCAGTAGCACCTGTGAGCTCAGTAAGCAACTCAACATCGCCTACGACGTCACCTACAGCCTGGCC TGCGTCCGCTGCGTCAATCCCTTTCTGTACGCCTTCATCGGGGTCAAGTTCCGCAACGATCTCTT CAAGCTCTTCAAGGACCTGGGCTGCCTCAGCCAGGAGCAGCTCCGGCAGTGGTCTTCCTGTCGGCAC ATCCGGCGCTCCTCCATGAGTGTGGAGGCCGAGACCACCACCACCTTCTCCCCATAG | DNA | Mutated hCCR7 | A207T 20100171270 |
| 183 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAQMVIGFLVPLLAMSFCYLVIIRTLLQARNFERNKAIKVIIAVVVVFIVFQLPYNGVVLAQ EHVEAFITIQVAQMVIGFLVPLLAMSFCYLVIIRTLLQARNFERNKAIKVIIAVVVVFIVFQLPYNGVVLAQ TVANFNITSSTCELSKQLNIAYDVTYSLACVRCCVNPFLYAFIGVKFRNDLFKLFKDLGCLSQEQLRQWSS CRHIRRSSMSVEAEFTTTFSP | PRT | Mutated hCCR7 | A207T 20100171270 |

FIGURE 1AG

| SEQ ID NO: | Sequence | Type | Organism | Name |
|---|---|---|---|---|
| 184 | ATGGACCTGGGGAAACCAATGAAAAGCGTGCTGGTGGTGGCTCTCCTTGTCATTTCCAGGTATGCC TGTGTCAAGATGAGGTCACGACGATTACATCGAGACAACAACCAGTGGACTACACTTGTTCGA GTCTTTGTGCTCCAAGAGGACGTGCGGAACTTTAAAGCCTGGTTCCTCCCTATCATGTACTCCATCA TTTGTTTCGTGGGCCTACTGGGCAATGGGCTGCTGGTCACCTATATCTATTTCAAGAGGCTCAAG ACCATGACCGATACCTACCTGCTCAACCTGCGGTGGCAGATCATCCTCTTCCTCTGACCCTTCCCTT CTGGCCTACAGCGGGCCAAGTCCTGGCATGCTCCTACTTCTTGCATGTCTCACTTTTGCAAGCTCATCTTTGCCATCT ACAAGATGAGCTTCTTCAGTGGCATGCTCCTACTTCTTGCATCAGCATTGACCGCTACGTGGCCAT GTCCAGGCTGCTCAGCTACTAGCCACGTCACCGCCAGCTCTCCATCCAGAGCTCTCATCAGCCAAGCTGTCCTGTGGG CATCTGGATACTAGCCACACGTTGCGATGCTCTCTCATCACAGAGACATGTGGAGGCTTTATCACCATCCAGGTGG AGTGAGCAAGCGTTGCGATGCGGCTTTCGTGCCCCCATGGCCATGAGCTTCTGTTACCTTGTCATCATCCGC CCCAGATGGTGATCGGCTTTCGTGCCCAATGGCCATGAGCTTCTGTTACCTTGTCATCATCCGC ACCCTGCTCCAGGCACGCAACTTTGAGCGCAACAAGGCCATCAAGGTACATCAAGGTGATCATCGCTGTGGTCGTGG TCTCATAGTCTTCCAGTGCCCTACAATGGGGTGTCCTGGCCAGACGGTGGCAACTTCAACAT CACCAGTAGCACCTGTGAGCTCAGTAAGCAACTCAACATGCTCAACATGCTCAACGGCTCACTCAGCCTGGCC TGCGTCCGCTGCTGCGTCAACCTGTTCTTGTACGCCTTCATCGGGTCAAGTTCCGCAACGATCTCTT CAAGCTCTTCAAGGACCTGGGCTGCCTCAGCCAGGAGCAGCTCCGGCAGTGGTCTTCCTGTGGCAC ATCCGGCGCTCCTCCATGAGTGTGAGGCCGAGACCACCACCACCTTCTCCCCATAG | DNA | Mutated hCCR7 | M208L 20100171271 |
| 185 | MDLGKPMKSVLVVALLVIFQVCLCQDEVTDDYIGDNTTVDYTLFESLCSKKDVRNFKAWFLPIMYSHCF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSSEQALRCSLIT EHVEAFITIQVAQMVIGFLVPLLAMSFCYLVIIRTLLQARNFERNKAIKVIIAVVVFIVFQLPYNGVVLAQ TVANFNITSSTCELSKQLNIAYDVTYSLACVRCCVNPFLYAFIGVKFRNDLFKLFKDLGCLSQEQLRQWSS CRHIRRSSSMSVEAETTTTFSP | PRT | Mutated hCCR7 | M208L 20100171271 |

FIGURE 1AH

| SEQ ID NO. | Sequence | Type | Organism | Name |
|---|---|---|---|---|
| 186 | ATGGACCTGGGGAAACCAATGAAAAGCGTGCTGGTGGTGGCTCTCCTTGTCATTTCCAGGTATGCCTGTGTCAAGATGAGGTCACGACGGATTACATCGGAGACGAACACCAGTGGACTACACTTGTTCGAGTCTTTGTGCTCCAAGAAGACGTGCGGAACTTTAAAGCCTGGTTCCTCCCTATCATGTACTCCATCATTTGTTTCGTGGCCTACTGGCCTGGGCAATGGGCTGGTTCGTGTTGACCTATCTATTTCAAGAGGCTCAAGACCATGACCGATACCTGCTCAACCTGGCAGGTGGCAGACACTCCTTCCTCCTGACCCTTCCCTTCTGGGCCTACAGCGCGGCCAAGTCCTGGGTCTTCGGTGTCCACTTTTGCAAGCTCATCTTTGCCATCTACAAGATGAGCTTTCAGTGGCATGCTCCACCGTCACCGCACCGTGCCCGGTCCTTCTCATCAGCAAGCTGTCCTGTGTGGCATCGTCCAGGCTGTCTCAGTTCACCAGCCACAGTGCTCTCTCGTACCCAGAGCTCTGTACCAGTGACCTGCAGAGGAGCAGCAGTGAGCAAGCAATGCGATGCTTCTGTGTCCCCCTGTGGCCATGAGCCTTTATCACCATCCAGTTGGCCCAGATGGTGATCGGCTTTCGGTCCTGCCGCAACAAGGCCATCAAGGTGATCATCGTGTGGTCGTGGACCCTGCTCCAGGCACCGAACTTTGAGCGCAACGTGCCCAGTCCCCTACAATGGGTCGGTCCTGGCCCAGAAACGCCTGTCCTGTGTCAACATCACAGCTGCCTCTCAATAGTCTTCCAGTGTGAGCTGCGTCAAGCTGAAGCAACTCAACATCGCCTACGACGTCACCTACAGCCTGGCCGTGCCGTCGAGCGACCCTTCTGTACGCTCAGCCAGGAGCCTCCGGCAGTCCGGCAGTGGTCTCCCTGTCGGCACCAAGCTCTTCAAGGACCTCCTCAGCCAGGAGCCGAGACCACCACCACCTCTCCCCATAG | DNA | Mutated hCCR7 | I213V 20100168569 |
| 187 | MDLGKPMKSVLVVALLVIFQVCLCQDEVTDDYIGDNTTVDYTLFESLCSKKDVRNFKAWFLPIMYSIICFVGLLGNGLVVLTYIYFKRLKTMTDTYLLNLAVADILFLLTLPFWAYSAAKSWVFGVHFCKLIFAIYKMSFSGMLLLCISIDRYVAQMVIGFLVPLLAMSFCYLVIIRTLLQARNFERNKAIKVIIAVVVFIVFQLPYNGVVLATEHVEAFITHQVAQMVIGFLVPLLAMSFCYLVIIRTLLQARNFERNKAIKVIIAVVVFIVFQLPYNGVLAQTVANFNITSSTCELSKQLNIAYDVTYSLACVRCCVNPFLYAFIGVKFRNDLFKLFKDLGCLSQEQLRQWSSCRHIRRSSMSVEAETTTTFSP | PRT | Mutated hCCR7 | I213V 20100168569 |

FIGURE 1AI

| SEQ ID NO. | Sequence | Type | Organism | Name |
|---|---|---|---|---|
| 188 | ATGGACCTGGGCAAACCAATGAAAAGCGTGCTGGTGGTGGCTCTCCTGTCATTTTCCAGGTATGCC TGTGTCAAGATGAGGTCACGACGGATTACATCGGAGACGAACAACAGCTGGACTACACTTGTTCGA GTCTTTGTGCTCCAAGAAGACGTGCGGAACTTTAAAGCCTGGTTCCTCCCTATCATGTACTCCATCA TTTGTTTCGTGGCCTACTGGCTGTTCGGCGTCAATGGGCTGGTGTTGACCTATCTATTTCAAGAGGTCAAG ACCATGACCGATACGTACCTGCTCAACCTGGCGGTCGCAGACATCCTCTTCCTCCTGACCCTTCCCTT CTGGGCCTACAGCGCGGCCAAGTCCTGGGTCTTCGGTGTCCACTTTTGCAAGCTCATCTTTGCCATCT ACAAGATGAGCTTCTTCAGTGGCATGCTCCTACTTCTTTGCATCAGCATTGACCGCTACGTGGCCATC GTCCAGGCTGTCTCAGCTCACCGCCACGTGCTCTCCATCCCGGTCCTTCTCATCAGCAAGCTGTCCTGTGG CATCTGGATACTAGCCACAGTGCTCTCTCTATCCAGAGTCTCGTACAGTGGAGGCCTTTATCACCATCCGC AGTGAGCAAGGATGCGATGCTTCTGGTCCCCGACTTTGAGCACGAACAAGGCCATCAAGGTGATCATCGTGGTCGTGG CCCAGATGGTGATCGGCTTTCTGGTCCCCCTGCTGGCCATGAGCTTCTGTTACCTTGTCATCATCCGC ACCCTGCTCCAGGCACGGAACTTTGAGCGCAACAAGGCCATCAAGGTGATCATCGTGGTCGTGG TCTTCATAGTCTTCCAGCTGCCCTACAATGGGGTCGTCCTGGCCCAGATGCGGTGCTCACTCACGAGCCTGGCC ACCAGTAGCACCTGTGAGCTCAGTAAGCAACTCAACATCGCCTACGACGTCACTGTCAGCCTGGCC TGCCTCCGCTGCCTGTCCCAAGGACCCTGCGCTCAGCCAGGAGGCCACCACCACCTTCTCCCCCATAG CAAGCTCTCAAGGACCTGGGCTGCCTCAGCCAGGAGGCCACCACCACCTTCTCCCCCATAG | DNA | Mutated hCCR7 | T2143 20100168568 |
| 189 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAQMVIGFLVPLLAMSFCYLVIIRTLQARNFERNKAIKVIIAVVVPFIVFQLPYNGVVLAQ MVIGFLVPLLAMSFCYLVIIRTLQARNFERNKAIKVIIAVVVPFIVFQLPYNGVVLAQ SEHVEAFITIQVAQMVIGFLVPLLAMSFCYLVIIRTLQARNFERNKAIKVIIAVVVPFIVFQLPYNGVVLAQ TVANFNITSSTCELSKQLNIAYDVTYSLACVRCCVNPFLYAFIGVKFRNDLFKLFKDLGCLSQEQLRQWSS CRHIRRSSMSVEAETTTTFSP | PRT | Mutated hCCR7 | T2143 20100168568 |

FIGURE 1AJ

| SEQ ID NO: | Sequence | Type | Organism | Name |
|---|---|---|---|---|
| 190 | ATGGACCTGGGGAAACCAATGAAAAGCGTGCTGGTGGCTCTCCTTGTCATTTTCCAGGTATGCC TGTGTCAAGATGAGGTCACGGACGATTACATCGGAGACAACACCAGTGGACTACACTTTGTTGA GTCTTGTGCTCAAGAAGGACGTGCGGAACTTTAAAGCCTGGTTCTCCATCATGTACTCCATCA TTTGTTTCGTGGGCCTACTACCTGCTCAACCTGGTCGTTGACCTATATCATTCAAGAGGCTCAAG ACCATGACCGATACCTACCAGCGCGGCCAAGTCCTGCGGTCTTCGGTCTTGCAAGTCATCTTGCCATCT CTGGGCCTACAGCGCGGCCAAGTCCTGCGGTCTTCGGTCTTGCATCAGCATTGACCGCTACGCATCTGGCCATC ACAAGATGAGCTCTTCAGTGCATGCTGCTCTACTTCTTTGCATCAGCATTGACCGCTACGGCCATC GTCCAGGCTGTCTCAGCTAGCCACAGTGCTCTCCATCCAGAGCTCCATCACACGCATGGAGGCTCCAGTCTGGG CATCTGGATACTACTGGCAAGCGATGCTCTCTCACACGCATGGAGGCTCCAGTCCATCCAGTCG CCCAGATGGTGATCGGCTTTCTGGTCCCCCTGCTGGCCATGAGCTTCTGTTACTTGTCATCATCCGC ACCCTGCCCAGGCACGCAACTTGGAGCGAACAAGGCATCAAGGTGATCATGCGTCGTGTGTGG TCTTCATAGTCTTCCAGCTGCCCTACAATGGGTGTCTGGCCCAGACGGTTGGCCAACTTCAACAT CACCAGTACGCACCTGTGAGCTCAGTAAGCAACTCAAACATGCCTACGAGTCACTCACAAGCCTGCC TGCCTCCGTCGCTCAAGGACCTGGCTGCCTCAGCCAGGAGCAGCTCGGCAGTGGTCTTCCTGTCGGCAC ATCCGGCGCTCCTCCATGAGTGTGGAGGCCGAGACCACCACCTTCTCCCCATAG | DNA | Mutated hCCR7 | E215A 20100168567 |
| 191 | MDLGKPMKSVLVVLALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF TAHVEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLYAFIGVKFRNDLFKLFKDLGCLSQEQLRQWS SCRHIRRSSMSVEAETTTFSP | PRT | Mutated hCCR7 | E215A 20100168567 |

FIGURE 1AK

| SEQ ID NO: | Sequence | Type | Organism | Name |
|---|---|---|---|---|
| 192 | ATGGACCTGGGGAAACCAATGAAAAGCGTGCTGGTGGTGGCTCTCCTTGTCATTTCCAGGTATGCC TGTGTCAAGATGAGGTCTCCAAGAGGTCACGGACGATTACATGGAGACAACACCACAGTGGACTACACTTGTTCGA GTCTTTGTGTGTGGGCCTACTGGGACAATGGGCTGCTGTGTTGACCTATGTTCAAGAGGCTCAAG TTTGTTCGTGTGCGATACCTACCTGCTCAACCTGGCGGTTGGCAGACATCCTCCTCTGACCCTTCCTT CTGGGCCTACAGCGCGGCAAGTCCTGGGCTTCGGTGTCCACTCTTTGCAAGCTCATCTTTGCCATCT ACAAGATGAGCTTCTTCAGTGCATGCTCCTACTTCTTTGCATCAGCATTGACCAAGCTGTCCTGTGGG CATCTGGATACTAGCCACAGTGCTCTCCATCCAGAGCTCCGTACAGTGACCTGACCATCCAGGAGCAGC AGTGAGCAAGCGATGCGGCTTCTGTCCTCCAGCAGGTGGAGGCCTTTATCGAAGCTTCTGTTACCTTGTCATCATCCGC CCCAGATGGTGATCGGCTTCTGTCCCAGCAGGTGGCCATGAGCTTCTGTTACCTTGTCATCATCCGC ACCCTGCTCCAGGCAGCGAACTTTGAGCGCAACAAGGCCATCAAGGTGATCATCGCTGTGGTCGTGG TCTTCATAGTCTTCCAGCTGCCCTACAATGGGGTTCTGCCCAGACGAGCAACTTCAACAT CACCAGTAGCACCTGTGAGCTCAGTAAGCAACTCAACATCGCCTACGACGTCACTACAGCCTGCC TGCCTCCGCTGCTGCGTCAAGACCTTCTTGTACGCCTTCATCGGCGTCAAGTTCCGCAACGATCTCTT CAAGCTCTTCAAGGAACCTGGGCTGCCTCAGCCAGGAGCCGAGACCACCACCTTCTCTCCCCATAG | DNA | Mutated hCCR7 | H2:i6Q 20110009485 |
| 193 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLLCISIDRYVAIVQAVSAHRHRARVLLISKLSCVGIWILATVLSIPELLYSDLQRSSSEQAMRCSLI TEQVEAFITIQVAQMVIGFLVPLLAMSFCYLVIIRTLLQARNFERNKAIKVIIAVVVFIVFQLPYNGVVLA QTVANFNITSSTCELSKQLNIAYDVTYSLACVRCCVNPFLFKLFKDLGCLSQEQLRQWS SCRHRRSSMSVEAETTTFTSP | PRT | Mutated hCCR7 | H2:i6Q 20110009485 |

FIGURE 1AL

| SEQ ID NO. | Sequence | Type | Organism | Name |
|---|---|---|---|---|
| 194 | ATGGACCTGGGGAAACCAATGAAAAGCGTGCTGGTGGTGGCTCTCCTTGTCATTTTCCAGGTATGCCTGTGTCAAGATGAGGTCACGGACGATTACATCGGAGACAACACCACAGTGGACTACACTTTGTTCGAGTCTTGTGTCGTGCTGTGTAAGAAGGACGTGCGGAATGGCTGCGGAACTTTAAAGCCTGTTCCTCCCTATCATGTACTCCATCATTGTTTCGTGGGCCTACTACCAGGCGATACCTACCTGCTCAACCTGGCTGTGGCGGATATCCTCTTTCTTCTGACCCTTCCTTACCATGACCGATACAGCGCGGCCAAGTCTGGCTTCTGGCGTGTCGCAGAACATCCTCTTCCTGACCATTGCCATCTCTGGGCCTACAGCGCGGCCAAGTCTTCAGTGGCATGCTCCTACTTGTTTGCATCAGCATTGACCGCTACGTGGCCATCACAAGATGAGCTTCTTCAGTCACCTACCAGTCTTCTTTGCATCAGCATTGACCGCTACGTGGCCATCGTCCAGGCTGTCCAGATGCAGGTTATCTTCCAGGTCCTGTGCCAGGATGAAGTCACAGATGATTACATTGGCGATAACACTTATCTCTATCTCTTCCATCACAGACCTGATACATTTAGACACTGATACAGTTATTCTGTATCTATCTCAGATGACATATGAGCAAGCGATGCGATGCTTTCTGGTCCCGTGCTTCTACCTGCTGCAAGAGAACATCCTCTTGCAAGCAAATGGCCATCAAGGCCATCAAGGTGATCATCGCTGTTGGTCGTGGACCCCAGAGTCTTCCAGCTGCCTACAATGGGTGTGTCCTGGCCAGACACCCTACGAGGTCACTCAAGCCTGGCCTGCTCCGCTGCGTCAAGGACCTGGCTGCTCAGCCAGGAGCTGCGCCAGGACCACCACCTTCTCCTGTCGGCACAAGCTCTTCAAGGACCTGGCTGCTCAGCCAGGAGACCACCACCTTCTCCCCATAG | DNA | Mutated hCCR7 | S295N 20110018205 |
| 195 | MDLGKPMKSVLVVALLVIFQVCLCQDEVTDDYIGDNTTVDYTLFESLCSKKDVRNFKAWFLPIMYSIICFVGLLGNGLVVLTYIYFKRLKTMTDTYLLNLAVADILFLLTLPFWAYSAAKSWVFGVHFCKLIFAIYKMSFTEHYEAFITIQVAQMVIGFLVPLLAMSFCYLVIIRTLLQARNFERNKAIKVIIAVVVVFIVFQLPYNGVVLAQTVANFNITNSTCELSKQLNIAVDVTYSLACVRCCVNPFLYAFIGVKFRNDLFKLFKDLGCLSQEQLRQWSSCRHIRRSSMSVEAETTTTFSP | PRT | Mutated hCCR7 | S295N 20110018205 |

FIGURE 1AM

| SEQ ID NO: | Sequence | Type | Organism | Name |
|---|---|---|---|---|
| 196 | ATGGACCTGGGGAAACCAATGAAAAGCGTGCTGGTGGTGGCTCTCCTTGTCATTTTCCAGGTATGCC TGTGTCAAGATGAGGTCACGGACGATTACATCGGAGACAACACCACAGTGGACTACACTTGTGTCGA GTCTTTGTGTCCAAGAAGGACGTGCGGAACTTTAAAGCCTGGTTCCTCCTATCATGTACTCCATCA TTTGTTTCGTGTGGGCCTACTACCGCTCAACCTGGCTGTCTGGTCGTGTGCAGACATCCTCTTCCTGAGGCTCAAG ACCATGACCGATACCTACCTGCTCAACCTGGCTGCCGTCGCAGACATCCTCTTCCTGCTCACCCTTCCCTT CTGGGCCTACAGCGCGGCAAGTCCTCAGTGGCATGCCTGCTCTGCAAGTCTTTGCACTCTTGCATCAGCAAC ACAAGATGAGCTTCTCAGTGGCACGTCCGCCACGGTGCCCGCGTCCTTCTCATCAGCAGTCCTGTGTGGG CATCTGGATACTAGCCACCACAGTGCTCTCCATCCAGAGCTCCGTACAGTGACCTCCAGAGGAGCAGC AGTGAGCAAGCGATGCAGTCTCTCCTCATCACAGAGCATGTGAGGCCTTTATCACCATCCAGGTGG CCCAGATGGTGATCGGCTTTGGCTCCGTGCTGGCCATGGCCATCTGTTACTTGTCATCATCCGC ACCCTCTCCAGGCACGCAACTTTGAGCGCAACAAGGCCAATCAAGGTGATCATCGCTGTGGTCGTGG TCTTCATAGTCTTCCAGTCGCCCTACAAATGGGGTGTCCTGGCCCAGAGACGGTGGCCAACTTCAACAT CACCAGTAGCAGCTGTGAGCTCAGTAAGCAACTCAACATCGCCTACGACGTCACCTACAGCCTGGCC TGGGTCCGCTGCTGCGTCAACCCTTTCTTGTACGCCTTCATCGGGGTCAAGTTCCGCAACGATCTT CAAGCTCTTCAAGGACCTGGGCTGCCTCAGCCAGGAGCAGCTCCGGCAGGTGTTCCTGTCGGCAC ATCCGGGCGTCCTCCATGAGTGTGGAGGCCGAGACCACCACCACCTTCTCCCCATAG | DNA | Mutated hCCR7 | T2975 20:100:8203 |
| 197 | MDLGKPMKSVLVVALLVIFQVCLCQDEVTDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF TEHVEAFITIQVAQMVIGFLVPLLAMSFCYLVPLLQARNFERNKAIKVIIAVVVFIVFQLPYNGVVLA QTVANFNITSSSCELSKQLNIAYDVTYSLACVRCCVNPFLYAFIGVKFRNDLFKLFKDLGCLSQEQLRQWS SCRHRRSSMSVEAETTTTFSP | PRT | Mutated hCCR7 | T2975 20:100:8203 |

FIGURE 1AN

| SEQ ID NO. | Sequence | Type | Organism | Name |
|---|---|---|---|---|
| 198 | ATGGACCTGGGCAAACCAATGAAAAGCGTGCTGGTGGTGGCTCTCCTTGTCATTTTCCAGGTATGCC TGTGTCAAGATGAGGTCACGGACGATTACATCGGAGACAACACCAGTGGACTACACTTGTTCGA GTCTTTGTGCTCCAAGAAGACGTGCGGAACTTTAAAGCCTGGTTCCTCCCATCATGTACTCCATCA TTTGTTTCGTGGCCTACTGGGCAATGGGCTGGTCGTTTGACCTATATCTATTTCAAGAGGCTCAAG ACCATGACCGATACCTACCTGCTCAACCTGGCGGTCGCAGACATCCTCTTCCTCCTGACCCTCCTT CTGGCCTACAGCGGCGCCAAGTCCTGGGTCTTCGGTGTCCACTTTGCAAGTCATCTTTGCCATCT ACAAGATGAGCTTCTCAGTTGGCATGCTCCTACTCTTTGCATCAGCATTGACCGCTACGTGGCCATC GTCCAGGCTGTCTCAGCTCACCGCCACAGTGCTCTCCATCCCGAGCTCCTCCATCAGCAAGTGCTCCTGTGG CATCTGGATACTACGCCAAGCATGCGATGCTTCTCTCATCACAGAGCATGTGAGGCCTTTATCACCATCCAGGTGG AGTGAGCAAGCAATGCGGCTTTCTGGTCCCCCTGCTGGCCATGAGCTTCTGTTACCTTGTCATCATCCGC ACCCTGCTCCAGGCACGCAACTTTGAGCGCAACAAGGCCATCAAGGTGATCATCCTGTGGTCGTGG TCTTCATAGTTCTTCCAGTGCCCTACAATGGGTGGTCGCCAGACGGTGCAACTTCAACAT ACCAGTAGCACCTGTGAGACCAGTAAGCAACTCAACATGCCTACGAGCTCACCTGCAGCCTGCC TGCGTCCGCTGCGTCAAGGACCTGGCTGCCTCAGCCAGGAGCCGCCACCACCTTCTCCCCATAG | DNA | Mutated hCCR7 | L300T 20110018204 |
| 199 | MDLGKPMKSVLVVALLVIFQVCLCQDEVTDDYIGDNTTVDYTLFESLCSKKDVRNFKAWFLPIMYSIICF VGLLGNGLVVLTYIYFKRLKTMTDTYLLNLAVADILFLLTLPFWAYSAAKSWVFGVHFCKLIFAIYKMSF FSGMLLLCISIDRYVAQMVGFLVPLLAMSFCYLVIIRTLLQARNFERNKAIKVIIAVVVFIVFQLPYNGVVLA QTVANFNITSSTCEFSKQLNIAYDVTYSLACVRCCVNPFLYAFIGVKFRNDLFKLFKDLGCLSQEQLRQWS SCRHIRRSSMSVEAETTTTFSP | PRT | Mutated hCCR7 | L300T 20110018204 |

FIGURE 1AO

| SEQ ID NO: | Sequence | Type | Organism | Name |
|---|---|---|---|---|
| 200 | ATGGACCCAGGGAAACCAGGAAAAAACGTGTGGTGGCTCTCCTTGTCATTTCCAGGTGTGCT TCTGCCAAGATGAGTGCTTCACGGATGACTACATCGGCGAGAATACCACGTGGACTACACCTGTACG AGTGCGGTGTGCTTCAAGAAGGATGTGCGGAACTTAAGGCCTGGTTCCTGCCTCTCATGTATTCTGTC ATCTGCTTCGTGGGCCTGCTCGGCAACGGCCTGGTGATACTGACGTACATCTATTTCAAGAGGCTCA AGACCATGACGGATACTGAGCGGATACCTCAACCTGGCCGTGGCAGACATCCTTTTCCTCCTAATTCTCC TTCTGGGCCTACAGCGAAGCCAAGTTCTTCAGCGGGATGCTGCTCCTATGCATCAGCATTGACCGCTACGTAGCC TCTATAAGTTAAGCTTCTTCAGGCCGTGTCGGTCACACGCCAACGCGTGTCCTGTGT GGGCATCTGGATGCTGCCCTTCCCTCACTCCGAGCGTGCTCTACAAGGCCTCAAGAACC AGCGGCGAGGACACGCTGAGATGCTCCTAGTGCCAAGTGGAGGCCTTGATCACCATCCAA GTGGCCCAGATGTTTTGGGTTCCAGTCCTATGCGTGGCTATGAGTTCTGCTACCTCATTATCAT CCGTACCTTGCTCCAGGCACGCAACTTGAGCGAACAAGGCCATCAAGGTGATCATTGCCGTGGTG GTAGTCTTCATAGTCTCCGCTGCTGCGTCAACTGGGCGTCCAGCTCAACATTGCTATGACGTCACCTACAGCCT ACATCACCAATAGCAGCTGCGAAACCAGCAAGCAGCTCAACAATTGCTATGACGTCACCTACAGCCT GGCCTCCGTCCGCTGCTGCGTCAACTGGGCGTCCAGCAGCGAACGGCTCCGGCACTGGTCTTCCTGCCG TCTTCAAGCTCTTCAAAGGACTTGGCGTCCAGCCAGGAACGGCTCCGGCACTGGTCTTCCTGCCG GCATGTACCGGAAGCGTCGGTGAGCATGGAGGCGGAGACAATGAGGCAGACCTTCTCCCGTAG | DNA | Murine CCR7 | pcDNA3.1 Neo-mouseCCR7 |
| 201 | MDPGKPRKNVLVVALLVIFQVCFCQDEVTDDYIGENTTVDYTLYESVCFKDVRNFKAWFLPLMYSVIC FVGLLGNGLVILTYIYFKRLKTMTDTYLLNLAVADILFLLILPFWAYSEAKSWIFGVYLCKGIFGIYKLSFF SGMLLLLCISIDRYVAIVQAVSAHRHRARVLLISKLSCVGIWMLALFLSIPELLYSGLQKNSGEDTLRCSLV SAQVEALITIQVAQMVFGFLVPMLAMSFCYLIIIRTLLQARNFERNKAIKVIIAVVVFITFQLPYNGVVLA QTVANFNITNSSCETSKQLNIAYDVTYSLASVRCCVNPFLYAFIGVKFRSDLPKLFKDLGCLSQERLRHWS SCRHVRNASVSMEAETTTFSP | PRT | Murine CCR7 | pcDNA3.1 Neo-mouseCCR7 |
| 202 | ACGGTGGACTACACCCTGTTCGAGTCGTTGTGCTTCAA | DNA | Synthetic Oligo | Y44F_V47L sense |
| 203 | TTGAAGCACAACGACTCGAACAGGGTGTAGTCCACCGT | DNA | Synthetic Oligo | Y44F_V47L_antisense |
| 204 | CAGCGGCCTCCAGAGGAGCAGCAGCGCGAGGACGCGATGAGATGCTC | DNA | Synthetic Oligo | K201R_N202S_G204S_T207A_L208M sense |
| 205 | GAGCATCTCATGCGTCCTCGCTGCTCCTCTGGAGGCCGCTG | DNA | Synthetic Oligo | K201R_N202S_G204S_T207A_L208M antisense |

FIGURE 1AP

| SEQ ID NO. | Sequence | Type | Organism | Name |
|---|---|---|---|---|
| 206 | ATGGACCCAGGAAACCCAGGAAAAACGTGCTGGTGGTGGCTCTCCTTGTCATTTTCCAGGTGTGCT TCTGCCAAGATGAGGTCACCGATGACTACATCGGCGATGACTACATCGGCGAGAATACCACCGTGGACTACACCCTGTTCGA GTCGTTGTGCTTCAAGAAGGATGTGCCGGAACTTTAAGGCCTGGTTCCTGCCTCATGTATTCTGTCA TCTGCTTCCGTGGGCCTGCTCCGCAACGGCGTCGGTACTGACGTACATCATCTTTTCCAAGAGGCTCAA GACCATGACGGATACCTGCTCAACCTGGCCGTGGCAGACATCCTTTTCCTCCTAATTCTTCCCT TCTGGGCCTACAGCGAAGCCAAGTCCTGGATCTTTGGCGTCTACCTGCCTATGCATCAGCATTGACCGCTACGTAGCC CTATAAGTTAAGCTTCTTCAGCGGCCGTGTCGGTCATCGCCACCGACGGTCTTCATCAGCAGCGGCCTTCTACAGCTGTCCTGTGT GGGCCATCTGGATGCTGCCCTCTTCCTTCCATCCGAGCGCTTCTACAGCGGCCTTCAGAAGAAC AGCGGCGAGGACACGCTGAGATGCTCAGTGCCCAAGTGGAGGCCTTGATCACCATCCAA GTGGCCCAGATGGTTTTGGGTTCCTAGTGCCTATGTGAGTTTCTGCTACTCATTATCAT CCGTACCTGCTCCAGGCACGCAACTTTGAGCGAACAAGGCCATCAAGGTGATCATTGCCGTGGTG GTAGTCGTTCATAGTCTTCCAGCGCCCTACAATGGGGTGGTCCTGGCTCAGACGGTGCCAACTTCA ACATCACCAATAGCAGTGCGAAACAGCAAGCAGCTCAACATTGCCTATGACGTCACCTACAGCCT TCTTCAAGCTCTTCAAGGACTTGGGCTGCCTCAGCCAGCATGAGAGGCGGAGACCATGGCTCCGGCACTGGTCTTCCTGCCG GCATGTACGGAACGCGTCGGTGAGCATGGAGGCGGAGACCACCAACCCTTCTCCCGTAG | DNA | Mutated Murine CCR7 | Y44F and V47L construct 20110094675 |
| 207 | MDPGKPRKNVLVVALLVIFQVCFCQDEVTDDYIGENTVDYTLFESLCPKKDVRNFKAWFPLMYSVICF VGLLGNGLVILTYIYFKRLKTMTDTYLLNLAVADILFLLILPFWAYSEAKSWIFGVYLCKGIFGIYKLSFFS GMLLLLCISIDRYVAIVQAVSAHRHRARVLLISKLSCVGIWMLALFLSIPELLYSGLQKNSGEDTLRCSLVS AQVEALITIQVAQMVFGFLVPMLAMSFCYLHRTLLQARNFERNKAIKVIIAVVVFIVFQLPYNGVVLAQ TVANFNITNSSCETSKQLNIAYDVTYSLASVRCCVNPFLYAFIGVKFRSDLFKLFKDLGCLSQERLRHWSS CRHVRNASVSMEAETTTTFSP | PRT | Mutated Murine CCR7 | Y44F and V47L construct 20110094675 |

FIGURE 1AQ

| SEQ ID NO: | Sequence | Type | Organism | Name |
|---|---|---|---|---|
| 208 | ATGGACCCAGGGAAACCAGGAAAACGTGCTGGTGGTGGCTCTCCTTGTCATTTCCAAGGTGCT TCTGCCAAGATGAGGTCACGATGACTACATGGCGAGAATACCACGGTGGACTACACCGTACG AGTCGGTGTGCTTCAAGAAGGATGTGCGGAACTTTAAGGCTGGTTCCTGCCCTCATGTATTCTGTC ATCTGCTTCGGTGGCCTGCTCGGCAACGGGCTGGTGATACTGAGGTACATCTATTCAAGAGGCTCA AGACCATGACGGATACGACTACCTGCTCAACCTGGCCGTGGCAGACATCCTTTTCCTCTAATTCTCC TTCTGGGCCTACAGCGAAGCAAGTCCTGGATCGTGTCGTGTCTATGCATCAGCATTGACGCTACGTAGCC TCTATAAGTTAAGCTTCTCAGGCGCCGTGTCGCGCATCATCGCCACCGCCGTGTTGTCTCACGAGGAGC AGCAGCGAGGACGCGATGAGATGTCACTGGTTCCTATGTCCTGCCAAGTGGAGGCCTTGATCACCATCCAA GTGCCCAGATGGTTTTGGGTTCCTAGTTGCTGGCAACGGAATCAAGGCCATCAAGGTGATCATTGCCGTGGTG CCGTACCTTGCTCCAGGCAGCTCCAGCTGCCCTACCAATGGGTGGTCCTGGCTCAGACGGTGGCCAACTTCA GTAGTCTTCATAGTCTTCCAGCTGCGAAACCAGCAAGCAGCTCAACATTGCCTATGGCGTCACCACAGCCT ACATCACCAATAGCAGCTGCGAGTGCGCGTCAAGGACTTGGCTGCCTCAGCCAGGCTGCCGGCACTGGTTCCTGCCG TCTTCAAGCTCTTCAAGGACTTGGGTGCCTCAGCCAGGCGGAGACCACCAACCTTCTCCCCGTAG | DNA | Mutated Murine CCR7 | K201R/N202S/G204S/T207A/L2 08M construct 20110094673 |
| 209 | MDPGKPRKNVLVVALLVIFQVCFCQDEVTDDYIGENTTVDYTLYESVCFKKDVRNFKAWFLPLMYSVIC FVGLLGNGLVILTIYFKRLKTMTDTYLLNLAVADLFLLILPFWAYSEAKSWIFGVYLCKGIFGIYKLSFF SGMLLLLCISIDRYVAIVQAVSAHRHRARVLLISKLSCVGIWMLALFLSIPELLYSGLQRSSSEDAMRCSLV SAQVEALFTIQVAQMVFGFLVPMLAMSFCYLIIIRTLLQARNFERNKAIKVIIAVVVFIVFQLPYNGVVLA QTVANFNITNSSCETSKQLNIAYDVTYSLASVRCCVNPFLYAFIGVKFRSDLFKLFKDLGCLSQERLRHWS SCRHVRNASVSMEAETTTFSP | PRT | Mutated Murine CCR7 | K201R/N202S/G204S/T207A/L2 08M construct 20110094673 |
| 210 | ACGGTGGACTACACCCTGTTCGAGTCGTTGTGCTTCAA | DNA | Synthetic Oligo | Y44F_V47L_sense |
| 211 | TTGAAGCACAACGACTCGAACAGGGTGTAGTCCACCGT | PRT | Synthetic Oligo | Y44F_V47L_antisense |

FIGURE 1AR

| SEQ ID NO. | Sequence | Type | Organism | Name |
|---|---|---|---|---|
| 212 | ATGGACCCAGGGAAACCCAGGAAAAACGTGCTGGTGGTGGCTCTCCTGTCATTTTCCAGGTGTGCT TCTGCCAAGATGAGGTCACGATGACTGAGTCACGATGACTACACGGTGACTACACCCTGTTCGA GTCGTTGTGTCTTCAAGAAGGATGTGCCAACGGGCTGTTAAGGCCTGTTCCTGCCTCTCATGTATTCTGTCA TCTGCTTCGTGTGGCCTGCTCCGCAACCTGCTCAACCTGGTGATACTGCAGTACATCATCTATTTCAAGAGGCTCAA GACCATGACGGATACAGCAGGAAGCCAAGTTCTGGATCGGTGCTGTGCTCCTATGCATCAGCATTGACCCTACGTAGCC CTATAAGTTAAGCTTCTTCAGCGGATGCTGCTGCTCCTGCCCCGTGCTTCTCATCAGCAAGCTGTCCTGTGT ATCGTCCAGCCGTGTCGGCTCATCGCCACCGACCTCCTTCCATCCCGGAGCTCAGTGCCCAAGTGGAGGCCTTGATCACCATCCA AGCAGCGAGACGCGATGAGATGTCACTGGTCATCTAGTGCGCTATGCTGCTATGAGTTTCTGCTACCTCATTATCAT GTGGGCCAAGATGGTTTTTGGTTCCTAGTGCACGAACTTTGAGCGGAACAAGGCCATCAAGGTGATCATTGCCGTGGTG GTAGTCTTCCAGCGCTTCCAGGCTCCAGTGCGCCTACAATGGGTGCTCTGGCTCAGACGGTGCCAACTTCA ACATCACCAATAGCAGCTGCGAAACCAGCAAGCAAGCTCAACATTGCCTATGACTGCATCACTACAGCCT GGCCTCCGTCCGCTCTGCGTCAACCTTCTTGTATGCCTCAGCCAGGAACGGCTCCGGCACTGGTCTTCCTGCCG TCTTCAAGCTCTTCAAGGACTTGGGCTGCCTCAGCCAGGAGCGGAGACCATGAGGCGGAGAACCACCACAACCTTCTCCCGTAG | DNA | Mutated Murine CCR7 | Y44F/V47L/ K201R/N202S/G204S/T IC50 Determination with Recombinantly Expressed Parental and Variants Antibodies

SEQUENCE LISTING

```
<160> NUMBER OF SEQ ID NOS: 213

<210> SEQ ID NO 1
<211> LENGTH: 702
<212> TYPE: DNA
<213> ORGANISM: Human

<400> SEQUENCE: 1
atggacatga gggtgcccgc tcagctcctg gggctcctgc tgctgtggct gagaggtgcg        60
cgctgttcct atgagctgac tcagccaccc tcagtgtccg tgtccccagg acagagagcc       120
agaatcacct gctctggaga taaattgggg gataaatatg cttcctggta tcagcagaag       180
ccaggccagt cccctctact ggtcatctat caagatagca agcggccctc agggatccct       240
gagcgattct ctggctccaa ctctggaaac acagccactc tgaccatcag cgggacccag       300
gctatggatg aggctgacta ttactgtcag gcgtggggca gcagcactgt gatattcggc       360
ggagggacca aactgaccgt cctaggtcag cccaaggcca accccactgt cactctgttc       420
ccgccctcct ctgaggagct ccaagccaac aaggccacac tagtgtgtct gatcagtgac       480 ttctaccogg gagctgtgac agtggcctgg aaggcagatg gcagcccegt caaggcggga       540 gtggagacca ccaaaccete caaacagagc aacaacaagt acgcggccag cagctacctg       600
agcctgacgc ccgagcagtg gaagtcccac agaagctaca gctgccaggt cacgcatgaa       660
gggagcaccg tggagaagac agtggcccct acagaatgtt ca                         702

<210> SEQ ID NO 2
<211> LENGTH: 234
<212> TYPE: PRT
<213> ORGANISM: Human

<400> SEQUENCE: 2

Met Asp Met Arg Val Pro Ala Gln Leu Leu Gly Leu Leu Leu Leu Trp
1               5                   10                  15
```

Leu Arg Gly Ala Arg Cys Ser Tyr Glu Leu Thr Gln Pro Pro Ser Val
                20                  25                  30

Ser Val Ser Pro Gly Gln Arg Ala Arg Ile Thr Cys Ser Gly Asp Lys
            35                  40                  45

Leu Gly Asp Lys Tyr Ala Ser Trp Tyr Gln Lys Pro Gly Gln Ser
    50                  55                  60

Pro Leu Leu Val Ile Tyr Gln Asp Ser Lys Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Gly Thr Gln Ala Met Asp Glu Ala Asp Tyr Tyr Cys Gln Ala Trp
            100                 105                 110

Gly Ser Ser Thr Val Ile Phe Gly Gly Gly Thr Lys Leu Thr Val Leu
        115                 120                 125

Gly Gln Pro Lys Ala Asn Pro Thr Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Gly Ser Pro
                165                 170                 175

Val Lys Ala Gly Val Glu Thr Thr Lys Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
        210                 215                 220

Glu Lys Thr Val Ala Pro Thr Glu Cys Ser
225                 230

<210> SEQ ID NO 3
<211> LENGTH: 33
<212> TYPE: DNA
<213> ORGANISM: Human

<400> SEQUENCE: 3
tctggagata aattggggga taaatatgct tcc                                    33

<210> SEQ ID NO 4
<211> LENGTH: 11
<212> TYPE: PRT
<213> ORGANISM: Human

<400> SEQUENCE: 4

Ser Gly Asp Lys Leu Gly Asp Lys Tyr Ala Ser
1               5                   10

<210> SEQ ID NO 5
<211> LENGTH: 21
<212> TYPE: DNA
<213> ORGANISM: Human

<400> SEQUENCE: 5
caagatagca agcggccctc a                                                 21

<210> SEQ ID NO 6
<211> LENGTH: 7
<212> TYPE: PRT
<213> ORGANISM: Human

<400> SEQUENCE: 6

Gln Asp Ser Lys Arg Pro Ser
1               5

<210> SEQ ID NO 7
<211> LENGTH: 27
<212> TYPE: DNA
<213> ORGANISM: Human

<400> SEQUENCE: 7
caggcgtggg gcagcagcac tgtgata                                        27

<210> SEQ ID NO 8
<211> LENGTH: 9
<212> TYPE: PRT
<213> ORGANISM: Human

<400> SEQUENCE: 8

Gln Ala Trp Gly Ser Ser Thr Val Ile
1               5

<210> SEQ ID NO 9
<211> LENGTH: 699
<212> TYPE: DNA
<213> ORGANISM: Human

<400> SEQUENCE: 9
atggacatga gggtgcccgc tcagctcctg gggctcctgc tgctgtggct gagaggtgcg      60
cgctgttatg agctgactca gccaccctca gtgtccgtgt ccccaggaca gagagccaga     120
atcacctgct ctggagataa attgggggat aaatatgctt cctggtatca gcagaagcca     180
ggccagtccc ctctactggt catctatcaa gatagcaagc ggccctcagg gatccctgag     240
cgattctctg gctccaactc tggaaacaca gccactctga ccatcagcgg gacccaggct     300
atggatgagg ctgactatta ctgtcaggcg tgggcagca gcactgtgat attcggcgga     360
gggaccaaac tgaccgtcct aggtcagccc aaggccaacc ccactgtcac tctgttcccg     420
ccctcctctg aggagctcca agccaacaag gccacactag tgtgtctgat cagtgacttc     480
tacccgggag ctgtgacagt ggcctggaag gcagatggca gccccgtcaa ggcgggagtg     540
gagaccacca aaccctccaa acagagcaac aacaagtacg cggccagcag ctacctgagc     600
ctgacgcccg agcagtggaa gtcccacaga agctacagct gccaggtcac gcatgaaggg     660
agcaccgtgg agaagacagt ggcccctaca gaatgttca                            699

<210> SEQ ID NO 10
<211> LENGTH: 233
<212> TYPE: PRT
<213> ORGANISM: Human

<400> SEQUENCE: 10

Met Asp Met Arg Val Pro Ala Gln Leu Leu Gly Leu Leu Leu Leu Trp
1               5                   10                  15

Leu Arg Gly Ala Arg Cys Tyr Glu Leu Thr Gln Pro Pro Ser Val Ser
                20                  25                  30

Val Ser Pro Gly Gln Arg Ala Arg Ile Thr Cys Ser Gly Asp Lys Leu
            35                  40                  45

Gly Asp Lys Tyr Ala Ser Trp Tyr Gln Gln Lys Pro Gly Gln Ser Pro
        50                  55                  60

-continued

Leu Leu Val Ile Tyr Gln Asp Ser Lys Arg Pro Ser Gly Ile Pro Glu
65                  70                  75                  80

Arg Phe Ser Gly Ser Asn Ser Gly Asn Thr Ala Thr Leu Thr Ile Ser
            85                  90                  95

Gly Thr Gln Ala Met Asp Glu Ala Asp Tyr Tyr Cys Gln Ala Trp Gly
        100                 105                 110

Ser Ser Thr Val Ile Phe Gly Gly Gly Thr Lys Leu Thr Val Leu Gly
        115                 120                 125

Gln Pro Lys Ala Asn Pro Thr Val Thr Leu Phe Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 11
<211> LENGTH: 33
<212> TYPE: DNA
<213> ORGANISM: Human

<400> SEQUENCE: 11
tctggagata aattggggga taaatatgct tcc          33

<210> SEQ ID NO 12
<211> LENGTH: 11
<212> TYPE: PRT
<213> ORGANISM: Human

<400> SEQUENCE: 12

Ser Gly Asp Lys Leu Gly Asp Lys Tyr Ala Ser
1               5                   10

<210> SEQ ID NO 13
<211> LENGTH: 21
<212> TYPE: DNA
<213> ORGANISM: Human

<400> SEQUENCE: 13
caagatagca agcggccctc a          21

<210> SEQ ID NO 14
<211> LENGTH: 7
<212> TYPE: PRT
<213> ORGANISM: Human

<400> SEQUENCE: 14

Gln Asp Ser Lys Arg Pro Ser
1               5

<210> SEQ ID NO 15
<211> LENGTH: 27
<212> TYPE: DNA

<213> ORGANISM: Human

<400> SEQUENCE: 15
caggcgtggg gcagcagcac tgtgata                                          27

<210> SEQ ID NO 16
<211> LENGTH: 9
<212> TYPE: PRT
<213> ORGANISM: Human

<400> SEQUENCE: 16

Gln Ala Trp Gly Ser Ser Thr Val Ile
1               5

<210> SEQ ID NO 17
<211> LENGTH: 702
<212> TYPE: DNA
<213> ORGANISM: Human

<400> SEQUENCE: 17
atggacatga gggtgcccgc tcagctcctg gggctcctgc tgctgtggct gagaggtgcg      60
cgctgttcct atgagctgac tcagccaccc tcagtgtccg tgtccccagg acagagagcc    120
agcatcacct gctctggaga taaattgggg gataaatatg cttcctggta tcagcagaag    180
ccaggccagt cccctctact ggtcatctat caagatggca gcggccctc agggatccct     240 gagcgattct ctggctccaa ctctggaaac acagccactc tgaccatcag cgggacccag    300
gctatggatg aggctgacta ttactgtcag gcgtggggca gcagcactgt gatattcggc    360
ggagggacca aactgaccgt cctaggtcag cccaaggcca cccccactgt cactctgttc    420
ccgccctcct ctgaggagct caagccaac aaggccacac tagtgtgtct gatcagtgac     480
ttctacccgg gagctgtgac agtggcctgg aaggcagatg gcagccccgt caaggcggga    540
gtggagacca ccaaaccctc caaacagagc aacaacaagt acgcggccag cagctacctg    600
agcctgacgc ccgagcagtg gaagtcccac agaagctaca gctgccaggt cacgcatgaa    660
gggagcaccg tggagaagac agtggcccct acagaatgtt ca                       702

<210> SEQ ID NO 18
<211> LENGTH: 234
<212> TYPE: PRT
<213> ORGANISM: Human

<400> SEQUENCE: 18

Met Asp Met Arg Val Pro Ala Gln Leu Leu Gly Leu Leu Leu Leu Trp
1               5                   10                  15

Leu Arg Gly Ala Arg Cys Ser Tyr Glu Leu Thr Gln Pro Pro Ser Val
            20                  25                  30

Ser Val Ser Pro Gly Gln Arg Ala Ser Ile Thr Cys Ser Gly Asp Lys
        35                  40                  45

Leu Gly Asp Lys Tyr Ala Ser Trp Tyr Gln Gln Lys Pro Gly Gln Ser
    50                  55                  60

Pro Leu Leu Val Ile Tyr Gln Asp Gly Lys Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Gly Thr Gln Ala Met Asp Glu Ala Asp Tyr Tyr Cys Gln Ala Trp
            100                 105                 110

Gly Ser Ser Thr Val Ile Phe Gly Gly Gly Thr Lys Leu Thr Val Leu

```
            115                 120                 125
Gly Gln Pro Lys Ala Asn Pro Thr Val Thr Leu Phe Pro Pro Ser Ser
        130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Gly Ser Pro
                165                 170                 175

Val Lys Ala Gly Val Glu Thr Thr Lys Pro Ser Lys Gln Ser Asn Asn
            180                 185                 190

Lys Tyr Ala Ala Ser Ser Tyr Leu Ser Leu Thr Pro Glu Gln Trp Lys
        195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 19
<211> LENGTH: 33
<212> TYPE: DNA
<213> ORGANISM: Human

<400> SEQUENCE: 19
tctggagata aattggggga taaatatgct tcc                                   33

<210> SEQ ID NO 20
<211> LENGTH: 11
<212> TYPE: PRT
<213> ORGANISM: Human

<400> SEQUENCE: 20

Ser Gly Asp Lys Leu Gly Asp Lys Tyr Ala Ser
1               5                   10

<210> SEQ ID NO 21
<211> LENGTH: 21
<212> TYPE: DNA
<213> ORGANISM: Human

<400> SEQUENCE: 21
caagatggca agcggccctc a                                                21

<210> SEQ ID NO 22
<211> LENGTH: 7
<212> TYPE: PRT
<213> ORGANISM: Human

<400> SEQUENCE: 22

Gln Asp Gly Lys Arg Pro Ser
1               5

<210> SEQ ID NO 23
<211> LENGTH: 27
<212> TYPE: DNA
<213> ORGANISM: Human

<400> SEQUENCE: 23
caggcgtggg gcagcagcac tgtgata                                          27

<210> SEQ ID NO 24
<211> LENGTH: 9
<212> TYPE: PRT
```

<213> ORGANISM: Human

<400> SEQUENCE: 24

Gln Ala Trp Gly Ser Ser Thr Val Ile
1               5

<210> SEQ ID NO 25
<211> LENGTH: 699
<212> TYPE: DNA
<213> ORGANISM: Human

<400> SEQUENCE: 25

| | | | | | |
|---|---|---|---|---|---|
| atggacatga | gggtgcccgc | tcagctcctg | gggctcctgc | tgctgtggct | gagaggtgcg | 60 |
| cgctgttcct | atgagctgac | tcagccaccc | tcagtgtccg | tgtccccagg | acagacagcc | 120 |
| agcatcacct | gctctggaaa | taaattgggg | gataaatatg | cttcctggta | tcatcagaag | 180 |
| ccaggccagt | cccctgtgct | ggtcatctat | caagataaca | gcggccctca | gggatccct  | 240 |
| gagcgattct | ctggctccaa | ctctgggaac | acagccactc | tgaccatcag | cgggacccag | 300 |
| actatggatg | aggctgacta | tttctgtcag | gcgtgggaca | ggactgtggt | attcggcgga | 360 |
| gggaccaaac | tgaccgtcct | aggtcagccc | aaggccaacc | ccactgtcac | tctgttcccg | 420 |
| ccctcctctg | aggagctcca | agccaacaag | gccacactag | tgtgtctgat | cagtgacttc | 480 |
| tacccgggag | ctgtgacagt | ggcctggaag | gcagatggca | gccccgtcaa | ggcgggagtg | 540 |
| gagaccacca | aaccctccaa | acagagcaac | aacaagtacg | cggccagcag | ctacctgagc | 600 |
| ctgacgcccg | agcagtggaa | gtcccacaga | agctacagct | gccaggtcac | gcatgaaggg | 660 |
| agcaccgtgg | agaagacagt | ggcccctaca | gaatgttca  |            |            | 699 |

<210> SEQ ID NO 26
<211> LENGTH: 233
<212> TYPE: PRT
<213> ORGANISM: Human

<400> SEQUENCE: 26

Met Asp Met Arg Val Pro Ala Gln Leu Leu Gly Leu Leu Leu Leu Trp
1               5                   10                  15

Leu Arg Gly Ala Arg Cys Ser Tyr Glu Leu Thr Gln Pro Pro Ser Val
                20                  25                  30

Ser Val Ser Pro Gly Gln Thr Ala Ser Ile Thr Cys Ser Gly Asn Lys
            35                  40                  45

Leu Gly Asp Lys Tyr Ala Ser Trp Tyr His Gln Lys Pro Gly Gln Ser
        50                  55                  60

Pro Val Leu Val Ile Tyr Gln Asp Asn Lys Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Gly Thr Gln Thr Met Asp Glu Ala Asp Tyr Phe Cys Gln Ala Trp
            100                 105                 110

Asp Arg Thr Val Val Phe Gly Gly Gly Thr Lys Leu Thr Val Leu Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

```
Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220

Lys Thr Val Ala Pro Thr Glu Cys Ser
225                 230

<210> SEQ ID NO 27
<211> LENGTH: 33
<212> TYPE: DNA
<213> ORGANISM: Human

<400> SEQUENCE: 27
tctggaaata aattggggga taaatatgct tcc                                33

<210> SEQ ID NO 28
<211> LENGTH: 11
<212> TYPE: PRT
<213> ORGANISM: Human

<400> SEQUENCE: 28

Ser Gly Asn Lys Leu Gly Asp Lys Tyr Ala Ser
1               5                   10

<210> SEQ ID NO 29
<211> LENGTH: 21
<212> TYPE: DNA
<213> ORGANISM: Human

<400> SEQUENCE: 29
caagataaca agcggccctc a                                             21

<210> SEQ ID NO 30
<211> LENGTH: 7
<212> TYPE: PRT
<213> ORGANISM: Human

<400> SEQUENCE: 30

Gln Asp Asn Lys Arg Pro Ser
1               5

<210> SEQ ID NO 31
<211> LENGTH: 24
<212> TYPE: DNA
<213> ORGANISM: Human

<400> SEQUENCE: 31
caggcgtggg acaggactgt ggta                                          24

<210> SEQ ID NO 32
<211> LENGTH: 8
<212> TYPE: PRT
<213> ORGANISM: Human

<400> SEQUENCE: 32

Gln Ala Trp Asp Arg Thr Val Val
1               5

<210> SEQ ID NO 33
<211> LENGTH: 699
```

```
<212> TYPE: DNA
<213> ORGANISM: Human

<400> SEQUENCE: 33
atggacatga gggtgcccgc tcagctcctg gggctcctgc tgctgtggct gagaggtgcg      60
cgctgttcct atgagctgac tcagccaccc tcagtgtccg tgtccccagg acagacagcc     120
agcatcacct gctctggaaa taaattgggg gataaatatg cttcctggta tcagcagaag     180
ccaggccagt cccctgtgct ggtcatctat caagataaca gcggccctc agggatccct      240
gagcgattct ctggctccaa ctctgggaac acagccactc tgaccatcag cgggacccag     300
actatggatg aggctgacta tttctgtcag gcgtgggaca ggactgtggt attcggcgga     360
gggaccaaac tgaccgtcct aggtcagccc aaggccaacc ccactgtcac tctgttcccg     420
ccctcctctg aggagctcca agccaacaag gccacactag tgtgtctgat cagtgacttc     480
tacccgggag ctgtgacagt ggcctggaag gcagatggca gccccgtcaa ggcgggagtg     540
gagaccacca accctccaa acagagcaac aacaagtacg cggccagcag ctacctgagc      600
ctgacgcccg agcagtggaa gtcccacaga agctacagct gccaggtcac gcatgaaggg     660
agcaccgtgg agaagacagt ggcccctaca gaatgttca                           699

<210> SEQ ID NO 34
<211> LENGTH: 233
<212> TYPE: PRT
<213> ORGANISM: Human

<400> SEQUENCE: 34

Met Asp Met Arg Val Pro Ala Gln Leu Leu Gly Leu Leu Leu Leu Trp
1               5                   10                  15

Leu Arg Gly Ala Arg Cys Ser Tyr Glu Leu Thr Gln Pro Pro Ser Val
            20                  25                  30

Ser Val Ser Pro Gly Gln Thr Ala Ser Ile Thr Cys Ser Gly Asn Lys
        35                  40                  45

Leu Gly Asp Lys Tyr Ala Ser Trp Tyr Gln Gln Lys Pro Gly Gln Ser
    50                  55                  60

Pro Val Leu Val Ile Tyr Gln Asp Asn Lys Arg Pro Ser Gly Ile Pro
65                  70                  75                  80

Glu Arg Phe Ser Gly Ser Asn Ser Gly Asn Thr Ala Thr Leu Thr Ile
                85                  90                  95

Ser Gly Thr Gln Thr Met Asp Glu Ala Asp Tyr Phe Cys Gln Ala Trp
            100                 105                 110

Asp Arg Thr Val Val Phe Gly Gly Gly Thr Lys Leu Thr Val Leu Gly
        115                 120                 125

Gln Pro Lys Ala Asn Pro Thr Val Thr Leu Phe Pro Pro Ser Ser Glu
    130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Gly Ser Pro Val
                165                 170                 175

Lys Ala Gly Val Glu Thr Thr Lys Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
    210                 215                 220
```

Lys Thr Val Ala Pro Thr Glu Cys Ser
225                 230

<210> SEQ ID NO 35
<211> LENGTH: 33
<212> TYPE: DNA
<213> ORGANISM: Human

<400> SEQUENCE: 35
tctggaaata aattggggga taaatatgct tcc                                    33

<210> SEQ ID NO 36
<211> LENGTH: 11
<212> TYPE: PRT
<213> ORGANISM: Human

<400> SEQUENCE: 36

Ser Gly Asn Lys Leu Gly Asp Lys Tyr Ala Ser
1               5                   10

<210> SEQ ID NO 37
<211> LENGTH: 21
<212> TYPE: DNA
<213> ORGANISM: Human

<400> SEQUENCE: 37
caagataaca agcggccctc a                                                 21

<210> SEQ ID NO 38
<211> LENGTH: 7
<212> TYPE: PRT
<213> ORGANISM: Human

<400> SEQUENCE: 38

Gln Asp Asn Lys Arg Pro Ser
1               5

<210> SEQ ID NO 39
<211> LENGTH: 24
<212> TYPE: DNA
<213> ORGANISM: Human

<400> SEQUENCE: 39
caggcgtggg acaggactgt ggta                                              24

<210> SEQ ID NO 40
<211> LENGTH: 8
<212> TYPE: PRT
<213> ORGANISM: Human

<400> SEQUENCE: 40

Gln Ala Trp Asp Arg Thr Val Val
1               5

<210> SEQ ID NO 41
<211> LENGTH: 1416
<212> TYPE: DNA
<213> ORGANISM: Human

<400> SEQUENCE: 41
atggacatga gggtgcccgc tcagctcctg gggctcctgc tgctgtggct gagaggtgcg      60
cgctgtcagg tgcagctggt ggagtctggg ggaggcgtgg tccagcctgg gaggtccctg     120
agactctcct gtgcagcgtc tggattcacc ttcagtagct atggcatgca ctgggtccgc     180

```
caggctccag gcaaggggct ggagtgggtg gcagttatat ggtatgatgg aagtaaaaaa    240
tattatgcag actccgtgaa gggccgattc accatctcca gagacaattc caaaaacaca    300
ctgtatctgc aaatgaacag actgagagcc gaggacacgg ctgtgtatta ctgtgcgaga    360
gatgggggta tagcagtatt tttacaggac aattggttcg acccctgggg ccagggaacc    420
ctggtcaccg tctctagtgc ctccaccaag ggcccatcgg tcttcccccT ggcgccctgc    480
tccaggagca cctccgagag cacagcggcc ctgggctgcc tggtcaagga ctacttcccc    540
gaaccggtga cggtgtcgtg gaactcaggc gctctgacca gcggcgtgca caccttccca    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttcccccca aaacccaagg acaccctcat gatctcccgg    840
accccTgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct   1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                              1416
```

<210> SEQ ID NO 42
<211> LENGTH: 472
<212> TYPE: PRT
<213> ORGANISM: Human

<400> SEQUENCE: 42

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Ser Ser Tyr Gly Met His Trp Val Arg Gln Ala Pro Gly
    50                  55                  60

Lys Gly Leu Glu Trp Val Ala Val Ile Trp Tyr Asp Gly Ser Lys Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Arg Leu Arg Ala Glu Asp
            100                 105                 110

Thr Ala Val Tyr Tyr Cys Ala Arg Asp Gly Gly Ile Ala Val Phe Leu
        115                 120                 125

Gln Asp Asn Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Cys
```

```
                145                 150                 155                 160
        Ser Arg Ser Thr Ser Glu Ser Thr Ala Ala Leu Gly Cys Leu Val Lys
                        165                 170                 175

Asp Tyr Phe Pro Glu Pro Val Thr Val Ser Trp Asn Ser Gly Ala Leu
                        180                 185                 190

Thr Ser Gly Val His Thr Phe Pro Ala Val Leu Gln Ser Ser Gly Leu
                        195                 200                 205

Tyr Ser Leu Ser Ser Val Val Thr Val Pro Ser Ser Asn Phe Gly Thr
                210                 215                 220

Gln Thr Tyr Thr Cys Asn Val Asp His Lys Pro Ser Asn Thr Lys Val
        225                 230                 235                 240

Asp Lys Thr Val Glu Arg Lys Cys Cys Val Glu Cys Pro Pro Cys Pro
                        245                 250                 255

Ala Pro Pro Val Ala Gly Pro Ser Val Phe Leu Phe Pro Pro Lys Pro
                        260                 265                 270

Lys Asp Thr Leu Met Ile Ser Arg Thr Pro Glu Val Thr Cys Val Val
                        275                 280                 285

Val Asp Val Ser His Glu Asp Pro Glu Val Gln Phe Asn Trp Tyr Val
                290                 295                 300

Asp Gly Val Glu Val His Asn Ala Lys Thr Lys Pro Arg Glu Glu Gln
        305                 310                 315                 320

Phe Asn Ser Thr Phe Arg Val Val Ser Val Leu Thr Val Val His Gln
                        325                 330                 335

Asp Trp Leu Asn Gly Lys Glu Tyr Lys Cys Lys Val Ser Asn Lys Gly
                        340                 345                 350

Leu Pro Ala Pro Ile Glu Lys Thr Ile Ser Lys Thr Lys Gly Gln Pro
                        355                 360                 365

Arg Glu Pro Gln Val Tyr Thr Leu Pro Pro Ser Arg Glu Glu Met Thr
                370                 375                 380

Lys Asn Gln Val Ser Leu Thr Cys Leu Val Lys Gly Phe Tyr Pro Ser
        385                 390                 395                 400

Asp Ile Ala Val Glu Trp Glu Ser Asn Gly Gln Pro Glu Asn Asn Tyr
                        405                 410                 415

Lys Thr Thr Pro Pro Met Leu Asp Ser Asp Gly Ser Phe Phe Leu Tyr
                        420                 425                 430

Ser Lys Leu Thr Val Asp Lys Ser Arg Trp Gln Gln Gly Asn Val Phe
                        435                 440                 445

Ser Cys Ser Val Met His Glu Ala Leu His Asn His Tyr Thr Gln Lys
                450                 455                 460

Ser Leu Ser Leu Ser Pro Gly Lys
        465                 470

<210> SEQ ID NO 43
<211> LENGTH: 15
<212> TYPE: DNA
<213> ORGANISM: Human

<400> SEQUENCE: 43
agctatggca tgcac                                                            15

<210> SEQ ID NO 44
<211> LENGTH: 5
<212> TYPE: PRT
<213> ORGANISM: Human

<400> SEQUENCE: 44
```

Ser Tyr Gly Met His
1               5

<210> SEQ ID NO 45
<211> LENGTH: 51
<212> TYPE: DNA
<213> ORGANISM: Human

<400> SEQUENCE: 45
gttatatggt atgatggaag taaaaaatat tatgcagact ccgtgaaggg c    51

<210> SEQ ID NO 46
<211> LENGTH: 17
<212> TYPE: PRT
<213> ORGANISM: Human

<400> SEQUENCE: 46

Val Ile Trp Tyr Asp Gly Ser Lys Lys Tyr Tyr Ala Asp Ser Val Lys
1               5                   10                  15
Gly

<210> SEQ ID NO 47
<211> LENGTH: 45
<212> TYPE: DNA
<213> ORGANISM: Human

<400> SEQUENCE: 47 gatggggta tagcagtatt tttacaggac aattggttcg acccc    45

<210> SEQ ID NO 48
<211> LENGTH: 15
<212> TYPE: PRT
<213> ORGANISM: Human

<400> SEQUENCE: 48

Asp Gly Gly Ile Ala Val Phe Leu Gln Asp Asn Trp Phe Asp Pro
1               5                   10                  15

<210> SEQ ID NO 49
<211> LENGTH: 1416
<212> TYPE: DNA
<213> ORGANISM: Human

<400> SEQUENCE: 49
atggacatga gggtgcccgc tcagctcctg gggctcctgc tgctgtggct gagaggtgcg    60
cgctgtcagg tgcagctggt ggagtctggg ggaggcgtgg tccagcctgg gaggtccctg   120
agactctcct gtgcagcgtc tggattcacc ttcagaagct atggcatgca ctgggtccgc   180
caggctccag gcaaggggct ggagtgggtg gcagttatat ggtatgatgg aagtaaaaaa   240
tattatgcag actccgtgaa gggccgattc accatctcca gagacaactc caaaaacaca   300
ctgtatctgc aaatgaacag actgagagcc gaggacacgg ctgtgtatta ctgtgcgaga   360 gatggggta tagcagtatt tttagaggac aattggttcg acccctgggg ccagggaacc   420
ctggtcaccg tctctagtgc ctccaccaag ggcccatcgg tcttcccect ggcgccctgc   480 tccaggagca cctccgagag cacagcggcc ctgggctgcc tggtcaagga ctacttcccc   540
gaaccggtga cggtgtcgtg gaactcaggc gctctgacca gcggcgtgca caccttccca   600
gctgtcctac agtcctcagg actctactcc ctcagcagcg tggtgaccgt gccctccagc   660
aacttcggca cccagaccta cacctgcaac gtagatcaca agcccagcaa caccaaggtg   720

-continued

```
gacaagacag ttgagcgcaa atgttgtgtc gagtgcccac cgtgcccagc accacctgtg    780
gcaggaccgt cagtcttcct cttcccccca aacccaagg acaccctcat gatctcccgg     840
accctgagg tcacgtgcgt ggtggtggac gtgagccacg aagaccccga ggtccagttc     900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct    1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                              1416
```

<210> SEQ ID NO 50
<211> LENGTH: 472
<212> TYPE: PRT
<213> ORGANISM: Human

<400> SEQUENCE: 50

```
Met Asp Met Arg Val Pro Ala Gln Leu Leu Gly Leu Leu Leu Leu Trp
1               5                   10                  15
Leu Arg Gly Ala Arg Cys Gln Val Gln Leu Val Glu Ser Gly Gly Gly
            20                  25                  30
Val Val Gln Pro Gly Arg Ser Leu Arg Leu Ser Cys Ala Ala Ser Gly
        35                  40                  45
Phe Thr Phe Arg Ser Tyr Gly Met His Trp Val Arg Gln Ala Pro Gly
    50                  55                  60
Lys Gly Leu Glu Trp Val Ala Val Ile Trp Tyr Asp Gly Ser Lys Lys
65                  70                  75                  80
Tyr Tyr Ala Asp Ser Val Lys Gly Arg Phe Thr Ile Ser Arg Asp Asn
                85                  90                  95
Ser Lys Asn Thr Leu Tyr Leu Gln Met Asn Arg Leu Arg Ala Glu Asp
            100                 105                 110
Thr Ala Val Tyr Tyr Cys Ala Arg Asp Gly Gly Ile Ala Val Phe Leu
        115                 120                 125
Glu Asp Asn Trp Phe Asp Pro Trp Gly Gln Gly Thr Leu Val Thr Val
    130                 135                 140
Ser Ser Ala Ser Thr Lys Gly Pro Ser Val Phe Pro Leu Ala Pro Cys
145                 150                 155                 160
Ser Arg Ser Thr Ser Glu Ser Thr Ala Ala Leu Gly Cys Leu Val Lys
                165                 170                 175
Asp Tyr Phe Pro Glu Pro Val Thr Val Ser Trp Asn Ser Gly Ala Leu
            180                 185                 190
Thr Ser Gly Val His Thr Phe Pro Ala Val Leu Gln Ser Ser Gly Leu
        195                 200                 205
Tyr Ser Leu Ser Ser Val Val Thr Val Pro Ser Ser Asn Phe Gly Thr
    210                 215                 220
Gln Thr Tyr Thr Cys Asn Val Asp His Lys Pro Ser Asn Thr Lys Val
225                 230                 235                 240
Asp Lys Thr Val Glu Arg Lys Cys Cys Val Glu Cys Pro Pro Cys Pro
```

-continued

```
                    245                 250                 255
Ala Pro Pro Val Ala Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser His Glu Asp Pro Glu Val Gln Phe Asn Trp Tyr Val
        290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
                340                 345                 350

Leu Pro Ala Pro Ile Glu Lys Thr Ile Ser Lys Thr Lys Gly Gln Pro
                355                 360                 365

Arg Glu Pro Gln Val Tyr Thr Leu Pro Pro Ser Arg Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
                420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470
```

<210> SEQ ID NO 51
<211> LENGTH: 15
<212> TYPE: DNA
<213> ORGANISM: Human

<400> SEQUENCE: 51
agctatggca tgcac                                            15

<210> SEQ ID NO 52
<211> LENGTH: 5
<212> TYPE: PRT
<213> ORGANISM: Human

<400> SEQUENCE: 52

Ser Tyr Gly Met His
1               5

<210> SEQ ID NO 53
<211> LENGTH: 51
<212> TYPE: DNA
<213> ORGANISM: Human

<400> SEQUENCE: 53
gttatatggt atgatggaag taaaaaatat tatgcagact ccgtgaaggg c     51

<210> SEQ ID NO 54
<211> LENGTH: 17
<212> TYPE: PRT

<213> ORGANISM: Human

<400> SEQUENCE: 54

Val Ile Trp Tyr Asp Gly Ser Lys Lys Tyr Tyr Ala Asp Ser Val Lys
1               5                   10                  15

Gly

<210> SEQ ID NO 55
<211> LENGTH: 45
<212> TYPE: DNA
<213> ORGANISM: Human

<400> SEQUENCE: 55 gatggggta tagcagtatt tttagaggac aattggttcg acccc            45

<210> SEQ ID NO 56
<211> LENGTH: 15
<212> TYPE: PRT
<213> ORGANISM: Human

<400> SEQUENCE: 56

Asp Gly Gly Ile Ala Val Phe Leu Glu Asp Asn Trp Phe Asp Pro
1               5                   10                  15

<210> SEQ ID NO 57
<211> LENGTH: 1416
<212> TYPE: DNA
<213> ORGANISM: Human

<400> SEQUENCE: 57

| | |
|---|---|
| atggacatga gggtgcccgc tcagctcctg gggctcctgc tgctgtggct gagaggtgcg | 60 |
| cgctgtcagg gcagctggt ggagtctggg ggaggcgtgg tccagcctgg gaggtccctg | 120 |
| agactctcct gtgcagcgtc tggattcacc ttcaggagct atggcatgca ctgggtccgc | 180 |
| caggctccag gcaaggggct ggagtgggtg gcagttatat ggtatgatgg aagtaaaaaa | 240 |
| tactatgcag actccgtgaa gggccgattc accatctcca gagacaattc caagaacacg | 300 |
| ctgtttctgc aaatgaacag cctgagagcc gaggacacgg ctgtgtatta ctgtgcgaga | 360 |
| gatggggta tagcagcatt tttacaggac aactggttcg acccctgggg ccagggaacc | 420 |
| ctggtcaccg tctctagtgc ctccaccaag ggcccatcgg tcttcccct ggcgccctgc | 480 |
| tccaggagca cctccgagag cacagcggcc ctgggctgcc tggtcaagga ctacttcccc | 540 |
| gaaccggtga cggtgtcgtg gaactcaggc gctctgacca gcggcgtgca caccttccca | 600 |
| gctgtcctac agtcctcagg actctactcc ctcagcagcg tggtgaccgt gccctccagc | 660 |
| aacttcggca cccagaccta cacctgcaac gtagatcaca agcccagcaa caccaaggtg | 720 |
| gacaagacag ttgagcgcaa atgttgtgtc gagtgcccac cgtgcccagc accacctgtg | 780 |
| gcaggaccgt cagtcttcct cttccccca aaacccaagg acaccctcat gatctcccgg | 840 |
| acccctgagg tcacgtgcgt ggtggtggac gtgagccacg agaccccga ggtccagttc | 900 |
| aactggtacg tggacggcgt ggaggtgcat aatgccaaga caaagccacg ggaggagcag | 960 |
| ttcaacagca cgttccgtgt ggtcagcgtc ctcaccgttg tgcaccagga ctggctgaac | 1020 |
| ggcaaggagt acaagtgcaa ggtctccaac aaaggcctcc cagcccccat cgagaaaacc | 1080 |
| atctccaaaa ccaaagggca gccccgagaa ccacaggtgt acaccctgcc cccatcccgg | 1140 |
| gaggagatga ccaagaacca ggtcagcctg acctgcctgg tcaaaggctt ctaccccagc | 1200 |
| gacatcgccg tggagtggga gagcaatggg cagccggaga caactacaa gaccacacct | 1260 |

-continued

```
cccatgctgg actccgacgg ctccttcttc ctctacagca agctcaccgt ggacaagagc    1320
aggtggcagc aggggaacgt cttctcatgc tccgtgatgc atgaggctct gcacaaccac    1380
tacacgcaga agagcctctc cctgtctccg ggtaaa                              1416
```

<210> SEQ ID NO 58
<211> LENGTH: 472
<212> TYPE: PRT
<213> ORGANISM: Human

<400> SEQUENCE: 58

```
Met Asp Met Arg Val Pro Ala Gln Leu Leu Gly Leu Leu Leu Leu Trp
1               5                   10                  15

Leu Arg Gly Ala Arg Cys Gln Gly Gln Leu Val Glu Ser Gly Gly Gly
                20                  25                  30

Val Val Gln Pro Gly Arg Ser Leu Arg Leu Ser Cys Ala Ala Ser Gly
            35                  40                  45

Phe Thr Phe Arg Ser Tyr Gly Met His Trp Val Arg Gln Ala Pro Gly
        50                  55                  60

Lys Gly Leu Glu Trp Val Ala Val Ile Trp Tyr Asp Gly Ser Lys Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Phe Leu Gln Met Asn Ser Leu Arg Ala Glu Asp
            100                 105                 110

Thr Ala Val Tyr Tyr Cys Ala Arg Asp Gly Gly Ile Ala Ala Phe Leu
        115                 120                 125

Gln Asp Asn Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
    210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
```

```
            340                 345                 350
Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470
```

<210> SEQ ID NO 59
<211> LENGTH: 15
<212> TYPE: DNA
<213> ORGANISM: Human

<400> SEQUENCE: 59
agctatggca tgcac                                                15

<210> SEQ ID NO 60
<211> LENGTH: 5
<212> TYPE: PRT
<213> ORGANISM: Human

<400> SEQUENCE: 60

Ser Tyr Gly Met His
1               5

<210> SEQ ID NO 61
<211> LENGTH: 51
<212> TYPE: DNA
<213> ORGANISM: Human

<400> SEQUENCE: 61
gttatatggt atgatggaag taaaaaatac tatgcagact ccgtgaaggg c           51

<210> SEQ ID NO 62
<211> LENGTH: 17
<212> TYPE: PRT
<213> ORGANISM: Human

<400> SEQUENCE: 62

Val Ile Trp Tyr Asp Gly Ser Lys Lys Tyr Tyr Ala Asp Ser Val Lys
1               5                   10                  15

Gly

<210> SEQ ID NO 63
<211> LENGTH: 45
<212> TYPE: DNA
<213> ORGANISM: Human

<400> SEQUENCE: 63
gatgggggta tagcagcatt tttacaggac aactggttcg acccc                 45

<210> SEQ ID NO 64
<211> LENGTH: 15
<212> TYPE: PRT
<213> ORGANISM: Human

<400> SEQUENCE: 64

Asp Gly Gly Ile Ala Ala Phe Leu Gln Asp Asn Trp Phe Asp Pro
1               5                   10                  15

<210> SEQ ID NO 65
<211> LENGTH: 1416
<212> TYPE: DNA
<213> ORGANISM: Human

<400> SEQUENCE: 65

| | | | | | |
|---|---|---|---|---|---|
| atggacatga | gggtgcccgc | tcagctcctg | gggctcctgc | tgctgtggct | gagaggtgcg | 60 |
| cgctgtcagg | tgcagctggt | ggagtctggg | ggaggcgtgg | tccagcctgg | gaggtccctg | 120 |
| agactctcct | gtgcagcgtc | tggattcacc | ttcaggagct | atggcatgca | ctgggtccgc | 180 |
| caggctccag | gcaaggggct | ggagtgggtg | gcagttatat | ggtatgatgg | aagtaaaaaa | 240 |
| tactatgcag | actccgtgaa | gggccgattc | accatctcca | gagacaattc | caagaacacg | 300 |
| ctgtttctgc | aaatgaacag | cctgagagcc | gaggacacgg | ctgtgtatta | ctgtgcgaga | 360 |
| gatgggggta | tagcagcatt | tttacaggac | aactggttcg | accctggggg | ccagggaacc | 420 |
| ctggtcaccg | tctctagtgc | ctccaccaag | ggcccatcgg | tcttccccct | ggcgccctgc | 480 |
| tccaggagca | cctccgagag | cacagcggcc | ctgggctgcc | tggtcaagga | ctacttcccc | 540 |
| gaaccggtga | cggtgtcgtg | gaactcaggc | gctctgacca | gcggcgtgca | caccttccca | 600 |
| gctgtcctac | agtcctcagg | actctactcc | ctcagcagcg | tggtgaccgt | gccctccagc | 660 |
| aacttcggca | cccagaccta | cacctgcaac | gtagatcaca | agcccagcaa | caccaaggtg | 720 |
| gacaagacag | ttgagcgcaa | atgttgtgtc | gagtgcccac | cgtgcccagc | accacctgtg | 780 |
| gcaggaccgt | cagtcttcct | cttcccccca | aaacccaagg | acaccctcat | gatctcccgg | 840 |
| acccctgagg | tcacgtgcgt | ggtggtggac | gtgagccacg | aagaccccga | ggtccagttc | 900 |
| aactggtacg | tggacggcgt | ggaggtgcat | aatgccaaga | caaagccacg | ggaggagcag | 960 |
| ttcaacagca | cgttccgtgt | ggtcagcgtc | ctcaccgttg | tgcaccagga | ctggctgaac | 1020 |
| ggcaaggagt | acaagtgcaa | ggtctccaac | aaaggcctcc | cagcccccat | cgagaaaacc | 1080 |
| atctccaaaa | ccaaagggca | gccccgagaa | ccacaggtgt | acaccctgcc | cccatcccgg | 1140 |
| gaggagatga | ccaagaacca | ggtcagcctg | acctgcctgg | tcaaaggctt | ctaccccagc | 1200 |
| gacatcgccg | tggagtggga | gagcaatggg | cagccggaga | acaactacaa | gaccacacct | 1260 |
| cccatgctgg | actccgacgg | ctccttcttc | ctctacagca | agctcaccgt | ggacaagagc | 1320 |
| aggtggcagc | aggggaacgt | cttctcatgc | tccgtgatgc | atgaggctct | gcacaaccac | 1380 |
| tacacgcaga | agagcctctc | cctgtctccg | ggtaaa | | | 1416 |

<210> SEQ ID NO 66
<211> LENGTH: 472
<212> TYPE: PRT
<213> ORGANISM: Human

<400> SEQUENCE: 66

Met Asp Met Arg Val Pro Ala Gln Leu Leu Gly Leu Leu Leu Leu Trp
1               5                   10                  15

```
Leu Arg Gly Ala Arg Cys Gln Val Gln Leu Val Glu Ser Gly Gly
                 20                  25                  30

Val Val Gln Pro Gly Arg Ser Leu Arg Leu Ser Cys Ala Ala Ser Gly
         35                  40                  45

Phe Thr Phe Arg Ser Tyr Gly Met His Trp Val Arg Gln Ala Pro Gly
     50                  55                  60

Lys Gly Leu Glu Trp Val Ala Val Ile Trp Tyr Asp Gly Ser Lys Lys
 65                  70                  75                  80

Tyr Tyr Ala Asp Ser Val Lys Gly Arg Phe Thr Ile Ser Arg Asp Asn
                 85                  90                  95

Ser Lys Asn Thr Leu Phe Leu Gln Met Asn Ser Leu Arg Ala Glu Asp
            100                 105                 110

Thr Ala Val Tyr Tyr Cys Ala Arg Asp Gly Gly Ile Ala Ala Phe Leu
            115                 120                 125

Gln Asp Asn Trp Phe Asp Pro Trp Gly Gln Gly Thr Leu Val Thr Val
        130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Asn Phe Gly Thr
210                 215                 220

Gln Thr Tyr Thr Cys Asn Val Asp His Lys Pro Ser Asn Thr Lys Val
225                 230                 235                 240

Asp Lys Thr Val Glu Arg Lys Cys Cys Val Glu Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Asn Ser Thr Phe Arg Val Val Ser Val Leu Thr Val Val His Gln
                325                 330                 335

Asp Trp Leu Asn Gly Lys Glu Tyr Lys Cys Lys Val Ser Asn Lys Gly
            340                 345                 350

Leu Pro Ala Pro Ile Glu Lys Thr Ile Ser Lys Thr Lys Gly Gln Pro
        355                 360                 365

Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Met Leu Asp Ser Asp Gly Ser Phe Phe Leu Tyr
            420                 425                 430

Ser Lys Leu Thr Val Asp Lys Ser Arg Trp Gln Gln Gly Asn Val Phe
```

-continued

```
                435                 440                 445
Ser Cys Ser Val Met His Glu Ala Leu His Asn His Tyr Thr Gln Lys
    450                 455                 460
Ser Leu Ser Leu Ser Pro Gly Lys
465                 470

<210> SEQ ID NO 67
<211> LENGTH: 15
<212> TYPE: DNA
<213> ORGANISM: Human

<400> SEQUENCE: 67
agctatggca tgcac                                                          15

<210> SEQ ID NO 68
<211> LENGTH: 5
<212> TYPE: PRT
<213> ORGANISM: Human

<400> SEQUENCE: 68

Ser Tyr Gly Met His
1               5

<210> SEQ ID NO 69
<211> LENGTH: 51
<212> TYPE: DNA
<213> ORGANISM: Human

<400> SEQUENCE: 69
gttatatggt atgatggaag taaaaaatac tatgcagact ccgtgaaggg c                  51

<210> SEQ ID NO 70
<211> LENGTH: 17
<212> TYPE: PRT
<213> ORGANISM: Human

<400> SEQUENCE: 70

Val Ile Trp Tyr Asp Gly Ser Lys Lys Tyr Tyr Ala Asp Ser Val Lys
1               5                   10                  15
Gly

<210> SEQ ID NO 71
<211> LENGTH: 45
<212> TYPE: DNA
<213> ORGANISM: Human

<400> SEQUENCE: 71 gatggggta tagcagcatt tttacaggac aactggttcg acccc                          45

<210> SEQ ID NO 72
<211> LENGTH: 15
<212> TYPE: PRT
<213> ORGANISM: Human

<400> SEQUENCE: 72

Asp Gly Gly Ile Ala Ala Phe Leu Gln Asp Asn Trp Phe Asp Pro
1               5                   10                  15

<210> SEQ ID NO 73
<211> LENGTH: 1416
<212> TYPE: DNA
<213> ORGANISM: Human
```

<400> SEQUENCE: 73

```
atggacatga gggtgcccgc tcagctcctg gggctcctgc tgctgtggct gagaggtgcg      60
cgctgtcagg ggcagctggt ggagtctggg ggaggcgtgg tccagcctgg aggtccctg     120
agactctcct gtgcagcgtc tggattcacc ttcaggagct atggcatgca ctgggtccgc    180
caggctccag gcaaggggct ggagtgggtg gcagttatat ggtatgatgg aagtaaaaaa    240
tactatgcag actccgtgaa gggccgattc accatctcca gagacaattc caagaacacg    300
ctgtatctgc aaatgaacag cctgagagcc gaggacacgg ctgtgtatta ctgtgcgaga    360
gatgggggta tagcagcatt tttacaggac aactggttcg accctgggg ccagggaacc     420
ctggtcaccg tctctagtgc ctccaccaag ggcccatcgg tcttccccct ggcgccctgc    480
tccaggagca cctccgagag cacagcggcc ctgggctgcc tggtcaagga ctacttcccc    540
gaaccggtga cggtgtcgtg aactcaggc gctctgacca gcggcgtgca ccttccca     600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttcccccca aaacccaagg acaccctcat gatctcccgg    840
acccctgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagccccat cgagaaaacc    1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa gaccacacct    1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416
```

<210> SEQ ID NO 74
<211> LENGTH: 472
<212> TYPE: PRT
<213> ORGANISM: Human

<400> SEQUENCE: 74

```
Met Asp Met Arg Val Pro Ala Gln Leu Leu Gly Leu Leu Leu Leu Trp
 1               5                  10                  15

Leu Arg Gly Ala Arg Cys Gln Gly Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Arg Ser Tyr Gly Met His Trp Val Arg Gln Ala Pro Gly
    50                  55                  60

Lys Gly Leu Glu Trp Val Ala Val Ile Trp Tyr Asp Gly Ser Lys Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110
```

```
Thr Ala Val Tyr Tyr Cys Ala Arg Asp Gly Gly Ile Ala Ala Phe Leu
            115                 120                 125
Gln Asp Asn Trp Phe Asp Pro Trp Gly Gln Gly Thr Leu Val Thr Val
130                 135                 140
Ser Ser Ala Ser Thr Lys Gly Pro Ser Val Phe Pro Leu Ala Pro Cys
145                 150                 155                 160
Ser Arg Ser Thr Ser Glu Ser Thr Ala Ala Leu Gly Cys Leu Val Lys
                165                 170                 175
Asp Tyr Phe Pro Glu Pro Val Thr Val Ser Trp Asn Ser Gly Ala Leu
            180                 185                 190
Thr Ser Gly Val His Thr Phe Pro Ala Val Leu Gln Ser Ser Gly Leu
        195                 200                 205
Tyr Ser Leu Ser Ser Val Val Thr Val Pro Ser Ser Asn Phe Gly Thr
    210                 215                 220
Gln Thr Tyr Thr Cys Asn Val Asp His Lys Pro Ser Asn Thr Lys Val
225                 230                 235                 240
Asp Lys Thr Val Glu Arg Lys Cys Cys Val Glu Cys Pro Pro Cys Pro
                245                 250                 255
Ala Pro Pro Val Ala Gly Pro Ser Val Phe Leu Phe Pro Pro Lys Pro
            260                 265                 270
Lys Asp Thr Leu Met Ile Ser Arg Thr Pro Glu Val Thr Cys Val Val
        275                 280                 285
Val Asp Val Ser His Glu Asp Pro Glu Val Gln Phe Asn Trp Tyr Val
    290                 295                 300
Asp Gly Val Glu Val His Asn Ala Lys Thr Lys Pro Arg Glu Glu Gln
305                 310                 315                 320
Phe Asn Ser Thr Phe Arg Val Val Ser Val Leu Thr Val Val His Gln
                325                 330                 335
Asp Trp Leu Asn Gly Lys Glu Tyr Lys Cys Lys Val Ser Asn Lys Gly
            340                 345                 350
Leu Pro Ala Pro Ile Glu Lys Thr Ile Ser Lys Thr Lys Gly Gln Pro
        355                 360                 365
Arg Glu Pro Gln Val Tyr Thr Leu Pro Pro Ser Arg Glu Glu Met Thr
    370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Met Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
    450                 455                 460
Ser Leu Ser Leu Ser Pro Gly Lys
465                 470
```

<210> SEQ ID NO 75
<211> LENGTH: 15
<212> TYPE: DNA
<213> ORGANISM: Human

<400> SEQUENCE: 75
agctatggca tgcac                                                15

<210> SEQ ID NO 76
<211> LENGTH: 5
<212> TYPE: PRT
<213> ORGANISM: Human

<400> SEQUENCE: 76

Ser Tyr Gly Met His
1               5

<210> SEQ ID NO 77
<211> LENGTH: 51
<212> TYPE: DNA
<213> ORGANISM: Human

<400> SEQUENCE: 77
gttatatggt atgatggaag taaaaaatac tatgcagact ccgtgaaggg c        51

<210> SEQ ID NO 78
<211> LENGTH: 17
<212> TYPE: PRT
<213> ORGANISM: Human

<400> SEQUENCE: 78

Val Ile Trp Tyr Asp Gly Ser Lys Lys Tyr Tyr Ala Asp Ser Val Lys
1               5                   10                  15
Gly

<210> SEQ ID NO 79
<211> LENGTH: 45
<212> TYPE: DNA
<213> ORGANISM: Human

<400> SEQUENCE: 79
gatgggggta tagcagcatt tttacaggac aactggttcg acccc             45

<210> SEQ ID NO 80
<211> LENGTH: 15
<212> TYPE: PRT
<213> ORGANISM: Human

<400> SEQUENCE: 80

Asp Gly Gly Ile Ala Ala Phe Leu Gln Asp Asn Trp Phe Asp Pro
1               5                   10                  15

<210> SEQ ID NO 81
<211> LENGTH: 1416
<212> TYPE: DNA
<213> ORGANISM: Human

<400> SEQUENCE: 81
atggacatga gggtgcccgc tcagctcctg ggctcctgc tgctgtggct gagaggtgcg      60
cgctgtcagg tgcagctggt ggagtctggg ggaggcgtgg tccagcctgg gaggtccctg    120
agactctcct gtgcagcgtc tggattcacc ttcaggagct atggcatgca ctgggtccgc    180
caggctccag gcaagggget ggagtgggtg gcagttatat ggtatgatgg aagtaaaaaa    240
tactatgcag actccgtgaa gggccgattc accatctcca gagacaattc caagaacacg    300
ctgtatctgc aaatgaacag cctgagagcc gaggacacgg ctgtgtatta ctgtgcgaga    360
gatgggggta tagcagcatt tttacaggac aactggttcg accccctgggg ccagggaacc    420 ctggtcaccg tctctagtgc ctccaccaag ggcccatcgg tcttcccccct ggcgccctgc    480

```
tccaggagca cctccgagag cacagcggcc ctgggctgcc tggtcaagga ctacttcccc    540
gaaccggtga cggtgtcgtg gaactcaggc gctctgacca gcggcgtgca caccttccca    600
gctgtcctac agtcctcagg actctactcc ctcagcagcg tggtgaccgt gccctccagc    660
aacttcggca cccagaccta cacctgcaac gtagatcaca agcccagcaa caccaaggtg    720
gacaagacag ttgagcgcaa atgttgtgtc gagtgcccac cgtgcccagc accacctgtg    780
gcaggaccgt cagtcttcct cttccccca  aaacccaagg acaccctcat gatctcccgg    840
accccctgagg tcacgtgcgt ggtggtggac gtgagccacg aagaccccga ggtccagttc    900
aactggtacg tggacggcgt ggaggtgcat aatgccaaga caaagccacg ggaggagcag    960
ttcaacagca cgttccgtgt ggtcagcgtc ctcaccgttg tgcaccagga ctggctgaac   1020
ggcaaggagt acaagtgcaa ggtctccaac aaaggcctcc cagcccccat cgagaaaacc   1080
atctccaaaa ccaaagggca gccccgagaa ccacaggtgt acaccctgcc cccatcccgg   1140
gaggagatga ccaagaacca ggtcagcctg acctgcctgg tcaaaggctt ctaccccagc   1200
gacatcgccg tggagtggga gagcaatggg cagccggaga caactacaa  gaccacacct   1260
cccatgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416
```

<210> SEQ ID NO 82
<211> LENGTH: 472
<212> TYPE: PRT
<213> ORGANISM: Human

<400> SEQUENCE: 82

```
Met Asp Met Arg Val Pro Ala Gln Leu Leu Gly Leu Leu Leu Leu Trp
1               5                   10                  15

Leu Arg Gly Ala Arg Cys Gln Val Gln Leu Val Glu Ser Gly Gly Gly
            20                  25                  30

Val Val Gln Pro Gly Arg Ser Leu Arg Leu Ser Cys Ala Ala Ser Gly
        35                  40                  45

Phe Thr Phe Arg Ser Tyr Gly Met His Trp Val Arg Gln Ala Pro Gly
    50                  55                  60

Lys Gly Leu Glu Trp Val Ala Val Ile Trp Tyr Asp Gly Ser Lys Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Gly Gly Ile Ala Ala Phe Leu
        115                 120                 125

Gln Asp Asn Trp Phe Asp Pro Trp Gly Gln Gly Thr Leu Val Thr Val
    130                 135                 140

Ser Ser Ala Ser Thr Lys Gly Pro Ser Val Phe Pro Leu Ala Pro Cys
145                 150                 155                 160

Ser Arg Ser Thr Ser Glu Ser Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205
```

-continued

```
Tyr Ser Leu Ser Ser Val Val Thr Val Pro Ser Ser Asn Phe Gly Thr
    210                 215                 220
Gln Thr Tyr Thr Cys Asn Val Asp His Lys Pro Ser Asn Thr Lys Val
225                 230                 235                 240
Asp Lys Thr Val Glu Arg Lys Cys Cys Val Glu Cys Pro Pro Cys Pro
                245                 250                 255
Ala Pro Pro Val Ala Gly Pro Ser Val Phe Leu Phe Pro Pro Lys Pro
                260                 265                 270
Lys Asp Thr Leu Met Ile Ser Arg Thr Pro Glu Val Thr Cys Val Val
            275                 280                 285
Val Asp Val Ser His Glu Asp Pro Glu Val Gln Phe Asn Trp Tyr Val
290                 295                 300
Asp Gly Val Glu Val His Asn Ala Lys Thr Lys Pro Arg Glu Glu Gln
305                 310                 315                 320
Phe Asn Ser Thr Phe Arg Val Val Ser Val Leu Thr Val Val His Gln
                325                 330                 335
Asp Trp Leu Asn Gly Lys Glu Tyr Lys Cys Lys Val Ser Asn Lys Gly
            340                 345                 350
Leu Pro Ala Pro Ile Glu Lys Thr Ile Ser Lys Thr Lys Gly Gln Pro
            355                 360                 365
Arg Glu Pro Gln Val Tyr Thr Leu Pro Pro Ser Arg Glu Glu Met Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Met Leu Asp Ser Asp Gly Ser Phe Phe Leu Tyr
            420                 425                 430
Ser Lys Leu Thr Val Asp Lys Ser Arg Trp Gln Gln Gly Asn Val Phe
            435                 440                 445
Ser Cys Ser Val Met His Glu Ala Leu His Asn His Tyr Thr Gln Lys
        450                 455                 460
Ser Leu Ser Leu Ser Pro Gly Lys
465                 470

<210> SEQ ID NO 83
<211> LENGTH: 15
<212> TYPE: DNA
<213> ORGANISM: Human

<400> SEQUENCE: 83
agctatggca tgcac                                                    15

<210> SEQ ID NO 84
<211> LENGTH: 5
<212> TYPE: PRT
<213> ORGANISM: Human

<400> SEQUENCE: 84

Ser Tyr Gly Met His
1               5

<210> SEQ ID NO 85
<211> LENGTH: 51
<212> TYPE: DNA
<213> ORGANISM: Human

<400> SEQUENCE: 85
```

```
gttatatggt atgatggaag taaaaaatac tatgcagact ccgtgaaggg c         51
```

<210> SEQ ID NO 86
<211> LENGTH: 17
<212> TYPE: PRT
<213> ORGANISM: Human

<400> SEQUENCE: 86

Val Ile Trp Tyr Asp Gly Ser Lys Lys Tyr Tyr Ala Asp Ser Val Lys
1               5                   10                  15

Gly

<210> SEQ ID NO 87
<211> LENGTH: 45
<212> TYPE: DNA
<213> ORGANISM: Human

<400> SEQUENCE: 87

```
gatgggggta tagcagcatt tttacaggac aactggttcg accccc             45
```

<210> SEQ ID NO 88
<211> LENGTH: 15
<212> TYPE: PRT
<213> ORGANISM: Human

<400> SEQUENCE: 88

Asp Gly Gly Ile Ala Ala Phe Leu Gln Asp Asn Trp Phe Asp Pro
1               5                   10                  15

<210> SEQ ID NO 89
<211> LENGTH: 990
<212> TYPE: DNA
<213> ORGANISM: Human

<400> SEQUENCE: 89

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccatcca gcagcttggg cacccagacc   240
tacatctgca acgtgaatca caagcccagc aacaccaagg tggacaagaa agttgagccc   300
aaatcttgtg acaaaactca cacatgccca ccgtgcccag cacctgaact cgcggggggca   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                     990
```

<210> SEQ ID NO 90
<211> LENGTH: 330
<212> TYPE: PRT
<213> ORGANISM: Human

<400> SEQUENCE: 90

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 91
<211> LENGTH: 708
<212> TYPE: DNA
<213> ORGANISM: Artificial Sequence
<220> FEATURE:
<223> OTHER INFORMATION: Antibody Sequence

<400> SEQUENCE: 91

```
atggacatga gggtgcccgc tcagctcctg gggctcctgc tgctgtggct gagaggtgcg      60
cgctgtgaca tccagatgac ccagagccca tctagtctct ctgcttccgt gggagatcgg    120
gttaccatta catgtagggc ctctcaagac attgggtcaa atctgaattg gtatcagcag    180
aaacccgaga agcacccaa atctctgatc tatgctacat cttctctgga ttccggggtc     240
ccctcacggt tctccggttc agggagcgga accgacttca cgcttacaat ctcaagcctt    300
cagccagagg attttgctac ctactactgt ctgcagtatg ccacaagccc tctcacattt    360
gggcagggaa ccaaggtcga gattaagcgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac     540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                 708
```

<210> SEQ ID NO 92
<211> LENGTH: 236
<212> TYPE: PRT
<213> ORGANISM: Artificial Sequence
<220> FEATURE:
<223> OTHER INFORMATION: Antibody Sequence

<400> SEQUENCE: 92

```
Met Asp Met Arg Val Pro Ala Gln Leu Leu Gly Leu Leu Leu Leu Trp
  1               5                  10                  15
Leu Arg Gly Ala Arg Cys Asp Ile Gln Met Thr Gln Ser Pro Ser Ser
                 20                  25                  30
Leu Ser Ala Ser Val Gly Asp Arg Val Thr Ile Thr Cys Arg Ala Ser
             35                  40                  45
Gln Asp Ile Gly Ser Asn Leu Asn Trp Tyr Gln Lys Pro Glu Lys
 50                  55                  60
Ala Pro Lys Ser Leu Ile Tyr Ala Thr Ser Ser Leu Asp Ser Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Leu Gln
            100                 105                 110
Tyr Ala Thr Ser Pro Leu Thr Phe Gly Gln Gly Thr Lys Val Glu Ile
            115                 120                 125
Lys Arg Thr Val Ala Ala Pro Ser Val Phe Ile Phe Pro Pro Ser Asp
130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
            195                 200                 205
Glu Lys His Lys Val Tyr Ala Cys Glu Val Thr His Gln Gly Leu Ser
        210                 215                 220
Ser Pro Val Thr Lys Ser Phe Asn Arg Gly Glu Cys
```

<210> SEQ ID NO 93
<211> LENGTH: 708
<212> TYPE: DNA
<213> ORGANISM: Artificial Sequence
<220> FEATURE:
<223> OTHER INFORMATION: Antibody Sequence

<400> SEQUENCE: 93

```
atggacatga gggtgcccgc tcagctcctg gggctcctgc tgctgtggct gagaggtgcg      60
cgctgtgaca tccagatgac ccagagccca tctagtctct ctgcttccgt gggagatcgg     120
gttaccatta catgtagggc ctctcaagac attgggtcaa atctgaattg gcttcaacag     180
acatcagatg gaagtattaa acgcctgatc tacgctacat cttctctgga ttccggggtc     240
ccctcacggt tctccggttc agggagcgga accgacttca cgcttacaat ctcaagcctt     300
cagccagagg attttgctac ctactactgt ctgcagtatg ccacaagccc tctcacattt     360
gggcagggaa ccaaggtcga gattaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcaccccat    660
cagggcctga gctcgcccgt cacaaagagc ttcaacaggg gagagtgt                   708
```

<210> SEQ ID NO 94
<211> LENGTH: 236
<212> TYPE: PRT
<213> ORGANISM: Artificial Sequence
<220> FEATURE:
<223> OTHER INFORMATION: Antibody Sequence

<400> SEQUENCE: 94

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Gly Ser Asn Leu Asn Trp Leu Gln Gln Thr Ser Asp Gly
    50                  55                  60

Ser Ile Lys Arg Leu Ile Tyr Ala Thr Ser Ser Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175
```

Gln Ser Gly Asn Ser Gln Glu Ser Val Thr Glu Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 95
<211> LENGTH: 708
<212> TYPE: DNA
<213> ORGANISM: Artificial Sequence
<220> FEATURE:
<223> OTHER INFORMATION: Antibody Sequence

<400> SEQUENCE: 95

```
atggacatga gggtgcccgc tcagctcctg gggctcctgc tgctgtggct gagaggtgcg    60
cgctgtgaca tccagatgac ccagagccca tctagtctct ctgcttccgt gggagatcgg   120
gttaccatta catgtagggc ctctcaagac attgggtcaa atctgaattg gctccagcag   180
aaacccgaga agcacccaa atctctgatc tatgctacat cttctctgga ttccggggtc    240
ccctcacggt tctccggttc agggagcgga accgacttca cgcttacaat ctcaagcctt   300
cagccagagg attttgctac ctactactgt ctgcagtatg ccacaagccc tctcacattt   360
gggcagggaa ccaaggtcga gattaagcgt acggtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
tcccaggaga gtgtcacaga gcaggacagc aaggacagca cctacagcct cagcagcacc   600
ctgacgctga gcaaagcaga ctacgagaaa cacaaagtct acgcctgcga agtcacccat   660
cagggcctga gctcgcccgt cacaaagagc ttcaacaggg gagagtgt               708
```

<210> SEQ ID NO 96
<211> LENGTH: 236
<212> TYPE: PRT
<213> ORGANISM: Artificial Sequence
<220> FEATURE:
<223> OTHER INFORMATION: Antibody Sequence

<400> SEQUENCE: 96

Met Asp Met Arg Val Pro Ala Gln Leu Leu Gly Leu Leu Leu Leu Trp
1               5                  10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Gly Ser Asn Leu Asn Trp Leu Gln Gln Lys Pro Glu Lys
    50                  55                  60

Ala Pro Lys Ser Leu Ile Tyr Ala Thr Ser Ser Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
        115                 120                 125

```
Lys Arg Thr Val Ala Ala Pro Ser Val Phe Ile Phe Pro Pro Ser Asp
        130                 135                 140
Glu Gln Leu Lys Ser Gly Thr Ala Ser Val Val Cys Leu Leu Asn Asn
145                 150                 155                 160
Phe Tyr Pro Arg Glu Ala Lys Val Gln Trp Lys Val Asp Asn Ala Leu
                165                 170                 175
Gln Ser Gly Asn Ser Gln Glu Ser Val Thr Glu Gln Asp Ser Lys Asp
            180                 185                 190
Ser Thr Tyr Ser Leu Ser Ser Thr Leu Thr Leu Ser Lys Ala Asp Tyr
        195                 200                 205
Glu Lys His Lys Val Tyr Ala Cys Glu Val Thr His Gln Gly Leu Ser
    210                 215                 220
Ser Pro Val Thr Lys Ser Phe Asn Arg Gly Glu Cys
225                 230                 235
```

<210> SEQ ID NO 97
<211> LENGTH: 708
<212> TYPE: DNA
<213> ORGANISM: Artificial Sequence
<220> FEATURE:
<223> OTHER INFORMATION: Antibody Sequence

<400> SEQUENCE: 97

```
atggacatga gggtgcccgc tcagctcctg gggctcctgc tgctgtggct gagaggtgcg      60
cgctgtgaca tccagatgac ccagagccca tctagtctct ctgcttccgt gggagatcgg     120
gttaccatta catgtagggc ctctcaagac attgggtcaa atctgaattg gtatcagcag     180
aaacccgaga agcacccaa aagactgatc tatgctacat cttctctgga ttccggggtc      240
ccctcacggt tctccggttc agggagcgga accgacttca cgcttacaat ctcaagcctt     300
cagccagagg attttgctac ctactactgt ctgcagtatg ccacaagccc tctcacattt     360
gggcagggaa ccaaggtcga gattaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac      540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708
```

<210> SEQ ID NO 98
<211> LENGTH: 236
<212> TYPE: PRT
<213> ORGANISM: Artificial Sequence
<220> FEATURE:
<223> OTHER INFORMATION: Anitbody Sequence

<400> SEQUENCE: 98

```
Met Asp Met Arg Val Pro Ala Gln Leu Leu Gly Leu Leu Leu Leu Trp
1               5                   10                  15
Leu Arg Gly Ala Arg Cys Asp Ile Gln Met Thr Gln Ser Pro Ser Ser
            20                  25                  30
Leu Ser Ala Ser Val Gly Asp Arg Val Thr Ile Thr Cys Arg Ala Ser
        35                  40                  45
Gln Asp Ile Gly Ser Asn Leu Asn Trp Tyr Gln Gln Lys Pro Glu Lys
    50                  55                  60
Ala Pro Lys Arg Leu Ile Tyr Ala Thr Ser Ser Leu Asp Ser Gly Val
```

Pro Ser Arg Phe Ser Gly Ser Gly Ser Gly Thr Asp Phe Thr Leu Thr
    65                  70                  75                  80

Ile Ser Ser Leu Gln Pro Glu Asp Phe Ala Thr Tyr Tyr Cys Leu Gln
                85                  90                  95

Tyr Ala Thr Ser Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

225                 230                 235

<210> SEQ ID NO 99
<211> LENGTH: 708
<212> TYPE: DNA
<213> ORGANISM: Artificial Sequence
<220> FEATURE:
<223> OTHER INFORMATION: Antibody Sequence

<400> SEQUENCE: 99
atggacatga gggtgcccgc tcagctcctg gggctcctgc tgctgtggct gagaggtgcg      60
cgctgtgaca tccagatgac ccagagccca tctagtctct ctgcttccgt gggagatcgg     120
gttaccatta catgtagggc ctctcaagac attgggtcaa atctgaattg gctccagcag     180
aaacccgaga agcacccaa aagactgatc tatgctacat cttctctgga ttccggggtc      240
ccctcacggt tctccggttc agggagcgga accgacttca cgcttacaat ctcaagcctt     300
cagccagagg attttgctac ctactactgt ctgcagtatg ccacaagccc tctcacattt     360
gggcagggaa ccaaggtcga gattaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgcctcca atcgggtaac      540 tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                  708

<210> SEQ ID NO 100
<211> LENGTH: 236
<212> TYPE: PRT
<213> ORGANISM: Artificial Sequence
<220> FEATURE:
<223> OTHER INFORMATION: Antibody Sequence

<400> SEQUENCE: 100

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
            35                  40                  45

Gln Asp Ile Gly Ser Asn Leu Asn Trp Leu Gln Gln Lys Pro Glu Lys
50                  55                  60

Ala Pro Lys Arg Leu Ile Tyr Ala Thr Ser Ser Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 101
<211> LENGTH: 708
<212> TYPE: DNA
<213> ORGANISM: Artificial Sequence
<220> FEATURE:
<223> OTHER INFORMATION: Antibody Sequence

<400> SEQUENCE: 101

```
atggacatga gggtgcccgc tcagctcctg gggctcctgc tgctgtggct gagaggtgcg      60
cgctgtgaca tccagatgac ccagagccca tctagtctct ctgcttccgt gggagatcgg     120
gttaccatta catgtagggc ctctcaagac attgggtcaa atctgaattg ctccagcag      180
aaacccggca agcacccaa aagactgatc tatgctacat cttctctgga ttccggggtc     240
ccctcacggt tctccggttc agggagcgga accgacttca cgcttacaat ctcaagcctt     300
cagccagagg attttgctac ctactactgt ctgcagtatg ccacaagccc tctcacattt     360
gggcagggaa ccaaggtcga gattaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac      540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgt                   708
```

<210> SEQ ID NO 102
<211> LENGTH: 236

```
<212> TYPE: PRT
<213> ORGANISM: Artificial Sequence
<220> FEATURE:
<223> OTHER INFORMATION: Antibody Sequence

<400> SEQUENCE: 102

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Gly Ser Asn Leu Asn Trp Leu Gln Gln Lys Pro Gly Lys
    50                  55                  60

Ala Pro Lys Arg Leu Ile Tyr Ala Thr Ser Ser Leu Asp Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 103
<211> LENGTH: 708
<212> TYPE: DNA
<213> ORGANISM: Artificial Sequence
<220> FEATURE:
<223> OTHER INFORMATION: Antibody Sequence

<400> SEQUENCE: 103
atggacatga gggtgcccgc tcagctcctg gggctcctgc tgctgtggct gagaggtgcg    60
cgctgtgaca tccagatgac ccagagccca tctagtctct ctgcttccgt gggagatcgg   120
gttaccatta catgtagggc ctctcaagac attgggtcaa atctgaattg gctccagcag   180
aaacccgaga agcacccaa aagactgatc tatgctacat cttctctgga ttccggggtc   240
ccctcacggt tctccggttc acggagcgga agcgactata cgcttacaat ctcaagcctt   300
cagccagagg attttgctac ctactactgt ctgcagtatg ccacaagccc tctcacattt   360
gggcagggaa ccaaggtcga gattaagcgt acgtggctg caccatctgt cttcatcttc   420
ccgccatctg atgagcagtt gaaatctgga actgcctctg ttgtgtgcct gctgaataac   480
ttctatccca gagaggccaa agtacagtgg aaggtggata acgccctcca atcgggtaac   540
```

```
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgt                708
```

<210> SEQ ID NO 104
<211> LENGTH: 236
<212> TYPE: PRT
<213> ORGANISM: Artificial Sequence
<220> FEATURE:
<223> OTHER INFORMATION: Antibody Sequence

<400> SEQUENCE: 104

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Gly Ser Asn Leu Asn Trp Leu Gln Gln Lys Pro Glu Lys
    50                  55                  60

Ala Pro Lys Arg Leu Ile Tyr Ala Thr Ser Ser Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 105
<211> LENGTH: 708
<212> TYPE: DNA
<213> ORGANISM: Artificial Sequence
<220> FEATURE:
<223> OTHER INFORMATION: Antibody Sequence

<400> SEQUENCE: 105

```
atggacatga gggtgcccgc tcagctcctg gggctcctgc tgctgtggct gagaggtgcg    60
cgctgtgaca tccagatgac ccagagccca tctagtctct ctgcttccgt gggagatcgg   120
gttaccatta catgtagggc ctctcaagac attgggtcaa atctgaattg gctccagcag   180
aaacccggca agcacccaa aagactgatc tatgctacat cttctctgga ttccggggtc   240
```

```
ccctcacggt tctccggttc acggagcgga agcgactata cgcttacaat ctcaagcctt      300
cagccagagg attttgctac ctactactgt ctgcagtatg ccacaagccc tctcacattt      360
gggcagggaa ccaaggtcga gattaagcgt acggtggctg caccatctgt cttcatcttc      420
ccgccatctg atgagcagtt gaaatctgga actgcctctg ttgtgtgcct gctgaataac      480
ttctatccca gagaggccaa agtacagtgg aaggtggata cgccctcca atcgggtaac       540 tcccaggaga gtgtcacaga gcaggacagc aaggacagca cctacagcct cagcagcacc      600
ctgacgctga gcaaagcaga ctacgagaaa cacaaagtct acgcctgcga agtcacccat      660
cagggcctga gctcgcccgt cacaaagagc ttcaacaggg gagagtgt                   708
```

<210> SEQ ID NO 106
<211> LENGTH: 236
<212> TYPE: PRT
<213> ORGANISM: Artificial Sequence
<220> FEATURE:
<223> OTHER INFORMATION: Antibody Sequence

<400> SEQUENCE: 106

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Gly Ser Asn Leu Asn Trp Leu Gln Lys Pro Gly Lys
    50                  55                  60

Ala Pro Lys Arg Leu Ile Tyr Ala Thr Ser Ser Leu Asp Ser Gly Val
65                  70                  75                  80

Pro Ser Arg Phe Ser Gly Ser Arg Ser Gly Ser Asp Tyr Thr Leu Thr
                85                  90                  95

Ile Ser Ser Leu Gln Pro Glu Asp Phe Ala Thr Tyr Tyr Cys Leu Gln
            100                 105                 110

Tyr Ala Thr Ser Pro Leu Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 107
<211> LENGTH: 1410
<212> TYPE: DNA
<213> ORGANISM: Artificial Sequence
<220> FEATURE:
<223> OTHER INFORMATION: Antibody Sequence

```
<400> SEQUENCE: 107
atggacatga gggtgcccgc tcagctcctg gggctcctgc tgctgtggct gagaggtgcg      60
cgctgtgaag tgcagcttgt ggagagcggt ggcggtctgg tgaagcccgg aggctcattg     120
agactctcat gcgccgcctc cggtttctct ttctcacgct atgcaatgac ttgggtgcgc     180
caggcccctg gtaaagggct ggaatgggtg tctacgatct ccgatggcgg ctcatatacg     240
tactatccag actcagagaa gaatagattc actatcagca gagacaatgc caagaacagc     300
ctctatctcc aaatgaatag tctgagggcc gaagatacag ccgtctatta ctgcgcacgg     360
cgggccgggc atatggtgac gacagatgcc atggattact ggggccaagg aaccatggtg     420
accgtctcta gtgcctccac caagggccca tcggtcttcc ccctggcgcc ctgctccagg     480
agcacctccg agagcacagc ggccctgggc tgcctggtca aggactactt ccccgaaccg     540
gtgacggtgt cgtggaactc aggcgctctg accagcggcg tgcacacctt cccagctgtc     600
ctacagtcct caggactcta ctccctcagc agcgtggtga ccgtgccctc cagcaacttc     660
ggcacccaga cctacacctg caacgtagat cacaagccca gcaacaccaa ggtggacaag     720
acagttgagc gcaaatgttg tgtcgagtgc ccaccgtgcc cagcaccacc tgtggcagga     780
ccgtcagtct tcctcttccc cccaaaaccc aaggacaccc tcatgatctc ccggacccct     840
gaggtcacgt gcgtggtggt ggacgtgagc acgaagacc ccgaggtcca gttcaactgg     900
tacgtggacg gcgtggaggt gcataatgcc aagacaaagc cacgggagga gcagttcaac     960
agcacgttcc gtgtggtcag cgtcctcacc gttgtgcacc aggactggct gaacggcaag    1020
gagtacaagt gcaaggtctc caacaaaggc ctcccagccc ccatcgagaa aaccatctcc    1080
aaaaccaaag ggcagccccg agaaccacag gtgtacaccc tgcccccatc ccgggaggag    1140
atgaccaaga accaggtcag cctgacctgc ctggtcaaag gcttctaccc cagcgacatc    1200
gccgtggagt gggagagcaa tgggcagccg gagaacaact acaagaccac acctcccatg    1260
ctggactccg acggctcctt cttcctctac agcaagctca ccgtggacaa gagcaggtgg    1320
cagcagggga acgtcttctc atgctccgtg atgcatgagg ctctgcacaa ccactacacg    1380
cagaagagcc tctccctgtc tccgggtaaa                                     1410

<210> SEQ ID NO 108
<211> LENGTH: 470
<212> TYPE: PRT
<213> ORGANISM: Artificial Sequence
<220> FEATURE:
<223> OTHER INFORMATION: Antibody Sequence

<400> SEQUENCE: 108

Met Asp Met Arg Val Pro Ala Gln Leu Leu Gly Leu Leu Leu Leu Trp
1               5                   10                  15

Leu Arg Gly Ala Arg Cys Glu Val Gln Leu Val Glu Ser Gly Gly Gly
            20                  25                  30

Leu Val Lys Pro Gly Gly Ser Leu Arg Leu Ser Cys Ala Ala Ser Gly
        35                  40                  45

Phe Ser Phe Ser Arg Tyr Ala Met Thr Trp Val Arg Gln Ala Pro Gly
    50                  55                  60

Lys Gly Leu Glu Trp Val Ser Thr Ile Ser Asp Gly Gly Ser Tyr Thr
65                  70                  75                  80

Tyr Tyr Pro Asp Ser Glu Lys Asn Arg Phe Thr Ile Ser Arg Asp Asn
                85                  90                  95
```

```
Ala Lys Asn Ser Leu Tyr Leu Gln Met Asn Ser Leu Arg Ala Glu Asp
            100                 105                 110

Thr Ala Val Tyr Tyr Cys Ala Arg Arg Ala Gly His Met Val Thr Thr
        115                 120                 125

Asp Ala Met Asp Tyr Trp Gly Gln Gly Thr Met Val Thr Val Ser Ser
130                 135                 140

Ala Ser Thr Lys Gly Pro Ser Val Phe Pro Leu Ala Pro Cys Ser Arg
145                 150                 155                 160

Ser Thr Ser Glu Ser Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Asn Phe Gly Thr Gln Thr
210                 215                 220

Tyr Thr Cys Asn Val Asp His Lys Pro Ser Asn Thr Lys Val Asp Lys
225                 230                 235                 240

Thr Val Glu Arg Lys Cys Cys Val Glu Cys Pro Pro Cys Pro Ala Pro
                245                 250                 255

Pro Val Ala Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Gln Phe Asn Trp Tyr Val Asp Gly
290                 295                 300

Val Glu Val His Asn Ala Lys Thr Lys Pro Arg Glu Glu Gln Phe Asn
305                 310                 315                 320

Ser Thr Phe Arg Val Val Ser Val Leu Thr Val Val His Gln Asp Trp
                325                 330                 335

Leu Asn Gly Lys Glu Tyr Lys Cys Lys Val Ser Asn Lys Gly Leu Pro
            340                 345                 350

Ala Pro Ile Glu Lys Thr Ile Ser Lys Thr Lys Gly Gln Pro Arg Glu
        355                 360                 365

Pro Gln Val Tyr Thr Leu Pro Pro Ser Arg Glu Glu Met Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Met Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
450                 455                 460

Ser Leu Ser Pro Gly Lys
465                 470

<210> SEQ ID NO 109
<211> LENGTH: 378
<212> TYPE: PRT
<213> ORGANISM: Human

<400> SEQUENCE: 109
```

Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
            35                  40                  45

Ser Lys Lys Asp Val Arg Asn Phe Lys Ala Trp Phe Leu Pro Ile Met
50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Lys Ser Trp Val Phe Gly Val His Phe
            115                 120                 125

Cys Lys Leu Ile Phe Ala Ile Tyr Lys Met Ser Phe Phe Ser Gly Met
130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
                195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
            245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
            325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
370                 375

<210> SEQ ID NO 110
<211> LENGTH: 35
<212> TYPE: DNA
<213> ORGANISM: Artificial Sequence
<220> FEATURE:

<223> OTHER INFORMATION: Synthetic Oligo

<400> SEQUENCE: 110
gacgattaca tcggagagaa caccacagtg gacta                              35

<210> SEQ ID NO 111
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 111
tagtccactg tggtgttctc tccgatgtaa tcgtc                              35

<210> SEQ ID NO 112
<211> LENGTH: 42
<212> TYPE: DNA
<213> ORGANISM: Artificial Sequence
<220> FEATURE:
<223> OTHER INFORMATION: Synthetic Oligo

<400> SEQUENCE: 112
cacagtggac tacactttgt atgagtcttt gtgctccaag aa                      42

<210> SEQ ID NO 113
<211> LENGTH: 42
<212> TYPE: DNA
<213> ORGANISM: Artificial Sequence
<220> FEATURE:
<223> OTHER INFORMATION: Synthetic Oligo

<400> SEQUENCE: 113
ttcttggagc acaaagactc atacaaagtg tagtccactg tg                      42

<210> SEQ ID NO 114
<211> LENGTH: 36
<212> TYPE: DNA
<213> ORGANISM: Artificial Sequence
<220> FEATURE:
<223> OTHER INFORMATION: Synthetic Oligo

<400> SEQUENCE: 114
tggactacac tttgttcgag tctgtgtgct ccaaga                             36

<210> SEQ ID NO 115
<211> LENGTH: 36
<212> TYPE: DNA
<213> ORGANISM: Artificial Sequence
<220> FEATURE:
<223> OTHER INFORMATION: Synthetic Oligo

<400> SEQUENCE: 115
tcttggagca cacagactcg aacaaagtgt agtcca                             36

<210> SEQ ID NO 116
<211> LENGTH: 36
<212> TYPE: DNA
<213> ORGANISM: Artificial Sequence
<220> FEATURE:
<223> OTHER INFORMATION: Synthetic Oligo

<400> SEQUENCE: 116
tcttggagca cacagactcg aacaaagtgt agtcca                             36

```
<210> SEQ ID NO 117
<211> LENGTH: 33
<212> TYPE: DNA
<213> ORGANISM: Artificial Sequence
<220> FEATURE:
<223> OTHER INFORMATION: Synthetic Oligo

<400> SEQUENCE: 117
ccgcacgtcc ttcttgaagc acaaagactc gaa                          33

<210> SEQ ID NO 118
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 118
gggcctacag cgaggccaag tcctg                                   25

<210> SEQ ID NO 119
<211> LENGTH: 25
<212> TYPE: DNA
<213> ORGANISM: Artificial Sequence
<220> FEATURE:
<223> OTHER INFORMATION: Synthetic Oligo

<400> SEQUENCE: 119
caggacttgg cctcgctgta ggccc                                   25

<210> SEQ ID NO 120
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 120
cggccaagtc ctggatcttc ggtgtccac                               29

<210> SEQ ID NO 121
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 121
gtggacaccg aagatccagg acttggccg                               29

<210> SEQ ID NO 122
<211> LENGTH: 41
<212> TYPE: DNA
<213> ORGANISM: Artificial Sequence
<220> FEATURE:
<223> OTHER INFORMATION: Synthetic Oligo

<400> SEQUENCE: 122
gtcctgggtc ttcggtgtct atttttgcaa gctcatcttt g                 41

<210> SEQ ID NO 123
<211> LENGTH: 41
<212> TYPE: DNA
<213> ORGANISM: Artificial Sequence
<220> FEATURE:
<223> OTHER INFORMATION: Synthetic Oligo
```

<400> SEQUENCE: 123
caaagatgag cttgcaaaaa tagacaccga agacccagga c                    41

<210> SEQ ID NO 124
<211> LENGTH: 34
<212> TYPE: DNA
<213> ORGANISM: Artificial Sequence
<220> FEATURE:
<223> OTHER INFORMATION: Synthetic Oligo

<400> SEQUENCE: 124
gggtcttcgg tgtccactta tgcaagctca tctt                            34

<210> SEQ ID NO 125
<211> LENGTH: 34
<212> TYPE: DNA
<213> ORGANISM: Artificial Sequence
<220> FEATURE:
<223> OTHER INFORMATION: Synthetic Oligo

<400> SEQUENCE: 125
aagatgagct tgcataagtg gacaccgaag accc                            34

<210> SEQ ID NO 126
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 126
gctcctgtac agtggcctcc agaggagca                                  29

<210> SEQ ID NO 127
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 127
tgctcctctg gaggccactg tacaggagc                                  29

<210> SEQ ID NO 128
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 128
cagtgacctc cagaagagca gcagtgagc                                  29

<210> SEQ ID NO 129
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 129
gctcactgct gctcttctgg aggtcactg                                  29

<210> SEQ ID NO 130
<211> LENGTH: 31

```
<212> TYPE: DNA
<213> ORGANISM: Artificial Sequence
<220> FEATURE:
<223> OTHER INFORMATION: Synthetic Oligo

<400> SEQUENCE: 130
gtgacctcca gaggaacagc agtgagcaag c                                  31

<210> SEQ ID NO 131
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 131
gcttgctcac tgctgttcct ctggaggtca c                                  31

<210> SEQ ID NO 132
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 132
tccagaggag cagcggtgag caagcgatg                                     29

<210> SEQ ID NO 133
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 133
catcgcttgc tcaccgctgc tcctctgga                                     29

<210> SEQ ID NO 134
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 134
ggagcagcag tgaggatgcg atgcgatgct c                                  31

<210> SEQ ID NO 135
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 135
gagcatcgca tcgcatcctc actgctgctc c                                  31

<210> SEQ ID NO 136
<211> LENGTH: 30
<212> TYPE: DNA
<213> ORGANISM: Artificial Sequence
<220> FEATURE:
<223> OTHER INFORMATION: Synthetic Oligo

<400> SEQUENCE: 136
```
aggagcagca gtgagcaaac gatgcgatcg                                30

<210> SEQ ID NO 137
<211> LENGTH: 30
<212> TYPE: DNA
<213> ORGANISM: Artificial Sequence
<220> FEATURE:
<223> OTHER INFORMATION: Synthetic Oligo

<400> SEQUENCE: 137
gcatcgcatc gtttgctcac tgctgctcct                                30

<210> SEQ ID NO 138
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 138
gcagtgagca agcgttgcga tgctctctc                                 29

<210> SEQ ID NO 139
<211> LENGTH: 29
<212> TYPE: DNA
<213> ORGANISM: Artificial Sequence
<220> FEATURE:
<223> OTHER INFORMATION: Synthetic Oligo

<400> SEQUENCE: 139
gagagagcat cgcaacgctt gctcactgc                                 29

<210> SEQ ID NO 140
<211> LENGTH: 33
<212> TYPE: DNA
<213> ORGANISM: Artificial Sequence
<220> FEATURE:
<223> OTHER INFORMATION: Synthetic Oligo

<400> SEQUENCE: 140
gatgcgatgc tctctcgtca cagagcatgt gga                            33

<210> SEQ ID NO 141
<211> LENGTH: 33
<212> TYPE: DNA
<213> ORGANISM: Artificial Sequence
<220> FEATURE:
<223> OTHER INFORMATION: Synthetic Oligo

<400> SEQUENCE: 141
tccacatgct ctgtgacgag agagcatcgc atc                            33

<210> SEQ ID NO 142
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 142
cgatgctctc tcatctcaga gcatgtggag g                              31

<210> SEQ ID NO 143
<211> LENGTH: 31
<212> TYPE: DNA
<213> ORGANISM: Artificial Sequence

```
<220> FEATURE:
<223> OTHER INFORMATION: Synthetic Oligo

<400> SEQUENCE: 143
cctccacatg ctctgagatg agagagcatc g                           31

<210> SEQ ID NO 144
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 144
gctctctcat cacagcgcat gtggaggcct t                           31

<210> SEQ ID NO 145
<211> LENGTH: 31
<212> TYPE: DNA
<213> ORGANISM: Artificial Sequence
<220> FEATURE:
<223> OTHER INFORMATION: Synthetic Oligo

<400> SEQUENCE: 145
aaggcctcca catgcgctgt gatgagagag c                           31

<210> SEQ ID NO 146
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 146
tctctcatca cagagcaggt ggaggccttt atcac                       35

<210> SEQ ID NO 147
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 147
gtgataaagg cctccacctg ctctgtgatg agaga                       35

<210> SEQ ID NO 148
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 148
caacttcaac atcaccaata gcacctgtga gctca                       35

<210> SEQ ID NO 149
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 149
tgagctcaca ggtgctattg gtgatgttga agttg                       35
```

<210> SEQ ID NO 150
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 150
caacatcacc agtagcagct gtgagctcag taagc                              35

<210> SEQ ID NO 151
<211> LENGTH: 35
<212> TYPE: DNA
<213> ORGANISM: Artificial Sequence
<220> FEATURE:
<223> OTHER INFORMATION: Synthetic Oligo

<400> SEQUENCE: 151
gcttactgag ctcacagctg ctactggtga tgttg                              35

<210> SEQ ID NO 152
<211> LENGTH: 40
<212> TYPE: DNA
<213> ORGANISM: Artificial Sequence
<220> FEATURE:
<223> OTHER INFORMATION: Synthetic Oligo

<400> SEQUENCE: 152
caccagtagc acctgtgaga ccagtaagca actcaacatc                         40

<210> SEQ ID NO 153
<211> LENGTH: 40
<212> TYPE: DNA
<213> ORGANISM: Artificial Sequence
<220> FEATURE:
<223> OTHER INFORMATION: Synthetic Oligo

<400> SEQUENCE: 153
gatgttgagt tgcttactgg tctcacaggt gctactggtg                         40

<210> SEQ ID NO 154
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 154
atggacctgg ggaaaccaat gaaaagcgtg ctggtggtgg ctctccttgt cattttccag   60
gtatgcctgt gtcaagatga ggtcacggac gattacatcg agacaacac cacagtggac   120
tacactttgt tcgagtcttt gtgctccaag aaggacgtgc ggaactttaa agcctggttc   180
ctccctatca tgtactccat catttgtttc gtgggcctac tgggcaatgg gctggtcgtg   240
ttgacctata tctatttcaa gaggctcaag accatgaccg atacctacct gctcaacctg   300
gcggtggcag acatcctctt cctcctgacc cttcccttct gggcctacag cgcggccaag   360
tcctgggtct tcggtgtcca cttttgcaag ctcatctttg ccatctacaa gatgagcttc   420
ttcagtggca tgctcctact tctttgcatc agcattgacc gctacgtggc catcgtccag   480
gctgtctcag ctcaccgcca ccgtgcccgc gtccttctca tcagcaagct gtcctgtgtg   540
ggcatctgga tactagccac agtgctctcc atcccagagc tcctgtacag tgacctccag   600
aggagcagca gtgagcaagc gatgcgatgc tctctcatca cagagcatgt ggaggccttt   660

-continued

```
atcaccatcc aggtggccca gatggtgatc ggctttctgg tcccctgct ggccatgagc    720 ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaaccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 155
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 155

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
```

```
        275                 280                 285
Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
370                 375

<210> SEQ ID NO 156
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 156
atggacctgg ggaaaccaat gaaaagcgtg ctggtggtgg ctctccttgt cattttccag     60
gtatgcctgt gtcaagatga ggtcacggac gattacatcg agagaacac acagtggac    120
tacactttgt tcgagtcttt gtgctccaag aaggacgtgc ggaactttaa agcctggttc   180
ctccctatca tgtactccat catttgtttc gtgggcctac tgggcaatgg gctggtcgtg    240
ttgacctata tctatttcaa gaggctcaag accatgaccg ataccatcct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca cagagcatgt ggaggccttt    660
atcaccatcc aggtggccca gatggtgatc ggctttctgg tccccctgct ggccatgagc    720
ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccct tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc ccccatag    1137

<210> SEQ ID NO 157
<211> LENGTH: 378
<212> TYPE: PRT
<213> ORGANISM: Artificial Sequence
<220> FEATURE:
<223> OTHER INFORMATION: mutated hCCR7

<400> SEQUENCE: 157

Met Asp Leu Gly Lys Pro Met Lys Ser Val Leu Val Val Ala Leu Leu
```

```
  1               5                  10                 15
Val Ile Phe Gln Val Cys Leu Cys Gln Asp Glu Val Thr Asp Asp Tyr
        20                  25                 30

Ile Gly Glu Asn Thr Thr Val Asp Tyr Thr Leu Phe Glu Ser Leu Cys
        35                  40                 45

Ser Lys Lys Asp Val Arg Asn Phe Lys Ala Trp Phe Leu Pro Ile Met
        50                  55                 60

Tyr Ser Ile Ile Cys Phe Val Gly Leu Leu Gly Asn Gly Leu Val Val
 65                  70                 75                  80

Leu Thr Tyr Ile Tyr Phe Lys Arg Leu Lys Thr Met Thr Asp Thr Tyr
                     85                 90                  95

Leu Leu Asn Leu Ala Val Ala Asp Ile Leu Phe Leu Leu Thr Leu Pro
                    100                105                 110

Phe Trp Ala Tyr Ser Ala Ala Lys Ser Trp Val Phe Gly Val His Phe
         115                 120                125

Cys Lys Leu Ile Phe Ala Ile Tyr Lys Met Ser Phe Phe Ser Gly Met
        130                 135                140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                    165                 170                 175

Leu Ser Cys Val Gly Ile Trp Ile Leu Ala Thr Val Leu Ser Ile Pro
        180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
        210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
        260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
        340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
        370                 375
```

<210> SEQ ID NO 158
<211> LENGTH: 1137
<212> TYPE: DNA
<213> ORGANISM: Artificial Sequence
<220> FEATURE:
<223> OTHER INFORMATION: Mutated hCCR7

-continued

<400> SEQUENCE: 158

```
atggacctgg ggaaaccaat gaaaagcgtg ctggtggtgg ctctccttgt catttttccag    60
gtatgcctgt gtcaagatga ggtcacggac gattacatcg agacaacac cacagtggac    120
tacactttgt atgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg atacctacct gctcaacctg    300
gcggtggcag acatcctctt cctcctgacc cttcccttct gggcctacag cgcggccaag    360
tcctgggtct cggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca cagagcatgt ggaggccttt    660
atcaccatcc aggtggccca gatggtgatc ggctttctgg tccccctgct ggccatgagc    720
ttctgttacc ttgtcatcat ccgcacccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaaccctt tcttgtacgc cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc cccatag      1137
```

<210> SEQ ID NO 159
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 159

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Tyr Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160
```

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
        370                 375

<210> SEQ ID NO 160
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 160
atggacctgg ggaaaccaat gaaaagcgtg ctggtggtgg ctctccttgt cattttccag      60
gtatgcctgt gtcaagatga ggtcacggac gattacatcg agacaacac cacagtggac     120 tacactttgt tcgagtctgt gtgctccaag aaggacgtgc ggaactttaa agcctggttc     180
ctccctatca tgtactccat catttgtttc gtgggcctac tgggcaatgg gctggtcgtg     240
ttgacctata tctatttcaa gaggctcaag accatgaccg atacctacct gctcaacctg     300
gcggtggcag acatcctctt cctcctgacc cttcccttct gggctacag gcgggccaag     360 tcctgggtct tcggtgtcca cttttgcaag ctcatctttg ccatctacaa gatgagcttc     420
ttcagtggca tgctcctact tctttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tgacctccag     600
aggagcagca gtgagcaagc gatgcgatgc tctctcatca gagcatgt ggaggccttt     660 atcaccatcc aggtgcccca gatggtgatc ggctttctgg tccccctgct ggccatgagc     720
ttctgttacc ttgtcatcat ccgcacctg ctccaggcac gcaactttga gcgcaacaag     780

-continued

```
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccct tccttgtacg ccttcatcgg cgtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 161
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 161

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Val Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300
```

```
Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
            325                 330                 335

Leu Phe Lys Leu Phe Lys Asp Leu Gly Cys Leu Ser Gln Glu Gln Leu
        340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
    370                 375
```

```
<210> SEQ ID NO 162
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 162
atggacctgg ggaaaccaat gaaaagcgtg ctggtggtgg ctctccttgt cattttccag      60
gtatgcctgt gtcaagatga ggtcacggac gattacatcg agacaacac cacagtggac     120 tacactttgt tcgagtcttt gtgcttcaag aaggacgtgc ggaactttaa agcctggttc    180
ctccctatca tgtactccat catttgtttc gtgggcctac tgggcaatgg gctggtcgtg   240
ttgacctata tctatttcaa gaggctcaag accatgaccg atacctacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga ctagccacag tgctctcc atcccagagc tcctgtacag tgacctccag    600
aggagcagca gtgagcaagc gatgcgatgc tctctcatca cagagcatgt ggaggccttt    660
atcaccatcc aggtgcccca gatggtgatc ggctttctgg tccccctgct ggccatgagc    720
ttctgttacc ttgtcatcat ccgcacctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggctgcgt ccgctgctgc    960 gtcaacccct tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

```
<210> SEQ ID NO 163
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 163

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30
```

Ile Gly Asp Asn Thr Thr Val Asp Tyr Thr Leu Phe Glu Ser Leu Cys
            35                  40                  45

Phe Lys Lys Asp Val Arg Asn Phe Lys Ala Trp Phe Leu Pro Ile Met
 50                  55                  60

Tyr Ser Ile Ile Cys Phe Val Gly Leu Leu Gly Asn Gly Leu Val Val
 65                  70                  75                  80

Leu Thr Tyr Ile Tyr Phe Lys Arg Leu Lys Thr Met Thr Asp Thr Tyr
                    85                  90                  95

Leu Leu Asn Leu Ala Val Ala Asp Ile Leu Phe Leu Leu Thr Leu Pro
                100                 105                 110

Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
            195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
                260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
370                 375

<210> SEQ ID NO 164
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 164
atggacctgg ggaaaccaat gaaaagcgtg ctggtggtgg ctctccttgt cattttccag      60
gtatgcctgt gtcaagatga ggtcacggac gattacatcg agacaacac cacagtggac     120

```
tacactttgt tcgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg atacctacct gctcaacctg    300
gcggtggcag acatcctctt cctcctgacc cttcccttct gggcctacag cgaggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca cagagcatgt ggaggccttt    660
atcaccatcc aggtggccca gatggtgatc ggctttctgg tcccctgct ggccatgagc     720 ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccct tcttgtacgc cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc cccatag       1137
```

<210> SEQ ID NO 165
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 165

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Glu Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
```

```
             180                 185                 190
Glu Leu Leu Tyr Ser Asp Leu Gln Arg Ser Ser Glu Gln Ala Met
    195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
                260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
            290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
    370                 375

<210> SEQ ID NO 166
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 166
atggacctgg ggaaaccaat gaaaagcgtg ctggtggtgg ctctccttgt cattttccag      60
gtatgcctgt gtcaagatga ggtcacggac gattacatcg agacaacac cacagtggac     120 tacactttgt tcgagtcttt tgtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg ataccacct gctcaacctg     300 gcggtggcag acatcctctt cctcctgacc cttcccttct gggctacag cgcggccaag     360 tcctggatct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca gagcatgtg ggaggccttt     660 atcaccatcc aggtggccca gatggtgatc ggctttctgg tccccctgct ggccatgagc    720
ttctgttacc ttgtcatcat ccgcaccctg ctccaggcac gcaactttga gcgcaacaag   780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
```

```
gtcaacccttt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 167
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 167

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Ile Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335
```

```
Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 168
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 168
atggacctgg ggaaaccaat gaaaagcgtg ctggtggtgg ctctccttgt cattttccag      60
gtatgcctgt gtcaagatga ggtcacggac gattacatcg agacaacac cacagtggac     120 tacactttgt tcgagtcttt gtgctccaag aaggacgtgc ggaactttaa agcctggttc     180
ctccctatca tgtactccat catttgtttc gtgggcctac tgggcaatgg gctggtcgtg     240
ttgacctata tctatttcaa gaggctcaag accatgaccg atacctacct gctcaacctg     300
gcggtggcag acatcctctt cctcctgacc cttcccttct gggcctacag cgcggccaag     360
tcctgggtct tcggtgtcta tttttgcaag ctcatctttg ccatctacaa gatgagcttc     420
ttcagtggca tgctcctact tctttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tgacctccag     600
aggagcagca gtgagcaagc gatgcgatgc tctctcatca cagagcatgt ggaggccttt     660
atcaccatcc aggtggccca gatggtgatc ggctttctgg tcccctgct ggccatgagc     720 ttctgttacc ttgtcatcat ccgcacctg ctccaggcac gcaactttga gcgcaacaag     780
gccatcaagg tgatcatcgc tgtggtcgtg gtcttcatag tcttccagct gccctacaat     840
ggggtggtcc tggcccagac ggtggccaac ttcaacatca ccagtagcac ctgtgagctc     900
agtaagcaac tcaacatcgc ctacgacgtc acctacagcc tggcctgcgt ccgctgctgc     960
gtcaacccct tccttgtacg cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc ccctag        1137

<210> SEQ ID NO 169
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 169

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60
```

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
            85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val Tyr Phe
            115                 120                 125

Cys Lys Leu Ile Phe Ala Ile Tyr Lys Met Ser Phe Phe Ser Gly Met
            130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
            165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
            195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
            245                 250                 255

Glu Arg Asn Lys Ala Ile Lys Val Ile Ala Val Val Val Val Phe
            260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
            325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
            370                 375

```
<210> SEQ ID NO 170
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 170
atggacctgg ggaaaccaat gaaaagcgtg ctggtggtgg ctctccttgt catttccag     60 gtatgcctgt gtcaagatga ggtcacggac gattacatcg agacaacac cacagtggac   120 tacactttgt tcgagtcttt gtgctccaag aaggacgtgc ggaactttaa agcctggttc   180
ctccctatca tgtactccat catttgtttc gtgggcctac tgggcaatgg gctggtcgtg   240
```

```
ttgacctata tctatttcaa gaggctcaag accatgaccg atacctacct gctcaacctg    300
gcggtggcag acatcctctt cctcctgacc cttcccttct gggcctacag cgcggccaag    360
tcctgggtct tcggtgtcca cttatgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca cagagcatgt ggaggccttt    660
atcaccatcc aggtgcccca gatggtgatc ggctttctgg tcccctgct ggccatgagc     720 ttctgttacc ttgtcatcat ccgcacccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaaccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag     1137
```

<210> SEQ ID NO 171
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 171

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Leu
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205
```

```
Arg Cys Ser Leu Ile Thr Glu His Val Glu Ala Phe Ile Thr Ile Gln
    210                 215                 220
Val Ala Gln Met Val Ile Gly Phe Leu Val Pro Leu Leu Ala Met Ser
225                 230                 235                 240
Phe Cys Tyr Leu Val Ile Ile Arg Thr Leu Leu Gln Ala Arg Asn Phe
                245                 250                 255
Glu Arg Asn Lys Ala Ile Lys Val Ile Ala Val Val Val Val Phe
                260                 265                 270
Ile Val Phe Gln Leu Pro Tyr Asn Gly Val Val Leu Ala Gln Thr Val
                275                 280                 285
Ala Asn Phe Asn Ile Thr Ser Ser Thr Cys Glu Leu Ser Lys Gln Leu
                290                 295                 300
Asn Ile Ala Tyr Asp Val Thr Tyr Ser Leu Ala Cys Val Arg Cys Cys
305                 310                 315                 320
Val Asn Pro Phe Leu Tyr Ala Phe Ile Gly Val Lys Phe Arg Asn Asp
                325                 330                 335
Leu Phe Lys Leu Phe Lys Asp Leu Gly Cys Leu Ser Gln Glu Gln Leu
                340                 345                 350
Arg Gln Trp Ser Ser Cys Arg His Ile Arg Arg Ser Ser Met Ser Val
                355                 360                 365
Glu Ala Glu Thr Thr Thr Thr Phe Ser Pro
                370                 375
```

<210> SEQ ID NO 172
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 172

```
atggacctgg ggaaaccaat gaaaagcgtg ctggtggtgg ctctccttgt cattttccag      60
gtatgcctgt gtcaagatga ggtcacggac gattacatcg agacaacac cacagtggac     120
tacactttgt tcgagtcttt gtgctccaag aaggacgtgc ggaactttaa agcctggttc     180
ctccctatca tgtactccat catttgtttc gtgggcctac tgggcaatgg gctggtcgtg     240
ttgacctata tctatttcaa gaggctcaag accatgaccg atacctacct gctcaacctg     300
gcggtggcag acatcctctt cctcctgacc cttcccttct gggcctacag cgcggccaag     360
tcctgggtct tcggtgtcca cttttgcaag ctcatctttg ccatctacaa gatgagcttc     420
ttcagtggca tgctcctact tctttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tggcctccag     600
aggagcagca gtgagcaagc gatgcgatgc tctctcatca gagcatgt ggaggccttt     660
atcaccatcc aggtggccca gatggtgatc ggctttctgg tccccctgct ggccatgagc     720
ttctgttacc ttgtcatcat ccgcaccctg ctccaggcac gcaactttga gcgcaacaag     780
gccatcaagg tgatcatcgc tgtggtcgtg gtcttcatag tcttccagct gccctacaat     840
ggggtggtcc tggcccagac ggtggccaac ttcaacatca ccagtagcac ctgtgagctc     900
agtaagcaac tcaacatcgc ctacgacgtc acctacagcc tggcctgcgt ccgctgctgc     960
gtcaaccctt tcttgtacgc cttcatcggc gtcaagttcc gcaacgatct cttcaagctc    1020
ttcaaggacc tgggctgcct cagccaggag cagctccggc agtggtcttc ctgtcggcac    1080
```

```
atccggcgct cctccatgag tgtggaggcc gagaccacca ccaccttctc cccatag        1137
```

<210> SEQ ID NO 173
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 173

```
Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp
            20                  25                  30

Tyr Ile Gly Asp Asn Thr Thr Val Asp Tyr Thr Leu Phe Glu Ser
        35                  40                  45

Leu Cys Ser Lys Lys Asp Val Arg Asn Phe Lys Ala Trp Phe Leu
    50                  55                  60

Pro Ile Met Tyr Ser Ile Ile Cys Phe Val Gly Leu Leu Gly Asn
65                  70                  75                  80

Gly Leu Val Val Leu Thr Tyr Ile Tyr Phe Lys Arg Leu Lys Thr
                85                  90                  95

Met Thr Asp Thr Tyr Leu Leu Asn Leu Ala Val Ala Asp Ile Leu
            100                 105                 110

Phe Leu Leu Thr Leu Pro Phe Trp Ala Tyr Ser Ala Ala Lys Ser
        115                 120                 125

Trp Val Phe Gly Val His Phe Cys Lys Leu Ile Phe Ala Ile Tyr
    130                 135                 140

Lys Met Ser Phe Phe Ser Gly Met Leu Leu Leu Leu Cys Ile Ser
145                 150                 155                 160

Ile Asp Arg Tyr Val Ala Ile Val Gln Ala Val Ser Ala His Arg
                165                 170                 175

His Arg Ala Arg Val Leu Leu Ile Ser Lys Leu Ser Cys Val Gly
            180                 185                 190

Ile Trp Ile Leu Ala Thr Val Leu Ser Ile Pro Glu Leu Leu Tyr
        195                 200                 205

Ser Gly Leu Gln Arg Ser Ser Ser Glu Gln Ala Met Arg Cys Ser
    210                 215                 220

Leu Ile Thr Glu His Val Glu Ala Phe Ile Thr Ile Gln
225                 230                 235

Val Ala Gln Met Val Ile Gly Phe Leu Val Pro Leu Leu Ala Met
225                 230                 235                 240

Phe Cys Tyr Leu Val Ile Ile Arg Thr Leu Leu Gln Ala Arg Asn
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
```

Glu Ala Glu Thr Thr Thr Thr Phe Ser Pro
    370             375

<210> SEQ ID NO 174
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 174

| | |
|---|---:|
| atggacctgg ggaaaccaat gaaaagcgtg ctggtggtgg ctctccttgt cattttccag | 60 |
| gtatgcctgt gtcaagatga ggtcacggac gattacatcg agacaacac cacagtggac | 120 |
| tacactttgt tcgagtcttt gtgctccaag aaggacgtgc ggaactttaa agcctggttc | 180 |
| ctccctatca tgtactccat catttgtttc gtgggcctac tgggcaatgg gctggtcgtg | 240 |
| ttgacctata tctatttcaa gaggctcaag accatgaccg ataccttacct gctcaacctg | 300 |
| gcggtggcag acatcctctt cctcctgacc cttcccttct gggcctacag cgcggccaag | 360 |
| tcctgggtct tcggtgtcca cttttgcaag ctcatctttg ccatctacaa gatgagcttc | 420 |
| ttcagtggca tgctcctact tctttgcatc agcattgacc gctacgtggc catcgtccag | 480 |
| gctgtctcag ctcaccgcca ccgtgccgc gtccttctca tcagcaagct gtcctgtgtg | 540 |
| ggcatctgga tactagccac agtgctctcc atcccagagc tcctgtacag tgacctccag | 600 |
| aagagcagca gtgagcaagc gatgcgatgc tctctcatca cagagcatgt ggaggccttt | 660 |
| atcaccatcc aggtggccca gatggtgatc ggctttctgg tcccctgct ggccatgagc | 720 |
| ttctgttacc ttgtcatcat ccgcacctg ctccaggcac gcaactttga gcgcaacaag | 780 |
| gccatcaagg tgatcatcgc tgtggtcgtg gtcttcatag tcttccagct gccctacaat | 840 |
| ggggtggtcc tggcccagac ggtggccaac ttcaacatca ccagtagcac ctgtgagctc | 900 |
| agtaagcaac tcaacatcgc ctacgacgtc acctacagcc tggcctgcgt ccgctgctgc | 960 |
| gtcaacccctt tcttgtacgc cttcatcggc gtcaagttcc gcaacgatct cttcaagctc | 1020 |
| ttcaaggacc tgggctgcct cagccaggag cagctccggc agtggtcttc ctgtcggcac | 1080 |
| atccggcgct cctccatgag tgtggaggcc gagaccacca ccaccttctc cccatag | 1137 |

<210> SEQ ID NO 175
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 175

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr

```
                    85                  90                  95
Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
            115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Lys Ser Ser Glu Gln Ala Met
            195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
            290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
            370                 375

<210> SEQ ID NO 176
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 176
atggacctgg ggaaaccaat gaaaagcgtg ctggtggtgg ctctccttgt catttttccag      60 gtatgcctgt gtcaagatga ggtcacggac gattacatcg agacaacac cacagtggac      120 tacactttgt tcgagtcttt gtgctccaag aaggacgtgc ggaactttaa agcctggttc      180
ctccctatca tgtactccat catttgtttc gtgggcctac tgggcaatgg gctggtcgtg      240
ttgacctata tctatttcaa gaggctcaag accatgaccg ataccctacct gctcaacctg      300 gcggtggcag acatcctctt cctcctgacc cttcccttct gggcctacag cgcggccaag      360
tcctgggtct tcggtgtcca cttttgcaag ctcatctttg ccatctacaa gatgagcttc      420
```

```
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggaacagca gtgagcaagc gatgcgatgc tctctcatca cagagcatgt ggaggccttt    660
atcaccatcc aggtggccca gatggtgatc ggctttctgg tccccctgct ggccatgagc    720
ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960 gtcaacccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 177
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 177

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Asn Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240
```

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 178
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 178

```
atggacctgg ggaaaccaat gaaaagcgtg ctggtggtgg ctctccttgt cattttccag      60
gtatgcctgt gtcaagatga ggtcacggac gattacatcg agacaacac acagtggac      120
tacactttgt tcgagtcttt gtgctccaag aaggacgtgc ggaactttaa agcctggttc     180
ctccctatca tgtactccat catttgtttc gtgggcctac tgggcaatgg gctggtcgtg     240
ttgaccctata tctatttcaa gaggctcaag accatgaccg ataccttacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc     420
ttcagtggca tgctcctact tcttttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagcg gtgagcaagc gatgcgatgc tctctcatca cagagcatgt ggaggccttt    660
atcaccatcc aggtgcccca gatggtgatc ggctttctgg tccccctgct ggccatgagc     720
ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggctgcgt ccgctgctgc    960
gtcaacccct tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 179
<211> LENGTH: 378

<212> TYPE: PRT
<213> ORGANISM: Artificial Sequence
<220> FEATURE:
<223> OTHER INFORMATION: Mutated hCCR7

<400> SEQUENCE: 179

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Gly Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375
```

<210> SEQ ID NO 180
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 180

```
atggacctgg ggaaaccaat gaaaagcgtg ctggtggtgg ctctccttgt cattttccag     60
gtatgcctgt gtcaagatga ggtcacggac gattacatcg agacaacac cacagtggac    120
tacactttgt tcgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg ataccctacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgaggatgc gatgcgatgc tctctcatca cagagcatgt ggaggccttt    660
atcaccatcc aggtggccca gatggtgatc ggctttctgg tcccccctgct ggccatgagc    720
ttctgttacc ttgtcatcat ccgcacccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 181
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 181

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110
```

Phe Trp Ala Tyr Ser Ala Ala Lys Ser Trp Val Gly Val His Phe
               115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
                180                 185                 190

Glu Leu Leu Tyr Ser Asp Leu Gln Arg Ser Ser Glu Asp Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
                260                 265                 270

Ile Val Phe Gln Leu Pro Tyr Asn Gly Val Val Leu Ala Gln Thr Val
275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
370                 375

<210> SEQ ID NO 182
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 182

```
atggacctgg ggaaaccaat gaaaagcgtg ctggtggtgg ctctccttgt cattttccag    60
gtatgcctgt gtcaagatga ggtcacggac gattacatcg agacaacac cacagtggac   120
tacactttgt tcgagtcttt tgctccaag aaggacgtgc ggaactttaa agcctggttc   180
ctccctatca tgtactccat catttgtttc gtgggcctac tgggcaatgg gctggtcgtg   240
ttgacctata tctatttcaa gaggctcaag accatgaccg atacctacct gctcaacctg   300
gcggtggcag acatcctctt cctcctgacc cttcccttct gggcctacag cgcggccaag   360
tcctgggtct tcggtgtcca ctttgcaag ctcatctttg ccatctacaa gatgagcttc   420
ttcagtggca tgctcctact tctttgcatc agcattgacc gctacgtggc catcgtccag   480
gctgtctcag ctcaccgcca ccgtgcccgc gtccttctca tcagcaagct gtcctgtgtg   540
```

```
ggcatctgga tactagccac agtgctctcc atcccagagc tcctgtacag tgacctccag    600
aggagcagca gtgagcaaac gatgcgatgc tctctcatca cagagcatgt ggaggccttt    660
atcaccatcc aggtggccca gatggtgatc ggctttctgg tcccctgct ggccatgagc     720 ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960 gtcaacccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 183
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 183

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Thr Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
```

```
                260               265                270
Ile Val Phe Gln Leu Pro Tyr Asn Gly Val Val Leu Ala Gln Thr Val
                275               280                285
Ala Asn Phe Asn Ile Thr Ser Ser Thr Cys Glu Leu Ser Lys Gln Leu
                290               295                300
Asn Ile Ala Tyr Asp Val Thr Tyr Ser Leu Ala Cys Val Arg Cys Cys
305             310                315                    320
Val Asn Pro Phe Leu Tyr Ala Phe Ile Gly Val Lys Phe Arg Asn Asp
                325               330                335
Leu Phe Lys Leu Phe Lys Asp Leu Gly Cys Leu Ser Gln Glu Gln Leu
                340               345                350
Arg Gln Trp Ser Ser Cys Arg His Ile Arg Arg Ser Ser Met Ser Val
                355               360                365
Glu Ala Glu Thr Thr Thr Thr Phe Ser Pro
                370           375
```

<210> SEQ ID NO 184
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 184

```
atggacctgg ggaaaccaat gaaaagcgtg ctggtggtgg ctctccttgt cattttccag      60
gtatgcctgt gtcaagatga ggtcacggac gattacatcg agacaacac cacagtggac     120
tacactttgt tcgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg atacctacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gttgcgatgc tctctcatca cagagcatgt ggaggccttt    660
atcaccatcc aggtggccca gatggtgatc ggctttctgg tccccctgct ggccatgagc    720
ttctgttacc ttgtcatcat ccgcacctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 185
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 185

```
Met Asp Leu Gly Lys Pro Met Lys Ser Val Leu Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
                35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Leu
        195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375
```

<210> SEQ ID NO 186
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 186

| | | | | | |
|---|---|---|---|---|---|
| atggacctgg | ggaaaccaat | gaaaagcgtg | ctggtggtgg | ctctccttgt | cattttccag | 60 |
| gtatgcctgt | gtcaagatga | ggtcacggac | gattacatcg | gagacaacac | cacagtggac | 120 |
| tacactttgt | tcgagtcttt | gtgctccaag | aaggacgtgc | ggaactttaa | agcctggttc | 180 |
| ctccctatca | tgtactccat | catttgtttc | gtgggcctac | tgggcaatgg | gctggtcgtg | 240 |
| ttgacctata | tctatttcaa | gaggctcaag | accatgaccg | ataccttcct | gctcaacctg | 300 |
| gcggtggcag | acatcctctt | cctcctgacc | cttcccttct | gggcctacag | cgcggccaag | 360 |
| tcctgggtct | tcggtgtcca | cttttgcaag | ctcatctttg | ccatctacaa | gatgagcttc | 420 |
| ttcagtggca | tgctcctact | tctttgcatc | agcattgacc | gctacgtggc | catcgtccag | 480 |
| gctgtctcag | ctcaccgcca | ccgtgcccgc | gtccttctca | tcagcaagct | gtcctgtgtg | 540 |
| ggcatctgga | tactagccac | agtgctctcc | atcccagagc | tcctgtacag | tgacctccag | 600 |
| aggagcagca | gtgagcaagc | gatgcgatgc | tctctcgtca | cagagcatgt | ggaggccttt | 660 |
| atcaccatcc | aggtggccca | gatggtgatc | ggctttctgg | tcccctgct | ggccatgagc | 720 |
| ttctgttacc | ttgtcatcat | ccgcaccctg | ctccaggcac | gcaactttga | gcgcaacaag | 780 |
| gccatcaagg | tgatcatcgc | tgtggtcgtg | gtcttcatag | tcttccagct | gccctacaat | 840 |
| ggggtggtcc | tggcccagac | ggtggccaac | ttcaacatca | ccagtagcac | ctgtgagctc | 900 |
| agtaagcaac | tcaacatcgc | ctacgacgtc | acctacagcc | tggcctgcgt | ccgctgctgc | 960 |
| gtcaaccctt | tcttgtacgc | cttcatcggc | gtcaagttcc | gcaacgatct | cttcaagctc | 1020 |
| ttcaaggacc | tgggctgcct | cagccaggag | cagctccggc | agtggtcttc | ctgtcggcac | 1080 |
| atccggcgct | cctccatgag | tgtggaggcc | gagaccacca | ccaccttctc | cccatag | 1137 |

<210> SEQ ID NO 187
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 187

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
            165                 170                 175

Leu Ser Cys Val Gly Ile Trp Ile Leu Ala Thr Val Leu Ser Ile Pro
        180                 185                 190

Glu Leu Leu Tyr Ser Asp Leu Gln Arg Ser Ser Glu Gln Ala Met
    195                 200                 205

Arg Cys Ser Leu Val Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
                260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
        370                 375

<210> SEQ ID NO 188
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 188
atggacctgg ggaaaccaat gaaaagcgtg ctggtggtgg ctctccttgt cattttccag     60
gtatgcctgt gtcaagatga ggtcacggac gattacatcg agacaacac cacagtggac    120 tacactttgt tcgagtcttt gtgctccaag aaggacgtgc ggaactttaa agcctggttc    180
ctccctatca tgtactccat catttgtttc gtgggcctac tgggcaatgg gctggtcgtg    240
ttgacctata tctatttcaa gaggctcaag accatgaccg ataccctacct gctcaacctg    300 gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatct cagagcatgt ggaggccttt    660
atcaccatcc aggtggccca gatggtgatc ggctttctgg tccccctgct ggccatgagc    720

```
ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccct tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 189
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 189

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Ser Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285
```

Ala Asn Phe Asn Ile Thr Ser Ser Thr Cys Glu Leu Ser Lys Gln Leu
                290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
                355                 360                 365

Glu Ala Glu Thr Thr Thr Thr Phe Ser Pro
                370                 375

<210> SEQ ID NO 190
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 190
atggacctgg ggaaaccaat gaaaagcgtg ctggtggtgg ctctccttgt cattttccag    60
gtatgcctgt gtcaagatga ggtcacggac gattacatcg agacaacac cacagtggac    120
tacactttgt tcgagtcttt tgctccaag aaggacgtgc ggaactttaa agcctggttc    180
ctccctatca tgtactccat catttgtttc gtgggcctac tgggcaatgg gctggtcgtg    240
ttgaccctata tctatttcaa gaggctcaag accatgaccg ataccctacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca gcgcgcatgt ggaggccttt    660
atcaccatcc aggtggccca gatggtgatc ggctttctgg tccccctgct ggccatgagc    720
ttctgttacc ttgtcatcat ccgcacctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagctc    900
agtaagcaac tcaacatcgc ctacgacgtc acctacagcc tggcctgcgt ccgctgctgc    960
gtcaacccct tctctgtacgc cttcatcggc gtcaagttcc gcaacgatct cttcaagctc    1020
ttcaaggacc tgggctgcct cagccaggag cagctccggc agtggtcttc ctgtcggcac    1080
atccggcgct cctccatgag tgtggaggcc gagaccacca ccaccttctc cccatag    1137

<210> SEQ ID NO 191
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 191

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Lys Ser Trp Val Phe Gly Val His Phe
        115                 120                 125

Cys Lys Leu Ile Phe Ala Ile Tyr Lys Met Ser Phe Phe Ser Gly Met
        130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Glu Gln Ala Met
        195                 200                 205

Arg Cys Ser Leu Ile Thr Ala His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
        260                 265                 270

Ile Val Phe Gln Leu Pro Tyr Asn Gly Val Val Leu Ala Gln Thr Val
        275                 280                 285

Ala Asn Phe Asn Ile Thr Ser Ser Thr Cys Glu Leu Ser Lys Gln Leu
        290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
        370                 375

<210> SEQ ID NO 192
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 192

```
atggacctgg ggaaaccaat gaaaagcgtg ctggtggtgg ctctccttgt cattttccag    60
gtatgcctgt gtcaagatga ggtcacggac gattacatcg agacaacaca cacagtggac   120
tacactttgt tcgagtcttt gtgctccaag aaggacgtgc ggaactttaa agcctggttc   180
ctccctatca tgtactccat catttgtttc gtgggcctac tgggcaatgg gctggtcgtg   240
ttgacctata tctatttcaa gaggctcaag accatgaccg atacctacct gctcaacctg   300
gcggtggcag acatcctctt cctcctgacc cttcccttct gggcctacag cgcggccaag   360
tcctgggtct tcggtgtcca cttttgcaag ctcatctttg ccatctacaa gatgagcttc   420
ttcagtggca tgctcctact tctttgcatc agcattgacc gctacgtggc catcgtccag   480
gctgtctcag ctcaccgcca ccgtgcccgc gtccttctca tcagcaagct gtcctgtgtg   540
ggcatctgga tactagccac agtgctctcc atcccagagc tcctgtacag tgacctccag   600
aggagcagca gtgagcaagc gatgcgatgc tctctcatca cagagcaggt ggaggccttt   660
atcaccatcc aggtgcccca gatggtgatc ggctttctgg tcccctgct ggccatgagc   720
ttctgttacc ttgtcatcat ccgcaccctg ctccaggcac gcaactttga gcgcaacaag   780
gccatcaagg tgatcatcgc tgtggtcgtg gtcttcatag tcttccagct gccctacaat   840
gggtggtcc tggcccagac ggtggccaac ttcaacatca ccagtagcac ctgtgagctc   900
agtaagcaac tcaacatcgc ctacgacgtc acctacagcc tggcctgcgt ccgctgctgc   960
gtcaaccctt tcttgtacgc cttcatcggc gtcaagttcc gcaacgatct cttcaagctc  1020
ttcaaggacc tgggctgcct cagccaggag cagctccggc agtggtcttc ctgtcggcac  1080
atccggcgct cctccatgag tgtggaggcc gagaccacca ccaccttctc cccatag     1137
```

<210> SEQ ID NO 193
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 193

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
```

```
                    165                 170                 175
Leu Ser Cys Val Gly Ile Trp Ile Leu Ala Thr Val Leu Ser Ile Pro
        180                 185                 190

Glu Leu Leu Tyr Ser Asp Leu Gln Arg Ser Ser Glu Gln Ala Met
    195                 200                 205

Arg Cys Ser Leu Ile Thr Glu Gln Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
                260                 265                 270

Ile Val Phe Gln Leu Pro Tyr Asn Gly Val Val Leu Ala Gln Thr Val
            275                 280                 285

Ala Asn Phe Asn Ile Thr Ser Ser Thr Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
370                 375
```

<210> SEQ ID NO 194
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 194

```
atggacctgg ggaaaccaat gaaaagcgtg ctggtggtgg ctctccttgt cattttccag      60
gtatgcctgt gtcaagatga ggtcacggac gattacatcg agacaacac cacagtggac     120
tacactttgt tcgagtcttt gtgctccaag aaggacgtgc ggaactttaa agcctggttc     180
ctccctatca tgtactccat catttgtttc gtgggcctac tgggcaatgg gctggtcgtg     240
ttgacctata tctatttcaa gaggctcaag accatgaccg ataccttacct gctcaacctg     300
gcggtggcag acatcctctt cctcctgacc cttcccttct gggcctacag cgcggccaag     360
tcctgggtct tcggtgtcca cttttgcaag ctcatctttg ccatctacaa gatgagcttc     420
ttcagtggca tgctcctact tcttttgcatc agcattgacc gctacgtggc catcgtccag     480
gctgtctcag ctcaccgcca ccgtgcccgc gtccttctca tcagcaagct gtcctgtgtg     540
ggcatctgga tactagccac agtgctctcc atcccagagc tcctgtacag tgacctccag     600
aggagcagca gtgagcaagc gatgcgatgc tctctcatca cagagcatgt ggaggccttt     660
atcaccatcc aggtggccca gatggtgatc ggctttctgg tccccctgct ggccatgagc     720
ttctgttacc ttgtcatcat ccgcacccctg ctccaggcac gcaactttga gcgcaacaag     780
gccatcaagg tgatcatcgc tgtggtcgtg gtcttcatag tcttccagct gccctacaat     840
```

-continued

```
ggggtggtcc tggcccagac ggtggccaac ttcaacatca ccaatagcac ctgtgagctc    900
agtaagcaac tcaacatcgc ctacgacgtc acctacagcc tggcctgcgt ccgctgctgc    960
gtcaacccct tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc cccatag      1137
```

<210> SEQ ID NO 195
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 195

```
Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190

Glu Leu Leu Tyr Ser Asp Leu Gln Arg Ser Ser Ser Glu Gln Ala Met
        195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Asn Ser Thr Cys Glu Leu Ser Lys Gln Leu
    290                 295                 300

Asn Ile Ala Tyr Asp Val Thr Tyr Ser Leu Ala Cys Val Arg Cys Cys
305                 310                 315                 320
```

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
            340                 345                 350

Arg Gln Trp Ser Ser Cys Arg His Ile Arg Arg Ser Ser Met Ser Val
        355                 360                 365

Glu Ala Glu Thr Thr Thr Thr Phe Ser Pro
    370                 375

<210> SEQ ID NO 196
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 196

| | |
|---|---:|
| atggacctgg ggaaaccaat gaaaagcgtg ctggtggtgg ctctccttgt cattttccag | 60 |
| gtatgcctgt gtcaagatga ggtcacggac gattacatcg agacaacac cacagtggac | 120 |
| tacactttgt tcgagtcttt gtgctccaag aaggacgtgc ggaactttaa agcctggttc | 180 |
| ctccctatca tgtactccat catttgtttc gtgggcctac tgggcaatgg gctggtcgtg | 240 |
| ttgacctata tctatttcaa gaggctcaag accatgaccg ataccacct gctcaacctg | 300 |
| gcggtggcag acatcctctt cctcctgacc cttcccttct gggcctacag cgcggccaag | 360 |
| tcctgggtct tcggtgtcca cttttgcaag ctcatctttg ccatctacaa gatgagcttc | 420 |
| ttcagtggca tgctcctact tctttgcatc agcattgacc gctacgtggc catcgtccag | 480 |
| gctgtctcag ctcaccgcca ccgtgcccgc gtccttctca tcagcaagct gtcctgtgtg | 540 |
| ggcatctgga ctactagccac agtgctctcc atcccagagc tcctgtacag tgacctccag | 600 |
| aggagcagca gtgagcaagc gatgcgatgc tctctcatca cagagcatgt ggaggccttt | 660 |
| atcaccatcc aggtggccca gatggtgatc ggctttctgg tcccctgct ggccatgagc | 720 |
| ttctgttacc ttgtcatcat ccgcaccctg ctccaggcac gcaactttga gcgcaacaag | 780 |
| gccatcaagg tgatcatcgc tgtggtcgtg gtcttcatag tcttccagct gccctacaat | 840 |
| ggggtggtcc tggcccagac ggtggccaac ttcaacatca ccagtagcag ctgtgagctc | 900 |
| agtaagcaac tcaacatcgc ctacgacgtc acctacagcc tggcctgcgt ccgctgctgc | 960 |
| gtcaaccctt tcttgtacgc cttcatcggc gtcaagttcc gcaacgatct cttcaagctc | 1020 |
| ttcaaggacc tgggctgcct cagccaggag cagctccggc agtggtcttc ctgtcggcac | 1080 |
| atccggcgct cctccatgag tgtggaggcc gagaccacca ccaccttctc cccatag | 1137 |

<210> SEQ ID NO 197
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 197

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

| | | | | | | | | | | | | |
|---|---|---|---|---|---|---|---|---|---|---|---|---|
|Ser|Lys|Lys|Asp|Val|Arg|Asn|Phe|Lys|Ala|Trp|Phe|Leu|Pro|Ile|Met|
|50| | | | |55| | | |60| | | | | |

Ser Lys Lys Asp Val Arg Asn Phe Lys Ala Trp Phe Leu Pro Ile Met
 50                  55                  60

Tyr Ser Ile Ile Cys Phe Val Gly Leu Leu Asn Gly Leu Val Val
 65                  70                  75                  80

Leu Thr Tyr Ile Tyr Phe Lys Arg Leu Lys Thr Met Thr Asp Thr Tyr
                     85                  90                  95

Leu Leu Asn Leu Ala Val Ala Asp Ile Leu Phe Leu Leu Thr Leu Pro
                100                 105                 110

Phe Trp Ala Tyr Ser Ala Ala Lys Ser Trp Val Phe Gly Val His Phe
             115                 120                 125

Cys Lys Leu Ile Phe Ala Ile Tyr Lys Met Ser Phe Phe Ser Gly Met
130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
             180                 185                 190

Glu Leu Leu Tyr Ser Asp Leu Gln Arg Ser Ser Glu Gln Ala Met
             195                 200                 205

Arg Cys Ser Leu Ile Thr Glu His Val Glu Ala Phe Ile Thr Ile Gln
210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
             260                 265                 270

Ile Val Phe Gln Leu Pro Tyr Asn Gly Val Val Leu Ala Gln Thr Val
             275                 280                 285

Ala Asn Phe Asn Ile Thr Ser Ser Cys Glu Leu Ser Lys Gln Leu
290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
             340                 345                 350

Arg Gln Trp Ser Ser Cys Arg His Ile Arg Arg Ser Ser Met Ser Val
             355                 360                 365

Glu Ala Glu Thr Thr Thr Thr Phe Ser Pro
370                 375

<210> SEQ ID NO 198
<211> LENGTH: 1137
<212> TYPE: DNA
<213> ORGANISM: Artificial Sequence
<220> FEATURE:
<223> OTHER INFORMATION: Mutated hCCR7

<400> SEQUENCE: 198
atggacctgg ggaaaccaat gaaaagcgtg ctggtggtgg ctctccttgt catttccag      60 gtatgcctgt gtcaagatga ggtcacggac gattacatcg agacaacac cacagtggac     120 tacactttgt tcgagtcttt tgtgctccaag aaggacgtgc ggaactttaa agcctggttc    180

```
ctccctatca tgtactccat catttgtttc gtgggcctac tgggcaatgg gctggtcgtg    240
ttgacctata tctatttcaa gaggctcaag accatgaccg atacctacct gctcaacctg    300
gcggtggcag acatcctctt cctcctgacc cttcccttct gggcctacag cgcggccaag    360
tcctgggtct tcggtgtcca cttttgcaag ctcatctttg ccatctacaa gatgagcttc    420
ttcagtggca tgctcctact tctttgcatc agcattgacc gctacgtggc catcgtccag    480
gctgtctcag ctcaccgcca ccgtgcccgc gtccttctca tcagcaagct gtcctgtgtg    540
ggcatctgga tactagccac agtgctctcc atcccagagc tcctgtacag tgacctccag    600
aggagcagca gtgagcaagc gatgcgatgc tctctcatca cagagcatgt ggaggccttt    660
atcaccatcc aggtggccca gatggtgatc ggctttctgg tcccccctgct ggccatgagc    720 ttctgttacc ttgtcatcat ccgcaccctg ctccaggcac gcaactttga gcgcaacaag    780
gccatcaagg tgatcatcgc tgtggtcgtg gtcttcatag tcttccagct gccctacaat    840
ggggtggtcc tggcccagac ggtggccaac ttcaacatca ccagtagcac ctgtgagacc    900
agtaagcaac tcaacatcgc ctacgacgtc acctacagcc tggcctgcgt ccgctgctgc    960
gtcaaccctt tcttgtacgc cttcatcggc gtcaagttcc gcaacgatct cttcaagctc   1020
ttcaaggacc tgggctgcct cagccaggag cagctccggc agtggtcttc ctgtcggcac   1080
atccggcgct cctccatgag tgtggaggcc gagaccacca ccaccttctc ccccatag     1137
```

```

<210> SEQ ID NO 199
<211> LENGTH: 378
<212> TYPE: PRT
<213> ORGANISM: Artificial Sequence
<220> FEATURE:
<223> OTHER INFORMATION: Mutated hCCR7

<400> SEQUENCE: 199

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Ile Leu Ala Thr Val Leu Ser Ile Pro
            180                 185                 190
```

```
Glu Leu Leu Tyr Ser Asp Leu Gln Arg Ser Ser Glu Gln Ala Met
            195                 200                 205

Arg Cys Ser Leu Ile Thr Glu His Val Glu Ala Phe Ile Thr Ile Gln
    210                 215                 220

Val Ala Gln Met Val Ile Gly Phe Leu Val Pro Leu Leu Ala Met Ser
225                 230                 235                 240

Phe Cys Tyr Leu Val Ile Ile Arg Thr Leu Leu Gln Ala Arg Asn Phe
                245                 250                 255

Glu Arg Asn Lys Ala Ile Lys Val Ile Ala Val Val Val Val Phe
                260                 265                 270

Ile Val Phe Gln Leu Pro Tyr Asn Gly Val Val Leu Ala Gln Thr Val
                275                 280                 285

Ala Asn Phe Asn Ile Thr Ser Ser Thr Cys Glu Thr Ser Lys Gln Leu
    290                 295                 300

Asn Ile Ala Tyr Asp Val Thr Tyr Ser Leu Ala Cys Val Arg Cys Cys
305                 310                 315                 320

Val Asn Pro Phe Leu Tyr Ala Phe Ile Gly Val Lys Phe Arg Asn Asp
                325                 330                 335

Leu Phe Lys Leu Phe Lys Asp Leu Gly Cys Leu Ser Gln Glu Gln Leu
                340                 345                 350

Arg Gln Trp Ser Ser Cys Arg His Ile Arg Arg Ser Ser Met Ser Val
            355                 360                 365

Glu Ala Glu Thr Thr Thr Thr Phe Ser Pro
    370                 375

<210> SEQ ID NO 200
<211> LENGTH: 1137
<212> TYPE: DNA
<213> ORGANISM: Murine CCR7

<400> SEQUENCE: 200
atggacccag ggaaacccag gaaaaacgtg ctggtggtgg ctctccttgt catttttccag      60 gtgtgcttct gccaagatga ggtcaccgat gactacatcg gcgagaatac cacggtggac     120
tacaccctgt acgagtcggt gtgcttcaag aaggatgtgc ggaactttaa ggcctggttc     180
ctgcctctca tgtattctgt catctgcttc gtgggcctgc tcggcaacgg gctggtgata     240
ctgacgtaca tctatttcaa gaggctcaag accatgacgg ataccttacct gctcaacctg     300 gccgtggcag acatcctttt cctcctaatt cttcccttct gggcctacag cgaagccaag     360
tcctggatct tggcgtcta cctgtgtaag gcatctttg catctataa gttaagcttc     420 ttcagcggga tgctgctgct cctatgcatc agcattgacc gctacgtagc catcgtccag     480
gccgtgtcgg ctcatcgcca ccgcgcccgc gtgcttctca tcagcaagct gtcctgtgtg     540
ggcatctgga tgctggccct cttcctctcc atcccggagc tgctctacag cggcctccag     600
aagaacagcg cgaggacac gctgagatgc tcactggtca gtgcccaagt ggaggccttg     660
atcaccatcc aagtggccca gatggttttt gggttcctag tgcctatgct ggctatgagt     720
ttctgctacc tcattatcat ccgtaccttg ctccaggcac gcaactttga gcggaacaag     780
gccatcaagg tgatcattgc cgtggtggta gtcttcatag tcttccagct gccctacaat     840
ggggtggtcc tggctcagac ggtggccaac ttcaacatca ccaatagcag ctgcgaaacc     900
agcaagcagc tcaacattgc ctatgacgtc acctacagcc tggcctccgt ccgctgctgc     960
gtcaaccctt tcttgtatgc cttcatcggc gtcaagttcc gcagcgacct cttcaagctc    1020
ttcaaggact gggctgcct cagccaggaa cggctccggc actggtcttc ctgccggcat    1080
```
gtacggaacg cgtcggtgag catggaggcg gagaccacca caaccttctc cccgtag    1137

<210> SEQ ID NO 201
<211> LENGTH: 378
<212> TYPE: PRT
<213> ORGANISM: Murine CCR7

<400> SEQUENCE: 201

Met Asp Pro Gly Lys Pro Arg Lys Asn Val Leu Val Val Ala Leu Leu
1               5                   10                  15

Val Ile Phe Gln Val Cys Phe Cys Gln Asp Glu Val Thr Asp Asp Tyr
                20                  25                  30

Ile Gly Glu Asn Thr Thr Val Asp Tyr Thr Leu Tyr Glu Ser Val Cys
            35                  40                  45

Phe Lys Lys Asp Val Arg Asn Phe Lys Ala Trp Phe Leu Pro Leu Met
    50                  55                  60

Tyr Ser Val Ile Cys Phe Val Gly Leu Leu Gly Asn Gly Leu Val Ile
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Ile Leu Pro
            100                 105                 110

Phe Trp Ala Tyr Ser Glu Ala Lys Ser Trp Ile Phe Gly Val Tyr Leu
        115                 120                 125

Cys Lys Gly Ile Phe Gly Ile Tyr Lys Leu Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Met Leu Ala Leu Phe Leu Ser Ile Pro
            180                 185                 190

Glu Leu Leu Tyr Ser Gly Leu Gln Lys Asn Ser Gly Glu Asp Thr Leu
        195                 200                 205

Arg Cys Ser Leu Val Ser Ala Gln Val Glu Ala Leu Ile Thr Ile Gln
    210                 215                 220

Val Ala Gln Met Val Phe Gly Phe Leu Val Pro Met Leu Ala Met Ser
225                 230                 235                 240

Phe Cys Tyr Leu Ile Ile Ile Arg Thr Leu Leu Gln Ala Arg Asn Phe
                245                 250                 255

Glu Arg Asn Lys Ala Ile Lys Val Ile Ala Val Val Val Val Val Phe
            260                 265                 270

Ile Val Phe Gln Leu Pro Tyr Asn Gly Val Val Leu Ala Gln Thr Val
        275                 280                 285

Ala Asn Phe Asn Ile Thr Asn Ser Ser Cys Glu Thr Ser Lys Gln Leu
    290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
            340                 345                 350

Arg His Trp Ser Ser Cys Arg His Val Arg Asn Ala Ser Val Ser Met
        355                 360                 365

Glu Ala Glu Thr Thr Thr Thr Phe Ser Pro
    370                 375

<210> SEQ ID NO 202
<211> LENGTH: 38
<212> TYPE: DNA
<213> ORGANISM: Artificial Sequence
<220> FEATURE:
<223> OTHER INFORMATION: Synthetic Oligo

<400> SEQUENCE: 202
acggtggact acaccctgtt cgagtcgttg tgcttcaa                        38

<210> SEQ ID NO 203
<211> LENGTH: 38
<212> TYPE: DNA
<213> ORGANISM: Artificial Sequence
<220> FEATURE:
<223> OTHER INFORMATION: Synthetic Oligo

<400> SEQUENCE: 203
ttgaagcaca acgactcgaa cagggtgtag tccaccgt                        38

<210> SEQ ID NO 204
<211> LENGTH: 45
<212> TYPE: DNA
<213> ORGANISM: Artificial Sequence
<220> FEATURE:
<223> OTHER INFORMATION: Synthetic Oligo

<400> SEQUENCE: 204
cagcggcctc cagaggagca gcagcgagga cgcgatgaga tgctc                45

<210> SEQ ID NO 205
<211> LENGTH: 45
<212> TYPE: DNA
<213> ORGANISM: Artificial Sequence
<220> FEATURE:
<223> OTHER INFORMATION: Synthetic Oligo

<400> SEQUENCE: 205
gagcatctca tcgcgtcctc gctgctgctc ctctggaggc cgctg                45

<210> SEQ ID NO 206
<211> LENGTH: 1137
<212> TYPE: DNA
<213> ORGANISM: Artificial Sequence
<220> FEATURE:
<223> OTHER INFORMATION: Mutated Murine CCR7

<400> SEQUENCE: 206
atggacccag ggaaacccag gaaaaacgtg ctggtggtgg ctctccttgt cattttccag    60
gtgtgcttct gccaagatga ggtcaccgat gactacatcg gcgagaatac cacggtggac    120
tacaccctgt tcgagtcgtt gtgcttcaag aaggatgtgc ggaactttaa ggcctggttc    180
ctgcctctca tgtattctgt catctgcttc gtgggcctgc tcggcaacgg gctggtgata    240
ctgacgtaca tctatttcaa gaggctcaag accatgacgg ataccacct gctcaacctg    300 gccgtggcag acatcctttt cctcctaatt cttcccttct gggcctacag cgaagccaag    360
tcctggatct ttggcgtcta cctgtgtaag gcatctttg catctataa gttaagcttc    420 ttcagcggga tgctgctgct cctatgcatc agcattgacc gctacgtagc catcgtccag    480
gccgtgtcgg ctcatcgcca ccgcgcccgc gtgcttctca tcagcaagct gtcctgtgtg    540

```
ggcatctgga tgctggccct cttcctctcc atcccggagc tgctctacag cggcctccag    600
aagaacagcg gcgaggacac gctgagatgc tcactggtca gtgcccaagt ggaggccttg    660
atcaccatcc aagtggccca gatggttttt gggttcctag tgcctatgct ggctatgagt    720
ttctgctacc tcattatcat ccgtaccttg ctccaggcac gcaactttga gcggaacaag    780
gccatcaagg tgatcattgc cgtggtggta gtcttcatag tcttccagct gccctacaat    840
ggggtggtcc tggctcagac ggtggccaac ttcaacatca ccaatagcag ctgcgaaacc    900
agcaagcagc tcaacattgc ctatgacgtc acctacagcc tggcctccgt ccgctgctgc    960 gtcaacccctt tcttgtatgc cttcatcggc gtcaagttcc gcagcgacct cttcaagctc   1020
ttcaaggact tgggctgcct cagccaggaa cggctccggc actggtcttc ctgccggcat   1080
gtacggaacg cgtcggtgag catggaggcg gagaccacca caaccttctc cccgtag       1137
```

<210> SEQ ID NO 207
<211> LENGTH: 378
<212> TYPE: PRT
<213> ORGANISM: Artificial Sequence
<220> FEATURE:
<223> OTHER INFORMATION: Mutated Murine CCR7

<400> SEQUENCE: 207

```
Met Asp Pro Gly Lys Pro Arg Lys Asn Val Leu Val Val Ala Leu Leu
1               5                   10                  15

Val Ile Phe Gln Val Cys Phe Cys Gln Asp Glu Val Thr Asp Asp Tyr
            20                  25                  30

Ile Gly Glu Asn Thr Thr Val Asp Tyr Thr Leu Phe Glu Ser Leu Cys
        35                  40                  45

Phe Lys Lys Asp Val Arg Asn Phe Lys Ala Trp Phe Leu Pro Leu Met
    50                  55                  60

Tyr Ser Val Ile Cys Phe Val Gly Leu Leu Gly Asn Gly Leu Val Ile
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Ile Leu Pro
            100                 105                 110

Phe Trp Ala Tyr Ser Glu Ala Lys Ser Trp Ile Phe Gly Val Tyr Leu
        115                 120                 125

Cys Lys Gly Ile Phe Gly Ile Tyr Lys Leu Ser Phe Phe Ser Gly Met
    130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Met Leu Ala Leu Phe Leu Ser Ile Pro
            180                 185                 190

Glu Leu Leu Tyr Ser Gly Leu Gln Lys Asn Ser Gly Glu Asp Thr Leu
        195                 200                 205

Arg Cys Ser Leu Val Ser Ala Gln Val Glu Ala Leu Ile Thr Ile Gln
    210                 215                 220

Val Ala Gln Met Val Phe Gly Phe Leu Val Pro Met Leu Ala Met Ser
225                 230                 235                 240

Phe Cys Tyr Leu Ile Ile Ile Arg Thr Leu Leu Gln Ala Arg Asn Phe
                245                 250                 255
```

Glu Arg Asn Lys Ala Ile Lys Val Ile Ala Val Val Val Phe
                260                 265                 270

Ile Val Phe Gln Leu Pro Tyr Asn Gly Val Val Leu Ala Gln Thr Val
            275                 280                 285

Ala Asn Phe Asn Ile Thr Asn Ser Ser Cys Glu Thr Ser Lys Gln Leu
        290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
            340                 345                 350

Arg His Trp Ser Ser Cys Arg His Val Arg Asn Ala Ser Val Ser Met
        355                 360                 365

Glu Ala Glu Thr Thr Thr Thr Phe Ser Pro
370                 375

<210> SEQ ID NO 208
<211> LENGTH: 1137
<212> TYPE: DNA
<213> ORGANISM: Artificial Sequence
<220> FEATURE:
<223> OTHER INFORMATION: Mutated Murine CCR7

<400> SEQUENCE: 208

```
atggacccag ggaaacccag gaaaaacgtg ctggtggtgg ctctccttgt catttcccag      60
gtgtgcttct gccaagatga ggtcaccgat gactacatcg cgagaatac cacggtggac     120
tacaccctgt acgagtcggt gtgcttcaag aaggatgtgc ggaactttaa ggcctggttc     180
ctgcctctca tgtattctgt catctgcttc gtgggcctgc tcggcaacgg gctggtgata     240
ctgacgtaca tctatttcaa gaggctcaag accatgacgg atacctacct gctcaacctg     300
gccgtggcag acatcctttt cctcctaatt cttcccttct gggcctacag cgaagccaag     360
tcctggatct ttggcgtcta cctgtgtaag gcatctttg catctataa gttaagcttc     420
ttcagcggga tgctgctgct cctatgcatc agcattgacc gctacgtagc catcgtccag     480
gccgtgtcgg ctcatcgcca ccgcgcccgc gtgcttctca tcagcaagct gtcctgtgtg     540
ggcatctgga tgctggccct cttcctctcc atcccggagc tgctctacag cggcctccag     600
aggagcagca gcgaggacgc gatgagatgc tcactggtca gtgcccaagt ggaggccttg     660
atcaccatcc aagtggccca gatggttttt gggttcctag tgcctatgct ggctatgagt     720
ttctgctacc tcattatcat ccgtaccttg ctccaggcac gcaactttga gcggaacaag     780
gccatcaagg tgatcattgc cgtggtggta gtcttcatag tcttccagct gccctacaat     840
ggggtggtcc tggctcagac ggtggccaac ttcaacatca ccaatagcag ctgcgaaacc     900
agcaagcagc tcaacattgc ctatgacgtc acctacagcc tggcctccgt ccgctgctgc     960
gtcaacccct tcttgtatgc cttcatcggc gtcaagttcc gcagcgacct cttcaagctc    1020
ttcaaggact tgggctgcct cagccaggaa cggctccggc actggtcttc ctgccggcat    1080
gtacggaacg cgtcggtgag catggaggcg agaccacca caaccttctc cccgtag       1137
```

<210> SEQ ID NO 209
<211> LENGTH: 378
<212> TYPE: PRT
<213> ORGANISM: Artificial Sequence
<220> FEATURE:
<223> OTHER INFORMATION: Mutated Murine CCR7

<400> SEQUENCE: 209

```
Met Asp Pro Gly Lys Pro Arg Lys Asn Val Leu Val Ala Leu Leu
 1               5                  10                  15

Val Ile Phe Gln Val Cys Phe Cys Gln Asp Glu Val Thr Asp Asp Tyr
            20                  25                  30

Ile Gly Glu Asn Thr Thr Val Asp Tyr Thr Leu Tyr Glu Ser Val Cys
            35                  40                  45

Phe Lys Lys Asp Val Arg Asn Phe Lys Ala Trp Phe Leu Pro Leu Met
 50                  55                  60

Tyr Ser Val Ile Cys Phe Val Gly Leu Leu Gly Asn Gly Leu Val Ile
 65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Ile Leu Pro
                100                 105                 110

Phe Trp Ala Tyr Ser Glu Ala Lys Ser Trp Ile Phe Gly Val Tyr Leu
            115                 120                 125

Cys Lys Gly Ile Phe Gly Ile Tyr Lys Leu Ser Phe Phe Ser Gly Met
 130                 135                 140

Leu Leu Leu Leu Cys Ile Ser Ile Asp Arg Tyr Val Ala Ile Val Gln
 145                 150                 155                 160

Ala Val Ser Ala His Arg His Arg Ala Arg Val Leu Leu Ile Ser Lys
                165                 170                 175

Leu Ser Cys Val Gly Ile Trp Met Leu Ala Leu Phe Leu Ser Ile Pro
            180                 185                 190

Glu Leu Leu Tyr Ser Gly Leu Gln Arg Ser Ser Ser Glu Asp Ala Met
            195                 200                 205

Arg Cys Ser Leu Val Ser Ala Gln Val Glu Ala Leu Ile Thr Ile Gln
 210                 215                 220

Val Ala Gln Met Val Phe Gly Phe Leu Val Pro Met Leu Ala Met Ser
 225                 230                 235                 240

Phe Cys Tyr Leu Ile Ile Ile Arg Thr Leu Leu Gln Ala Arg Asn Phe
                245                 250                 255

Glu Arg Asn Lys Ala Ile Lys Val Ile Ile Ala Val Val Val Val Phe
            260                 265                 270

Ile Val Phe Gln Leu Pro Tyr Asn Gly Val Val Leu Ala Gln Thr Val
            275                 280                 285

Ala Asn Phe Asn Ile Thr Asn Ser Ser Cys Glu Thr Ser Lys Gln Leu
 290                 295                 300

Asn Ile Ala Tyr Asp Val Thr Tyr Ser Leu Ala Ser Val Arg Cys Cys
 305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
            340                 345                 350

Arg His Trp Ser Ser Cys Arg His Val Arg Asn Ala Ser Val Ser Met
            355                 360                 365

Glu Ala Glu Thr Thr Thr Thr Phe Ser Pro
 370                 375
```

<210> SEQ ID NO 210
<211> LENGTH: 38
<212> TYPE: DNA

<213> ORGANISM: Artificial Sequence
<220> FEATURE:
<223> OTHER INFORMATION: Synthetic Oligo

<400> SEQUENCE: 210

```
acggtggact acaccctgtt cgagtcgttg tgcttcaa                                38
```

<210> SEQ ID NO 211
<211> LENGTH: 38
<212> TYPE: DNA
<213> ORGANISM: Artificial Sequence
<220> FEATURE:
<223> OTHER INFORMATION: Synthetic Oligo

<400> SEQUENCE: 211

```
ttgaagcaca acgactcgaa cagggtgtag tccaccgt                                38
```

<210> SEQ ID NO 212
<211> LENGTH: 1137
<212> TYPE: DNA
<213> ORGANISM: Artificial Sequence
<220> FEATURE:
<223> OTHER INFORMATION: Mutated Murine CCR7

<400> SEQUENCE: 212

```
atggacccag ggaaacccag gaaaaacgtg ctggtggtgg ctctccttgt cattttccag          60
gtgtgcttct gccaagatga ggtcaccgat gactacatcg gcgagaatac cacggtggac         120
tacaccctgt tcgagtcgtt gtgcttcaag aaggatgtgc ggaactttaa ggcctggttc         180
ctgcctctca tgtattctgt catctgcttc gtgggcctgc tcggcaacgg gctggtgata         240
ctgacgtaca tctatttcaa gaggctcaag accatgacgg ataccttacct gctcaacctg         300
gccgtggcag acatcctttt cctcctaatt cttcccttct gggcctacag cgaagccaag         360
tcctggatct ttggcgtcta cctgtgtaag gcatctttg catctataa gttaagcttc         420
ttcagcggga tgctgctgct cctatgcatc agcattgacc gctacgtagc catcgtccag         480
gccgtgtcgg ctcatcgcca ccgcgcccgc gtgcttctca tcagcaagct gtcctgtgtg         540
ggcatctgga tgctggccct cttcctctcc atcccggagc tgctctacag cggcctccag         600
aggagcagca gcgaggacgc gatgagatgc tcactggtca gtgcccaagt ggaggccttg         660
atcaccatcc aagtgcccca gatggttttt gggttcctag tgcctatgct ggctatgagt         720
ttctgctacc tcattatcat ccgtaccttg ctccaggcac gcaactttga gcggaacaag         780
gccatcaagg tgatcattgc cgtggtggta gtcttcatag tcttccagct gccctacaat         840
ggggtggtcc tggctcagac ggtggccaac ttcaacatca ccaatagcag ctgcgaaacc         900
agcaagcagc tcaacattgc ctatgacgtc acctacagcc tggcctccgt ccgctgctgc         960
gtcaaccctt tcttgtatgc cttcatcggc gtcaagttcc gcagcgacct cttcaagctc        1020
ttcaaggact gggctgcct cagccaggaa cggctccggc actggtcttc ctgccggcat        1080
gtacggaacg cgtcggtgag catggaggcg gagaccacca caaccttctc cccgtag          1137
```

<210> SEQ ID NO 213
<211> LENGTH: 378
<212> TYPE: PRT
<213> ORGANISM: Artificial Sequence
<220> FEATURE:
<223> OTHER INFORMATION: Mutated Murine CCR7

<400> SEQUENCE: 213

Met Asp Pro Gly Lys Pro Arg Lys Asn Val Leu Val Val Ala Leu Leu

```
1               5                   10                  15
Val Ile Phe Gln Val Cys Phe Cys Gln Asp Glu Val Thr Asp Asp Tyr
                20                  25                  30

Ile Gly Glu Asn Thr Thr Val Asp Tyr Thr Leu Phe Glu Ser Leu Cys
                35                  40                  45

Phe Lys Lys Asp Val Arg Asn Phe Lys Ala Trp Phe Leu Pro Leu Met
                50                  55                  60

Tyr Ser Val Ile Cys Phe Val Gly Leu Leu Gly Asn Gly Leu Val Ile
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Ile Leu Pro
                100                 105                 110

Phe Trp Ala Tyr Ser Glu Ala Lys Ser Trp Ile Phe Gly Val Tyr Leu
                115                 120                 125

Cys Lys Gly Ile Phe Gly Ile Tyr Lys Leu Ser Phe Phe Ser Gly Met
                130                 135                 140

Leu Leu Leu Leu Cys Ile Ser Ile Asp Arg Tyr Val Ala Ile Val Gln
145                 150                 155                 160

Ala Val Ser Ala His Arg His Arg Ala Arg Val Leu Leu Ile Ser Lys
                165                 170                 175

Leu Ser Cys Val Gly Ile Trp Met Leu Ala Leu Phe Leu Ser Ile Pro
                180                 185                 190

Glu Leu Leu Tyr Ser Gly Leu Gln Arg Ser Ser Ser Glu Asp Ala Met
                195                 200                 205

Arg Cys Ser Leu Val Ser Ala Gln Val Glu Ala Leu Ile Thr Ile Gln
                210                 215                 220

Val Ala Gln Met Val Phe Gly Phe Leu Val Pro Met Leu Ala Met Ser
225                 230                 235                 240

Phe Cys Tyr Leu Ile Ile Ile Arg Thr Leu Leu Gln Ala Arg Asn Phe
                245                 250                 255

Glu Arg Asn Lys Ala Ile Lys Val Ile Ile Ala Val Val Val Val Phe
                260                 265                 270

Ile Val Phe Gln Leu Pro Tyr Asn Gly Val Val Leu Ala Gln Thr Val
                275                 280                 285

Ala Asn Phe Asn Ile Thr Asn Ser Ser Cys Glu Thr Ser Lys Gln Leu
                290                 295                 300

Asn Ile Ala Tyr Asp Val Thr Tyr Ser Leu Ala Ser Val Arg Cys Cys
305                 310                 315                 320

Val Asn Pro Phe Leu Tyr Ala Phe Ile Gly Val Lys Phe Arg Ser Asp
                325                 330                 335

Leu Phe Lys Leu Phe Lys Asp Leu Gly Cys Leu Ser Gln Glu Arg Leu
                340                 345                 350

Arg His Trp Ser Ser Cys Arg His Val Arg Asn Ala Ser Val Ser Met
                355                 360                 365

Glu Ala Glu Thr Thr Thr Thr Phe Ser Pro
370                 375
```

METHODS AND COMPOSITIONS RELATING TO ANTI-CCR7 ANTIGEN BINDING PROTEINS

CROSS-REFERENCE TO RELATED APPLICATIONS

This application is a continuation application which claims the benefit of U.S. application Ser. No. 14/776,670, filed Sep. 14, 2015, which is a national stage application under 35 U.S.C. § 371 of International Application No. PCT/US2014/026537, having an international filing date of Mar. 14, 2014, which claims the benefit of U.S. Provisional Application Ser. No. 61/962,296, filed Mar. 15, 2013, which is incorporated in its entirety by reference herein.

REFERENCE TO THE SEQUENCE LISTING

The present application is being filed along with a Sequence Listing in electronic format via EFS-Web. The Sequence Listing is provided as a text file entitled A-1814-US-CNT_SequenceListing.txt, created Jul. 31, 2017, which is 242,953 bytes in size. The information in the electronic format of the Sequence Listing is incorporated herein by reference in its entirety.

BACKGROUND

CCR7 and its ligands CCL19 and CCL21 play non-redundant roles in regulating the migration, organization, and activation of dendritic cells and naïve T and B cells in secondary and tertiary (disease-associated) lymphoid structures.

CCR7 activity has been implicated in a diverse variety of disease states, including chronic inflammatory conditions (Moschovakis et al., 2012, Eur J Immunol. 42:1949-55), atherosclerosis (Luchtefeld et al., 2010, Circulation 122:1621-28), HIV infection (Evans et al., 2012, Cytokine Growth Factor Rev. 23:151-57), and cancer (Ben-Baruch, 2009, Cell Adhesion Migration 3:328-33).

SUMMARY OF THE INVENTION

In one aspect, the present invention provides an isolated anti-CCR7 antigen binding protein, wherein said antigen binding protein comprises either: the light chain variable domain sequence of antibody 6B4.1, 6B5.1, 6E1.2, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8; or the heavy chain variable domain sequence of 6B4.1, 6B5.1, 6E1.2, 6E1.2 HC G2V, 6E1.2 HC F80Y, 6E1.2 HC G2V F80Y or MAB22_HC_V1; or the heavy chain variable domain and the light chain variable domain of antibody 6B4.1, 6B5.1, or 6E1.2; or a light chain variable domain sequence that is at least 90%, 95%, 97%, or 99% identical to the light chain variable domain sequence of 6B4.1, 6B5.1, 6E1.2, 6B4.1 LC desS, or 6E1.2 LC H36Q; or a heavy chain variable domain sequence that is at least 90%, 95%, 97%, or 99% identical to the heavy chain variable domain sequence of 6B4.1, 6B5.1, or 6E1.2; or a light chain variable domain sequence and a heavy chain variable domain sequence that each is at least 90%, 95%, 97%, or 99% identical to the light chain variable domain sequence and the heavy chain variable domain sequence, respectively, of antibody 6B4.1, 6B5.1, or 6E1.2; or a light chain variable domain sequence that differs at no more than 15, 12, 10, 8, 5, or 3 amino acid positions from the light chain variable domain sequence of 6B4.1, 6B5.1, 6E1.2, 6B4.1 LC desS, or 6E1.2 LC H36Q; or a heavy chain variable domain sequence that differs at no more than 15, 12, 10, 8, 5, or 3 amino acid positions from the heavy chain variable domain sequence of 6B4.1, 6B5.1, or 6E1.2; or a light chain variable domain sequence and a heavy chain variable domain sequence that each differs at no more than 15, 12, 10, 8, 5, or 3 amino acid positions from the light chain variable domain sequence and the heavy chain variable domain sequence, respectively, of 6B4.1, 6B5.1, or 6E1.2; or a light chain variable domain sequence that is encoded by a nucleic acid sequence that is at least 90%, 95%, 97%, or 99% identical to the nucleic acid sequence encoding the light chain variable domain sequence of 6B4.1, 6B5.1, 6E1.2, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8 as provided in FIG. 1; or a heavy chain variable domain sequence that is encoded by a nucleic acid sequence that is at least 90%, 95%, 97%, or 99% identical to the nucleic acid sequence encoding the heavy chain variable domain sequence of 6B4.1, 6B5.1, 6E1.2, 6E1.2 HC G2V, 6E1.2 HC F80Y, 6E1.2 HC G2V F80Y or MAB22_HC_V1, as provided in FIG. 1; or a light chain variable domain sequence that is encoded by a nucleic acid sequence that is at least 90%, 95%, 97%, or 99% identical to the nucleic acid sequence encoding the light chain variable domain sequence of 6B4.1, 6B5.1, 6E1.2, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8 as provided in FIG. 1, and a heavy chain variable domain sequence that is encoded by a nucleic acid sequence that is at least 90%, 95%, 97%, or 99% identical to the nucleic acid sequence encoding the heavy chain variable domain sequence of 6B4.1, 6B5.1, 6E1.2, 6E1.2 HC G2V, 6E1.2 HC F80Y, 6E1.2 HC G2V F80Y or MAB22_HC_V1, as provided in FIG. 1; or a light chain variable domain sequence that is encoded by a nucleic acid sequence that hybridizes under moderately stringent, stringent, or highly stringent conditions to the nucleic acid sequence encoding the light chain variable domain sequence of 6B4.1, 6B5.1, 6E1.2, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8 as provided in FIG. 1; or a heavy chain variable domain sequence that is encoded by a nucleic acid sequence that hybridizes under moderately stringent, stringent, or highly stringent conditions to the nucleic acid sequence encoding the heavy chain variable domain sequence of 6B4.1, 6B5.1, 6E1.2, 6E1.2 HC G2V, 6E1.2 HC F80Y, 6E1.2 HC G2V F80Y or MAB22_HC_V1, as provided in FIG. 1; or a light chain variable domain sequence that is encoded by a nucleic acid sequence that hybridizes under moderately stringent, stringent, or highly stringent conditions to the nucleic acid sequence encoding the light chain variable domain sequence of 6B4.1, 6B5.1, 6E1.2, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8 as provided in FIG. 1, and a heavy chain variable domain sequence that is encoded by a nucleic acid sequence that hybridizes under moderately stringent, stringent, or highly stringent conditions to the nucleic acid sequence encoding the heavy chain variable domain sequence of the same antibody 6B4.1, 6B5.1, 6E1.2, 6E1.2

HC G2V, 6E1.2 HC F80Y, 6E1.2 HC G2V F80Y or MAB22_HC_V1; or CDR1, CDR2, and CDR3 of the light chain variable domain sequence of 6B4.1, 6B5.1, 6E1.2, 6B4.1 LC desS, 6E1.2 LC H36Q; or CDR1, CDR2, and CDR3 of the heavy chain variable domain sequence of 6B4.1, 6B5.1, 6E1.2, 6E1.2 HC G2V, 6E1.2 HC F80Y, or 6E1.2 HC G2V F80Y; or CDR1, CDR2, and CDR3 of the light chain variable domain sequence, and CDR1, CDR2, and CDR3 of the heavy chain variable domain sequence, of 6B4.1, 6B5.1, or 6E1.2; or light chain variable domain CDR1, CDR2, and CDR3 sequences that each differs at no more than 3, 2, or 1 amino acid positions from the light chain variable domain CDR1, CDR2, and CDR3 sequences, respectively, of the light chain variable domain sequence of 6B4.1, 6B5.1, 6E1.2, 6B4.1 LC desS, 6E1.2 LC H36Q; or heavy chain variable domain CDR1, CDR2, and CDR3 sequences that each differs at no more than 3, 2, or 1 amino acid positions from the heavy chain variable domain CDR1, CDR2, and CDR3 sequences, respectively, of the heavy chain variable domain sequence of 6B4.1, 6B5.1, 6E1.2, 6E1.2 HC G2V, 6E1.2 HC F80Y, or 6E1.2 HC G2V F80Y; or light chain variable domain CDR1, CDR2, and CDR3 sequences that each differs at no more than 3, 2, or 1 amino acid positions from the light chain variable domain CDR1, CDR2, and CDR3 sequences, respectively, of the light chain variable domain sequence of antibody 6B4.1, 6B5.1, or 6E1.2, and heavy chain variable domain CDR1, CDR2, and CDR3 sequences that each differs at no more than 3, 2, or 1 amino acid positions from the heavy chain variable domain CDR1, CDR2, and CDR3 sequences, respectively, of the heavy chain variable domain sequence of the same antibody 6B4.1, 6B5.1, or 6E1.2.

In one embodiment, the anti-CCR7 antigen binding protein comprises: the light chain sequence of 6B4.1 LC or of 6B4.1 LC desS and the heavy chain sequence of 6B4.1 HC, as shown in FIG. 1; or the light chain sequence of 6B5.1 LC and the heavy chain sequence of 6B5.1 HC, as shown in FIG. 1; or the light chain sequence of 6E1.2 LC or of 6E1.2 LC H36Q and the heavy chain sequence of 6E1.2, 6E1.2 HC G2V, 6E1.2 HC F80Y, or 6E1.2 HC G2V F80Y, as shown in FIG. 1; or the light chain sequence of MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8 and the heavy chain sequence of MAB22_HC_V1.

In another embodiment, the isolated anti-CCR7 antigen binding protein competes for binding to a human CCR7 with antibody 6B4.1, 6B5.1, or 6E1.2.

In another embodiment, the antigen binding protein comprises either: a light chain variable domain that differs from the light chain variable domain of antibody 6B4.1, 6B5.1, or 6E1.2 only in that one or more non-germline amino acid residues are replaced with the corresponding germline residues; a heavy chain variable domain that differs from the heavy chain variable domain of antibody 6B4.1, 6B5.1, or 6E1.2 only in that one or more non-germline amino acid residues are replaced with the corresponding germline residues; or a light chain variable domain that differs from the light chain variable domain of antibody 6B4.1, 6B5.1, or 6E1.2 only in that one or more non-germline amino acid residues are replaced with the corresponding germline residues, and a heavy chain variable domain that differs from the heavy chain variable domain of the same antibody 6B4.1, 6B5.1, or 6E1.2 only in that one or more non-germline amino acid residues are replaced with the corresponding germline residues.

In another embodiment, the isolated CCR7 antigen binding protein comprises: a human antibody; a humanized antibody; a chimeric antibody; a monoclonal antibody; a polyclonal antibody; a recombinant antibody; an antigen-binding antibody fragment; a single chain antibody; a diabody; a triabody; a tetrabody; a Fab fragment; a F(ab')2 fragment; a domain antibody; an IgD antibody; an IgE antibody; an IgM antibody; an IgG1 antibody; an IgG2 antibody; an IgG3 antibody; an IgG4 antibody; or an IgG4 antibody having at least one mutation in a hinge region that alleviates a tendency to form intra-H chain disulfide bond.

In another embodiment, the isolated anti-CCR7 antigen binding protein inhibits binding of CCL19 or CCL21 to CCR7.

In another aspect, the present invention provides an isolated polynucleotide comprising a sequence that encodes the light chain, the heavy chain, or both of an isolated anti-CCR7 antigen binding protein.

In one embodiment, the isolated polynucleotide comprises a light chain variable domain nucleic acid sequence and/or a heavy chain variable domain nucleic acid sequence of FIG. 1.

In another aspect, the present invention provides a plasmid comprising the isolated polynucleotide.

In one embodiment, the plasmid is an expression vector.

In another aspect, the present invention provides an isolated cell comprising the isolated polynucleotide.

In another embodiment, a chromosome of the cell comprises the polynucleotide.

In another embodiment, the cell is a hybridoma.

In another embodiment, an expression vector comprises said polynucleotide.

In another embodiment, the cell is a CHO cell.

In another embodiment, the cell is a bacterial cell.

In another embodiment, the cell is an *E. coli* cell.

In another embodiment, the cell is a yeast cell.

In another embodiment, the cell is an animal cell.

In another embodiment, the cell is a human cell.

In another aspect, the present invention provides a method of making an anti-CCR7 antigen binding protein, comprising incubating the isolated cell under conditions that allow it to express the antigen binding protein.

In another aspect, the present invention provides a pharmaceutical composition comprising the anti-CCR7 antigen binding protein.

BRIEF DESCRIPTION OF THE FIGURE

FIG. 1A-AR provides nucleic acid and amino acid sequences of the antibodies and other polypeptides disclosed herein. Variable domain sequences of light and heavy chain antibody sequences are underlined.

DETAILED DESCRIPTION

Figure 2:
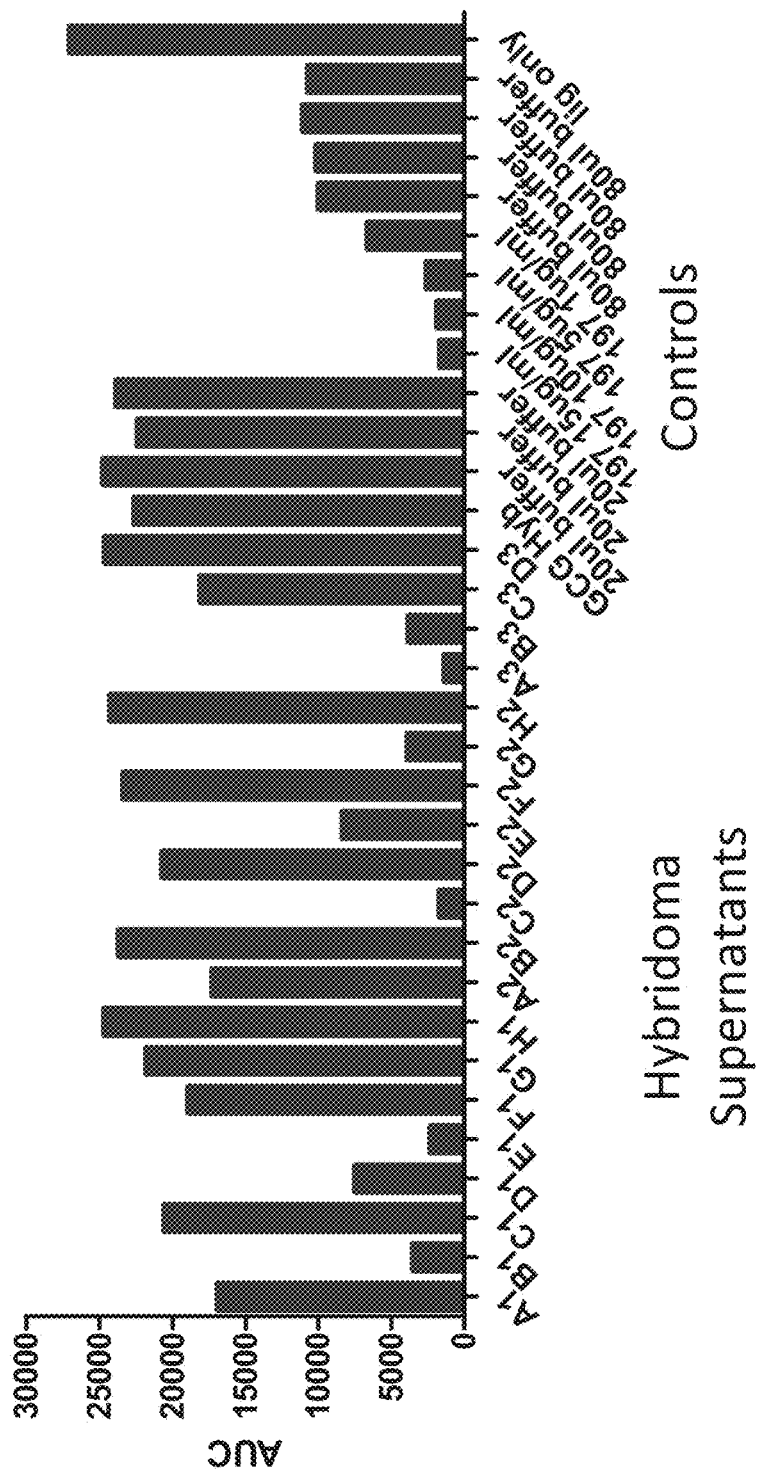
FIG. 2 provides the results of a hybridoma supernatant screen.

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, the terminology and techniques of cell and tissue culture, molecular biology, immunology, microbiology, genetics, protein and nucleic acid chemistry, manufacturing, formulation, pharmacology, and medicine described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art, or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

This invention is not limited to the particular methodology, protocols, reagents, etc., described herein. The terminology used herein is for the purpose of describing particular embodiments only, and is not intended to limit the scope of the present invention as defined by the claims.

Other than in the operating examples, or where otherwise indicated, all numbers expressing quantities of ingredients or reaction conditions used herein should be understood as modified in all instances by the term "about" as that term would be interpreted by the person skilled in the relevant art.

Definitions

The term "polynucleotide" or "nucleic acid" includes nucleotide polymers of any length. They can be, for example, single-stranded, double-stranded, or triple-stranded, or a combination of single- and/or double- and/or triple-stranded. Where a nucleotide polymer comprises more than one strand, each strand is itself understood to be a polynucleotide or nucleic acid. Where a nucleotide polymer is double-stranded, typically each of the strands is complementary to the other, although their complementarity need not be perfect and in some instances is sufficient to allow the stable association or hybridization of the two strands only under certain hybridization conditions. The nucleotides comprising the polynucleotide can be naturally-occurring or artificial nucleotide analogs, such as, for example, ribonucleotides, deoxyribonucleotides, or modified forms of either type of nucleotide, or a combination of different types of nucleotides and/or nucleotide analogs. Said modifications include, for example, base modifications, such as bromouridine and inosine derivatives, ribose modifications, such as 2',3'-dideoxyribose, and internucleotide linkage modifications, such as phosphorothioate, phosphorodithioate, phosphoroselenoate, phosphorodiselenoate, phosphoroanilothioate, phoshoraniladate and phosphoroamidate. The terms "polynucleotide" and "nucleic acid" include nucleotide polymers that have been covalently or non-covalently modified by the addition of one or more non-polynucleotide chemical entities, such as, for example, labels, (e.g., radiolabels), fluorescent labels, haptens or antigenic labels as well as nucleotide polymers that have been covalently or non-covalently bound to a solid object or surface, such as a hybridization membrane (e.g., a nitrocellulose hybridization membrane), a bead, a vessel wall, or the like.

The term "oligonucleotide" refers generally to shorter polynucleotide or nucleic acid sequences. The length of a particular oligonucleotide will depend on how it is made and/or its intended use. Typically, it refers to a polynucleotide comprising 200 or fewer nucleotides. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be, for example, single-, double-, or triple-stranded. Single stranded oligonucleotides may be sense or antisense oligonucleotides. Oligonucleotides have many uses, including, for example, as PCR primers, cloning primers, adapters for joining two or more polynucleotides, and hybridization probes.

An "isolated nucleic acid molecule" means a DNA or RNA of genomic, mRNA, cDNA, or synthetic origin, or some combination thereof, which is at least partially removed from its natural environment. Examples of isolated nucleic acid molecules include nucleic acids that have sequences found in nature but that are produced synthetically, naturally-occurring nucleic acids that are not associated with all or a portion of a polynucleotide in which the isolated polynucleotide is found in nature, naturally-occurring nucleic acids that are linked to a polynucleotide to which they are not linked in nature, and naturally-occurring nucleic acids that have been at least partially removed from their natural cellular environment. For purposes of this disclosure, it should be understood that "a nucleic acid molecule comprising" a particular nucleotide sequence does not encompass intact naturally-occurring chromosomes. Isolated nucleic acid molecules "comprising" specified nucleic acid sequences may include other sequences as well, such as, for example, one or more other coding sequences, operably linked regulatory sequences that control or affect expression of the coding region of the recited nucleic acid sequences, vector or plasmid sequences, sequences controlling or affecting replication of the nucleic acid, restriction sites, primer binding sites, and the like.

Unless specified otherwise, the left-hand end of any single-stranded polynucleotide sequence provided herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

The term "control sequence" refers to a polynucleotide sequence that can affect the expression and/or processing of a coding sequence to which it is ligated. The nature of such control sequences may depend upon the host organism. In particular embodiments, control sequences for prokaryotes may include a promoter, a ribosomal binding site, and a transcription termination sequence. Examples of control sequences for eukaryotes include promoters comprising one or a plurality of recognition sites for transcription factors, transcription enhancer sequences, and transcription termination sequences. The term "control sequences" can refer to leader sequences and/or fusion partner sequences as well.

The term "vector" means any molecule or entity (e.g., nucleic acid, plasmid, bacteriophage or virus) used to transfer protein coding information into a host cell.

The terms "expression vector," "expression plasmid," and "expression construct" each refers to a vector that is suitable for transformation of a host cell and contains nucleic acid sequences that allows (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

As used herein, "operably linked" means that the components to which the term is applied are in a relationship that allows them to carry out their inherent or desired functions under suitable conditions. An example of a control sequence that is "operably linked" to a protein coding sequence in a vector is an enhancer region that is ligated (either directly or via intermediary sequences) to the protein coding sequence such that expression of the protein coding sequence is achieved under conditions compatible with the transcriptional activity of the enhancer region.

The term "host cell" means a cell capable of expressing, under the correct conditions, a coding sequence of interest. The term includes the progeny of the parent cell, whether or not the progeny is identical in morphology or in genetic make-up to the original parent cell, so long as the coding sequence of interest is present. A "host cell" can be a cell that has been transformed, or is capable of being transformed, with a nucleic acid sequence and thereby express a coding sequence of interest.

The term "transduction" means the transfer of genes from one bacterium to another, usually by bacteriophage. "Transduction" also refers to the acquisition and transfer of eukaryotic cellular sequences by replication defective retroviruses.

The term "transfection" means the uptake of foreign or exogenous DNA by a cell, and a cell has been "transfected" when the exogenous DNA has been introduced into the cell. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197. Such techniques can be used to introduce one or more exogenous DNA moieties into suitable host cells. Depending on the technique used to make the transfected cell and the desired use of the transfected cell, a cell can be transfected either stably or transiently.

The term "transformation" refers to a change in a cell's genetic characteristics, and a cell has been transformed when it has been modified to contain new DNA or RNA. For example, a cell is transformed where it is genetically modified from its native state by introducing new genetic material via, for example, transfection or transduction, or via another technique, such as a chemical, ballistic, or electroporation technique. Following transformation, the transforming DNA may recombine with that of the cell by physically integrating into a chromosome of the cell, or may be maintained transiently as an episomal element without being replicated and/or stably propagated during cellular division, or it may replicate independently as a plasmid. A cell is considered to have been "stably transformed" when the transforming DNA is replicated as part of the host cell's cycle of cell division.

The terms "polypeptide" or "protein" are used interchangeably herein to refer to a polymer of amino acid residues. The terms also apply to amino acid polymers in which one or more amino acid residues is an analog, derivative, or mimetic of a naturally occurring amino acid, as well as to naturally occurring amino acid polymers. The terms also encompass amino acid polymers that have been modified. Such modifications include any naturally-occurring or artificial modification of a polypeptide. Some such modifications will alter the sequence of the polypeptide, but others will not. Examples of such modifications include the addition of carbohydrate residues and phosphorylation. Polypeptides and proteins can be produced and/or modified by a naturally-occurring and non-recombinant cell or they can be produced by a genetically-engineered or recombinant cell. "Polypeptides" and "proteins" comprise molecules having the amino acid sequence of a native protein, or molecules having deletions from, additions to, and/or substitutions of one or more amino acids of, the native sequence. The terms "polypeptide" and "protein" specifically encompass CCR7 antigen-binding proteins, antibodies, or sequences that have deletions from, additions to, and/or substitutions of one or more amino acids of an antigen-binding protein. The term "polypeptide fragment" refers to a polypeptide that has an amino-terminal deletion, a carboxyl-terminal deletion, and/or an internal deletion as compared with the full-length protein. Such fragments may also contain modified amino acids as compared with the full-length protein. In certain embodiments, fragments are about five to 500 amino acids long. For example, fragments may be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a CCR7-binding antibody, useful fragments include but are not limited to a CDR region, a variable domain of a heavy or light chain, a portion of an antibody chain or just its variable region including two CDRs, and the like.

An "isolated protein" (1) is free of at least some other proteins or cellular components with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent bonds) with a polypeptide with which it is not associated in nature, or (6) does not occur in nature. An "isolated protein" can constitute at least about 5%, at least about 10%, at least about 25%, or at least about 50% of a given sample. Genomic DNA, cDNA, mRNA or other RNA, of synthetic origin, or any combination thereof may encode such an isolated protein. In some embodiments, the isolated protein is substantially free from proteins or polypeptides or other contaminants that are found in its natural environment that would interfere with its therapeutic, diagnostic, prophylactic, research or other use.

A "variant" of a polypeptide (e.g., of an antigen binding protein or of an antibody) comprises an amino acid sequence wherein one or more amino acid residues are inserted into, deleted from and/or substituted into the amino acid sequence relative to another polypeptide sequence. A fusion protein comprising all or part of a polypeptide is one example of a variant of the polypeptide.

A "derivative" of a polypeptide is a polypeptide (e.g., an antigen binding protein, or an antibody) that has been chemically modified in some manner distinct from the insertion, deletion, and/or substitution of amino acids, e.g., via conjugation to another chemical moiety. An antigen binding protein that contains all or most of either the light- or heavy-chain variable domain of an antibody, but lacks most or all of the other variable domain of the antibody, is an example of a derivative of the antibody.

The term "naturally occurring" as used throughout the specification in connection with biological materials such as polypeptides, nucleic acids, host cells, and the like, refers to materials which are found in nature.

An "antigen binding protein" as used herein means a protein that specifically binds a specified target antigen, such as CCR7 or human CCR7.

An antigen binding protein, such as an antibody or antibody fragment, variant, or derivative, is said to "specifically bind" its target antigen when it binds immunospecifically to its target antigen. In some embodiments, a specifically binding antigen binding protein has a dissociation constant ($K_D$) of 1 to $10 \times 10^{-8}$ M. The antibody specifically binds antigen with "high affinity" when the $K_D$ is 1 to $10 \times 10^{-9}$ M, and with "very high affinity" when the $K_D$ is 1 to $10 \times 10^{-10}$ M. In one embodiment, the antibody has a $K_D$ of 1 to $10 \times 10^{-9}$ M and an off-rate of about $1 \times 10^{-4}$/sec. In one embodiment, the off-rate is about $1 \times 10^{-5}$/sec. In other embodiments, the antibodies will bind to CCR7, or human CCR7, with a $K_D$ of between about $10^{-8}$ M and $10^{-10}$ M, and in yet another embodiment it will bind with a $K_D$ of 1 to $2 \times 10^{-10}$.

"Antigen binding region" means the portion of an antibody or other antigen binding protein, or a fragment, derivative, or variant thereof, that specifically binds a specified antigen. An antigen binding region can include one or more "complementarity determining regions" ("CDRs"). Certain antigen binding regions also include one or more "framework" regions. Residues within the framework regions of some antibodies and other antigen binding proteins can contribute directly to the specific binding of the antibody or antigen binding protein to its antigen, but typically framework regions aid in maintaining a conformation of the CDRs that allows binding between the antigen binding region and the antigen.

In certain aspects, recombinant antigen binding proteins that bind CCR7, or human CCR7, are provided. In this context, a "recombinant protein" is a protein made using recombinant techniques, e.g., through the expression of a recombinant nucleic acid. Methods and techniques for the production of recombinant proteins are well known in the art.

The term "antibody" refers to an intact antigen-binding immunoglobulin of any kind, or a fragment thereof that itself specifically binds to the antibody's target antigen, and includes, for example, chimeric, humanized, fully human, and bispecific antibodies. An "antibody" is a type of an antigen binding protein. In some embodiments, an intact antibody comprises two full-length heavy chains and two full-length light chains. In other embodiments, an intact antibody includes fewer chains such as antibodies naturally occurring in camelids, which may comprise only heavy chains. In other embodiments, a fragment or derivative of an antibody is made that lacks part or all of the antibody's light chains or light chain variable regions. In other embodiments, a fragment or derivative of an antibody is made that lacks some or all of the antibody's heavy chains. Such derivatives or fragments typically will comprise one or more linker or other amino acid sequences to join the light chains or light chain fragments and/or allow them to adopt a conformation that allows for binding of the fragment or derivative to its antigen.

The amino acid sequences of an antibody may be derived solely from a single source, or may be "chimeric"; that is, different portions of the antibody may be derived from two different antibodies as described further below. The antigen binding proteins, antibodies, or binding fragments may be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and mutations thereof.

The term "light chain" includes full-length light chain as well as fragments, derivatives, and variants thereof having a variable region sequence that is sufficient, in combination, as needed, with a suitable heavy chain or heavy chain fragment, derivative, or variant, to confer specific binding to an antigen. A full-length light chain includes a variable region domain, $V_L$, and a constant region domain, $C_L$. Examples of light chains include kappa light chains and lambda light chains.

The term "heavy chain" includes a full-length heavy chain as well as fragments, derivatives, and variants thereof having a variable region sequence that is sufficient, in combination, as needed, with a suitable light chain or light chain fragment, derivative, or variant, to confer specific binding to an antigen. A full-length heavy chain includes a variable region domain, $V_H$, and three constant region domains, $C_{H1}$, $C_{H2}$, and $C_{H3}$. Heavy chains may be of any isotype, including IgG (including IgG1, IgG2, IgG3 and IgG4 subtypes), IgA (including IgA1 and IgA2 subtypes), IgM and IgE, as well as derivatives and variants thereof.

The term "immunologically functional fragment" of an antibody or immunoglobulin chain (heavy or light chain), as used herein, is an antigen binding protein comprising a portion (regardless of how that portion is obtained or synthesized) of an antibody that lacks at least some of the amino acids present in a full-length chain but which is capable of specifically binding to an antigen. Such fragments are biologically active in that they bind specifically to the target antigen. In some embodiment, such a fragment will retain at least one CDR present in the full-length light or heavy chain, and in some embodiments will comprise a single heavy chain and/or light chain or portion thereof. These biologically active fragments may be produced by, for example, recombinant DNA techniques or by enzymatic or chemical cleavage of antigen binding proteins, including of intact antibodies. Immunologically functional immunoglobulin fragments include, but are not limited to, Fab, Fab', F(ab')2, Fv, domain antibodies and single-chain antibodies, and may be derived from any mammalian source, including but not limited to human, mouse, rat, camelid or rabbit. It is contemplated further that a functional portion of the antigen binding proteins disclosed herein, for example, one or more CDRs, could be covalently bound to a second protein or to a small molecule to create a therapeutic agent directed to a particular target in the body, possessing bifunctional therapeutic properties, or having a prolonged serum half-life.

"Single-chain antibodies" are Fv molecules in which the heavy and light chain variable regions have been connected by a flexible linker to form a single polypeptide chain, which forms an antigen-binding region. Single chain antibodies are discussed in detail in International Patent Application Publication No. WO 88/01649 and U.S. Pat. No. 4,946,778 and No. 5,260,203, the disclosures of which are incorporated by reference.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antigen binding protein" or "bivalent antibody" comprises two antigen binding sites. In some embodiments, the two binding sites have the same antigen specificities. In other embodiments, the bivalent antigen binding proteins and bivalent antibodies are bispecific.

A multispecific antigen binding protein" or "multispecific antibody" is one that specifically binds more than one antigen or epitope.

A "bispecific," "dual-specific" or "bifunctional" antigen binding protein or antibody is a hybrid antigen binding protein or antibody, respectively, having two antigen binding sites that each specifically binds to a different epitope. The two epitopes can be present on the same molecule (e.g., on the CCR7 protein) or on different molecules (e.g., on the CCR7 protein and on CCL19 OR CCL21). Bispecific antigen binding proteins and antibodies are a species of multispecific antigen binding protein or multispecific antibody and may be produced by a variety of methods including, but not limited to, fusion of hybridomas or linking of Fab' fragments. See, e.g., Songsivilai and Lachmann, 1990, Clin. Exp. Immunol. 79:315-321; Kostelny et al., 1992, J. Immunol. 148:1547-1553.

The terms "inhibitory antigen binding protein," "inhibitory antibody," "antagonistic antigen binding protein," "antagonistic antibody," "neutralizing antigen binding protein" and "neutralizing antibody" refers to an antigen binding protein or antibody, respectively, that specifically binds to its target and thereby reduces or prevents a biological activity of the target, such as, for example, its ability to bind with a ligand, receptor, binding partner, regulatory molecule, or substrate, catalyze a reaction, send or propagate a signal, or phosphorylate or de-phosphorylate itself or another protein.

The term "compete" when used in the context of antigen binding proteins (e.g., neutralizing antigen binding proteins or neutralizing antibodies) that bind to the same target means competition between antigen binding proteins is determined by an assay in which the antigen binding protein (e.g., antibody or immunologically functional fragment thereof) under test prevents, reduces or inhibits specific binding of a reference antigen binding protein (e.g., a ligand, or a reference antibody) to a common antigen (e.g., CCR7 or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176: 546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins, an epitope that overlaps the epitope as the reference antigen binding proteins, and epitopes that do not overlap but that allow for steric hindrance to occur between the test and reference antigen binding proteins. A specific method for determining competitive binding is provided in the examples herein. Usually, when a competing antigen binding protein is present in excess, it will inhibit specific binding of a reference antigen binding protein to a common antigen by at least 20%, 25%, 30%, 35%, 40%, 45%, 50%, 55%, 60%, 65%, 70% or 75%. In some instance, binding is inhibited by at least 80%, 85%, 90%, 95%, or 97% or more.

The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies.

The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a polypeptide, amino acid residues that are not contiguous to one another in the polypeptide sequence but that within in context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) must be addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al., 1988, SIAM J. Applied Math. 48:1073.

In calculating percent identity, the sequences being compared are aligned in a way that gives the largest match between the sequences. The computer program used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. USA. 89:10915-10919 for the BLOSUM 62 comparison matrix) is also used by the algorithm.

Parameters for determining percent identity for polypeptides or nucleotide sequences using the GAP program are the following:
Algorithm: Needleman et al., 1970, J. Mol. Biol. 48:443-453;
Comparison matrix: BLOSUM 62 from Henikoff et al., 1992, supra;
Gap Penalty: 12 (but with no penalty for end gaps)
Gap Length Penalty: 4
Threshold of Similarity: 0

Certain alignment schemes for aligning two amino acid sequences may result in matching of only a short region of the two sequences, and this small aligned region may have very high sequence identity even though there is no significant relationship between the two full-length sequences. Accordingly, the selected alignment method (GAP program) can be adjusted if so desired to result in an alignment that spans at least 50 contiguous amino acids of the target polypeptide.

As used herein, "substantially pure" means that the described species of molecule is the predominant species present, that is, on a molar basis it is more abundant than any other individual species in the same mixture. In certain embodiments, a substantially pure molecule is a composition wherein the object species comprises at least 50% (on a molar basis) of all macromolecular species present. In other embodiments, a substantially pure composition will comprise at least 80%, 85%, 90%, 95%, or 99% of all macromolecular species present in the composition. In other embodiments, the object species is purified to essential homogeneity wherein contaminating species cannot be detected in the composition by conventional detection methods and thus the composition consists of a single detectable macromolecular species.

The term "treating" refers to any indicia of success in the prevention, prophylaxis, treatment or amelioration of an injury, pathology, disease or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods presented herein successfully treat inflammatory conditions by decreasing the incidence of inflammation, causing remission of inflammation and/or ameliorating a symptom associated with inflammation.

An "effective amount" of a therapeutic treatment is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with symptoms or their underlying cause. In some embodiments, the effective amount is a therapeutically effective amount or a prophylactically effective amount. A "therapeutically effective amount" is an amount sufficient to remedy a disease state (e.g. inflammation) or symptoms, particularly a state or symptoms associated with the disease state, or otherwise prevent, hinder, retard or reverse the progression of the disease state or any other undesirable symptom associated with the disease in any way whatsoever. A "prophylactically effective amount" is an amount of a pharmaceutical composition that, when administered to a subject, will have the intended prophylactic effect, e.g., preventing or delaying the onset (or reoccurrence) of inflammation, or reducing the likelihood of the onset (or reoccurrence) of inflammation or inflammation symptoms. The full therapeutic or prophylactic effect does not necessarily occur by administration of one dose, and may occur only after administration of a series of doses. Thus, a therapeutically or prophylactically effective amount may be administered in one or more administrations.

"Amino acid" includes its normal meaning in the art. The twenty naturally-occurring amino acids and their abbreviations follow conventional usage. See, Immunology—A Synthesis, 2nd Edition, (E. S. Golub and D. R. Green, eds.), Sinauer Associates: Sunderland, Mass. (1991), incorporated herein by reference for any purpose. Stereoisomers (e.g., D-amino acids) of the twenty conventional amino acids, unnatural amino acids such as [alpha]-, [alpha]-disubstituted amino acids, N-alkyl amino acids, and other unconventional amino acids may also be suitable components for polypeptides and are included in the phrase "amino acid." Examples of unconventional amino acids include: 4-hydroxyproline, [gamma]-carboxyglutamate, [epsilon]-N,N,N-trimethyllysine, [epsilon]-N-acetyllysine, O-phosphoserine, N-acetylserine, N-formylmethionine, 3-methylhistidine, 5-hydroxylysine, [sigma]-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

The term "CCR7 mediated disease" includes, but is not limited to, inflammatory, infectious, and autoimmune diseases. An "autoimmune disease" as used herein refers to disease states and conditions wherein a patient's immune response is directed toward the patient's own constituents. For example, CCR7 mediated diseases include, but are not limited to, Acquired Immune Deficiency Syndrome (AIDS), rheumatoid arthritis including juvenile rheumatoid arthritis, inflammatory bowel diseases including ulcerative colitis and Crohn's disease, multiple sclerosis, Addison's disease, diabetes (type I), diabetes (type 2), insulin resistance, metabolic syndrome, heart disease, coronary artery disease, epididymitis, glomerulonephritis, Graves' disease, Guillain-Barre syndrome, Hashimoto's disease, hemolytic anemia, systemic lupus erythematosus (SLE), lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies including ankylosing spondylitis, thyroiditis, vasculitis, atherosclerosis, coronary artery disease, and heart disease. The term "CCR7 mediated disease" also encompasses any medical condition associated with increased levels of CCL19 or CCL21 or CCR7 or increased sensitivity to CCL19 OR CCL21.

Antigen Binding Proteins

In one aspect, the present invention provides antigen binding proteins (e.g., antibodies, antibody fragments, antibody derivatives, antibody muteins, and antibody variants), that bind to CCR7, e.g., human CCR7.

Antigen binding proteins in accordance with the present invention include antigen binding proteins that inhibit a biological activity of CCR7. Examples of such biological activities include binding a signaling molecule (e.g. CCL19 or CCL21), and transducing a signal in response to binding a signaling molecule.

Different antigen binding proteins may bind to different domains or epitopes of CCR7 or act by different mechanisms of action. Examples include but are not limited to antigen binding proteins that interfere with binding of CCL19 or CCL21 to CCR7 or that inhibit signal transduction. The site of action may be, for example, intracellular (e.g., by interfering with an intracellular signaling cascade) or extracellular. An antigen binding protein need not completely inhibit a CCL19 or CCL21 induced activity to find use in the present invention; rather, antigen binding proteins that reduce a particular activity of CCL19 or CCL21 are contemplated for use as well. (Discussions herein of particular mechanisms of action for CCR7-binding antigen binding proteins in treating particular diseases are illustrative only, and the methods presented herein are not bound thereby.)

In another aspect, the present invention provides CCR7 antigen binding proteins that comprise a light chain variable region and/or a heavy chain variable region selected from the sequences provided herein, or that comprise one or more CDR sequences selected from the sequences provided herein. Examples of antigen binding proteins of the present invention include antigen binding proteins, antibodies, and antibody derivatives and fragments comprising all or part of the sequences of 6B4.1, 6B5.1, 6E1.2, 6B4.1 LC desS, 6E1.2 HC G2V, 6E1.2 HC F80Y, 6E1.2 HC G2V F80Y, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, MAB22_KLC_V8, and/or MAB22_HC_V1, as disclosed herein. Specific examples of such antigen binding proteins include antibody 6B4.1 [SEQ ID NO:2 and 42], antibody 6B5.1 [SEQ ID NO:18 and 50], antibody 6E1.2 [SEQ ID NO:26 and 58], and antibody mAb 22 [SEQ ID NO:92 and 108]. Specific fragments of these antibodies that are found in various embodiments of the invention include their signal sequences, variable domains, CDRs, framework regions, and constant regions. In one such embodiment, the antigen binding protein comprises the heavy chain variable domain of 6B4.1 HC, 6B5.1 HC, 6E1.2 HC, 6E1.2 HC G2V, 6E1.2 HC F80Y, 6E1.2 HC G2V F80Y or MAB22_HC_V1. In another such embodiment, the antigen binding protein comprises the light chain variable domain of 6B4.1 LC, 6B5.1 LC, 6E1.2 LC, 6B4.1 LC desS, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, or MAB22_KLC_V8. In another such embodiment, the antigen binding protein comprises the light chain variable domain and the heavy chain variable domain of antibody 6B4.1, 6B5.1, 6E1.2, or the heavy chain variable domain of 6B4.1 and the light chain variable domain of 6B4.1 LC desS, or the light chain variable domain of 6E1.2 LC and the heavy chain variable domain of 6E1.2 HC G2V, 6E1.2 HC F80Y, or 6E1.2 HC G2V F80Y, or the heavy chain variable domain of 6E1.2 HC and the light chain variable domain of 6E1.2 LC H36Q. In another such embodiment, the antigen binding protein comprises the heavy chain CDR sequences of antibody 6B4.1 HC, 6B5.1 HC, or 6E1.2 HC. In another such embodiment, the antigen binding protein comprises the light chain CDR sequences of antibody 6B4.1, 6B5.1, or 6E1.2. In another such embodiment, the antigen binding protein comprises the heavy chain CDR sequences and the light chain CDR sequences of antibody 6B4.1 LC, 6B5.1 LC, or 6E1.2 LC. In some such embodiments, the antigen binding protein is an antibody or an antigen-binding fragment of an antibody.

In another embodiment, the present invention provides a CCR7 antigen binding protein comprising a light chain variable domain comprising a sequence of amino acids that differs from the sequence of a light chain variable domain disclosed herein only at 15, 14, 13, 12, 11, 10, 9, 8, 7, 6, 5, 4, 3, 2, or 1 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain selected from the light chain variable domain sequences disclosed herein. In another embodiment, the light chain variable domain comprises a sequence of amino acids that is encoded by a nucleotide sequence that is at least 70%, 75%, 80%, 85%, 90%, 95%, 97%, or 99% identical to a nucleotide sequence disclosed herein. In another embodiment, the light chain variable domain comprises a sequence of amino acids that is encoded by a polynucleotide that hybridizes under moderately stringent conditions to the complement of a polynucleotide disclosed herein. In another embodiment, the light chain variable domain comprises a sequence of amino acids that is encoded by a polynucleotide that hybridizes under moderately stringent conditions to the complement of a polynucleotide disclosed herein. In another embodiment, the light chain variable domain comprises a sequence of amino acids that is encoded by a polynucleotide that hybridizes under moderately stringent conditions to a complement of a light chain polynucleotide disclosed herein.

In another embodiment, the present invention provides a CCR7 antigen binding protein comprising a heavy chain variable domain comprising a sequence of amino acids that differs from the sequence of a heavy chain variable domain selected disclosed herein only at 15, 14, 13, 12, 11, 10, 9, 8, 7, 6, 5, 4, 3, 2, or 1 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain sequence disclosed herein. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence disclosed herein. In another embodiment, the heavy chain variable domain comprises a sequence of amino acids that is encoded by a polynucleotide that hybridizes under moderately stringent conditions to the complement of a polynucleotide disclosed herein. In another embodiment, the heavy chain variable domain comprises a sequence of amino acids that is encoded by a polynucleotide that hybridizes under moderately stringent conditions to the complement of a polynucleotide disclosed herein. In another embodiment, the heavy chain variable domain comprises a sequence of amino acids that is encoded by a polynucleotide that hybridizes under moderately stringent conditions to a complement of a heavy chain polynucleotide disclosed herein.

Particular embodiments of antigen binding proteins of the present invention comprise one or more amino acid sequences that are identical to the amino acid sequences of one or more of the CDRs and/or FRs disclosed herein. In one embodiment, the antigen binding protein comprises a light chain CDR1 sequence disclosed herein. In another embodiment, the antigen binding protein comprises a light chain CDR2 sequence disclosed herein. In another embodiment, the antigen binding protein comprises a light chain CDR3 sequence disclosed herein. In another embodiment, the antigen binding protein comprises a heavy chain CDR1 sequence disclosed herein. In another embodiment, the antigen binding protein comprises a heavy chain CDR2 sequence disclosed herein. In another embodiment, the antigen binding protein comprises a heavy chain CDR3 sequence disclosed herein. In another embodiment, the antigen binding protein comprises a light chain FR1 sequence disclosed herein. In another embodiment, the antigen binding protein comprises a light chain FR2 sequence disclosed herein. In another embodiment, the antigen binding protein comprises a light chain FR3 sequence disclosed herein. In another embodiment, the antigen binding protein comprises a light chain FR4 sequence disclosed herein. In another embodiment, the antigen binding protein comprises a heavy chain FR1 sequence disclosed herein. In another embodiment, the antigen binding protein comprises a heavy chain FR2 sequence disclosed herein. In another embodiment, the antigen binding protein comprises a heavy chain FR3 sequence disclosed herein. In another embodiment, the antigen binding protein comprises a heavy chain FR4 sequence disclosed herein.

In one embodiment, the present invention provides an antigen binding protein that comprises one or more CDR sequences that each differs from a CDR sequence disclosed herein by no more than 5, 4, 3, 2, or 1 amino acid residues.

In another embodiment, the present invention provides antibodies that cross-compete with one or more of the antibodies described herein for binding to the extracellular domain of human CCR7, wherein two antibodies "cross-compete" if each antibody reduces the binding of the other by at least 80%.

The nucleotide sequences or amino acid sequences disclosed herein can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al.1985, Gene 37:73; Craik, BioTechniques, Jan. 12-19, 1985; Smith et al., 1981, Genetic Engineering: Principles and Methods, Plenum Press; and U.S. Pat. Nos. 4,518,584 and 4,737,462. These and other methods can be used to make, for example, derivatives of anti-CCR7 antibodies that have a desired property, for example, increased affinity, avidity, or specificity for CCR7, increased activity or stability in vivo or in vitro, or reduced in vivo side-effects as compared to the underivatized antibody.

Other derivatives of anti-CCR7 antibodies within the scope of this invention include covalent or aggregative conjugates of anti-CCR7 antibodies, or fragments thereof, with other proteins or polypeptides, such as by expression of recombinant fusion proteins comprising heterologous polypeptides fused to the N-terminus or C-terminus of an anti-CCR7 antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide Asp-Tyr-Lys-Asp-Asp-Asp-Asp-Lys (DYKDDDDK) as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more antigen binding proteins may be employed as CCR7 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have CCR7 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11.

One embodiment of the present invention is directed to a dimer comprising two fusion proteins created by fusing a CCR7 binding fragment of an anti-CCR7 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-CCR7 antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-CCR7 antibody fragment or derivative fused to a leucine zipper peptide are expressed in suitable host cells, and the soluble oligomeric anti-CCR7 antibody fragments or derivatives that form are recovered from the culture supernatant.

In another aspect, the present invention provides an antigen binding protein that binds to the ligand binding domain of human CCR7. Antigen binding proteins that bind to the ligand binding domain can be made using any technique known in the art. For example, such antigen binding proteins can be isolated using the full-length CCR7 polypeptide (e.g., in a membrane-bound preparation), a soluble extracellular domain fragment of CCR7, or a smaller fragment of the CCR7 extracellular domain comprising or consisting of the ligand binding domain. Antigen binding proteins so isolated can be screened to determine their binding specificity using any method known in the art. Examples of suitable assays are assays that test the antigen binding proteins for the ability to inhibit binding of CCL19 or CCL21 to cells expressing CCR7, or that test antigen binding proteins for the ability to reduce a biological or cellular response that results from the binding of CCL19 or CCL21 to cell surface CCR7 receptors.

In another aspect, the present invention provides an antigen binding protein that binds to the same epitope as a reference antibody disclosed herein, for example, 6B4.1, 6B5.1, or 6E1.2. In one embodiment, the antigen binding protein competes for binding to human CCR7 with the reference antibody. In another embodiment, the antigen binding protein and the reference antibody cross-compete for binding to human CCR7. In another embodiment, the epitope of the reference antibody and of the antigen binding protein is determined by solving the X-ray crystal structure of the antibody or antigen binding protein bound to human CCR7, for example, to a soluble fragment of human CCR7. In one such embodiment, the epitope is defined as those residues on the surface of human CCR7 that show at least a 10% reduction in solvent accessibility when the reference antibody or the antigen binding protein is bound to it as compared to when it is bound to neither. In one embodiment, the epitope substantially overlaps the CCL19 or CCL21 binding domain of human CCR7.

In another aspect, the present invention provides an antigen binding protein that demonstrates species selectivity. In one embodiment, the antigen binding protein binds to one or more mammalia CCR7s, for example, to human CCR7 and to one or more of mouse, rat, guinea pig, hamster, gerbil, cat, rabbit, dog, goat, sheep, cow, horse, camel, and non-human primate CCR7. In another embodiment, the antigen binding protein binds to one or more primate CCR7s, for example, to human CCR7 and to one or more of cynomologous, marmoset, rhesus, and chimpanzee CCR7s. In another embodiment, the antigen binding protein binds specifically to human, cynomologous, marmoset, rhesus, or chimpanzee CCR7. In another embodiment, the antigen binding protein does not bind to one or more of mouse, rat, guinea pig, hamster, gerbil, cat, rabbit, dog, goat, sheep, cow, horse, camel, and non-human primate CCR7. In another embodiment, the antigen binding protein does not bind to a New World monkey species such as a marmoset. In another embodiment, the antigen binding protein does not exhibit specific binding to any naturally occurring protein other tha CCR7. In another embodiment, the antigen binding protein does not exhibit specific binding to any naturally occurring protein other than mammalia CCR7. In another embodiment, the antigen binding protein does not exhibit specific binding to any naturally occurring protein other than primate CCR7. In another embodiment, the antigen binding protein does not exhibit specific binding to any naturally occurring protein other than human CCR7. In another embodiment, the antigen binding protein specifically binds to mouse, rat, cynomolgus monkey, and human CCR7. In another embodiment, the antigen binding protein specifically binds to mouse, rat, cynomolgus monkey, and human CCR7 with a similar binding affinity. In another embodiment, the antigen binding protein blocks binding of human CCL19 or CCL21 with mouse, rat, cynomolgus monkey, and human CCR7. In another embodiment, the antigen binding protein blocks binding of human CCL19 OR CCL21 with mouse, rat, cynomolgus monkey, and human CCR7 with similar $K_i$.

One may determine the selectivity of an antigen binding protein for a CCR7 using methods well known in the art and following the teachings of the specification. For example, one may determine the selectivity using Western blot, FACS, ELISA or RIA.

Antigen-binding fragments of antigen binding proteins of the invention may be produced by conventional techniques. Examples of such fragments include, but are not limited to, Fab and F(ab')2 fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. patent application Ser. No. 10/194,975 (published Feb. 27, 2003), U.S. Pat. Nos. 5,869,619, 5,225,539, 5,821,337, 5,859,205, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with a CCR7 polypeptide, such that antibodies directed against the CCR7 polypeptide are generated in the animal. One example of a suitable immunogen is a soluble human CCR7, such as a polypeptide comprising its extracellular domain or other immunogenic fragment. Examples of techniques for production and use of transgenic animals for the production of human or partially human antibodies are described in U.S. Pat. Nos. 5,814,318, 5,569,825, and 5,545,806, Davis et al., 2003, Production of human antibodies from transgenic mice in Lo, ed. Antibody Engineering: Methods and Protocols, Humana Press, NJ:191-200, Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20.

In another aspect, the present invention provides monoclonal antibodies that bind to CCR7. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and 5194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with a CCR7 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds a CCR7 polypeptide. Such hybridoma cell lines, and anti-CCR7 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block an CCL19 or CCL21 induced activity. Examples of such screens are provided in the examples below.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to CCR7.

Antigen binding proteins directed against a CCR7 can be used, for example, in assays to detect the presence of CCR7 polypeptides, either in vitro or in vivo. The antigen binding proteins also may be employed in purifying CCR7 proteins by immunoaffinity chromatography. Those antigen binding proteins that additionally can block binding of CCL19 or CCL21 to CCR7 may be used to inhibit a biological activity that results from such binding. Blocking antigen binding proteins can be used in the methods of the present invention. Such antigen binding proteins that function as CCL19 or CCL21 antagonists may be employed in treating any CCL19- or CCL21-induced condition, including but not limited to lupus, SLE, and arthritis. In one embodiment, a human anti-CCR7 monoclonal antibody generated by procedures involving immunization of transgenic mice is employed in treating such conditions.

Antigen binding proteins may be employed in an in vitro procedure, or administered in vivo to inhibit an CCL19 or CCL21-induced biological activity. Disorders caused or exacerbated (directly or indirectly) by the interaction of CCL19 or CCL21 with cell surface CCR7, examples of which are provided herein, thus may be treated. In one embodiment, the present invention provides a therapeutic method comprising in vivo administration of an CCL19 or CCL21 blocking antigen binding protein to a mammal in need thereof in an amount effective for reducing an CCL19 or CCL21-induced biological activity.

Antigen binding proteins of the invention include partially human and fully human monoclonal antibodies that inhibit a biological activity of CCL19 or CCL21. One embodiment is directed to a human monoclonal antibody that at least partially blocks binding of CCL19 or CCL21 to a cell that expresses human CCR7. In one embodiment, the antibodies are generated by immunizing a transgenic mouse with a CCR7 immunogen. In another embodiment, the immunogen is a human CCR7 polypeptide (e.g., a soluble fragment comprising all or part of the CCR7 extracellular domain). Hybridoma cell lines derived from such immunized mice, wherein the hybridoma secretes a monoclonal antibody that binds CCR7, also are provided herein.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble CCR7 polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (Cloning Vectors: A Laboratory Manual, Elsevier, New York, 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of CCR7 bound thereto. Polypeptides contemplated for use herein include substantially homogeneous recombinant mammalian anti-CCR7 antibody polypeptides substantially free of contaminating endogenous materials.

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-CCR7 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-CCR7 antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides (VL and VH). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different VL and VH -comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein include, but are not limited to, scFvs comprising one or more variable domain sequences, or one or more CDR sequences from one or more variable domain sequences, disclosed herein.

In some embodiments, antigen binding proteins (e.g., antibodies, antibody fragments, and antibody derivatives) of the invention comprise a light chain and/or a heavy chain antibody constant region. Any antibody constant regions known in the art can be used. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol.178:303-16.

Accordingly, the antigen binding proteins of the present invention include those comprising, for example, one or more of the variable domain sequences disclosed herein and having a desired isotype (for example, IgA, IgG1, IgG2, IgG3, IgG4, IgM, IgE, and IgD), as well as Fab or F(ab')2 fragments thereof. Moreover, if an IgG4 is desired, it may also be desired to introduce a point mutation (CPSCP ->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Techniques for deriving antigen binding proteins having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

In another embodiment, the present invention provides an antigen binding protein that has a low dissociation rate from CCR7. In one embodiment, the antigen binding protein has a $K_{off}$ of $1 \times 10^{-4}$ s$^{-1}$ or lower. In another embodiment, the $K_{off}$ is $5 \times 10^{-5}$ s$^{-1}$ or lower. In another embodiment, the $K_{off}$ is substantially the same as an antibody disclosed herein. In another embodiment, the antigen binding protein binds to CCR7 with substantially the same $K_{off}$ as an antibody disclosed herein. In another embodiment, the antigen binding protein binds to CCR7 with substantially the same $K_{off}$ as an antibody that comprises one or more CDRs from an antibody disclosed herein.

In another aspect, the present invention provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO 00/09560, published Feb. 24, 2000, incorporated by reference.

The present invention further provides multi-specific antigen binding proteins, for example, bispecific antigen binding protein, e.g., antigen binding protein that bind to two different epitopes of CCR7, or to an epitope of CCR7 and an epitope of another molecule, via two different antigen binding sites or regions. Moreover, bispecific antigen binding protein as disclosed herein can comprise a CCR7 binding site from one of the herein-described antibodies and a second CCR7 binding region from another of the herein-described antibodies, including those described herein by reference to other publications. Alternatively, a bispecific antigen binding protein may comprise an antigen binding site from one of the herein described antibodies and a second antigen binding site from another CCR7 antibody that is known in the art, or from an antibody that is prepared by known methods or the methods described herein.

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. Nos. 4,474,893, 6,106,833), and chemical coupling of antibody fragments (Brennan et al.,1985, Science 229:81; Glennie et al.,1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immnol. 148:1547) or other lock and key interactive domain structures as described in U.S. Pat. No. 5,582,996. Additional useful techniques include those described in Kortt et al., 1997, supra; U.S. Pat. Nos. 5,959,083; and 5,807,706.

In another aspect, the antigen binding protein of the present invention comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. U.S. Pat. App. No. 20030195154.

In another aspect, the present invention provides methods of screening for a molecule that binds to CCR7 using the antigen binding proteins of the present invention. Any suitable screening technique can be used. In one embodiment, a CCR7 molecule, or a fragment thereof to which an antigen binding protein of the present invention binds, is contacted with the antigen binding protein of the invention and with another molecule, wherein the other molecule binds to CCR7 if it reduces the binding of the antigen binding protein to CCR7. Binding of the antigen binding protein can be detected using any suitable method, e.g., an ELISA. Detection of binding of the antigen binding protein to CCR7 can be simplified by detectably labeling the antigen binding protein, as discussed above. In another embodiment, the CCR7-binding molecule is further analyzed to determine whether it inhibits CCR7-mediated signaling.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with CCR7. The nucleic acid may be isolated by conventional procedures such as polymerase chain reaction (PCR).

Representative nucleic acid sequences encoding some of the antibodies of the invention are disclosed herein. Particular nucleic acid sequences encoding the variable domains of 6B4.1, 6B5.1, 6E1.2, 6B4.1 LC desS, 6E1.2 HC G2V, 6E1.2 HC F80Y, 6E1.2 HC G2V F80Y, 6E1.2 LC H36Q, MAB22_KLC-V1, MAB22_KLC_V2, MAB22_KLC_V3, MAB22_KLC_V4, MAB22_KLC_V5, MAB22_KLC_V6, MAB22_KLC_V7, MAB22_KLC_V8, and MAB22_HC_V1, are disclosed herein. The skilled artisan will appreciate that, due to the degeneracy of the genetic code, each of the polypeptide sequences disclosed herein is encoded by a large number of nucleic acid sequences. The present invention provides each degenerate nucleotide sequence encoding each antigen binding protein or other polypeptide of the invention.

The invention further provides nucleic acids that hybridize to other nucleic acids (e.g., nucleic acids comprising a nucleotide sequence disclosed herein) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to CCR7 or blocking the binding of CCL19 or CCL21 to CCR7).

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein, or a desired fragment, variant, or derivative thereof, is mutated such that it encodes an amino acid sequence comprising one or more deletions, substitutions, or additions of amino acid residues. In another embodiment, one or more mutations are introduced into a nucleic acid that selectively change the biological activity (e.g., binding of CCR7, inhibiting CCL19 or CCL21 binding, etc.) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a CCR7 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Methods of Making Anti-CCR7 Antigen Binding Proteins

A host cell comprising sequences that encode an anti-CCR7 antigen binding protein of the invention can be used to make the anti-CCR7 antigen binding protein. Typically, expression vectors used in a host cell will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the anti-CCR7 antigen binding protein coding sequence(s); the oligonucleotide sequence encodes polyHis (such as hexaHis), or another "tag" such as FLAG, HA (hemaglutinin influenza virus), or myc, for which commercially available antibodies exist. This tag is typically fused to the polypeptide upon expression of the polypeptide, and can serve as a means for affinity purification or detection of the anti-CCR7 antigen binding protein from the host cell. Affinity purification can be accomplished, for example, by column chromatography using antibodies against the tag as an affinity matrix. Optionally, the tag can subsequently be removed from the purified anti-CCR7 antigen binding protein polypeptide by various means such as using certain peptidases for cleavage.

Flanking sequences may be homologous (i.e., from the same species and/or strain as the host cell), heterologous (ie., from a species other than the host cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Whether all or only a portion of the flanking sequence is known, it may be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagene® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various viral origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Preferred selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to CCR7 polypeptide. As a result, increased quantities of a polypeptide such as an anti-CCR7 antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the invention will typically contain a promoter that is recognized by the host organism and operably linked to the molecule encoding the anti-CCR7 antigen binding protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising an anti-CCR7 antigen binding protein of the invention by removing the promoter from the source DNA by restriction enzyme digestion and inserting the desired promoter sequence into the vector.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-10); CMV promoter (Thomsen et al., 1984, Proc. Natl. Acad. USA 81:659-663); the promoter contained in the 3' long terminal repeat of Rous sarcoma virus (Yamamoto, et al., 1980, Cell 22:787-97); herpes thymidine kinase promoter (Wagner et al., 1981, Proc. Natl. Acad. Sci. U.S.A. 78:144445); promoter and regulatory sequences from the metallothionine gene (Brinster et al., 1982, Nature 296:39-42); and prokaryotic promoters such as the beta-lactamase promoter (Villa-Kamaroff et al., 1978, Proc. Natl. Acad. Sci. U.S.A., 75:3727-31); or the tac promoter (DeBoer et al., 1983, Proc. Natl. Acad. Sci. U.S.A., 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:63946; Ornitz et al., 1986, Cold Spring Harbor Symp. Quant. Biol. 50:399409 (1986); MacDonald, 1987, Hepatology 7:425-515); the insulin gene control region that is active in pancreatic beta cells (Hanahan, 1985, Nature 315:115-22); the immunoglobulin gene control region that is active in lymphoid cells (Grosschedl et al., 1984, Cell 38:647-58; Adames et al., 1985, Nature 318:533-38; Alexander et al., 1987, Mol. Cell. Biol, 7:1436-44); the mouse mammary tumor virus control region that is active in testicular, breast, lymphoid and mast cells (Leder et al., 1986, Cell 45:485-95); the albumin gene control region that is active in liver (Pinkert et al., 1987, Genes and Devel. 1:268-76); the alpha-feto-protein gene control region that is active in liver (Krumlauf et al., 1985, Mol. Cell. Biol., 5:1639-48; Hammer et al., 1987, Science 235:53-58); the alpha 1-antitrypsin gene control region that is active in liver (Kelsey et al., 1987, Genes and Devel. 1:161-71); the beta-globin gene control region that is active in myeloid cells (Mogram et al., 1985, Nature 315:33840; Kollias et al., 1986, Cell 46:89-94); the myelin basic protein gene control region that is active in oligodendrocyte cells in the brain (Readhead et al., 1987, Cell 48:703-12); the myosin light chain-2 gene control region that is active in skeletal muscle (Sani, 1985, Nature 314:283-86); and the gonadotropic releasing hormone gene control region that is active in the hypothalamus (Mason et al., 1986, Science 234:1372-78).

An enhancer sequence may be inserted into the vector to increase transcription of DNA encoding light chain or heavy chain comprising an anti-CCR7 antigen binding protein of the invention by higher eukaryotes. Enhancers are cis-acting elements of DNA, usually about 10-300 bp in length, that act on the promoter to increase transcription Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer may be positioned in the vector either 5' or 3' to a coding sequence, it is typically located at a site 5' from the promoter.

A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al. (1984, Nature 312: 768); the interleukin-4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846; the signal sequence of human IgK; and the signal sequence of human growth hormone.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an anti-CCR7 antibody has been inserted into the proper site of the vector, the completed vector may be inserted into a suitable host cell for amplification and/or polypeptide expression. The transformation of an expression vector for an anti-CCR7 antigen binding protein into a selected host cell may be accomplished by well known methods including transfection, infection, calcium phosphate co-precipitation, electroporation, microinjection, lipofection, DEAE-dextran mediated transfection, or other known techniques. The method selected will in part be a function of the type of host cell to be used.

A host cell, when cultured under appropriate conditions, synthesizes an anti-CCR7 antigen binding protein that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels and constitutively produce antibodies with CCR7 binding properties. In another embodiment, a cell line from the B cell lineage that does not make its own antibody but has a capacity to make and secrete a heterologous antibody can be selected.

Formulations

In some embodiments, the invention provides pharmaceutical compositions comprising a therapeutically effective amount of one or a plurality of the antibodies of the invention together with a pharmaceutically acceptable diluent, carrier, solubilizer, emulsifier, preservative, and/or adjuvant. Preferably, acceptable formulation materials are nontoxic to recipients at the dosages and concentrations employed. In preferred embodiments, pharmaceutical compositions comprising a therapeutically effective amount of anti-CCR7 antibodies are provided.

In certain embodiments, acceptable formulation materials preferably are nontoxic to recipients at the dosages and concentrations employed.

In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See REMINGTON'S PHARMACEUTICAL SCIENCES, 18th Edition, (A. R. Gennaro, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the invention.

In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In certain embodiments of the invention, anti-CCR7 antigen binding protein compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the, anti-CCR7 antigen binding protein product may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising the desired anti-CCR7 antigen binding protein in a pharmaceutically acceptable vehicle. A particularly suitable vehicle for parenteral injection is sterile distilled water in which the , anti-CCR7 antigen binding protein is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody molecule.

Pharmaceutical compositions of the invention can be formulated for inhalation. In these embodiments, anti-CCR7 antigen binding proteins are advantageously formulated as a dry, inhalable powder. In preferred embodiments, anti-CCR7 antigen binding protein inhalation solutions may also be formulated with a propellant for aerosol delivery. In certain embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. Anti-CCR7 antigen binding proteins that are administered in this fashion can be formulated with or without carriers customarily used in the compounding of solid dosage forms such as tablets and capsules. In certain embodiments, a capsule may be designed to release the active portion of the formulation at the point in the gastrointestinal tract when bioavailability is maximized and presystemic degradation is minimized. Additional agents can be included to facilitate absorption of the anti-CCR7 antigen binding protein. Diluents, flavorings, low melting point waxes, vegetable oils, lubricants, suspending agents, tablet disintegrating agents, and binders may also be employed.

A pharmaceutical composition of the invention is preferably provided to comprise an effective quantity of one or a plurality of anti-CCR7 antigen binding proteins in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving anti-CCR7 antigen binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, Biopolymers 22:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., supra) or poly-D(−)-3-hydroxybutyric acid (European Patent Application Publication No. EP 133,988). Sustained release compositions may also include liposomes that can be prepared by any of several methods known in the art. See e.g., Eppstein et al., 1985, Proc. Natl. Acad. Sci. USA 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain both a first container having a dried protein and a second container having an aqueous formulation. In certain embodiments of this invention, kits containing single and multi-chambered pre-filled syringes (e.g., liquid syringes and lyosyringes) are provided.

Indications

The methods and compositions of the present invention (including, for example, anti-CCR7 antigen binding proteins, antibodies, antibody fragments, antibody derivatives, and other molecules of the present invention) can be used to treat a wide range of diseases, conditions, and indications. Examples of types of diseases that can be treated include inflammatory conditions, cancerous conditions, and conditions and complications arising from tissue or organ transplantation.

CCR7 activity is implicated in Inflammatory bowel diseases (IBDs) such as Crohn's disease and ulcerative colitis. Crohn's disease is chronic and debilitating inflammatory bowel disease that is thought to reflect a overly-active TH1-mediated immune response to the flora of the gut. The lesions of Crohn's disease can appear anywhere in the bowel and occasionally elsewhere in the gastrointestinal tract. Ulcerative colitis lesions, on the other hand, usually appear in the colon. The nature of the lesions is also different, but the diseases are sufficiently similar that is sometimes difficult to distinguish them clinically. See, e.g., U.S. Pat. No. 6,558,661. The compositions and methods described herein can be used to treat IBD patients, and/or reduce, prevent, or eliminate one or more symptoms or complications of IBD.

Inhibition of CCR7 activity has been implicated in tissue or organ transplant rejection (Lo et al., 2011, Transplantation 91:70-77; Liu et al., 2011, Eur J Immunol. 41:611-23; Yuling et al., Am J Transplant 8:1401-12). The compositions and methods described herein can be used to treat tissue or organ transplant recipients, for example, kidney, heart, skin, or lung transplant recipients, and/or reduce, prevent, or eliminate one or more complications of transplant surgery.

CCR7 activity has been implicated in asthma, allergic airway inflammation, airway smooth muscle hyperplasia, and fibrotic lung diseases (Gomperts et al., 2007, J Leukoc Biol. 82:449-56; Kawakami et al., 2012, Cell Immunol. 2575:24-32; Saunders et al., 2009, Clin Exp Allergy 39:1684-92). The compositions and methods described herein can be used to treat patients with asthma, allergic airway inflammation, airway smooth muscle hyperplasia, or fibrotic lung diseases, and/or to reduce, prevent, or eliminate one or more symptoms or complications of these diseases.

CCR7 activity has been implicated in rheumatoid arthritis (Moschovakis et al., 2012, Eur J Immunol. 42:1949-55). The compositions and methods described herein can be used to treat patients with rheumatoid arthritis, and/or to reduce, prevent, or eliminate one or more symptoms or complications of rheumatoid arthritis.

CCR7 activity has been implicated in multiple sclerosis (Aung et al., 2010, J Neuroimmunol. 226:158-64). The compositions and methods described herein can be used to treat patients with multiple sclerosis, and/or to reduce, prevent, or eliminate one or more symptoms or complications of multiple sclerosis.

CCR7 activity has been implicated in atherosclerosis (Luchtefeld et al., 2010, Circulation 122:1621-28). The compositions and methods described herein can be used to treat patients with atherosclerosis, and/or to reduce, prevent, or eliminate one or more symptoms or complications of atherosclerosis.

CCR7 activity has been implicated in HIV infection (Evans et al., 2012, Cytokine Growth Factor Rev. 23:151-

57). The compositions and methods described herein can be used to treat patients infected with HIV, including patients having AIDS, or patients at risk of contracting HIV or of developing AIDS, and/or to reduce, prevent, or eliminate one or more symptoms or complications of HIV or AIDS. CCR7 activity has been implicated in certain aspects of the development and spread of cancer (Ben-Baruch, 2009, 3:328-33).mThe compositions and methods described herein can be used to treat patients with cancer, and/or to reduce, prevent, or eliminate one or more symptoms or complications of cancer. In one particular embodiment, the compositions and/or methods of the present invention are used to prevent, reduce, slow, or reverse the metastatic spread of cancer in a patient.

Therapeutic Methods and Administration of Antigen Binding Proteins

In one aspect, the present invention provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of CCR7 and/or CCL19 and/or CCL21. In some such conditions, the expression or activity level is too high, and the treatment comprises administering a CCR7 antagonist as described herein. In other such conditions, the expression or activity level is too low, and the treatment comprises administering a CCR7 agonist as described herein. In other such conditions, the levels of CCR7 and/or CCL19 and/or CCL21 activity are not necessarily elevated, but the subject is more sensitive to them.

In another aspect, the present invention provides methods of identifying subjects who are more likely to benefit from treatment using the compositions and/or methods of treatment of the present invention. Such methods can enable a caregiver to better tailor a therapeutic regimen to a particular subject's needs and reduce the likelihood of an ineffective or counterproductive course of treatment. In one embodiment, the present invention provides a method of determining whether a subject is a candidate for treatment using a composition or method as described herein comprising determining whether a target cell type in the subject expresses CCR7, wherein if the target cell type expresses CCR7, then the subject is a candidate for treatment. In another embodiment, the method comprises determining the approximate average number of CCR7 molecules per target cell, wherein $10^2$, $10^3$, $10^4$, $10^5$, or $10^6$ CCR7 per cell indicates that the subject is a candidate for treatment. The approximate average number of CCR7 molecules per target cell can be determined using any technique known in the art, for example, by staining a sample comprising cells of the target cell type with a CCR7 binding molecule, and detecting the amount of CCR7 binding molecule bound to the sample, where the amount of CCR7 binding molecule detected is proportional to the average number of CCR7 molecules in the sample. In another embodiment, the method comprises comparing the approximate average number of CCR7 molecules per target cell to a reference standard, wherein if the approximate average number of CCR7 molecules per target cell is greater than the reference standard, then the subject is more likely to benefit from treatment using the compositions and/or methods of treatment of the present invention. In another aspect, the method comprises determining whether CCL19 or CCL21 is present at elevated levels in the tissue of interest, e.g., in the vicinity of immune cells expressing CCR7. In another aspect, the method comprises determining whether a molecule downstream of CCR7 is altered or activated in a CCR7-dependent fashion.

Certain methods provided herein comprise administering a CCR7 binding antigen binding protein to a subject, thereby reducing an CCL19 or CCL21-induced biological response that plays a role in a particular condition. In particular embodiments, methods of the invention involve contacting endogenous CCR7 with a CCR7 binding antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient a CCR7 antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds CCR7 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second CCR7-inhibiting substance, an anti-inflammatory substance, an anti-angiogenic substance, a chemotherapeutic substance, or an analgesic substance. In various particular embodiments, the composition comprises one, two, three, four, five, or six physiologically active agents in addition to a CCR7 binding antigen binding protein.

In one embodiment, the pharmaceutical composition comprise an antigen binding protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, 16th Ed. (1980) and 20th Ed. (2000), Mack Publishing Company, Easton, Pa.

Kits for use by medical practitioners include a CCR7-inhibiting substance of the invention and a label or other instructions for use in treating any of the conditions discussed herein. In one embodiment, the kit includes a sterile preparation of one or more CCR7 binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

A CCR7 inhibiting substance of the invention may be administered, for example, once or more than once, e.g., at regular intervals over a period of time. In particular embodiments, an antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

Particular embodiments of the present invention involve administering to a subject an antigen binding protein at a dosage of from about 1 ng of antigen binding protein per kg of subject's weight per day ("1 ng/kg/day") to about 100 mg/kg/day, from about 500 ng/kg/day to about 50 mg/kg/day, from about 5 µg/kg/day to about 20 mg/kg/day, and from about 5 mg/kg/day to about 20 mg/kg/day to a subject. In additional embodiments, an antigen binding protein is administered to adults one time per week, two times per week, three times per week, four times per week, five times per week, six times per week, or seven or more times per week, to treat a CCR7 mediated disease, condition or disorder, e.g., a medical disorder disclosed herein. If injected, the effective amount of antigen binding protein per adult dose may range from, for example, 1-20 mg/m$^2$, or from about 5-12 mg/m$^2$. Alternatively, a flat dose may be administered; the amount may range from 1-300 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of antigen binding protein to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antigen binding protein administered two or three times per week.

Particular embodiments of the methods provided herein involve subcutaneous injection of from 0.5 mg to 10 mg, preferably from 3 to 5 mg, of an antigen binding protein, once or twice per week. Another embodiment is directed to pulmonary administration (e.g., by nebulizer) of 3 or more mg of antigen binding protein once a week.

Examples of therapeutic regimens provided herein comprise subcutaneous injection of an antigen binding protein once a week, at a dose of 1.5 to 3 mg, to treat a condition in which CCR7 signaling plays a role. Examples of such conditions are provided herein and are known in the art. Administration of antigen binding protein can be continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of a CCR7 inhibitor of the present invention per kilogram body mass of the subject (mg/kg). The dose can be administered once to the subject, or more than once at a certain interval, for example, once a day, three times a week, twice a week, once a week, once every two weeks, once every three weeks, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an antigen binding protein is administered to the subject in an amount and for a time sufficient to maintain the concentration of the antigen binding protein at or above a desired level, to maintain the amount, concentration, or other state of a biomarker at a desired level, or to induce an improvement, preferably a sustained improvement, in at least one symptom or other indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

Combination Therapies

Treatments exist for most CCR7 mediated diseases, even though many of these treatments are effective only to a limited extent or for only a subset of patients, and/or have substantial toxicities that limit patient tolerance of treatment. The CCR7 inhibitors described herein can be combined with other existing therapies for CCR7-mediated diseases.

In one embodiment, a patient suffering from an inflammatory bowel disease (IBD), such as Crohn's disease or ulcerative colitis, can be concurrently treated with a therapy for IBD plus an anti-CCR7 antibody as described herein. Existing therapies for IBD include sulfasalazine, 5-aminosalicylic acid and its derivatives (such as olsalazine, balsalazide, and mesalamine), anti-IFN-γ antibodies, anti-TNF antibodies (including infliximab, adalimumab, golimumab, and certolizumab pegol), corticosteroids for oral or parenteral administration (including prednisone, methylprednisone, budesonide, or hydrocortisone), adrenocorticotropic hormone, antibiotics (including metronidazole, ciprofloxacin, or rifaximin), azathioprine, 6-mercaptopurine, methotrexate, cyclosporine, tacrolimus, and thalidomide.

In other embodiments, a patient suffering from rheumatoid arthritis can be concurrently treated with a drug used for RA therapy plus an anti-CCR7 antibody as described herein. Therapies for rheumatoid arthritis (RA) include non-steroidal anti-inflammatory drugs (NSAIDs) (such aspirin and cyclooxygenase-2 (COX-2) inhibitors), disease modifying anti-inflammatory drugs (DMARDs)(such as methotrexate, leflunomide, and sulfasalazine), anti-malarials (such as hydroxychloroquine), cyclophosphamide, D-penicillamine, azathioprine, gold salts, tumor necrosis factor inhibitors (such as etanercept, infliximab, adalimumab, golimumab, and certolizumab pegol), CD20 inhibitors such as rituximab, IL-1 antagonists such as anakinra, IL-6 inhibitors such as tocilizumab, inhibitors of Janus kinases (JAK)(such as tofacitinib), abatacept, and glucocorticoids, among others.

EXAMPLES

Example 1

Preparation of Human Monoclonal Antibodies

Immunizations were conducted using one or more suitable forms of CCR7 antigen, including: (1) CHO/AM1D cells engineered to stably express huCCR7, (2) murine L1.2 cells engineered to stably express full length human CCR7, and (3) 293T cells transiently transfected with human CCR7.

A suitable amount of immunogen (i.e., 3-4×10$^6$ cells/mouse of stably transfected CHO cells, transiently transfected 293T cells as mentioned above, or other CCR7-expressing cell type was used for initial immunization in XENOMOUSE™ (Amgen, Thousand Oaks, Calif.) according to the methods disclosed in U.S. patent application Ser. No. 08/759,620, filed Dec. 3, 1996 and International Patent Application Nos. WO 98/24893, and WO 00/76310, the disclosures of which are incorporated by reference. Following the initial immunization, subsequent boost immunizations of immunogen (2.0×10$^6$ CCR7 transfected cells/mouse) were administered on a schedule and for the duration necessary to induce a suitable anti-CCR7 titer in the mice. Titers were determined by a suitable method, for example, fluorescence activated cell sorting (FACS).

Animals exhibiting suitable titers were identified, and lymphocytes were obtained from draining lymph nodes and, if necessary, pooled for each cohort. Lymphocytes were dissociated from lymphoid tissue by grinding in a suitable medium (for example, Dulbecco's Modified Eagle Medium; DMEM; obtainable from Invitrogen, Carlsbad, Calif.) to release the cells from the tissues, and suspended in DMEM. B cells were selected and/or expanded using standard methods, and fused with suitable fusion partner, for example, nonsecretory myeloma P3X63Ag8.653 cells (American Type Culture Collection CRL 1580; Kearney et al, (1979) J. Immunol. 123:1548-1550), using techniques that were known in the art.

In one suitable fusion method, lymphocytes were mixed with fusion partner cells at a ratio of 1:4. The cell mixture was gently pelleted by centrifugation at 400×g for 4 minutes, the supernatant decanted, and the cell mixture gently mixed. Fusion was induced with PEG/DMSO (polyethylene glycol/dimethyl sulfoxide; obtained from Sigma-Aldrich, St. Louis Mo.; 1 ml per million of lymphocytes). PEG/DMSO was slowly added with gentle agitation over one minute followed, by one minute of mixing. IDMEM (DMEM without glutamine; 2 ml per million of B cells), was then added over 2 minutes with gentle agitation, followed by additional IDMEM (8 ml per million B-cells) which was added over 3 minutes.

The fused cells were pelleted (400×g 6 minutes) and resuspended in 20 ml Selection media (for example, DMEM containing Azaserine and Hypoxanthine [HA] and other supplemental materials as necessary) per million B-cells. Cells were incubated for 20-30 minutes at 37° C. and then resuspended in 200 ml selection media and cultured for three to four days in T175 flasks prior to 96 well plating.

Cells were distributed into 96-well plates using standard techniques to maximize clonality of the resulting colonies. An alternative method was also employed and the fused cells were directly plated clonally into 384-well plates to ensure monoclonality from the start. After several days of culture, supernatants were collected and subjected to screening assays as detailed in the examples below, including confirmation of binding to human CCR7 receptor. Positive cells were further selected and subjected to standard cloning and subcloning techniques. Clonal lines were expanded in vitro, and the secreted human antibodies obtained for analysis.

In this manner, mice were immunized with cells expressing full length CCR7 cells with a range of 11-17 immunizations over a period of approximately one to two and one half months. Several hybrdidoma lines secreting CCR7-specific antibodies were obtained, and the antibodies were further characterized.

Among the antibodies generated in this way were 6B4.1, 6B5.1, and 6E1.2.

Example 2

Selection of Binding Antibodies by FMAT

After 14 days of culture, hybridoma supernatants were screened for CCR7-specific monoclonal antibodies by Fluorometric Microvolume Assay Technology (FMAT) by screening against either the CHO AM1/D/huCCR7 cell line or recombinant HEK293T cells that were transfected with human CCR7 and counter-screening against parental CHO/AM1D or HEK293T cells. Briefly, the cells in Freestyle media (Invitrogen; Carlsbad, Calif.) were seeded into 384-well FMAT plates in a volume of 50 µL/well at a density of 3500 cells/well for the stable transfectants, and at a density of 8500 cells/well for the parental cells, and cells were incubated overnight at 37° C. 20 µL/well of supernatant was then added, and the plates were incubated for approximately one hour at 4° C., after which 10 μL/well of anti-human IgG-Cy5 secondary antibody was added at a concentration of 2.8 μg/ml (400 ng/ml final concentration). Plates were then incubated for one hour at 4° C., and fluorescence was read using an FMAT Cellular Detection System (Applied Biosystems, Grand Island, N.Y.).

In total, 81 hybridoma supernatants were identified as binding to the CCR7 receptor expressing cells but not to parental cells by the FMAT method. These supernatants were then tested in the CCR7 functional assays as described below.

Example 3

Preparation of Humanized Antibodies

Normal mice (i.e., mice with a murine immune system) were immunized with human CCR7-expressing cells. Murine anti-human CCR7 antibodies were isolated from these mice, among them the blocking antibody MAb 22. MAb22 was chimerized by replacing heavy chain constant region residues with their human counterparts, generating MAb22_HC_V1 and MAb22_LC_V1. This antibody retained its ability to bind human CCR7. The light chain of this antibody was further altered to generate a series of humanized MAb 22 variants by altering framework regions 1, 2, 3, and 4. This produced sequences MAb22_KLC_V2, MAb22_KLC_V3, MAb22_KLC_V4, MAb22_KLC_V5, MAb22_KLC_V6, MAb22_KLC_V7, and MAb22_KLC_V8.

Example 4

Functional Screening to Identify Antibody Antagonists

Figure 3:
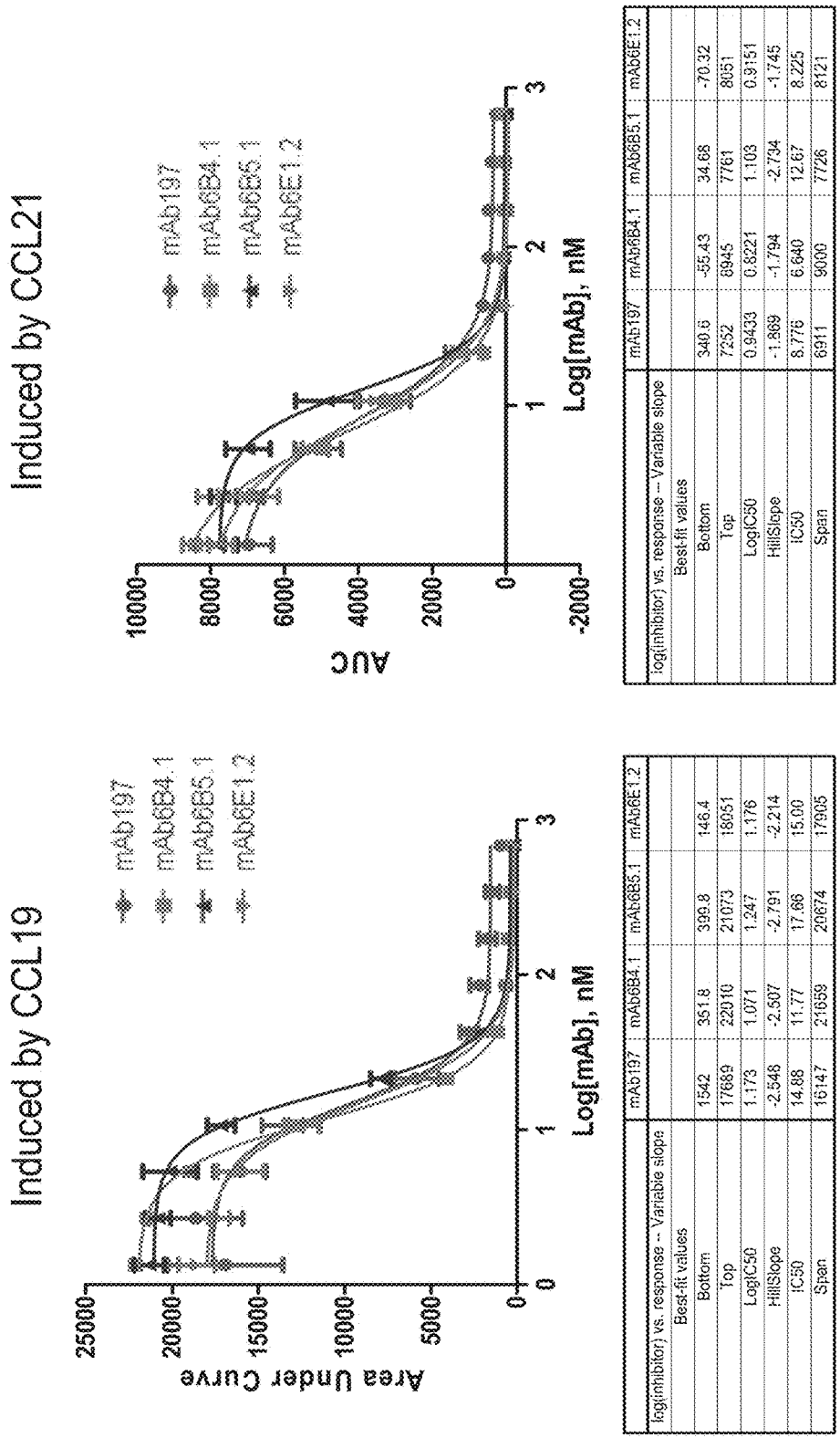
FIG. 3 provides graphs for determining the IC50 of antibodies mAb197, 6B4.1, 6B5.1, and 6E1.2 for inhibition of CCR7 activity induced by CCL19 or by CCL21.
Figure 4:
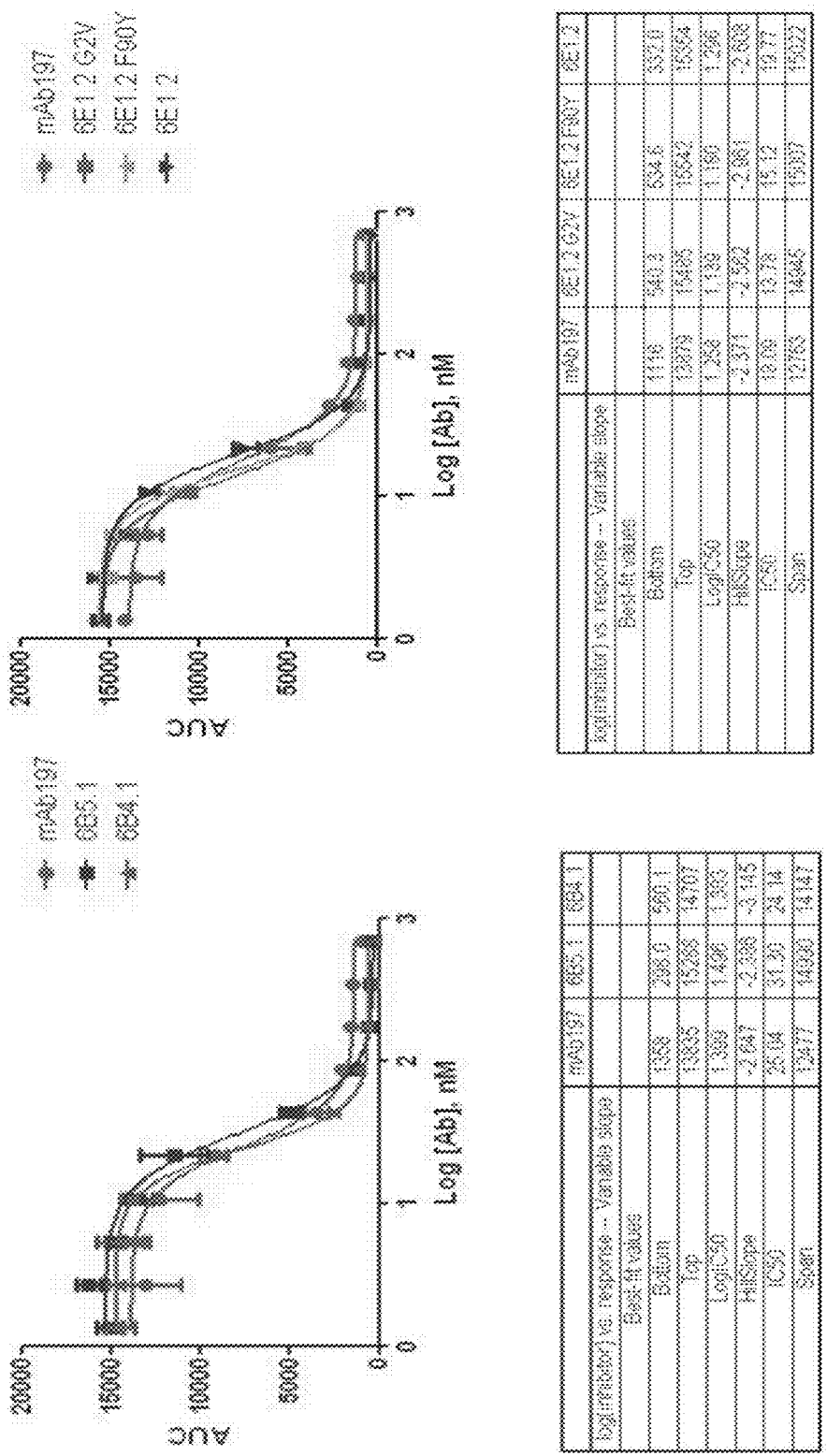
FIG. 4 provides IC50 determinations for antibodies mAB197, 6B5.1, 6B4.1, 6E1.2, 6E1.2 G2V, and 6E1.2 F90Y.

Hybridoma supernatants were screened for the ability to block CCL19-dependant or CCL21-dependant CCR7 signaling. The functional assay used was either a human or cyno CCR7 dependant aequorin-based reporter system using engineered CHO cell lines. The assay was performed by seeding 96 well plates with 60,000 cell/well and growing them at 37° C. overnight. On day two, growth medium was removed and an assay buffer containing 30 μM coelenterazine was added to the cells. Cells were then incubated for 3 hours at 34° C. Hybridoma supernatants or control samples were then spiked into each well and incubated for an additional 30 minutes at 34° C. CCL19 ligand was then added at an ECso concentration (approximately 113.6nM). Alternatively, the CCL21 ligand was used at an ECso concentration (approximately 166.7 nM). The level of aequorin activity is then assayed by detecting blue light emitted at a wavelength of 469 nm on a mini FLASH machine. Antibodies which blocked CCL19- or CCL21-dependant CCR7 signaling were identified as those samples that reduced the level of activated aequorin leading to a reduction in signal intensity. Data Generated on hybridoma supernatants is shown in FIG. 2; antagonists were identified as those samples that cause a 50% or greater reduction in signal as compared to the negative control. In a similar approach, the same assay was used to determine the $IC_{50}$ activity of the purified antibody samples. Data are shown in FIGS. 3 and 4.

Example 5

Epitope Mapping

A series of mutated variants of human CCR7 was made. Each variant contained changes to its extracellular domain (ECD), extracellular loop (ECL) 1, ECL2, or ECL3 that converted hCCR7 amino acid residues into their corresponding murine CCR7 residues. In the ECD, mutations were introduced at positions D35E, F44Y, L47V and S49F. In ECL1, mutations were made in the A118E, V123I, H127Y and F128L positions. In ECL2, mutations were made in the D198G, R201K, S202N, S204G, Q206D, A207T, M208L, I213V, T214S, E215A and H216Q positions. For ECL3, mutations were made at positions S295N, T297S and L300T.

Mutations were made using the following oligos:

```
D35E sense:
GAC GAT TAC ATC GGA GAG AAC ACC ACA GTG GAC TA

D35E antisense:
TAG TCC ACT GTG GTG TTC TCT CCG ATG TAA TCG TC

F44Y sense:
CAC AGT GGA CTA CAC TTT GTA TGA GTC TTT GTG CTC
CAA GAA

F44Y antisense:
TTC TTG GAG CAC AAA GAC TCA TAC AAA GTG TAG TCC
ACT GTG

L47V sense:
TGG ACT ACA CTT TGT TCG AGT CTG TGT GCT CCA AGA

L47V antisense:
TCT TGG AGC ACA CAG ACT CGA ACA AAG TGT AGT CCA

S49F sense:
TTC GAG TCT TTG TGC TTC AAG AAG GAC GTG CGG

S49F antisense:
CCG CAC GTC CTT CTT GAA GCA CAA AGA CTC GAA

A118E sense:
GGG CCT ACA GCG AGG CCA AGT CCT G

A118 antisense:
CAG GAC TTG GCC TCG CTG TAG GCC C

V123I sense:
CGG CCA AGT CCT GGA TCT TCG GTG TCC AC

V123I antisense:
GTG GAC ACC GAA GAT CCA GGA CTT GGC CG

H127Y sense:
GTC CTG GGT CTT CGG TGT CTA TTT TTG CAA GCT CAT
CTT TG

H127Y antisense:
CAA AGA TGA GCT TGC AAA AAT AGA CAC CGA AGA CCC
AGG AC

F128L sense:
GGG TCT TCG GTG TCC ACT TAT GCA AGC TCA TCT T

F128L antisense:
AAG ATG AGC TTG CAT AAG TGG ACA CCG AAG ACC C

D198G sense:
GCT CCT GTA CAG TGG CCT CCA GAG GAG CA

D198G antisense:
TGC TCC TCT GGA GGC CAC TGT ACA GGA GC

R201K sense:
CAG TGA CCT CCA GAA GAG CAG CAG TGA GC

R201K antisense:
GCT CAC TGC TGC TCT TCT GGA GGT CAC TG
```

-continued

```
S202N sense:
GTG ACC TCC AGA GGA ACA GCA GTG AGC AAG C

S202N antisense:
GCT TGC TCA CTG CTG TTC CTC TGG AGG TCA C

S204G sense:
TCC AGA GGA GCA GCG GTG AGC AAG CGA TG

S204G antisense:
CAT CGC TTG CTC ACC GCT GCT CCT CTG GA

Q206D sense:
GGA GCA GCA GTG AGG ATG CGA TGC GAT GCT C

Q206D antisense:
GAG CAT CGC ATC GCA TCC TCA CTG CTG CTC C

A207T sense:
AGG AGC AGC AGT GAG CAA ACG ATG CGA TCG

A207T antisense:
GCA TCG CAT CGT TTG CTC ACT GCT GCT CCT

M208L sense:
GCA GTG AGC AAG CGT TGC GAT GCT CTC TC

M208L antisense:
GAG AGA GCA TCG CAA CGC TTG CTC ACT GC

I213V sense:
GAT GCG ATG CTC TCT CGT CAC AGA GCA TGT GGA

I213V antisense:
TCC ACA TGC TCT GTG ACG AGA GAG CAT CGC ATC

T214S sense:
CGA TGC TCT CTC ATC TCA GAG CAT GTG GAG G

T214S antisense:
CCT CCA CAT GCT CTG AGA TGA GAG AGC ATC G

E215A sense:
GCT CTC TCA TCA CAG CGC ATG TGG AGG CCT T

E215A antisense:
AAG GCC TCC ACA TGC GCT GTG ATG AGA GAG C

H216Q sense:
TCT CTC ATC ACA GAG CAG GTG GAG GCC TTT ATC AC

H216Q antisense:
GTG ATA AAG GCC TCC ACC TGC TCT GTG ATG AGA GA

S295N sense:
CAA CTT CAA CAT CAC CAA TAG CAC CTG TGA GCT CA

S295 antisense:
TGA GCT CAC AGG TGC TAT TGG TGA TGT TGA AGT TG

T297S sense:
CAA CAT CAC CAG TAG CAG CTG TGA GCT CAG TAA GC

T297S antisense:
GCT TAC TGA GCT CAC AGC TGC TAC TGG TGA TGT TG

L300T sense:
CAC CAG TAG CAC CTG TGA GAC CAG TAA GCA ACT CAA
CAT C

L300T antisense:
GAT GTT GAG TTG CTT ACT GGT CTC ACA GGT GCT ACT
GGT G
```

The oligos were diluted to 50 ng/μl concentration. PCR reactions were set up using 100 ng template DNA pcDNA3.1 Neo-hCCR7 (20100121357):

```
ATGGACCTGGGGAAACCAATGAAAAGCGTGCTGGTGGTGGCTCTCCTTGT
CATTTTCCAGGTATGCCTGTGTCAAGATGAGGTCACGGACGATTACATCG
GAGACAACACCACAGTGGACTACACTTTGTTCGAGTCTTTGTGCTCCAAG
AAGGACGTGCGGAACTTTAAAGCCTGGTTCCTCCCTATCATGTACTCCAT
CATTTGTTTCGTGGGCCTACTGGGCAATGGGCTGGTCGTGTTGACCTATA
TCTATTTCAAGAGGCTCAAGACCATGACCGATACCTACCTGCTCAACCTG
GCGGTGGCAGACATCCTCTTCCTCCTGACCCTTCCCTTCTGGGCCTACAG
CGCGGCCAAGTCCTGGGTCTTCGGTGTCCACTTTTGCAAGCTCATCTTTG
CCATCTACAAGATGAGCTTCTTCAGTGGCATGCTCCTACTTCTTTGCATC
AGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGA
TACTAGCCACAGTGCTCTCCATCCCAGAGCTCCTGTACAGTGACCTCCAG
AGGAGCAGCAGTGAGCAAGCGATGCGATGCTCTCTCATCACAGAGCATGT
GGAGGCCTTTATCACCATCCAGGTGGCCCAGATGGTGATCGGCTTTCTGG
TCCCCCTGCTGGCCATGAGCTTCTGTTACCTTGTCATCATCCGCACCCTG
CTCCAGGCACGCAACTTTGAGCGCAACAAGGCCATCAAGGTGATCATCGC
TGTGGTCGTGGTCTTCATAGTCTTCCAGCTGCCCTACAATGGGGTGGTCC
TGGCCCAGACGGTGGCCAACTTCAACATCACCAGTAGCACCTGTGAGCTC
AGTAAGCAACTCAACATCGCCTACGACGTCACCTACAGCCTGGCCTGCGT
CCGCTGCTGCGTCAACCCCTTTCTTGTACGCCTTCATCGGCGTCAAGTTCC
GCAACGATCTCTTCAAGCTCTTCAAGGACCTGGGCTGCCTCAGCCAGGAG
CAGCTCCGGCAGTGGTCTTCCTGTCGGCACATCCGGCGCTCCTCCATGAG
TGTGGAGGCCGAGACCACCACCACCTTCTCCCCATAG

MDLGKPMKSVLVVALLVIFQVCLCQDEVTDDYIGDNTTVDYTLFESLCSK
KDVRNFKAWFLPIMYSIICFVGLLGNGLVVLTYIYFKRLKTMTDTYLLNL
AVADILFLLTLPFWAYSAAKSWVFGVHFCKLIFAIYKMSFFSGMLLLLCI
SIDRYVAIVQAVSAHRHRARVLLISKLSCVGIWILATVLSIPELLYSDLQ
RSSSEQAMRCSLITEHVEAFITIQVAQMVIGFLVPLLAMSFCYLVIIRTL
LQARNFERNKAIKVIIAVVVVFIVFQLPYNGVVLAQTVANFNITSSTCEL
SKQLNIAYDVTYSLACVRCCVNPFLYAFIGVKFRNDLFKLFKDLGCLSQE
QLRQWSSCRHIRRSSMSVEAETTTTFSP*
```

For each individual mutation, a PCR product was generated using a QuikChange Multi Site-Site Directed Mutagenesis Kit (Cat# 200531) (Stratagene, La Jolla, Calif.) according to manufacturer's instructions. The resulting PCR products were DpnI digested and then transformed into Top10 chemically competent cells (Invitrogen, Grand Island, N.Y.). Individual colonies were picked for each construct and sequenced. Clones with the correct sequences were scaled up and re-sequenced. The final clone DNA sequences and translated protein sequences follow:

D35E 20100122625
ATGGACCTGGGGAAACCAATGAAAAGCGTGCTGGTGGTGGCTCTCCTTGTCATTTTCCAGGT
ATGCCTGTGTCAAGATGAGGTCACGGACGATTACATCGGAGAGAACACCACAGTGGACTAC
ACTTTGTTCGAGTCTTTGTGCTCCAAGAAGGACGTGCGGAACTTTAAAGCCTGGTTCCTCCCT
ATCATGTACTCCATCATTTGTTTCGTGGGCCTACTGGGCAATGGGCTGGTCGTGTTGACCTAT
ATCTATTTCAAGAGGCTCAAGACCATGACCGATACCTACCTGCTCAACCTGGCGGTGGCAGA
CATCCTCTTCCTCCTGACCCTTCCCTTCTGGGCCTACAGCGCGGCCAAGTCCTGGGTCTTCGG
TGTCCACTTTTGCAAGCTCATCTTTGCCATCTACAAGATGAGCTTCTTCAGTGGCATGCTCCT
ACTTCTTTGCATCAGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGATACTAGCCACAG
TGCTCTCCATCCCAGAGCTCCTGTACAGTGACCTCCAGAGGAGCAGCAGTGAGCAAGCGATG
CGATGCTCTCTCATCACAGAGCATGTGGAGGCCTTTATCACCATCCAGGTGGCCCAGATGGT
GATCGGCTTTCTGGTCCCCCTGCTGGCCATGAGCTTCTGTTACCTTGTCATCATCCGCACCCT
GCTCCAGGCACGCAACTTTGAGCGCAACAAGGCCATCAAGGTGATCATCGCTGTGGTCGTGG
TCTTCATAGTCTTCCAGCTGCCCTACAATGGGGTGGTCCTGGCCCAGACGGTGGCCAACTTC
AACATCACCAGTAGCACCTGTGAGCTCAGTAAGCAACTCAACATCGCCTACGACGTCACCTA
CAGCCTGGCCTGCGTCCGCTGCTGCGTCAACCCCTTTCTTGTACGCCTTCATCGGCGTCAAGTT
CCGCAACGATCTCTTCAAGCTCTTCAAGGACCTGGGCTGCCTCAGCCAGGAGCAGCTCCGGC
AGTGGTCTTCCTGTCGGCACATCCGGCGCTCCTCCATGAGTGTGGAGGCCGAGACCACCACC
ACCTTCTCCCCATAG

MDLGKPMKSVLVVALLVIFQVCLCQDEVTDDYIGENTTVDYTLFESLCSKKDVRNFKAWFLPIM
YSIICFVGLLGNGLVVLTYIYFKRLKTMTDTYLLNLAVADILFLLTLPFWAYSAAKSWVFGVHFC
KLIFAIYKMSFFSGMLLLLCISIDRYVAIVQAVSAHRHRARVLLISKLSCVGIWILATVLSIPELLYS
DLQRSSSEQAMRCSLITEHVEAFITIQVAQMVIGFLVPLLAMSFCYLVIIRTLLQARNFERNKAIKV
IIAVVVFIVFQLPYNGVVLAQTVANFNITSSTCELSKQLNIAYDVTYSLACVRCCVNPFLYAFIG
VKFRNDLFKLFKDLGCLSQEQLRQWSSCRHIRRSSMSVEAETTTTFSP

F44Y 20100128285
ATGGACCTGGGGAAACCAATGAAAAGCGTGCTGGTGGTGGCTCTCCTTGTCATTTTCCAGGT
ATGCCTGTGTCAAGATGAGGTCACGGACGATTACATCGGAGACAACACCACAGTGGACTAC
ACTTTGTATGAGTCTTTGTGCTCCAAGAAGGACGTGCGGAACTTTAAAGCCTGGTTCCTCCC
TATCATGTACTCCATCATTTGTTTCGTGGGCCTACTGGGCAATGGGCTGGTCGTGTTGACCTA
TATCTATTTCAAGAGGCTCAAGACCATGACCGATACCTACCTGCTCAACCTGGCGGTGGCAG
ACATCCTCTTCCTCCTGACCCTTCCCTTCTGGGCCTACAGCGCGGCCAAGTCCTGGGTCTTCG
GTGTCCACTTTTGCAAGCTCATCTTTGCCATCTACAAGATGAGCTTCTTCAGTGGCATGCTCC
TACTTCTTTGCATCAGCATTGACCGCTACGTGGCCATCGTCCAGGCTGTCTCAGCTCACCGCC
ACCGTGCCCGCGTCCTTCTCATCAGCAAGCTGTCCTGTGTGGGCATCTGGATACTAGCCACA
GTGCTCTCCATCCCAGAGCTCCTGTACAGTGACCTCCAGAGGAGCAGCAGTGAGCAAGCGAT
GCGATGCTCTCTCATCACAGAGCATGTGGAGGCCTTTATCACCATCCAGGTGGCCCAGATGG
TGATCGGCTTTCTGGTCCCCCTGCTGGCCATGAGCTTCTGTTACCTTGTCATCATCCGCACCC
TGCTCCAGGCACGCAACTTTGAGCGCAACAAGGCCATCAAGGTGATCATCGCTGTGGTCGTG
GTCTTCATAGTCTTCCAGCTGCCCTACAATGGGGTGGTCCTGGCCCAGACGGTGGCCAACTT
CAACATCACCAGTAGCACCTGTGAGCTCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLYESLCSKKDVRNFKAWFLPI

MYSIICFVGLLGNLVVLTYIYFKRLKTMTDTYLLNLAVADILFLLTLPFWAYSAAKSWVFGVHF

CKLIFAIYKMSFFSGMLLLLCISIDRYVAIVQAVSAHRHRARVLLISKLSCVGIWILATVLSIPELLY

SDLQRSSSEQAMRCSLITEHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

L47V 20100122626
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTGTGTGCTCCAAGAAGGACGTGCGGAACTTTAAAGCCTGGTTCCTCCC

TATCATGTACTCCATCATTTGTTTCGTGGGCCTACTGGGCAATGGGCTGGTCGTGTTGACCTA

TATCTATTTCAAGAGGCTCAAGACCATGACCGATACCTACCTGCTCAACCTGGCGGTGGCAG

ACATCCTCTTCCTCCTGACCCTTCCCTTCTGGGCCTACAGCGCGGCCAAGTCCTGGGTCTTCG

GTGTCCACTTTTGCAAGCTCATCTTTGCCATCTACAAGATGAGCTTCTTCAGTGGCATGCTCC

TACTTCTTTGCATCAGCATTGACCGCTACGTGGCCATCGTCCAGGCTGTCTCAGCTCACCGCC

ACCGTGCCCGCGTCCTTCTCATCAGCAAGCTGTCCTGTGTGGGCATCTGGATACTAGCCACA

GTGCTCTCCATCCCAGAGCTCCTGTACAGTGACCTCCAGAGGAGCAGCAGTGAGCAAGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESVCSKKDVRNFKAWFLPI

MYSIICFVGLLGNLVVLTYIYFKRLKTMTDTYLLNLAVADILFLLTLPFWAYSAAKSWVFGVHF

CKLIFAIYKMSFFSGMLLLLCISIDRYVAIVQAVSAHRHRARVLLISKLSCVGIWILATVLSIPELLY

SDLQRSSSEQAMRCSLITEHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

S49F 20100122627
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTTCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

```
ATCTATTTCAAGAGGCTCAAGACCATGACCGATACCTACCTGCTCAACCTGGCGGTGGCAGA
CATCCTCTTCCTCCTGACCCTTCCCTTCTGGGCCTACAGCGCGGCCAAGTCCTGGGTCTTCGG
TGTCCACTTTTGCAAGCTCATCTTTGCCATCTACAAGATGAGCTTCTTCAGTGGCATGCTCCT
ACTTCTTTGCATCAGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGATACTAGCCACAG
TGCTCTCCATCCCAGAGCTCCTGTACAGTGACCTCCAGAGGAGCAGCAGTGAGCAAGCGATG
CGATGCTCTCTCATCACAGAGCATGTGGAGGCCTTTATCACCATCCAGGTGGCCCAGATGGT
GATCGGCTTTCTGGTCCCCCTGCTGGCCATGAGCTTCTGTTACCTTGTCATCATCCGCACCCT
GCTCCAGGCACGCAACTTTGAGCGCAACAAGGCCATCAAGGTGATCATCGCTGTGGTCGTGG
TCTTCATAGTCTTCCAGCTGCCCTACAATGGGGTGGTCCTGGCCCAGACGGTGGCCAACTTC
AACATCACCAGTAGCACCTGTGAGCTCAGTAAGCAACTCAACATCGCCTACGACGTCACCTA
CAGCCTGGCCTGCGTCCGCTGCTGCGTCAACCCTTTCTTGTACGCCTTCATCGGCGTCAAGTT
CCGCAACGATCTCTTCAAGCTCTTCAAGGACCTGGGCTGCCTCAGCCAGGAGCAGCTCCGGC
AGTGGTCTTCCTGTCGGCACATCCGGCGCTCCTCCATGAGTGTGGAGGCCGAGACCACCACC
ACCTTCTCCCCATAG
MDLGKPMKSVLVVALLVIFQVCLCQDEVTDDYIGDNTTVDYTLFESLCFKKDVRNFKAWFLPI
MYSIICFVGLLGNGLVVLTYIYFKRLKTMTDTYLLNLAVADILFLLTLPFWAYSAAKSWVFGVHF
CKLIFAIYKMSFFSGMLLLLCISIDRYVAIVQAVSAHRHRARVLLISKLSCVGIWILATVLSIPELLY
SDLQRSSSEQAMRCSLITEHVEAFITIQVAQMVIGFLVPLLAMSFCYLVIIRTLLQARNFERNKAIK
VIIAVVVVFIVFQLPYNGVVLAQTVANFNITSSTCELSKQLNIAYDVTYSLACVRCCVNPFLYAFI
GVKFRNDLFKLFKDLGCLSQEQLRQWSSCRHIRRSSMSVEAETTTTFSP
A118E 20100130760
ATGGACCTGGGGAAACCAATGAAAAGCGTGCTGGTGGTGGCTCTCCTTGTCATTTTCCAGGT
ATGCCTGTGTCAAGATGAGGTCACGGACGATTACATCGGAGACAACACCACAGTGGACTAC
ACTTTGTTCGAGTCTTTGTGCTCCAAGAAGGACGTGCGGAACTTTAAAGCCTGGTTCCTCCCT
ATCATGTACTCCATCATTTGTTTCGTGGGCCTACTGGGCAATGGGCTGGTCGTGTTGACCTAT
ATCTATTTCAAGAGGCTCAAGACCATGACCGATACCTACCTGCTCAACCTGGCGGTGGCAGA
CATCCTCTTCCTCCTGACCCTTCCCTTCTGGGCCTACAGCGAGGCCAAGTCCTGGGTCTTCGG
TGTCCACTTTTGCAAGCTCATCTTTGCCATCTACAAGATGAGCTTCTTCAGTGGCATGCTCCT
ACTTCTTTGCATCAGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGATACTAGCCACAG
TGCTCTCCATCCCAGAGCTCCTGTACAGTGACCTCCAGAGGAGCAGCAGTGAGCAAGCGATG
CGATGCTCTCTCATCACAGAGCATGTGGAGGCCTTTATCACCATCCAGGTGGCCCAGATGGT
GATCGGCTTTCTGGTCCCCCTGCTGGCCATGAGCTTCTGTTACCTTGTCATCATCCGCACCCT
GCTCCAGGCACGCAACTTTGAGCGCAACAAGGCCATCAAGGTGATCATCGCTGTGGTCGTGG
TCTTCATAGTCTTCCAGCTGCCCTACAATGGGGTGGTCCTGGCCCAGACGGTGGCCAACTTC
AACATCACCAGTAGCACCTGTGAGCTCAGTAAGCAACTCAACATCGCCTACGACGTCACCTA
CAGCCTGGCCTGCGTCCGCTGCTGCGTCAACCCTTTCTTGTACGCCTTCATCGGCGTCAAGTT
CCGCAACGATCTCTTCAAGCTCTTCAAGGACCTGGGCTGCCTCAGCCAGGAGCAGCTCCGGC
AGTGGTCTTCCTGTCGGCACATCCGGCGCTCCTCCATGAGTGTGGAGGCCGAGACCACCACC
ACCTTCTCCCCATAG
```

-continued

MDLGKPMKSVLVVALLVIFQVCLCQDEVTDDYIGDNTTVDYTLFESLCSKKDVRNFKAWFLPIM
YSIICFVGLLGNGLVVLTYIYFKRLKTMTDTYLLNLAVADILFLLTLPFWAYSEAKSWVFGVHFC
KLIFAIYKMSFFSGMLLLLCISIDRYVAIVQAVSAHRHRARVLLISKLSCVGIWILATVLSIPELLYS
DLQRSSSEQAMRCSLITEHVEAFITIQVAQMVIGFLVPLLAMSFCYLVIIRTLLQARNFERNKAIKV
IIAVVVFIVFQLPYNGVVLAQTVANFNITSSTCELSKQLNIAYDVTYSLACVRCCVNPFLYAFIG
VKFRNDLFKLFKDLGCLSQEQLRQWSSCRHIRRSSMSVEAETTTTFSP

V123I 20100126473
ATGGACCTGGGGAAACCAATGAAAAGCGTGCTGGTGGTGGCTCTCCTTGTCATTTTCCAGGT
ATGCCTGTGTCAAGATGAGGTCACGGACGATTACATCGGAGACAACACCACAGTGGACTAC
ACTTTGTTCGAGTCTTTGTGCTCCAAGAAGGACGTGCGGAACTTTAAAGCCTGGTTCCTCCCT
ATCATGTACTCCATCATTTGTTTCGTGGGCCTACTGGGCAATGGGCTGGTCGTGTTGACCTAT
ATCTATTTCAAGAGGCTCAAGACCATGACCGATACCTACCTGCTCAACCTGGCGGTGGCAGA
CATCCTCTTCCTCCTGACCCTTCCCTTCTGGGCCTACAGCGCGGCCAAGTCCTGGATCTTCGG
TGTCCACTTTTGCAAGCTCATCTTTGCCATCTACAAGATGAGCTTCTTCAGTGGCATGCTCCT
ACTTCTTTGCATCAGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGATACTAGCCACAG
TGCTCTCCATCCCAGAGCTCCTGTACAGTGACCTCCAGAGGAGCAGCAGTGAGCAAGCGATG
CGATGCTCTCTCATCACAGAGCATGTGGAGGCCTTTATCACCATCCAGGTGGCCCAGATGGT
GATCGGCTTTCTGGTCCCCCTGCTGGCCATGAGCTTCTGTTACCTTGTCATCATCCGCACCCT
GCTCCAGGCACGCAACTTTGAGCGCAACAAGGCCATCAAGGTGATCATCGCTGTGGTCGTGG
TCTTCATAGTCTTCCAGCTGCCCTACAATGGGGTGGTCCTGGCCCAGACGGTGGCCAACTTC
AACATCACCAGTAGCACCTGTGAGCTCAGTAAGCAACTCAACATCGCCTACGACGTCACCTA
CAGCCTGGCCTGCGTCCGCTGCTGCGTCAACCCCTTTCTTGTACGCCTTCATCGGCGTCAAGTT
CCGCAACGATCTCTTCAAGCTCTTCAAGGACCTGGGCTGCCTCAGCCAGGAGCAGCTCCGGC
AGTGGTCTTCCTGTCGGCACATCCGGCGCTCCTCCATGAGTGTGGAGGCCGAGACCACCACC
ACCTTCTCCCCATAG

MDLGKPMKSVLVVALLVIFQVCLCQDEVTDDYIGDNTTVDYTLFESLCSKKDVRNFKAWFLPIM
YSIICFVGLLGNGLVVLTYIYFKRLKTMTDTYLLNLAVADILFLLTLPFWAYSAAKSWIFGVHFC
KLIFAIYKMSFFSGMLLLLCISIDRYVAIVQAVSAHRHRARVLLISKLSCVGIWILATVLSIPELLYS
DLQRSSSEQAMRCSLITEHVEAFITIQVAQMVIGFLVPLLAMSFCYLVIIRTLLQARNFERNKAIKV
IIAVVVFIVFQLPYNGVVLAQTVANFNITSSTCELSKQLNIAYDVTYSLACVRCCVNPFLYAFIG
VKFRNDLFKLFKDLGCLSQEQLRQWSSCRHIRRSSMSVEAETTTTFSP

H127Y 20100135009
ATGGACCTGGGGAAACCAATGAAAAGCGTGCTGGTGGTGGCTCTCCTTGTCATTTTCCAGGT
ATGCCTGTGTCAAGATGAGGTCACGGACGATTACATCGGAGACAACACCACAGTGGACTAC
ACTTTGTTCGAGTCTTTGTGCTCCAAGAAGGACGTGCGGAACTTTAAAGCCTGGTTCCTCCCT
ATCATGTACTCCATCATTTGTTTCGTGGGCCTACTGGGCAATGGGCTGGTCGTGTTGACCTAT
ATCTATTTCAAGAGGCTCAAGACCATGACCGATACCTACCTGCTCAACCTGGCGGTGGCAGA
CATCCTCTTCCTCCTGACCCTTCCCTTCTGGGCCTACAGCGCGGCCAAGTCCTGGGTCTTCGG
TGTCTATTTTTGCAAGCTCATCTTTGCCATCTACAAGATGAGCTTCTTCAGTGGCATGCTCCT
ACTTCTTTGCATCAGCATTGACCGCTACGTGGCCATCGTCCAGGCTGTCTCAGCTCACCGCCA
CCGTGCCCGCGTCCTTCTCATCAGCAAGCTGTCCTGTGTGGGCATCTGGATACTAGCCACAG

```
TGCTCTCCATCCCAGAGCTCCTGTACAGTGACCTCCAGAGGAGCAGCAGTGAGCAAGCGATG

CGATGCTCTCTCATCACAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVYFC

KLIFAIYKMSFFSGMLLLLCISIDRYVAIVQAVSAHRHRARVLLISKLSCVGIWILATVLSIPELLYS

DLQRSSSEQAMRCSLITEHVEAFITIQVAQMVIGFLVPLLAMSFCYLVIIRTLLQARNFERNKAIKV

IIAVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

F128L 20100126472
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTATGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHLC

KLIFAIYKMSFFSGMLLLLCISIDRYVAIVQAVSAHRHRARVLLISKLSCVGIWILATVLSIPELLYS

DLQRSSSEQAMRCSLITEHVEAFITIQVAQMVIGFLVPLLAMSFCYLVIIRTLLQARNFERNKAIKV
```

IIAVVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

D198G 20110009482
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGGCCTCCAGAGGAGCAGCAGTGAGCAAGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCCTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

GLQRSSSEQAMRCSLITEHVEAFITIQVAQMVIGFLVPLLAMSFCYLVIIRTLLQARNFERNKAIKV

IIAVVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

R201K 20100171268
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAAGAGCAGCAGTGAGCAAGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

```
TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQKSSSEQAMRCSLITEHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

S202N 20110009483
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAACAGCAGTGAGCAAGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRNSSEQAMRCSLITEHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

S204G 20100171269
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC
```

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCGGTGAGCAAGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSGEQAMRCSLITEHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

Q206D 20110009484
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGGATGCGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

```
CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEDAMRCSLITEHVEAFITIQVAQMVIGFLVPLLAMSFCYLVIIRTLLQARNFERNKAIKV

IIAVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

A207T 20100171270
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAACGAT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCCTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQTMRCSLITEHVEAFITIQVAQMVIGFLVPLLAMSFCYLVIIRTLLQARNFERNKAIKV

IIAVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

M208L 20100171271
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG
```

-continued

```
TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGTT

GCGATGCTCTCTCATCACAGAGCATGTGGAGGCCTTTATCACCATCCAGGTGGCCCAGATGG

TGATCGGCTTTCTGGTCCCCCTGCTGGCCATGAGCTTCTGTTACCTTGTCATCATCCGCACCC

TGCTCCAGGCACGCAACTTTGAGCGCAACAAGGCCATCAAGGTGATCATCGCTGTGGTCGTG

GTCTTCATAGTCTTCCAGCTGCCCTACAATGGGGTGGTCCTGGCCCAGACGGTGGCCAACTT

CAACATCACCAGTAGCACCTGTGAGCTCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG
```

MDLGKPMKSVLVVALLVIFQVCLCQDEVTDDYIGDNTTVDYTLFESLCSKKDVRNFKAWFLPIM
YSIICFVGLLGNGLVVLTYIYFKRLKTMTDTYLLNLAVADILFLLTLPFWAYSAAKSWVFGVHFC
KLIFAIYKMSFFSGMLLLLCISIDRYVAIVQAVSAHRHRARVLLISKLSCVGIWILATVLSIPELLYS
DLQRSSSEQALRCSLITEHVEAFITIQVAQMVIGFLVPLLAMSFCYLVIIRTLLQARNFERNKAIKV
IIAVVVFIVFQLPYNGVVLAQTVANFNITSSTCELSKQLNIAYDVTYSLACVRCCVNPFLYAFIG
VKFRNDLFKLFKDLGCLSQEQLRQWSSCRHIRRSSMSVEAETTTTFSP

I213V 20100168569

```
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCGTCACAGAGCATGTGGAGGCCTTTATCACCATCCAGGTGGCCCAGATGG

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG
```

MDLGKPMKSVLVVALLVIFQVCLCQDEVTDDYIGDNTTVDYTLFESLCSKKDVRNFKAWFLPIM
YSIICFVGLLGNGLVVLTYIYFKRLKTMTDTYLLNLAVADILFLLTLPFWAYSAAKSWVFGVHFC

-continued

KLIFAIYKMSFFSGMLLLLCISIDRYVAIVQAVSAHRHRARVLLISKLSCVGIWILATVLSIPELLYS

DLQRSSSEQAMRCSLVTEHVEAFITIQVAQMVIGFLVPLLAMSFCYLVIIRTLLQARNFERNKAIK

VIIAVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

T214S 20100168568
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCTCAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLISEHVEAFITIQVAQMVIGFLVPLLAMSFCYLVIIRTLLQARNFERNKAIKV

IIAVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP

E215A 20100168567
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGCGCATGTGGAGGCCTTTATCACCATCCAGGTGGCCCAGATGGT

```
GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLITAHVEAFITIQVAQMVIGFLVPLLAMSFCYLVIIRTLLQARNFERNKAIK

VIIAVVVVFIVFQLPYNGVVLAQTVANFNITSSTCELSKQLNIAYDVTYSLACVRCCVNPFLYAFI

GVKFRNDLFKLFKDLGCLSQEQLRQWSSCRHIRRSSMSVEAETTTTFSP

H216Q 20110009485
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGAGCAGGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGCTCAGTAAGCAACTCAACATCGCCTACGACGTCACCTA

CAGCCTGGCCTGCGTCCGCTGCTGCGTCAACCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLITEQVEAFITIQVAQMVIGFLVPLLAMSFCYLVIIRTLLQARNFERNKAIKV

IIAVVVVFIVFQLPYNGVVLAQTVANFNITSSTCELSKQLNIAYDVTYSLACVRCCVNPFLYAFIG

VKFRNDLFKLFKDLGCLSQEQLRQWSSCRHIRRSSMSVEAETTTTFSP
```

S295N 20110018205
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAATAGCACCTGTGAGCTCAGTAAGCAACTCAACATCGCCTACGACGTCACCTA

CAGCCTGGCCTGCGTCCGCTGCTGCGTCAACCCCTTTCTTGTACGCCTTCATCGGCGTCAAGTT

CCGCAACGATCTCTTCAAGCTCTTCAAGGACCTGGGCTGCCTCAGCCAGGAGCAGCTCCGGC

AGTGGTCTTCCTGTCGGCACATCCGGCGCTCCTCCATGAGTGTGGAGGCCGAGACCACCACC

ACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLITEHVEAFITIQVAQMVIGFLVPLLAMSFCYLVIIRTLLQARNFERNKAIKV

IIAVVVFIVFQLPYNGVVLAQTVANFNITNSTCELSKQLNIAYDVTYSLACVRCCVNPFLYAFIG

VKFRNDLFKLFKDLGCLSQEQLRQWSSCRHIRRSSMSVEAETTTTFSP

T297S 20110018203
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

-continued

AACATCACCAGTAGCAGCTGTGAGCTCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLITEHVEAFITIQVAQMVIGFLVPLLAMSFCYLVIIRTLLQARNFERNKAIKV

IIAVVVVFIVFQLPYNGVVLAQTVANFNITSSSCELSKQLNIAYDVTYSLACVRCCVNPFLYAFIG

VKFRNDLFKLFKDLGCLSQEQLRQWSSCRHIRRSSMSVEAETTTTFSP

L300T 20110018204
ATGGACCTGGGGAAACCAATGAAAAGCGTGCTGGTGGTGGCTCTCCTTGTCATTTTCCAGGT

ATGCCTGTGTCAAGATGAGGTCACGGACGATTACATCGGAGACAACACCACAGTGGACTAC

ACTTTGTTCGAGTCTTTGTGCTCCAAGAAGGACGTGCGGAACTTTAAAGCCTGGTTCCTCCCT

ATCATGTACTCCATCATTTGTTTCGTGGGCCTACTGGGCAATGGGCTGGTCGTGTTGACCTAT

ATCTATTTCAAGAGGCTCAAGACCATGACCGATACCTACCTGCTCAACCTGGCGGTGGCAGA

CATCCTCTTCCTCCTGACCCTTCCCTTCTGGGCCTACAGCGCGGCCAAGTCCTGGGTCTTCGG

TGTCCACTTTTGCAAGCTCATCTTTGCCATCTACAAGATGAGCTTCTTCAGTGGCATGCTCCT

ACTTCTTTGCATCAGCATTGACCGCTACGTGGCCATCGTCCAGGCTGTCTCAGCTCACCGCCA

CCGTGCCCGCGTCCTTCTCATCAGCAAGCTGTCCTGTGTGGGCATCTGGATACTAGCCACAG

TGCTCTCCATCCCAGAGCTCCTGTACAGTGACCTCCAGAGGAGCAGCAGTGAGCAAGCGATG

CGATGCTCTCTCATCACAGAGCATGTGGAGGCCTTTATCACCATCCAGGTGGCCCAGATGGT

GATCGGCTTTCTGGTCCCCCTGCTGGCCATGAGCTTCTGTTACCTTGTCATCATCCGCACCCT

GCTCCAGGCACGCAACTTTGAGCGCAACAAGGCCATCAAGGTGATCATCGCTGTGGTCGTGG

TCTTCATAGTCTTCCAGCTGCCCTACAATGGGGTGGTCCTGGCCCAGACGGTGGCCAACTTC

AACATCACCAGTAGCACCTGTGAGACCAGTAAGCAACTCAACATCGCCTACGACGTCACCT

ACAGCCTGGCCTGCGTCCGCTGCTGCGTCAACCCTTTCTTGTACGCCTTCATCGGCGTCAAGT

TCCGCAACGATCTCTTCAAGCTCTTCAAGGACCTGGGCTGCCTCAGCCAGGAGCAGCTCCGG

CAGTGGTCTTCCTGTCGGCACATCCGGCGCTCCTCCATGAGTGTGGAGGCCGAGACCACCAC

CACCTTCTCCCCATAG

MDLGKPMKSVLVVALLVIFQVCLCQDEVTDDYIGDNTTVDYTLFESLCSKKDVRNFKAWFLPIM

YSIICFVGLLGNGLVVLTYIYFKRLKTMTDTYLLNLAVADILFLLTLPFWAYSAAKSWVFGVHFC

KLIFAIYKMSFFSGMLLLLCISIDRYVAIVQAVSAHRHRARVLLISKLSCVGIWILATVLSIPELLYS

DLQRSSSEQAMRCSLITEHVEAFITIQVAQMVIGFLVPLLAMSFCYLVIIRTLLQARNFERNKAIKV

IIAVVVVFIVFQLPYNGVVLAQTVANFNITSSTCETSKQLNIAYDVTYSLACVRCCVNPFLYAFIG

VKFRNDLFKLFKDLGCLSQEQLRQWSSCRHIRRSSMSVEAETTTTFSP*

293T cells were transfected with each of the 22 constructs using Fugene HD Transfection Reagent (Cat #: 04709705001) (Roche Applied Sciences, Indianapolis, Ind.), according to manufacturer's protocol. DNA to Fugene HD ratio used was 1:3. Controls for the transfection were pcDNA3.1 Neo-hCCR7 (20100121357) listed above, and pcDNA3.1 Neo-mouseCCR7 (20060298628):

ATGGACCCAGGGAAACCCAGGAAAAACGTGCTGGTGGTGGCTCTCCTTGT

CATTTTCCAGGTGTGCTTCTGCCAAGATGAGGTCACCGATGACTACATCG

GCGAGAATACCACGGTGGACTACACCCTGTACGAGTCGGTGTGCTTCAAG

```
AAGGATGTGCGGAACTTTAAGGCCTGGTTCCTGCCTCTCATGTATTCTGT

CATCTGCTTCGTGGGCCTGCTCGGCAACGGGCTGGTGATACTGACGTACA

TCTATTTCAAGAGGCTCAAGACCATGACGGATACCTACCTGCTCAACCTG

GCCGTGGCAGACATCCTTTTCCTCCTAATTCTTCCCTTCTGGGCCTACAG

CGAAGCCAAGTCCTGGATCTTTGGCGTCTACCTGTGTAAGGGCATCTTTG

GCATCTATAAGTTAAGCTTCTTCAGCGGGATGCTGCTGCTCCTATGCATC

AGCATTGACCGCTACGTAGCCATCGTCCAGGCCGTGTCGGCTCATCGCCA

CCGCGCCCGCGTGCTTCTCATCAGCAAGCTGTCCTGTGTGGGCATCTGGA

TGCTGGCCCTCTTCCTCTCCATCCCGGAGCTGCTCTACAGCGGCCTCCAG

AAGAACAGCGGCGAGGACACGCTGAGATGCTCACTGGTCAGTGCCCAAGT

GGAGGCCTTGATCACCATCCAAGTGGCCCAGATGGTTTTTGGGTTCCTAG

TGCCTATGCTGGCTATGAGTTTCTGCTACCTCATTATCATCCGTACCTTG

CTCCAGGCACGCAACTTTGAGCGGAACAAGGCCATCAAGGTGATCATTGC

CGTGGTGGTAGTCTTCATAGTCTTCCAGCTGCCCTACAATGGGGTGGTCC

TGGCTCAGACGGTGGCCAACTTCAACATCACCAATAGCAGCTGCGAAACC

AGCAAGCAGCTCAACATTGCCTATGACGTCACCTACAGCCTGGCCTCCGT

CCGCTGCTGCGTCAACCCTTTCTTGTATGCCTTCATCGGCGTCAAGTTCC

GCAGCGACCTCTTCAAGCTCTTCAAGGACTTGGGCTGCCTCAGCCAGGAA

CGGCTCCGGCACTGGTCTTCCTGCCGGCATGTACGGAACGCGTCGGTGAG

CATGGAGGCGGAGACCACCACAACCTTCTCCCCGTAG

MDPGKPRKNVLVVALLVIFQVCFCQDEVTDDYIGENTTVDYTLYESVCFK

KDVRNFKAWFLPLMYSVICFVGLLGNGLVILTYIYFKRLKTMTDTYLLNL

AVADILFLLILPFWAYSEAKSWIFGVYLCKGIFGIYKLSFFSGMLLLCI

SIDRYVAIVQAVSAHRHRARVLLISKLSCVGIWMLALFLSIPELLYSGLQ

KNSGEDTLRCSLVSAQVEALITIQVAQMVFGFLVPMLAMSFCYLIIIRTL

LQARNFERNKAIKVIIAVVVVFIVFQLPYNGVVLAQTVANFNITNSSCET

SKQLNIAYDVTYSLASVRCCVNPFLYAFIGVKFRSDLFKLFKDLGCLSQE

RLRHWSSCRHVRNASVSMEAETTTTFSP
```

After 48 hours, transfected cells were harvested and washed with PBS+5%FBS two times. Cells were counted using the Nexcelom Cell Counter (Nexcelom Bioscience, Lawrence, Mass.), and 250,000 cells per well were plated in a 96 well round bottom plate. Cells transfected with each construct were stained in duplicate as follows: unstained control, 6B4.1 primary Ab followed by Goat anti-human-PE secondary Ab, 6B5.1 primary Ab followed by Goat anti-human-PE secondary Ab, mAb197 primary Ab (R&D Systems, Minneapolis, Minn.) followed by Goat anti-mouse-PE secondary Ab, and the controls of secondary Ab Goat anti-mouse-PE only and Goat anti-human-PE only. The cells were visualized by flow cytometry and geo means were generated and analyzed.

Figure 5:
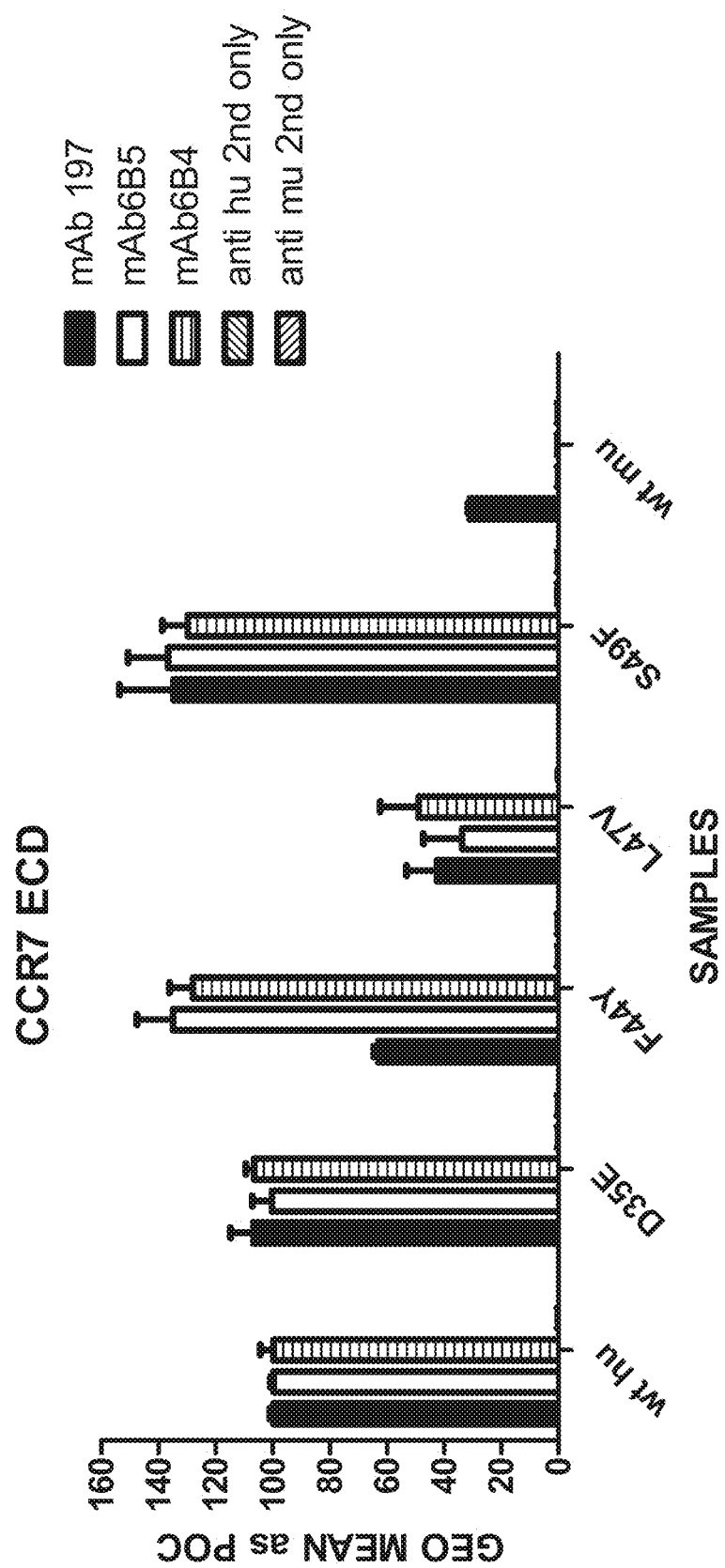
FIG. 5 provides epitope mapping data for antibodies mAb197, 6B4.1, and 6B5.1.

FIG. 5 shows that mAb197 showed lower binding, as compared to 6B4.1 and 6B5.1, to the CDR construct having the F44Y mutation, demonstrating that antibodies 6B4.1and 6B5.1 each bound to an epitope different than that of mAb197. All three antibodies bound to the D35 variant about as well as each bound to wild-type human CCR7, less well to the L47V variant, and better to the S49F variant. Of these antibodies, only mAb197 bound to wild-type murine CCR7.

Figure 6:
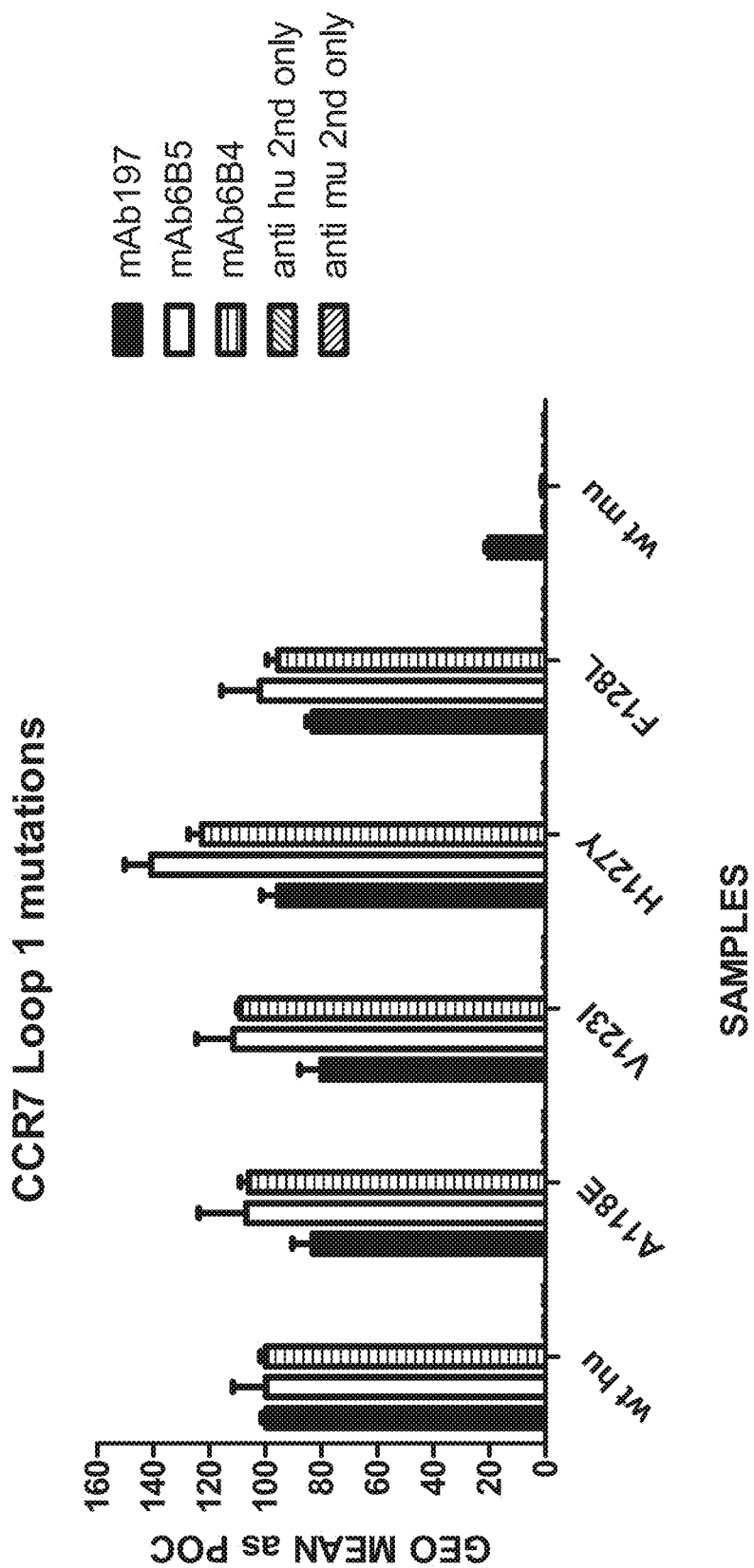
FIG. 6 provides epitope mapping data for antibodies mAb197, 6B4.1, and 6B5.1.

FIG. 6 shows that no obvious differences occurred in binding to variants within ECL1. Each of the three antibodies bound roughly as well to each mutant as it bound to wild-type human CCR7.

Figure 7:
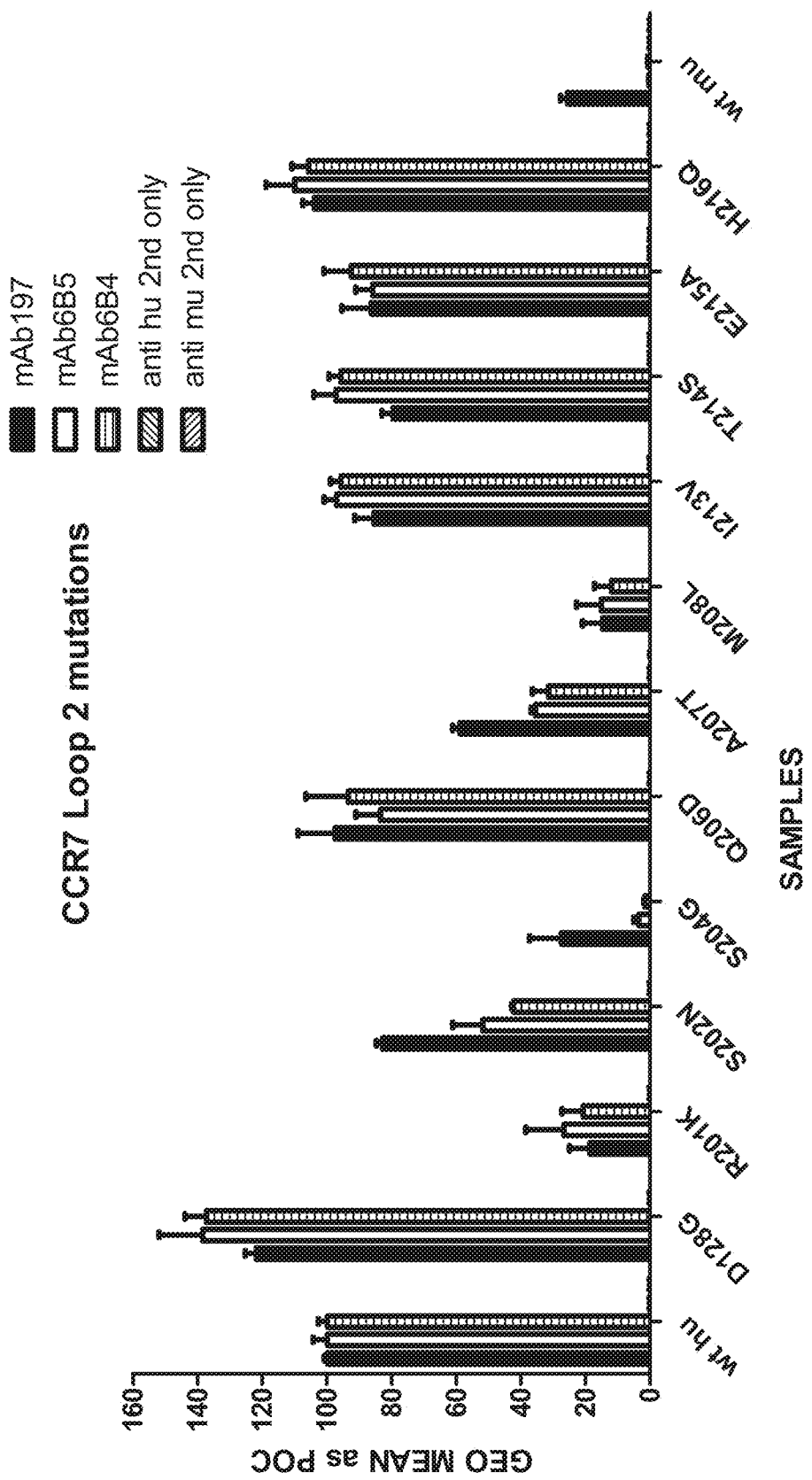
FIG. 7 provides epitope mapping data for antibodies mAb197, 6B4.1, and 6B5.1.

FIG. 7 shows that mAb197 showed less of a reduction in binding to the S202N, S204G, and A207T variants of ECL2 (as compared to its binding to wild-type human CCR7) than the reduction showed by either 6B.4 or 6B.5, although all three antibodies bound less well to these variants, and to the R201K and M208L variants, than they bound to wild-type human CCR7.

Figure 8:
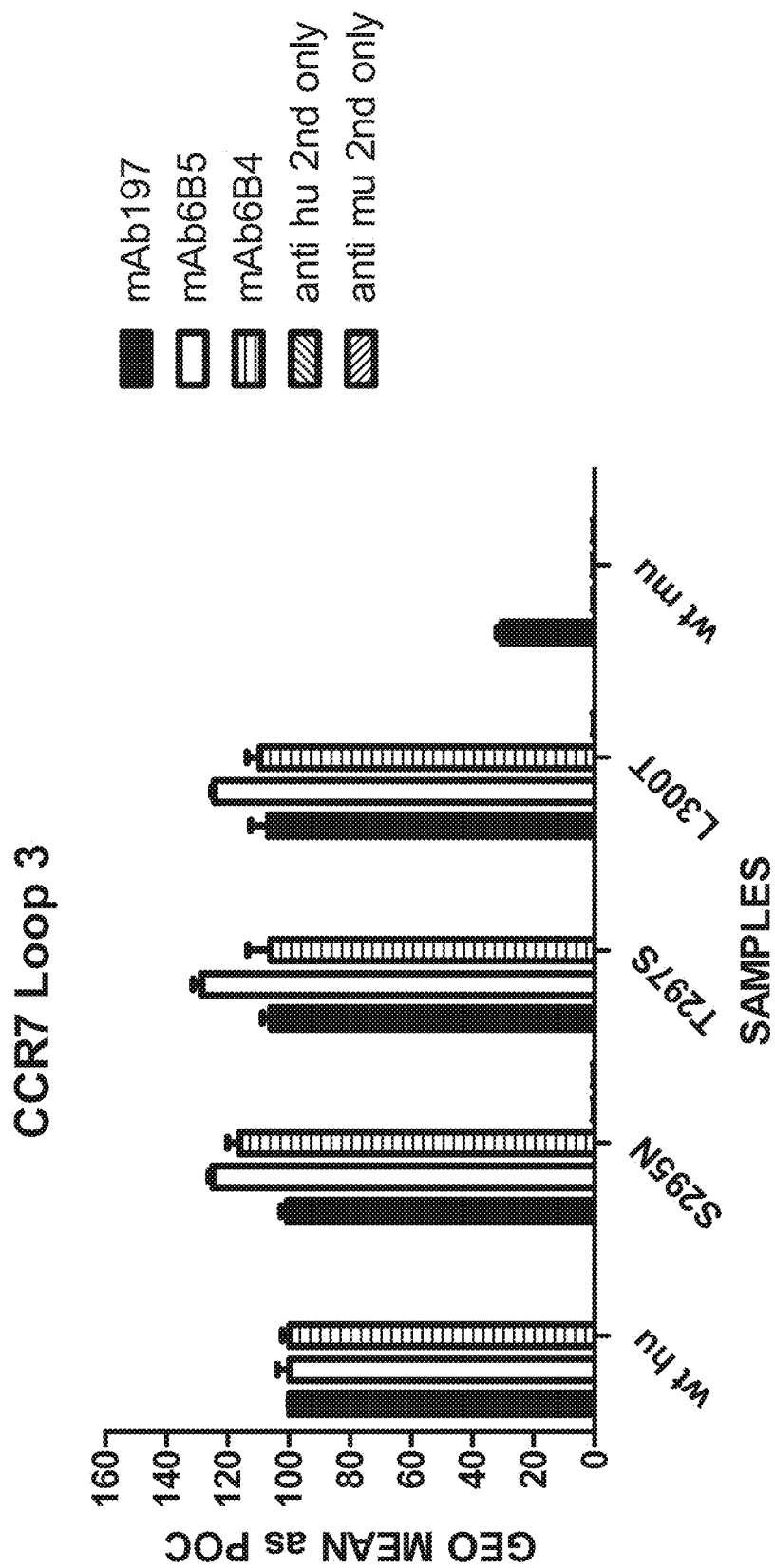
FIG. 8 provides epitope mapping data for antibodies mAb197, 6B4.1, and 6B5.1.

FIG. 8 shows that all three antibodies bound about as well to each of the tested ECL3 variants as it bound to wild-type human CCR7. Again, only mAb197 bound to the wild-type murine CCR7 receptor.

Reciprocal constructs were made in which a wild-type murine CCR7 sequence was mutated to replace certain of its amino acid residues with the residue found at the homologous position in wild-type human CCR7.

The following mutations were made: Y44F, V47L, K201R, N202S, G204S, T207A, L208M. These amino acid changes were used in the following combinations as individual constructs:

1) Y44F and V47L mutations
2) K201R/N202S/G204S/T207A/L208M
3) All of the above: Y44F/V47L/K201R/N202S/G204S/T207A/L208M The following oligos were made:

Y44F_V47L sense:
ACGGTGGACTACACCCTGTTCGAGTCGTTGTGCTTCAA

Y44F_V47L_antisense:
TTGAAGCACAACGACTCGAACAGGGTGTAGTCCACCGT

K201R_N202S_G204S_T207A_L208M sense:
CAGCGGCCTCCAGAGGAGCAGCAGCGAGGACGCGATGAGATGCTC K201R_N202S_G204S_T207A_L208M antisense:
GAGCATCTCATCGCGTCCTCGCTGCTGCTCCTCTGGAGGCCGCTG The oligos were diluted to 50 ng/□l concentration. PCR reactions were set up using 100 ng template DNA pcDNA3.1 Neo-mCCR7 (20060298628). For each individual mutation, a PCR product was generated using a QuikChange Multi Site-Site Directed Mutagenesis Kit (Cat #200531) (Stratagene, La Jolla, Calif.) according to manufacturer's instructions. The resulting PCR products were Dpnl digested and then transformed into Top10 chemically competent cells (Invitrogen, Grand Island, N.Y.). Individual colonies were picked for each construct and sequenced. Clones with the correct sequences were scaled up and re-sequenced. The final clone DNA sequences and translated protein sequences follow:

Y44F and V47L construct 20110094675 ("YV"):
ATGGACCCAGGGAAACCCAGGAAAAACGTGCTGGTGGTGGCTCTCCTTGT

CATTTTCCAGGTGTGCTTCTGCCAAGATGAGGTCACCGATGACTACATCG

GCGAGAATACCACGGTGGACTACACCCTGTTCGAGTCGTTGTGCTTCAAG

AAGGATGTGCGGAACTTTAAGGCCTGGTTCCTGCCTCTCATGTATTCTGT

CATCTGCTTCGTGGGCCTGCTCGGCAACGGGCTGGTGATACTGACGTACA

-continued

```
TCTATTTCAAGAGGCTCAAGACCATGACGGATACCTACCTGCTCAACCTG
GCCGTGGCAGACATCCTTTTCCTCCTAATTCTTCCCTTCTGGGCCTACAG
CGAAGCCAAGTCCTGGATCTTTGGCGTCTACCTGTGTAAGGGCATCTTTG
GCATCTATAAGTTAAGCTTCTTCAGCGGGATGCTGCTGCTCCTATGCATC
AGCATTGACCGCTACGTAGCCATCGTCCAGGCCGTGTCGGCTCATCGCCA
CCGCGCCCGCGTGCTTCTCATCAGCAAGCTGTCCTGTGTGGGCATCTGGA
TGCTGGCCCTCTTCCTCTCCATCCCGGAGCTGCTCTACAGCGGCCTCCAG
AAGAACAGCGGCGAGGACACGCTGAGATGCTCACTGGTCAGTGCCCAAGT
GGAGGCCTTGATCACCATCCAAGTGGCCCAGATGGTTTTTGGGTTCCTAG
TGCCTATGCTGGCTATGAGTTTCTGCTACCTCATTATCATCCGTACCTTG
CTCCAGGCACGCAACTTTGAGCGGAACAAGGCCATCAAGGTGATCATTGC
CGTGGTGGTAGTCTTCATAGTCTTCCAGCTGCCCTACAATGGGGTGGTCC
TGGCTCAGACGGTGGCCAACTTCAACATCACCAATAGCAGCTGCGAAACC
AGCAAGCAGCTCAACATTGCCTATGACGTCACCTACAGCCTGGCCTCCGT
CCGCTGCTGCGTCAACCCTTTCTTGTATGCCTTCATCGGCGTCAAGTTCC
GCAGCGACCTCTTCAAGCTCTTCAAGGACTTGGGCTGCCTCAGCCAGGAA
CGGCTCCGGCACTGGTCTTCCTGCCGGCATGTACGGAACGCGTCGGTGAG
CATGGAGGCGGAGACCACCACAACCTTCTCCCCGTAG
MDPGKPRKNVLVVALLVIFQVCFCQDEVTDDYIGENTTVDYTLFESLCFK
KDVRNFKAWFLPLMYSVICFVGLLGNGLVILTYIYFKRLKTMTDTYLLNL
AVADILFLLILPFWAYSEAKSWIFGVYLCKGIFGIYKLSFFSGMLLLLCI
SIDRYVAIVQAVSAHRHRARVLLISKLSCVGIWMLALFLSIPELLYSGLQ
KNSGEDTLRCSLVSAQVEALITIQVAQMVFGFLVPMLAMSFCYLIIIRTL
LQARNFERNKAIKVIIAVVVVFIVFQLPYNGVVLAQTVANFNITNSSCET
SKQLNIAYDVTYSLASVRCCVNPFLYAFIGVKFRSDLFKLFKDLGCLSQE
RLRHWSSCRHVRNASVSMEAETTTTFSP
K201R/N202S/G204S/T207A/L208M construct
20110094673 ("KNGTL"):
ATGGACCCAGGGAAACCCAGGAAAAACGTGCTGGTGGTGGCTCTCCTTGT
CATTTTCCAGGTGTGCTTCTGCCAAGATGAGGTCACCGATGACTACATCG
GCGAGAATACCACGGTGGACTACACCCTGTACGAGTCGGTGTGCTTCAAG
AAGGATGTGCGGAACTTTAAGGCCTGGTTCCTGCCTCTCATGTATTCTGT
CATCTGCTTCGTGGGCCTGCTCGGCAACGGGCTGGTGATACTGACGTACA
TCTATTTCAAGAGGCTCAAGACCATGACGGATACCTACCTGCTCAACCTG
GCCGTGGCAGACATCCTTTTCCTCCTAATTCTTCCCTTCTGGGCCTACAG
CGAAGCCAAGTCCTGGATCTTTGGCGTCTACCTGTGTAAGGGCATCTTTG
GCATCTATAAGTTAAGCTTCTTCAGCGGGATGCTGCTGCTCCTATGCATC
AGCATTGACCGCTACGTAGCCATCGTCCAGGCCGTGTCGGCTCATCGCCA
CCGCGCCCGCGTGCTTCTCATCAGCAAGCTGTCCTGTGTGGGCATCTGGA
TGCTGGCCCTCTTCCTCTCCATCCCGGAGCTGCTCTACAGCGGCCTCCAG
AGGAGCAGCAGCGAGGACGCGATGAGATGCTCACTGGTCAGTGCCCAAGT
GGAGGCCTTGATCACCATCCAAGTGGCCCAGATGGTTTTTGGGTTCCTAG
TGCCTATGCTGGCTATGAGTTTCTGCTACCTCATTATCATCCGTACCTTG
CTCCAGGCACGCAACTTTGAGCGGAACAAGGCCATCAAGGTGATCATTGC
CGTGGTGGTAGTCTTCATAGTCTTCCAGCTGCCCTACAATGGGGTGGTCC
TGGCTCAGACGGTGGCCAACTTCAACATCACCAATAGCAGCTGCGAAACC
AGCAAGCAGCTCAACATTGCCTATGACGTCACCTACAGCCTGGCCTCCGT
CCGCTGCTGCGTCAACCCTTTCTTGTATGCCTTCATCGGCGTCAAGTTCC
GCAGCGACCTCTTCAAGCTCTTCAAGGACTTGGGCTGCCTCAGCCAGGAA
CGGCTCCGGCACTGGTCTTCCTGCCGGCATGTACGGAACGCGTCGGTGAG
CATGGAGGCGGAGACCACCACAACCTTCTCCCCGTAG
MDPGKPRKNVLVVALLVIFQVCFCQDEVTDDYIGENTTVDYTLYESVCFK
KDVRNFKAWFLPLMYSVICFVGLLGNGLVILTYIYFKRLKTMTDTYLLNL
AVADILFLLILPFWAYSEAKSWIFGVYLCKGIFGIYKLSFFSGMLLLLCI
SIDRYVAIVQAVSAHRHRARVLLISKLSCVGIWMLALFLSIPELLYSGLQ
RSSSEDAMRCSLVSAQVEALITIQVAQMVFGFLVPMLAMSFCYLIIIRTL
LQARNFERNKAIKVIIAVVVVFIVFQLPYNGVVLAQTVANFNITNSSCET
SKQLNIAYDVTYSLASVRCCVNPFLYAFIGVKFRSDLFKLFKDLGCLSQE
RLRHWSSCRHVRNASVSMEAETTTTFSP
```

Using construct 20110094673, another round of QuikChange Site directed mutagenesis was run using the following oligos in order to get all 7 mutations in one construct:

```
Y44F_V47L sense:
ACGGTGGACTACACCCTGTTCGAGTCGTTGTGCTTCAA

Y44F_V47L antisense:
TTGAAGCACAACGACTCGAACAGGGTGTAGTCCACCGT

Y44F/V47L/K201R/N202S/G204S/T207A/L208M construct
20110105423 ("YVKNGTL"):
ATGGACCCAGGGAAACCCAGGAAAAACGTGCTGGTGGTGGCTCTCCTTGT
CATTTTCCAGGTGTGCTTCTGCCAAGATGAGGTCACCGATGACTACATCG
GCGAGAATACCACGGTGGACTACACCCTGTTCGAGTCGTTGTGCTTCAAG
AAGGATGTGCGGAACTTTAAGGCCTGGTTCCTGCCTCTCATGTATTCTGT
CATCTGCTTCGTGGGCCTGCTCGGCAACGGGCTGGTGATACTGACGTACA
TCTATTTCAAGAGGCTCAAGACCATGACGGATACCTACCTGCTCAACCTG
GCCGTGGCAGACATCCTTTTCCTCCTAATTCTTCCCTTCTGGGCCTACAG
CGAAGCCAAGTCCTGGATCTTTGGCGTCTACCTGTGTAAGGGCATCTTTG
GCATCTATAAGTTAAGCTTCTTCAGCGGGATGCTGCTGCTCCTATGCATC
AGCATTGACCGCTACGTAGCCATCGTCCAGGCCGTGTCGGCTCATCGCCA
CCGCGCCCGCGTGCTTCTCATCAGCAAGCTGTCCTGTGTGGGCATCTGGA
TGCTGGCCCTCTTCCTCTCCATCCCGGAGCTGCTCTACAGCGGCCTCCAG
AGGAGCAGCAGCGAGGACGCGATGAGATGCTCACTGGTCAGTGCCCAAGT
GGAGGCCTTGATCACCATCCAAGTGGCCCAGATGGTTTTTGGGTTCCTAG
TGCCTATGCTGGCTATGAGTTTCTGCTACCTCATTATCATCCGTACCTTG
```

```
-continued
CTCCAGGCACGCAACTTTGAGCGGAACAAGGCCATCAAGGTGATCATTGC

CGTGGTGGTAGTCTTCATAGTCTTCCAGCTGCCCTACAATGGGGTGGTCC

TGGCTCAGACGGTGGCCAACTTCAACATCACCAATAGCAGCTGCGAAACC

AGCAAGCAGCTCAACATTGCCTATGACGTCACCTACAGCCTGGCCTCCGT

CCGCTGCTGCGTCAACCCTTTCTTGTATGCCTTCATCGGCGTCAAGTTCC

GCAGCGACCTCTTCAAGCTCTTCAAGGACTTGGGCTGCCTCAGCCAGGAA

CGGCTCCGGCACTGGTCTTCCTGCCGGCATGTACGGAACGCGTCGGTGAG

CATGGAGGCGGAGACCACCACAACCTTCTCCCCGTAG

MDPGKPRKNVLVVALLVIFQVCFCQDEVTDDYIGENTTVDYTLFESLCFK

KDVRNFKAWFLPLMYSVICFVGLLGNGLVILTYIYFKRLKTMTDTYLLNL

AVADILFLLILPFWAYSEAKSWIFGVYLCKGIFGIYKLSFFSGMLLLLCI

SIDRYVAIVQAVSAHRHRARVLLISKLSCVGIWMLALFLSIPELLYSGLQ

RSSSEDAMRCSLVSAQVEALITIQVAQMVFGFLVPMLAMSFCYLIIIRTL

LQARNFERNKAIKVIIAVVVVFIVFQLPYNGVVLAQTVANFNITNSSCET

SKQLNIAYDVTYSLASVRCCVNPFLYAFIGVKFRSDLFKLFKDLGCLSQE

RLRHWSSCRHVRNASVSMEAETTTTFSP
```

293T cells were transfected with each of the 22 constructs using Fugene HD Transfection Reagent (Cat #: 04709705001) (Roche Applied Sciences, Indianapolis, Ind.) according to manufacturer's protocol. DNA to Fugene HD ratio used was 1:3. Controls for the transfection were wild type pcDNA3.1 Neo-hCCR7 (20100121357) listed above, and wild type pcDNA3.1 Neo-mouseCCR7 (20060298628). After 48 hours, transfected cells were harvested and washed with PBS+5% FBS two times. Cells were counted using the Nexcelom Cell Counter (Nexcelom Bioscience, Lawrence, Mass.), and 250,000 cells per well were plated in a 96 well round bottom plate. Cells transfected with each construct were stained in duplicate as follows: unstained control, 6B4.1 primary Ab followed by Goat anti-human-PE secondary Ab, 6B5.1 primary Ab followed by Goat anti-human-PE secondary Ab, mAb197 primary Ab followed by Goat anti-mouse-PE secondary Ab, and the controls of secondary Ab Goat anti-mouse-PE only and Goat anti-human-PE only. The cells were visualized by flow cytometry and geo means were generated and analyzed.

As previously determined, of the three tested antibodies, only mAb197 bound to wild-type murine CCR7, while all three bound to wild-type human CCR7. mAb197 was the only tested antibody to bind the YV construct. Both 6B.4 and 6B.5 bound to the KNGTL construct, and in fact bound to it better than mAb197. All three antibodies also bound to construct YVKNGTL, but mAb197 bound better than either 6B.4 or 6B.5.

What is claimed is:

1. An isolated CCR7 antigen binding protein, comprising:
   a. the light chain variable domain sequence of 6B5.1 LC (SEQ ID NO:18), as shown underlined in FIG. 1, and the heavy chain variable domain sequence of 6B5.1 HC (SEQ ID NO:50), as shown underlined in FIG. 1; or
   (b) the light chain CDR 1, 2, and 3 sequences of 6B5.1 (SEQ ID NO:20, 22, and 24, respectively), and the heavy chain CDR 1, 2, and 3 sequences of 6B5.1 (SEQ ID NO:52, 54, and 56, respectively).

2. The isolated CCR7 antigen binding protein of claim 1, wherein said CCR7 antigen binding protein is an anti-CCR7 antibody, and wherein said antibody comprises the sequences 6B5.1 LC (SEQ ID NO:18) and 6B5.1 HC (SEQ ID NO:50).

3. The isolated CCR7 antigen binding protein of claim 1 wherein said antigen binding protein comprises:
   a. a human antibody;
   b. a humanized antibody;
   c. a chimeric antibody;
   d. a monoclonal antibody;
   e. a polyclonal antibody;
   f. a recombinant antibody;
   g. an antigen-binding antibody fragment;
   h. a single chain antibody;
   i. a diabody;
   j. a triabody;
   k. a tetrabody;
   l. a Fab fragment;
   m. a F(ab')2 fragment;
   n. a domain antibody;
   o. an IgD antibody;
   p. an IgE antibody;
   q. an IgM antibody;
   r. an IgG1 antibody;
   s. an IgG2 antibody;
   t. an IgG3 antibody;
   u. an IgG4 antibody; or
   v. an IgG4 antibody having at least one mutation in a hinge region that alleviates a tendency to form intra-H chain disulfide bond.

4. The isolated CCR7 antigen binding protein of claim 1 wherein said antigen binding protein inhibits binding of CCL19 or CCL21 to CCR7.

5. A pharmaceutical composition comprising the CCR7 antigen binding protein of claim 1.

* * * * *